(12) United States Patent
Martinez et al.

(10) Patent No.: US 11,350,648 B2
(45) Date of Patent: Jun. 7, 2022

(54) COMPOSITIONS AND RELATED METHODS FOR AGRICULTURE

(71) Applicant: Flagship Pioneering Innovations V, Inc., Cambridge, MA (US)

(72) Inventors: Ignacio Martinez, Lexington, MA (US); Zachary Garo Armen, Boston, MA (US); Jonathan Friedlander, Cambridge, MA (US); Christine Cezar, Sammamish, WA (US); Barry Andrew Martin, Boston, MA (US); Maier Steve Avendano Amado, Cambridge, MA (US)

(73) Assignee: Flagship Pioneering Innovations V, Inc., Cambridge, MA (US)

( * ) Notice: Subject to any disclaimer, the term of this patent is extended or adjusted under 35 U.S.C. 154(b) by 63 days.

(21) Appl. No.: 16/480,228

(22) PCT Filed: Jan. 24, 2018

(86) PCT No.: PCT/US2018/015025
§ 371 (c)(1),
(2) Date: Jul. 23, 2019

(87) PCT Pub. No.: WO2018/140479
PCT Pub. Date: Aug. 2, 2018

(65) Prior Publication Data
US 2020/0129565 A1    Apr. 30, 2020

Related U.S. Application Data

(60) Provisional application No. 62/583,736, filed on Nov. 9, 2017, provisional application No. 62/450,017, filed on Jan. 24, 2017.

(51) Int. Cl.
*A61K 35/741* (2015.01)
*A23K 20/153* (2016.01)
(Continued)

(52) U.S. Cl.
CPC ............ *A23K 20/153* (2016.05); *A01G 31/00* (2013.01); *A01K 53/00* (2013.01); *A01K 67/033* (2013.01);
(Continued)

(58) Field of Classification Search
CPC ..................................................... A61K 35/741
See application file for complete search history.

(56) References Cited

U.S. PATENT DOCUMENTS 5,631,024 A    5/1997   Kevan et al.
8,334,366 B1  12/2012   Hughes et al.
(Continued)

FOREIGN PATENT DOCUMENTS

CN    1499932 A    5/2004
CN  101636073 A    1/2010
(Continued)

OTHER PUBLICATIONS

Al-Ghamdi et al., "Effect of gut bacterial isolates from *Apis mellifera jementica* on *Paenibacillus larvae* infected bee larvae," Saudi J Biol Sci. 25(2):383-87 (2018).
(Continued)

*Primary Examiner* — Rosanne Kosson
(74) *Attorney, Agent, or Firm* — Clark & Elbing LLP

(57) ABSTRACT

Provided herein are agents, compositions, and methods for agricultural use, e.g., for altering the level, activity, or metabolism of one or more microorganisms resident in a host nematode or arthropod (e.g., honeybee or silkworm), the alteration resulting in an increase in the fitness of the host. The invention features a composition that includes an agent (e.g., phage, peptide, small molecule, antibiotic, or combinations thereof) that can alter the host's microbiota in a manner that is beneficial to the host. By promoting favorable microbial levels, microbial activity, microbial (Continued)

metabolism, and/or microbial diversity, the agents described herein may be used to increase the fitness of a variety of beneficial nematodes or arthropods, such as bees and silkworms, utilized in agriculture and commerce.

6 Claims, 5 Drawing Sheets

Specification includes a Sequence Listing.

(51) Int. Cl.
| | |
|---|---|
| A61K 35/74 | (2015.01) |
| A61K 35/745 | (2015.01) |
| A01G 31/00 | (2018.01) |
| A01K 53/00 | (2006.01) |
| A01K 67/033 | (2006.01) |
| A23K 50/90 | (2016.01) |
| A61K 35/747 | (2015.01) |

(52) U.S. Cl.
CPC .............. *A23K 50/90* (2016.05); *A61K 35/74* (2013.01); *A61K 35/745* (2013.01); *A61K 35/747* (2013.01)

(56) References Cited

U.S. PATENT DOCUMENTS

| | | |
|---|---|---|
| 10,086,024 B2 | 10/2018 | Kovarik |
| 2008/0295207 A1 | 11/2008 | Baum et al. |
| 2009/0285937 A1 | 11/2009 | Vadis et al. |
| 2011/0145939 A1 | 6/2011 | O'Neill |
| 2011/0150780 A1 | 6/2011 | Krieger et al. |
| 2011/0209228 A1 | 8/2011 | Cocks et al. |
| 2011/0229937 A1 | 9/2011 | Pompejus et al. |
| 2011/0263487 A1 | 10/2011 | Meagher |
| 2014/0349917 A1 | 11/2014 | Eckert et al. |
| 2017/0015716 A1 | 1/2017 | Walensky et al. |
| 2017/0151293 A1* | 6/2017 | Kovarik ............... A61K 35/747 |
| 2019/0015528 A1 | 1/2019 | Moran et al. |

FOREIGN PATENT DOCUMENTS

| | | |
|---|---|---|
| CN | 106472882 A | 3/2017 |
| CN | 106962696 A | 7/2017 |
| CN | 107028037 A | 8/2017 |
| CN | 108782465 A | 11/2018 |
| CN | 108783118 A | 11/2018 |
| CN | 108812552 A | 11/2018 |
| CN | 108813226 A | 11/2018 |
| CN | 109055268 A | 12/2018 |
| EP | 2949220 A1 | 12/2015 |
| FR | 2985664 A1 | 7/2013 |
| JP | H2-222654 A | 9/1990 |
| JP | 2010-136668 A | 6/2010 |
| JP | 2010-525809 A | 7/2010 |
| JP | 2013-158315 A | 8/2013 |
| KR | 2010-0125747 A | 12/2010 |
| KR | 2012-0123975 A | 11/2012 |
| KR | 2013-0101370 A | 9/2013 |
| MD | 1193 Y | 9/2017 |
| RU | 2305935 C1 | 9/2007 |
| RU | 2511304 C2 | 4/2014 |
| RU | 2552672 C1 | 6/2015 |
| RU | 2579266 C1 | 4/2016 |
| WO | WO-88/00976 A1 | 2/1988 |
| WO | WO-95/16776 A1 | 6/1995 |
| WO | WO-2005/034863 A2 | 4/2005 |
| WO | WO-2008/084074 A2 | 7/2008 |
| WO | WO-2014/097338 A1 | 6/2014 |
| WO | WO-2015/020516 A1 | 2/2015 |
| WO | WO-2015/100432 A2 | 7/2015 |
| WO | WO-2015/191744 A1 | 12/2015 |
| WO | WO-2016/004312 A1 | 1/2016 |
| WO | WO-2018/051344 A1 | 3/2018 |

OTHER PUBLICATIONS

Alberoni et al., "Beneficial microorganisms for honey bees: problems and progresses," Appl Microbiol Biotechnol. 100(22):9469-82 (2016).

Alberoni et al., "Impact of beneficial bacteria supplementation on the gut microbiota, colony development and productivity of *Apis mellifera* L.," Beneficial Microbes. 9(2):269-78 (2018).

Amos, "UBC students give bees a chance," University of British Columbia News, <http://news.ubc.ca/2015/09/18/ubc-students-give-bees-a-chance/>, dated Sep. 18, 2015 (3 pages).

Anderson et al., "An emerging paradigm of colony health: microbial balance of the honey bee and hive (*Apis mellifera*)" Insect Soc. 58:431-44 (2011).

Audisio et al., "Effect of *Lactobacillus johnsonii* CRL1647 on different parameters of honeybee colonies and bacterial populations of the bee gut," Benef Microbes. 6(5):687-95 (2015).

Audisio, "Gram-positive bacteria with probiotic potential for the *Apis mellifera* L. honey bee: the experience in the northwest of Argentina," Probiotics & Antimicro Prot. 9(1):22-31 (2017).

Baffoni et al., "Effect of dietary supplementation of *Bifidobacterium* and *Lactobacillus* strains in *Apis mellifera* L. against *Nosema ceranae*," Beneficial Microbes. 7(1):45-51 (2016).

Broderick et al., "Gut-associated microbes of *Drosophila melanogaster*," Gut Microbes. 3(4): 307-321 (2012).

Camiletti et al. "*Drosophila* As a Genetically Tractable Model for Social Insect Behavior," Front Ecol Evol. 4:1-9 (2016).

Chan et al., "Changes in protein expression during honey bee larval development," Genome Biol. 9(10):R156 (2008) (14 pages).

Chmiel et al. "Deleterious Effects of Neonicotinoid Pesticides on *Drosophila melanogaster* Immune Pathways," mBio. 10(5): (2019) (14 pages).

Corby-Harris et al., "The bacterial communities associated with honey bee (*Apis mellifera*) foragers," PLoS One. 9(4):e95056 (2014) (13 pages).

Crotti et al., "Microbial symbionts of honeybees: a promising tool to improve honeybee health," N Biotechnol. 30(6):716-22 (2013).

Crotti et al., "Microbial symbionts: a resource for the management of insect-related problems," Microb Biotechnol. 5(3):307-17 (2012).

Daisley et al. "Neonicotinoid-induced pathogen susceptibility is mitigated by *Lactobacillus plantarum* immune stimulation in a *Drosophila melanogaster* model," Sci Rep. 7(1): 2703 (2017) (13 pages).

Dearden et al. "Patterns of conservation and change in honey bee developmental genes," Genome Res. 16(11):1376-1384 (2006).

Dike et al., "Production of L-methionine by Bacillus cereus isolated from different soil eocvars in Owerri, South East Nigeria," Euro J Exp Biol 2(2):311-314 (2012).

Dong et al. "Overproduction of Aromatic Amino Acids from Cyanobacteria," The Summer Undergraduate Research Fellowship (SURF) Symposium, Aug. 2, West Lafayette, IN. (Abstract only) (2018).

Donkersley et al., "Bacterial communities associated with honeybee food stores are correlated with land use" Ecology and Evolution. 8(10):4743-56 (2018).

Douglas, "The *Drosophila* model for microbiome research," available in PMC Jun. 20, 2019, published in final edited form as: Lab Anim (NY). 47(6):157-164 (2018) (19 pages).

El Khoury et al., "Deleterious interaction between honeybees (*Apis mellifera*) and its microsporidian intracellular parasite *Nosema ceranae* was mitigated by administrating either endogenous or allochthonous gut microbiota strains," Front Ecol Evol. 6:58 (2018) (15 pages).

Evans et al., "Bacterial probiotics induce an immune response in the honey bee (Hymenoptera: Apidae)," J Econ Entomol. 97(3):752-6 (2004) (6 pages).

Forsgren et al., "Novel lactic acid bacteria inhibiting *Paenibacillus larvae* in honey bee larvae," Apidologie. 41(1):99-108 (2010).

Galang et al. "Analysis of the *Drosophila melanogaster* anti-ovarian response to honey bee queen mandibular pheromone," Insect Mol Biol. 28(1): 99-111 (2019).

Hamdi et al., "Gut microbiome dysbiosis and honeybee health," Journal of Applied Entomology. 135(7):524-533 (2011) (11 pages).

(56) References Cited

OTHER PUBLICATIONS

Hütter et al. "Amino Acid Overproduction," Industrial Aspects of Biochemistry and Genetics. 87:49-59(1985).
International Preliminary Reporton Patentability for PCT Application No. PCT/US2018/015025, dated Jul. 30, 2019 (7 pages).
International Search Report and Written Opinion for International Application No. PCT/US2018/015025, dated Apr. 13, 2018 (13 pages).
International Search Report and Written Opinion for International Application No. PCT/US2018/015077, dated Apr. 23, 2018 (16 pages).
Kaznowski et al., "The effects of probiotic supplementation on the content of intestinal microflora and chemical composition of worker honey bees (*Apis mellifera*)" J Apic Res. 44(1):10-4 (2005) (6 pages).
Kikuchi et al., "Symbiont-mediated insecticide resistance," Proc Natl Acad Sci U.S.A. 109(22):8618-22 (2012).
Kim et al. "Physiological responses of insects to microbial fermentation products: insights from the interactions between *Drosophila* and acetic acid," available in PMC Apr. 1, 2019, published in final edited form as: J Insect Physiol. 106(Pt 1 ):13-19 (2018) (20 pages).
Liu et al., "Disruption of methionine metabolism in *Drosophila melanogaster* impacts histone methylation and results in loss of viability," G3 (Bethesda). 6(1):121-32 (2015).
McCaughey et al., "Amino Acids and Protein Adequacy for Honey Bees of Pollens from Desert Plants and Other Floral Sources," Apidologie 11 (1): 75-86 (1980).
Mondal et al., "Methionine Production by Microorganisms," Folia Microbiol (Praha). 41(6):465-472 (1996).
Odunfa et al., "Evaluation of lysine and methionine production in some Lactobacilli and yeasts from ogi," Int J Food Microbiol 631 (1-2): 159-63 (2001).
Patruica et al., "The effect of using prebiotic and probiotic products on intestinal micro-flora of the honeybee (*Apis mellifera carpatica*)" Bull Entomol Res. 102(6):619-23 (2012).
Ptaszynska et al., "Are commerical probiotics and prebiotics effective in the treatment and prevention of honeybee nosemosis C?," Parasitol Res. 115:397-406 (2016) (11 pages).
Rodriguez et al. "Engineering *Escherichia coli* to overproduce aromatic amino acids and derived compounds," Microb Cell Fact. 13(1):126 (2014) (15 pages).
Sahm et al. "Metabolic design in amino acid producing bacterium *Corynebacterium glutamicum*," FEMS Microbiology Reviews. 16(2-3): 243-52 (1995).
Sanchez et al. "Our microbes not only produce antibiotics, they also overproduce amino acids," J Antibiot. 71:26-36 (2018).
Sannasi, "Inhibition of ovary development of the fruit-fly, *Drosophila melanogaster* by synthetic queen substance," Life Sci. 8(14): 785-789 (1969).
Santo Domingo et al., "Characterization of the Cricket Hindgut Microbiota with Fluorescently Labeled rRNA-Targeted Oligonucleotide Probes," Appl Environ Microbiol. 64(2):752-5 (1998).
Schneider, "Using *Drosophila* as a model insect," Nat Rev Genet. 1(3):218-26 (2000).
Schwarz et al., "Early gut colonizers shape parasite susceptibility and microbiota composition in honey bee workers," Proc Natl Acad Sci U S A. 113(33):9345-50 (2016).
Shapira, "Gut Microbiotas and Host Evolution: Scaling Up Symbiosis," Trends Ecol Evol. 31(7):539-549 (2016).
Sharma et al., "Metabolism of 1-naphthyl-N-methyl carbamate (carbaryl) by bacterial isolates from honey bees and the effect of bacterial inoculations on carbaryl tolerance in bees," J Appl Bacteriol. 81:235-41 (1996).
Shin et al. "*Drosophila* Microbiome Modulates Host Developmental and Metabolic Homeostasis via Insulin Signaling," Science. 334(6056): 670-674 (2011) (6 pages).
Singh et al., "Microbial Degradation of Organophosphorus Compounds," FEMS Microbiol Rev. 30(3):428-71 (2006).
Sokolowski, "Social Interactions in "Simple" Model Systems," Neuron. 65(6): 780-94 (2010).
Storelli et al., "Lactobacillus plantarum Promotes *Drosophila* Systemic Growth by Modulating Hormonal Signals Through TOR-Dependent Nutrient Sensing," Cell Metab. 14(3): 403-414 (2011).
Tower, "Lactobacillus plantarum Gives *Drosophila* the Grow Signal," Cell Metab. 14(3): 283-284 (2011).
Trinder et al., "*Drosophila melanogaster* as a High-Throughput Model for Host-Microbiota Interactions," Front Microbiol. 8:751 (2017) (8 pages).
Trinder et al., "Probiotic Lactobacillus rhamnosus Reduces Organophosphate Pesticide Absorption and Toxicity to *Drosophila melanogaster*," Appl Environ Microbiol. 82(20):6204-13 (2016).
Trotschel et al., "Characterization of methionine export in Corynebacterium glutamicum," J Bacteriol. 187(11):3786-94 (2005).
Zheng et al., "Honeybee Gut Microbiota Promotes Host Weight Gain via Bacterial Metabolism and Hormonal Signaling," Proc Natl Acad Sci USA. 114(18):4775-4780 (2017).

\* cited by examiner

Fig. 2A  Males

Fig. 2B  Females

SEQUENCE LISTING

<160> NUMBER OF SEQ ID NOS: 198

<210> SEQ ID NO 1
<211> LENGTH: 1505
<212> TYPE: DNA
<213> ORGANISM: Snodgrassella alvi

<400> SEQUENCE: 1

```
gagagtttga tcctggctca gattgaacgc tggcggcatg ccttacacat gcaagtcgaa      60
cggcagcacg gagagcttgc tctctggtgg cgagtggcga acgggtgagt aatgcatcgg     120
aacgtaccga gtaatggggg ataactgtcc gaaaggatgg ctaataccgc atacgccctg     180 aggggaaag cggggatcg aaagacctcg cgttatttga gcggccgatg ttggattagc      240
tagttggtgg ggtaaaggcc taccaaggcg acgatccata gcgggtctga gaggatgatc     300
cgccacattg ggactgagac acggcccaaa ctcctacggg aggcagcagt ggggaatttt     360
ggacaatggg gggaaccctg atccagccat gccgcgtgtc tgaagaaggc cttcgggttg     420
taaaggactt ttgttaggga agaaaagccg ggtgttaata ccatctggtg ctgacggtac     480
ctaaagaata agcaccggct aactacgtgc cagcagccgc ggtaatacgt agggtgcgag     540
cgttaatcgg aattactggg cgtaaagcga gcgcagacgg ttaattaagt cagatgtgaa     600
atccccgagc tcaacttggg acgtgcattt gaaactggtt aactagagtg tgtcagaggg     660
aggtagaatt ccacgtgtag cagtgaaatg cgtagagatg tggaggaata ccgatggcga     720
aggcagcctc ctgggataac actgacgttc atgctcgaaa gcgtgggtag caaacaggat     780
tagataccct ggtagtccac gccctaaacg atgacaatta gctgttggga cactagatgt     840
cttagtagcg aagctaacgc gtgaaattgt ccgcctgggg agtacggtcg caagattaaa     900
actcaaagga attgacgggg acccgcacaa gcggtggatg atgtggatta attcgatgca     960
acgcgaagaa ccttacctgg tcttgacatg tacggaatct cttagagata ggagagtgcc    1020
ttcgggaacc gtaacacagg tgctgcatgg ctgtcgtcag ctcgtgtcgt gagatgttgg    1080
gttaagtccc gcaacgagcg caaccttgt cattagttgc catcattaag ttgggcactc    1140
taatgagact gccggtgaca aaccggagga aggtggggat gacgtcaagt cctcatggcc    1200
cttatgacca gggcttcaca cgtcatacaa tggtcggtac agagggtagc gaagccgcga    1260
ggtgaagcca atctcagaaa gccgatcgta gtccggattg cactctgcaa ctcgagtgca    1320
tgaagtcgga atcgctagta atcgcaggtc agcatactgc ggtgaatacg ttcccgggtc    1380
ttgtacacac cgcccgtcac accatgggag tgggggatac cagaattggg tagactaacc    1440
gcaaggaggt cgcttaacac ggtatgcttc atgactgggg tgaagtcgta acaaggtagc    1500
``` cgtag                                                                  1505

<210> SEQ ID NO 2
<211> LENGTH: 1541
<212> TYPE: DNA
<213> ORGANISM: Gilliamella apicola

<400> SEQUENCE: 2
ttaaattgaa gagtttgatc atggctcaga ttgaacgctg gcggcaggct taacacatgc    60
aagtcgaacg gtaacatgag tgcttgcact tgatgacgag tggcggacgg gtgagtaaag   120
tatggggatc tgccgaatgg agggggacaa cagttggaaa cgactgctaa taccgcataa   180
agttgagaga ccaaagcatg ggaccttcgg gccatgcgcc atttgatgaa cccatatggg   240
attagctagt tggtagggta atggcttacc aaggcgacga tctctagctg gtctgagagg   300
atgaccagcc acactggaac tgagacacgg tccagactcc tacgggaggc agcagtgggg   360
aatattgcac aatgggggaa accctgatgc agccatgccg cgtgtatgaa gaaggccttc   420
gggttgtaaa gtactttcgg tgatgaggaa ggtggtgtat ctaataggtg catcaattga   480
cgttaattac agaagaagca ccggctaact ccgtgccagc agccgcggta atacggaggg   540
tgcgagcgtt aatcggaatg actgggcgta aagggcatgt aggcggataa ttaagttagg   600
tgtgaaagcc ctgggctcaa cctaggaatt gcacttaaaa ctggttaact agagtattgt   660
agaggaaggt agaattccac gtgtagcggt gaaatgcgta gagatgtgga ggaataccgg   720
tggcgaaggc ggccttctgg acagatactg acgctgagat gcgaaagcgt ggggagcaaa   780
caggattaga taccctggta gtccacgctg taaacgatgt cgatttggag tttgttgcct   840
agagtgatgg gctccgaagc taacgcgata aatcgaccgc ctggggagta cggccgcaag   900
gttaaaactc aaatgaattg acgggggccc gcacaagcgg tggagcatgt ggtttaattc   960
gatgcaacgc gaagaacctt acctggtctt gacatccaca gaatcttgca gagatgcggg  1020
agtgccttcg ggaactgtga gacaggtgct gcatggctgt cgtcagctcg tgttgtgaaa  1080
tgttgggtta agtcccgcaa cgagcgcaac ccttatcctt tgttgccatc ggttaggccg  1140
ggaactcaaa ggagactgcc gttgataaag cggaggaagg tggggacgac gtcaagtcat  1200
catggccctt acgaccaggg ctacacacgt gctacaatgg cgtatacaaa gggaggcgac  1260
ctcgcgagag caagcggacc tcataaagta cgtctaagtc cggattggag tctgcaactc  1320
gactccatga agtcggaatc gctagtaatc gtgaatcaga atgtcacggt gaatacgttc  1380
ccgggccttg tacacaccgc ccgtcacacc atggagtgg gttgcaccag aagtagatag  1440
cttaaccttc ggagggcgt ttaccacggt gtggtccatg actggggtga agtcgtaaca  1500
aggtaaccgt aggggaacct gcggttggat cacctcctta c                      1541

<210> SEQ ID NO 3
<211> LENGTH: 1528
<212> TYPE: DNA
<213> ORGANISM: Bartonella apis

<400> SEQUENCE: 3
aagccaaaat caaattttca acttgagagt ttgatcctgg ctcagaacga acgctggcgg    60
caggcttaac acatgcaagt cgaacgcact tttcggagtg agtggcagac gggtgagtaa   120
cgcgtgggaa tctacctatt tctacggaat aacgcagaga aatttgtgct aataccgtat   180
acgtccttcg ggagaaagat ttatcggaga tagatgagcc cgcgttggat tagctagttg   240

```
gtgaggtaat ggcccaccaa ggcgacgatc catagctggt ctgagaggat gaccagccac      300
attgggactg agacacggcc cagactccta cgggaggcag cagtggggaa tattggacaa      360
tgggcgcaag cctgatccag ccatgccgcg tgagtgatga aggccctagg gttgtaaagc      420
tctttcaccg gtgaagataa tgacggtaac cggagaagaa gccccggcta acttcgtgcc      480
agcagccgcg gtaatacgaa gggggctagc gttgttcgga tttactgggc gtaaagcgca      540
cgtaggcgga tatttaagtc aggggtgaaa tcccggggct caaccccgga actgcctttg      600
atactggata tcttgagtat ggaagaggta agtggaattc cgagtgtaga ggtgaaattc      660
gtagatattc ggaggaacac cagtggcgaa ggcggcttac tggtccatta ctgacgctga      720
ggtgcgaaag cgtggggagc aaacaggatt agataccctg gtagtccacg ctgtaaacga      780
tgaatgttag ccgttggaca gtttactgtt cggtggcgca gctaacgcat aaacattcc       840 gcctggggag tacggtcgca agattaaaac tcaaaggaat tgacggggc ccgcacaagc       900 ggtggagcat gtggtttaat tcgaagcaac gcgcagaacc ttaccagccc ttgacatccc      960
gatcgcggat ggtggagaca ccgtctttca gttcggctgg atcggtgaca ggtgctgcat     1020
ggctgtcgtc agctcgtgtc gtgagatgtt gggttaagtc ccgcaacgag cgcaacccc     1080 gcccttagtt gccatcattt agttgggcac tctaagggga ctgccggtga taagccgaga     1140
ggaaggtggg gatgacgtca agtcctcatg gcccttacgg gctgggctac acacgtgcta     1200
caatggtggt gacagtgggc agcgagaccg cgaggtcgag ctaatctcca aaagccatct     1260
cagttcggat tgcactctgc aactcgagtg catgaagttg gaatcgctag taatcgtgga     1320
tcagcatgcc acggtgaata cgttcccggg ccttgtacac accgcccgtc acaccatggg     1380
agttggtttt acccgaaggt gctgtgctaa ccgcaaggag gcaggcaacc acggtagggt     1440
cagcgactgg ggtgaagtcg taacaaggta gccgtagggg aacctgcggc tggatcacct     1500
cctttctaag gaagatgaag aattggaa                                        1528

<210> SEQ ID NO 4
<211> LENGTH: 1390
<212> TYPE: DNA
<213> ORGANISM: Parasaccharibacter apium
<220> FEATURE:
<221> NAME/KEY: misc_feature
<222> LOCATION: (643)..(756)
<223> OTHER INFORMATION: n is a, g, c, or t

<400> SEQUENCE: 4
ctaccatgca agtcgcacga aacctttcgg ggttagtggc ggacgggtga gtaacgcgtt       60
aggaacctat ctggaggtgg gggataacat cgggaaactg gtgctaatac cgcatgatgc      120
ctgagggcca aaggagagat ccgccattgg aggggcctgc gttcgattag ctagttggtt      180
gggtaaaggc tgaccaaggc gatgatcgat agctggtttg agaggatgat cagccacact      240
gggactgaga cacggcccag actcctacgg gaggcagcag tggggaatat tggacaatgg      300
gggcaaccct gatccagcaa tgccgcgtgt gtgaagaagg cttcggatt gtaaagcact      360 ttcactaggg aagatgatga cggtacctag agaagaagcc ccggctaact cgtgccagc      420 agccgcggta atacgaaggg ggctagcgtt gctcggaatg actgggcgta aagggcgcgt      480
aggctgtttg tacagtcaga tgtgaaatcc ccgggcttaa cctgggaact gcatttgata      540
cgtgcagact agagtccgag agagggttgt ggaattccca gtgtagaggt gaaattcgta      600
gatattggga agaacaccgg ttgcgaaggc ggcaacctgg ctnnnnnnnn nnnnnnnnnn      660
nnnnnnnnnn nnnnnnnnnn nnnnnnnnnn nnnnnnnnnn nnnnnnnnnn nnnnnnnnnn      720
```

| | |
|---|---|
| nnnnnnnnnn nnnnnnnnnn nnnnnnnnnn nnnnnngagc taacgcgtta agcacaccgc | 780 |
| ctggggagta cggccgcaag gttgaaactc aaaggaattg acgggggccc gcacaagcgg | 840 |
| tggagcatgt ggtttaattc gaagcaacgc gcagaacctt accagggctt gcatggggag | 900 |
| gctgtattca gagatggata tttcttcgga cctcccgcac aggtgctgca tggctgtcgt | 960 |
| cagctcgtgt cgtgagatgt tgggttaagt cccgcaacga gcgcaaccct tgtctttagt | 1020 |
| tgccatcacg tctgggtggg cactctagag agactgccgg tgacaagccg gaggaaggtg | 1080 |
| gggatgacgt caagtcctca tggcccttat gtcctgggct acacacgtgc tacaatggcg | 1140 |
| gtgacagagg gatgctacat ggtgacatgg tgctgatctc aaaaaaccgt ctcagttcgg | 1200 |
| attgtactct gcaactcgag tgcatgaagg tggaatcgct agtaatcgcg gatcagcatg | 1260 |
| ccgcggtgaa tacgttcccg ggccttgtac acaccgcccg tcacaccatg ggagttggtt | 1320 |
| tgaccttaag ccggtgagcg aaccgcaagg aacgcagccg accaccggtt cgggttcagc | 1380 |
| gactggggga | 1390 |

<210> SEQ ID NO 5
<211> LENGTH: 1549
<212> TYPE: DNA
<213> ORGANISM: Enterococcus

<400> SEQUENCE: 5

| | |
|---|---|
| aggtgatcca gccgcacctt ccgatacggc taccttgtta cgacttcacc ccaatcatct | 60 |
| atcccacctt aggcggctgg ctccaaaaag gttacctcac cgactcgggt gttacaaac | 120 |
| tctcgtggtg tgacgggcgg tgtgtacaag gcccgggaac gtattcaccg cggcgtgctg | 180 |
| atccgcgatt actagcgatt ccggcttcat gcaggcgagt tgcagcctgc aatccgaact | 240 |
| gagagaagct ttaagagatt tgcatgacct cgcggtctag cgactcgttg tacttcccat | 300 |
| tgtagcacgt gtgtagccca ggtcataagg ggcatgatga tttgacgtca tccccacctt | 360 |
| cctccggttt gtcaccggca gtctcgctag agtgcccaac taaatgatgg caactaacaa | 420 |
| taagggttgc gctcgttgcg ggacttaacc caacatctca cgacacgagc tgacgacaac | 480 |
| catgcaccac ctgtcacttt gtccccgaag ggaaagctct atctctagag tggtcaaagg | 540 |
| atgtcaagac ctggtaaggt tcttcgcgtt gcttcgaatt aaaccacatg ctccaccgct | 600 |
| tgtgcgggcc ccgtcaatt cctttgagtt tcaaccttgc ggtcgtactc cccaggcgga | 660 |
| gtgcttaatg cgtttgctgc agcactgaag ggcggaaacc ctccaacact tagcactcat | 720 |
| cgtttacggc gtggactacc agggtatcta atcctgtttg ctccccacgc tttcgagcct | 780 |
| cagcgtcagt tacagaccag agagccgcct tcgccactgg tgttcctcca tatatctacg | 840 |
| catttcaccg ctacacatgg aattccactc tcctcttctg cactcaagtc tcccagtttc | 900 |
| caatgaccct ccccggttga gccggggct ttcacatcag acttaagaaa ccgcctgcgc | 960 |
| tcgctttacg cccaataaat ccggacaacg cttgccacct acgtattacc gcggctgctg | 1020 |
| gcacgtagtt agccgtggct ttctggttag ataccgtcag gggacgttca gttactaacg | 1080 |
| tccttgttct tctctaacaa cagagtttta cgatccgaaa accttcttca ctcacgcggc | 1140 |
| gttgctcggt cagactttcg tccattgccg aagattccct actgctgcct cccgtaggag | 1200 |
| tctgggccgt gtctcagtcc cagtgtggcc gatcaccctc tcaggtcggc tatgcatcgt | 1260 |
| ggccttggtg agccgttacc tcaccaacta gctaatgcac gcgggtcca tccatcagcg | 1320 |
| acacccgaaa gcgcctttca ctcttatgcc atgcggcata aactgttatg cggtattagc | 1380 |

```
acctgtttcc aagtgttatc ccoctctgat gggtaggtta cccacgtgtt actcacccgt    1440
ccgccactcc tctttccaat tgagtgcaag cactcgggag gaaagaagcg ttcgacttgc    1500
atgtattagg cacgccgcca gcgttcgtcc tgagccagga tcaaactct               1549

<210> SEQ ID NO 6
<211> LENGTH: 1541
<212> TYPE: DNA
<213> ORGANISM: Delftia

<400> SEQUENCE: 6
cagaaaggag gtgatccagc cgcaccttcc gatacggcta ccttgttacg acttcacccc     60
agtcacgaac cccgccgtgg taagcgccct ccttgcggtt aggctaccta cttctggcga    120
gacccgctcc catggtgtga cgggcggtgt gtacaagacc cgggaacgta ttcaccgcgg    180
catgctgatc cgcgattact agcgattccg acttcacgca gtcgagttgc agactgcgat    240
ccggactacg actggtttta tgggattagc tcccoctcgc gggttggcaa ccctctgtac    300
cagccattgt atgacgtgtg tagccccacc tataagggcc atgaggactt gacgtcatcc    360
ccaccttcct ccggtttgtc accggcagtc tcattagagt gctcaactga atgtagcaac    420
taatgacaag ggttgcgctc gttgcgggac ttaacccaac atctcacgac acgagctgac    480
gacagccatg cagcacctgt gtgcaggttc tctttcgagc acgaatccat ctctggaaac    540
ttcctgccat gtcaaaggtg ggtaaggttt tcgcgttgc atcgaattaa accacatcat    600
ccaccgcttg tgcgggtccc cgtcaattcc tttgagtttc aaccttgcgg ccgtactccc    660
caggcggtca acttcacgcg ttagcttcgt tactgagaaa actaattccc aacaaccagt    720
tgacatcgtt tagggcgtgg actaccaggg tatctaatcc tgtttgctcc ccacgctttc    780
gtgcatgagc gtcagtacag gtccagggga ttgccttcgc catcggtgtt cctccgcata    840
tctacgcatt tcactgctac acgcggaatt ccatccccct ctaccgtact ctagccatgc    900
agtcacaaat gcagttccca ggttgagccc ggggatttca catctgtctt acataaccgc    960
ctgcgcacgc tttacgccca gtaattccga ttaacgctcg caccctacgt attaccgcgg   1020
ctgctggcac gtagttagcc ggtgcttatt cttacggtac cgtcatgggc cccctgtatt   1080
agaaggagct ttttcgttcc gtacaaaagc agtttacaac ccgaaggcct tcatcctgca   1140
cgcggcattg ctggatcagg cttcgccca ttgtccaaaa ttccccactg ctgcctcccg    1200
taggagtctg ggccgtgtct cagtcccagt gtggctggtc gtcctctcag accagctaca   1260
gatcgtcggc ttggtaagct tttatcccac caactaccta atctgccatc ggccgctcca   1320
atcgcgcgag gcccgaaggg ccccgctttt catcctcaga tcgtatgcgg tattagctac   1380
tctttcgagt agttatcccc cacgactggg cacgttccga tgtattactc acccgttcgc   1440
cactcgtcag cgtccgaaga cctgttaccg ttcgacttgc atgtgtaagg catgccgcca   1500
gcgttcaatc tgagccagga tcaaactcta cagttcgatc t                       1541

<210> SEQ ID NO 7
<211> LENGTH: 1502
<212> TYPE: DNA
<213> ORGANISM: Pelomonas
<220> FEATURE:
<221> NAME/KEY: misc_feature
<222> LOCATION: (192)..(193)
<223> OTHER INFORMATION: n is a, c, g, or t
<220> FEATURE:
<221> NAME/KEY: misc_feature
<222> LOCATION: (832)..(833)
<223> OTHER INFORMATION: n is a, c, g, or t
```

<400> SEQUENCE: 7

```
atcctggctc agattgaacg ctggcggcat gccttacaca tgcaagtcga acggtaacag      60
gttaagctga cgagtggcga acgggtgagt aatatatcgg aacgtgccca gtcgtggggg     120
ataactgctc gaaagagcag ctaataccgc atacgacctg agggtgaaag cggggatcg      180
caagacctcg cnngattgga gcggccgata tcagattagg tagttggtgg ggtaaaggcc     240
caccaagcca acgatctgta gctggtctga gaggacgacc agccacactg ggactgagac     300
acggcccaga ctcctacggg aggcagcagt ggggaatttt ggacaatggg cgcaagcctg     360
atccagccat gccgcgtgcg ggaagaaggc cttcgggttg taaaccgctt ttgtcaggga     420
agaaaaggtt ctggttaata cctgggactc atgacggtac ctgaagaata agcaccggct     480
aactacgtgc cagcagccgc ggtaatacgt agggtgcaag cgttaatcgg aattactggg     540
cgtaaagcgt gcgcaggcgg ttatgcaaga cagaggtgaa atccccgggc tcaacctggg     600
aactgccttt gtgactgcat agctagagta cggtagaggg ggatgaatt  ccgcgtgtag     660
cagtgaaatg cgtagatatg cggaggaaca ccgatggcga aggcaatccc ctggacctgt     720
actgacgctc atgcacgaaa gcgtggggag caaacaggat tagataccct ggtagtccac     780
gccctaaacg atgtcaactg gttgttggga gggtttcttc tcagtaacgt anntaacgcg     840
tgaagttgac cgcctgggga gtacggccgc aaggttgaaa ctcaaaggaa ttgacgggga     900
cccgcacaag cggtggatga tgtggtttaa ttcgatgcaa cgcgaaaaac cttacctacc     960
cttgacatgc caggaatcct gaagagattt gggagtgctc gaaagagaac ctggacacag    1020
gtgctgcatg gccgtcgtca gctcgtgtcg tgagatgttg ggttaagtcc cgcaacgagc    1080
gcaacccttg tcattagttg ctacgaaagg cactctaat  gagactgccg gtgacaaacc    1140
ggaggaaggt ggggatgacg tcaggtcatc atggccctta tgggtagggc tacacacgtc    1200
atacaatggc cggacagag  ggctgccaac ccgcgagggg gagctaatcc cagaaacccg    1260
gtcgtagtcc ggatcgtagt ctgcaactcg actgcgtgaa gtcggaatcg ctagtaatcg    1320
cggatcagct tgccgcggtg aatacgttcc cgggtcttgt acacaccgcc cgtcacacca    1380
tgggagcggg ttctgccaga agtagttagc ctaaccgcaa ggagggcgat taccacggca    1440
gggttcgtga ctggggtgaa gtcgtaacaa ggtagccgta tcggaaggtg cggctggatc    1500
ac                                                                   1502
```

<210> SEQ ID NO 8
<211> LENGTH: 34
<212> TYPE: PRT
<213> ORGANISM: Lactococcus lactis

<400> SEQUENCE: 8

```
Ile Thr Ser Ile Ser Leu Cys Thr Pro Gly Cys Lys Thr Gly Ala Leu
1               5                   10                  15

Met Gly Cys Asn Met Lys Thr Ala Thr Cys His Cys Ser Ile His Val
            20                  25                  30

Ser Lys
```

<210> SEQ ID NO 9
<211> LENGTH: 22
<212> TYPE: PRT
<213> ORGANISM: Staphylococcus epidermis

<400> SEQUENCE: 9

```
Ile Ala Ser Lys Phe Ile Cys Thr Pro Gly Cys Ala Lys Thr Gly Ser
1               5                   10                  15

Phe Asn Ser Tyr Cys Cys
            20
```

<210> SEQ ID NO 10
<211> LENGTH: 44
<212> TYPE: PRT
<213> ORGANISM: Pediococcus acidilactici

<400> SEQUENCE: 10

```
Lys Tyr Tyr Gly Asn Gly Val Thr Cys Gly Lys His Ser Cys Ser Val
1               5                   10                  15

Asp Trp Gly Lys Ala Thr Thr Cys Ile Ile Asn Asn Gly Ala Met Ala
            20                  25                  30

Trp Ala Thr Gly Gly His Gln Gly Asn His Lys Cys
            35                  40
```

<210> SEQ ID NO 11
<211> LENGTH: 44
<212> TYPE: PRT
<213> ORGANISM: Enterococcus faecium

<400> SEQUENCE: 11

```
Ala Thr Arg Ser Tyr Gly Asn Gly Val Tyr Cys Asn Asn Ser Lys Cys
1               5                   10                  15

Trp Val Asn Trp Gly Glu Ala Lys Glu Asn Ile Ala Gly Ile Val Ile
            20                  25                  30

Ser Gly Trp Ala Ser Gly Leu Ala Gly Met Gly His
            35                  40
```

<210> SEQ ID NO 12
<211> LENGTH: 39
<212> TYPE: PRT
<213> ORGANISM: Streptococcus lactis

<400> SEQUENCE: 12

```
Gly Thr Trp Asp Asp Ile Gly Gln Gly Ile Gly Arg Val Ala Tyr Trp
1               5                   10                  15

Val Gly Lys Ala Met Gly Asn Met Ser Asp Val Asn Gln Ala Ser Arg
            20                  25                  30

Ile Asn Arg Lys Lys Lys His
            35
```

<210> SEQ ID NO 13
<211> LENGTH: 48
<212> TYPE: PRT
<213> ORGANISM: Lactobacillus johnsonii

<400> SEQUENCE: 13

```
Asn Arg Trp Gly Asp Thr Val Leu Ser Ala Ala Ser Gly Ala Gly Thr
1               5                   10                  15

Gly Ile Lys Ala Cys Lys Ser Phe Gly Pro Trp Gly Met Ala Ile Cys
            20                  25                  30

Gly Val Gly Gly Ala Ala Ile Gly Gly Tyr Phe Gly Tyr Thr His Asn
            35                  40                  45
```

<210> SEQ ID NO 14
<211> LENGTH: 70
<212> TYPE: PRT
<213> ORGANISM: Enterococcus faecalis

```
<400> SEQUENCE: 14

Met Ala Lys Glu Phe Gly Ile Pro Ala Ala Val Ala Gly Thr Val Leu
1               5                   10                  15

Asn Val Val Glu Ala Gly Gly Trp Val Thr Thr Ile Val Ser Ile Leu
            20                  25                  30

Thr Ala Val Gly Ser Gly Gly Leu Ser Leu Leu Ala Ala Ala Gly Arg
        35                  40                  45

Glu Ser Ile Lys Ala Tyr Leu Lys Lys Glu Ile Lys Lys Lys Gly Lys
50                  55                  60

Arg Ala Val Ile Ala Trp
65                  70

<210> SEQ ID NO 15
<211> LENGTH: 51
<212> TYPE: PRT
<213> ORGANISM: Staphylococcus aureus

<400> SEQUENCE: 15

Met Ser Trp Leu Asn Phe Leu Lys Tyr Ile Ala Lys Tyr Gly Lys Lys
1               5                   10                  15

Ala Val Ser Ala Ala Trp Lys Tyr Lys Gly Lys Val Leu Glu Trp Leu
            20                  25                  30

Asn Val Gly Pro Thr Leu Glu Trp Val Trp Gln Lys Leu Lys Lys Ile
        35                  40                  45

Ala Gly Leu
    50

<210> SEQ ID NO 16
<211> LENGTH: 43
<212> TYPE: PRT
<213> ORGANISM: Lactococcus garvieae

<400> SEQUENCE: 16

Ile Gly Gly Ala Leu Gly Asn Ala Leu Asn Gly Leu Gly Thr Trp Ala
1               5                   10                  15

Asn Met Met Asn Gly Gly Gly Phe Val Asn Gln Trp Gln Val Tyr Ala
            20                  25                  30

Asn Lys Gly Lys Ile Asn Gln Tyr Arg Pro Tyr
        35                  40

<210> SEQ ID NO 17
<211> LENGTH: 103
<212> TYPE: PRT
<213> ORGANISM: Escherichia coli

<400> SEQUENCE: 17

Met Arg Thr Leu Thr Leu Asn Glu Leu Asp Ser Val Ser Gly Gly Ala
1               5                   10                  15

Ser Gly Arg Asp Ile Ala Met Ala Ile Gly Thr Leu Ser Gly Gln Phe
            20                  25                  30

Val Ala Gly Gly Ile Gly Ala Ala Ala Gly Gly Val Ala Gly Gly Ala
        35                  40                  45

Ile Tyr Asp Tyr Ala Ser Thr His Lys Pro Asn Pro Ala Met Ser Pro
50                  55                  60

Ser Gly Leu Gly Gly Thr Ile Lys Gln Lys Pro Glu Gly Ile Pro Ser
65                  70                  75                  80

Glu Ala Trp Asn Tyr Ala Ala Gly Arg Leu Cys Asn Trp Ser Pro Asn
```

Asn Leu Ser Asp Val Cys Leu
            100

<210> SEQ ID NO 18
<211> LENGTH: 339
<212> TYPE: PRT
<213> ORGANISM: Streptococcus phage Cp1

<400> SEQUENCE: 18

Met Val Lys Lys Asn Asp Leu Phe Val Asp Val Ser His Asn Gly
1               5                   10                  15

Tyr Asp Ile Thr Gly Ile Leu Glu Gln Met Gly Thr Thr Asn Thr Ile
                20                  25                  30

Ile Lys Ile Ser Glu Ser Thr Thr Tyr Leu Asn Pro Cys Leu Ser Ala
            35                  40                  45

Gln Val Glu Gln Ser Asn Pro Ile Gly Phe Tyr His Phe Ala Arg Phe
    50                  55                  60

Gly Gly Asp Val Ala Glu Ala Glu Arg Glu Ala Gln Phe Phe Leu Asp
65                  70                  75                  80

Asn Val Pro Met Gln Val Lys Tyr Leu Val Leu Asp Tyr Glu Asp Asp
                85                  90                  95

Pro Ser Gly Asp Ala Gln Ala Asn Thr Asn Ala Cys Leu Arg Phe Met
                100                 105                 110

Gln Met Ile Ala Asp Ala Gly Tyr Lys Pro Ile Tyr Tyr Ser Tyr Lys
            115                 120                 125

Pro Phe Thr His Asp Asn Val Asp Tyr Gln Gln Ile Leu Ala Gln Phe
    130                 135                 140

Pro Asn Ser Leu Trp Ile Ala Gly Tyr Gly Leu Asn Asp Gly Thr Ala
145                 150                 155                 160

Asn Phe Glu Tyr Phe Pro Ser Met Asp Gly Ile Arg Trp Trp Gln Tyr
                165                 170                 175

Ser Ser Asn Pro Phe Asp Lys Asn Ile Val Leu Leu Asp Asp Glu Glu
            180                 185                 190

Asp Asp Lys Pro Lys Thr Ala Gly Thr Trp Lys Gln Asp Ser Lys Gly
    195                 200                 205

Trp Trp Phe Arg Arg Asn Asn Gly Ser Phe Pro Tyr Asn Lys Trp Glu
210                 215                 220

Lys Ile Gly Gly Val Trp Tyr Tyr Phe Asp Ser Lys Gly Tyr Cys Leu
225                 230                 235                 240

Thr Ser Glu Trp Leu Lys Asp Asn Glu Lys Trp Tyr Tyr Leu Lys Asp
                245                 250                 255

Asn Gly Ala Met Ala Thr Gly Trp Val Leu Val Gly Ser Glu Trp Tyr
            260                 265                 270

Tyr Met Asp Asp Ser Gly Ala Met Val Thr Gly Trp Val Lys Tyr Lys
    275                 280                 285

Asn Asn Trp Tyr Tyr Met Thr Asn Glu Arg Gly Asn Met Val Ser Asn
            290                 295                 300

Glu Phe Ile Lys Ser Gly Lys Gly Trp Tyr Phe Met Asn Thr Asn Gly
305                 310                 315                 320

Glu Leu Ala Asp Asn Pro Ser Phe Thr Lys Glu Pro Asp Gly Leu Ile
                325                 330                 335

Thr Val Ala

<210> SEQ ID NO 19
<211> LENGTH: 296
<212> TYPE: PRT
<213> ORGANISM: Streptococcus phage Dp-1

<400> SEQUENCE: 19

Met Gly Val Asp Ile Glu Lys Gly Val Ala Trp Met Gln Ala Arg Lys
1               5                   10                  15

Gly Arg Val Ser Tyr Ser Met Asp Phe Arg Asp Gly Pro Asp Ser Tyr
            20                  25                  30

Asp Cys Ser Ser Ser Met Tyr Tyr Ala Leu Arg Ser Ala Gly Ala Ser
        35                  40                  45

Ser Ala Gly Trp Ala Val Asn Thr Glu Tyr Met His Ala Trp Leu Ile
    50                  55                  60

Glu Asn Gly Tyr Glu Leu Ile Ser Glu Asn Ala Pro Trp Asp Ala Lys
65                  70                  75                  80

Arg Gly Asp Ile Phe Ile Trp Gly Arg Lys Gly Ala Ser Ala Gly Ala
                85                  90                  95

Gly Gly His Thr Gly Met Phe Ile Asp Ser Asp Asn Ile Ile His Cys
            100                 105                 110

Asn Tyr Ala Tyr Asp Gly Ile Ser Val Asn Asp His Asp Glu Arg Trp
        115                 120                 125

Tyr Tyr Ala Gly Gln Pro Tyr Tyr Val Tyr Arg Leu Thr Asn Ala
    130                 135                 140

Asn Ala Gln Pro Ala Glu Lys Lys Leu Gly Trp Gln Lys Asp Ala Thr
145                 150                 155                 160

Gly Phe Trp Tyr Ala Arg Ala Asn Gly Thr Tyr Pro Lys Asp Glu Phe
                165                 170                 175

Glu Tyr Ile Glu Glu Asn Lys Ser Trp Phe Tyr Phe Asp Gln Gly
            180                 185                 190

Tyr Met Leu Ala Glu Lys Trp Leu Lys His Thr Asp Gly Asn Trp Tyr
        195                 200                 205

Trp Phe Asp Arg Asp Gly Tyr Met Ala Thr Ser Trp Lys Arg Ile Gly
    210                 215                 220

Glu Ser Trp Tyr Tyr Phe Asn Arg Asp Gly Ser Met Val Thr Gly Trp
225                 230                 235                 240

Ile Lys Tyr Tyr Asp Asn Trp Tyr Tyr Cys Asp Ala Thr Asn Gly Asp
                245                 250                 255

Met Lys Ser Asn Ala Phe Ile Arg Tyr Asn Asp Gly Trp Tyr Leu Leu
            260                 265                 270

Leu Pro Asp Gly Arg Leu Ala Asp Lys Pro Gln Phe Thr Val Glu Pro
    275                 280                 285

Asp Gly Leu Ile Thr Ala Lys Val
    290                 295

<210> SEQ ID NO 20
<211> LENGTH: 233
<212> TYPE: PRT
<213> ORGANISM: Bacillus phage gamma

<400> SEQUENCE: 20

Met Glu Ile Gln Lys Lys Leu Val Asp Pro Ser Lys Tyr Gly Thr Lys
1               5                   10                  15

Cys Pro Tyr Thr Met Lys Pro Lys Tyr Ile Thr Val His Asn Thr Tyr
            20                  25                  30

Asn Asp Ala Pro Ala Glu Asn Glu Val Ser Tyr Met Ile Ser Asn Asn

```
            35                  40                  45
Asn Glu Val Ser Phe His Ile Ala Val Asp Asp Lys Lys Ala Ile Gln
 50                  55                  60

Gly Ile Pro Leu Glu Arg Asn Ala Trp Ala Cys Gly Asp Gly Asn Gly
 65                  70                  75                  80

Ser Gly Asn Arg Gln Ser Ile Ser Val Glu Ile Cys Tyr Ser Lys Ser
                 85                  90                  95

Gly Gly Asp Arg Tyr Tyr Lys Ala Glu Asp Asn Ala Val Asp Val Val
                100                 105                 110

Arg Gln Leu Met Ser Met Tyr Asn Ile Pro Ile Glu Asn Val Arg Thr
            115                 120                 125

His Gln Ser Trp Ser Gly Lys Tyr Cys Pro His Arg Met Leu Ala Glu
        130                 135                 140

Gly Arg Trp Gly Ala Phe Ile Gln Lys Val Lys Asn Gly Asn Val Ala
145                 150                 155                 160

Thr Thr Ser Pro Thr Lys Gln Asn Ile Ile Gln Ser Gly Ala Phe Ser
                165                 170                 175

Pro Tyr Glu Thr Pro Asp Val Met Gly Ala Leu Thr Ser Leu Lys Met
                180                 185                 190

Thr Ala Asp Phe Ile Leu Gln Ser Asp Gly Leu Thr Tyr Phe Ile Ser
            195                 200                 205

Lys Pro Thr Ser Asp Ala Gln Leu Lys Ala Met Lys Glu Tyr Leu Asp
        210                 215                 220

Arg Lys Gly Trp Trp Tyr Glu Val Lys
225                 230

<210> SEQ ID NO 21
<211> LENGTH: 481
<212> TYPE: PRT
<213> ORGANISM: Staphylococcus phage phi MR11

<400> SEQUENCE: 21

Met Gln Ala Lys Leu Thr Lys Glu Phe Ile Glu Trp Leu Lys Thr
 1               5                  10                  15

Ser Glu Gly Lys Gln Phe Asn Val Asp Leu Trp Tyr Gly Phe Gln Cys
                 20                  25                  30

Phe Asp Tyr Ala Asn Ala Gly Trp Lys Val Leu Phe Gly Leu Leu Leu
             35                  40                  45

Lys Gly Leu Gly Ala Lys Asp Ile Pro Phe Ala Asn Asn Phe Asp Gly
 50                  55                  60

Leu Ala Thr Val Tyr Gln Asn Thr Pro Asp Phe Leu Ala Gln Pro Gly
 65                  70                  75                  80

Asp Met Val Val Phe Gly Ser Asn Tyr Gly Ala Gly Tyr Gly His Val
                 85                  90                  95

Ala Trp Val Ile Glu Ala Thr Leu Asp Tyr Ile Ile Val Tyr Glu Gln
                100                 105                 110

Asn Trp Leu Gly Gly Gly Trp Thr Asp Arg Ile Glu Gln Pro Gly Trp
            115                 120                 125

Gly Trp Glu Lys Val Thr Arg Arg Gln His Ala Tyr Asp Phe Pro Met
        130                 135                 140

Trp Phe Ile Arg Pro Asn Phe Lys Ser Glu Thr Ala Pro Arg Ser Ile
145                 150                 155                 160

Gln Ser Pro Thr Gln Ala Ser Lys Glu Thr Ala Lys Pro Gln Pro
                165                 170                 175
```

```
Lys Ala Val Glu Leu Lys Ile Ile Lys Asp Val Val Lys Gly Tyr Asp
                180                 185                 190

Leu Pro Lys Arg Gly Gly Asn Pro Lys Gly Ile Val Ile His Asn Asp
            195                 200                 205

Ala Gly Ser Lys Gly Ala Thr Ala Glu Ala Tyr Arg Asn Gly Leu Val
210                 215                 220

Asn Ala Pro Leu Ser Arg Leu Glu Ala Gly Ile Ala His Ser Tyr Val
225                 230                 235                 240

Ser Gly Asn Thr Val Trp Gln Ala Leu Asp Glu Ser Gln Val Gly Trp
                245                 250                 255

His Thr Ala Asn Gln Leu Gly Asn Lys Tyr Tyr Tyr Gly Ile Glu Val
                260                 265                 270

Cys Gln Ser Met Gly Ala Asp Asn Ala Thr Phe Leu Lys Asn Glu Gln
            275                 280                 285

Ala Thr Phe Gln Glu Cys Ala Arg Leu Leu Lys Lys Trp Gly Leu Pro
290                 295                 300

Ala Asn Arg Asn Thr Ile Arg Leu His Asn Glu Phe Thr Ser Thr Ser
305                 310                 315                 320

Cys Pro His Arg Ser Ser Val Leu His Thr Gly Phe Asp Pro Val Thr
                325                 330                 335

Arg Gly Leu Leu Pro Glu Asp Lys Gln Leu Gln Leu Lys Asp Tyr Phe
                340                 345                 350

Ile Lys Gln Ile Arg Val Tyr Met Asp Gly Lys Ile Pro Val Ala Thr
            355                 360                 365

Val Ser Asn Glu Ser Ser Ala Ser Ser Asn Thr Val Lys Pro Val Ala
370                 375                 380

Ser Ala Trp Lys Arg Asn Lys Tyr Gly Thr Tyr Tyr Met Glu Glu Asn
385                 390                 395                 400

Ala Arg Phe Thr Asn Gly Asn Gln Pro Ile Thr Val Arg Lys Ile Gly
                405                 410                 415

Pro Phe Leu Ser Cys Pro Val Ala Tyr Gln Phe Gln Pro Gly Gly Tyr
                420                 425                 430

Cys Asp Tyr Thr Glu Val Met Leu Gln Asp Gly His Val Trp Val Gly
            435                 440                 445

Tyr Thr Trp Glu Gly Gln Arg Tyr Tyr Leu Pro Ile Arg Thr Trp Asn
450                 455                 460

Gly Ser Ala Pro Pro Asn Gln Ile Leu Gly Asp Leu Trp Gly Glu Ile
465                 470                 475                 480

Ser

<210> SEQ ID NO 22
<211> LENGTH: 239
<212> TYPE: PRT
<213> ORGANISM: Streptococcus phage B30

<400> SEQUENCE: 22

Met Val Ile Asn Ile Glu Gln Ala Ile Ala Trp Met Ala Ser Arg Lys
1               5                   10                  15

Gly Lys Val Thr Tyr Ser Met Asp Tyr Arg Asn Gly Pro Ser Ser Tyr
                20                  25                  30

Asp Cys Ser Ser Ser Val Tyr Phe Ala Leu Arg Ser Ala Gly Ala Ser
            35                  40                  45

Asp Asn Gly Trp Ala Val Asn Thr Glu Tyr Glu His Asp Trp Leu Ile
50                  55                  60
```

```
Lys Asn Gly Tyr Val Leu Ile Ala Glu Asn Thr Asn Trp Asn Ala Gln
 65                  70                  75                  80

Arg Gly Asp Ile Phe Ile Trp Gly Lys Arg Gly Ala Ser Ala Gly Ala
                 85                  90                  95

Phe Gly His Thr Gly Met Phe Val Asp Pro Asp Asn Ile Ile His Cys
            100                 105                 110

Asn Tyr Gly Tyr Asn Ser Ile Thr Val Asn Asn His Asp Glu Ile Trp
        115                 120                 125

Gly Tyr Asn Gly Gln Pro Tyr Val Tyr Ala Tyr Arg Tyr Ser Gly Lys
    130                 135                 140

Gln Ser Asn Ala Lys Val Asp Asn Lys Ser Val Val Ser Lys Phe Glu
145                 150                 155                 160

Lys Glu Leu Asp Val Asn Thr Pro Leu Ser Asn Ser Asn Met Pro Tyr
                165                 170                 175

Tyr Glu Ala Thr Ile Ser Glu Asp Tyr Tyr Val Glu Ser Lys Pro Asp
            180                 185                 190

Val Asn Ser Thr Asp Lys Glu Leu Leu Val Ala Gly Thr Arg Val Arg
        195                 200                 205

Val Tyr Glu Lys Val Lys Gly Trp Ala Arg Ile Gly Ala Pro Gln Ser
    210                 215                 220

Asn Gln Trp Val Glu Asp Ala Tyr Leu Ile Asp Ala Thr Asp Met
225                 230                 235

<210> SEQ ID NO 23
<211> LENGTH: 495
<212> TYPE: PRT
<213> ORGANISM: Staphylococcus phage K

<400> SEQUENCE: 23

Met Ala Lys Thr Gln Ala Glu Ile Asn Lys Arg Leu Asp Ala Tyr Ala
  1               5                  10                  15

Lys Gly Thr Val Asp Ser Pro Tyr Arg Val Lys Lys Ala Thr Ser Tyr
                 20                  25                  30

Asp Pro Ser Phe Gly Val Met Glu Ala Gly Ala Ile Asp Ala Asp Gly
             35                  40                  45

Tyr Tyr His Ala Gln Cys Gln Asp Leu Ile Thr Asp Tyr Val Leu Trp
         50                  55                  60

Leu Thr Asp Asn Lys Val Arg Thr Trp Gly Asn Ala Lys Asp Gln Ile
 65                  70                  75                  80

Lys Gln Ser Tyr Gly Thr Gly Phe Lys Ile His Glu Asn Lys Pro Ser
                 85                  90                  95

Thr Val Pro Lys Lys Gly Trp Ile Ala Val Phe Thr Ser Gly Ser Tyr
            100                 105                 110

Glu Gln Trp Gly His Ile Gly Ile Val Tyr Asp Gly Asn Thr Ser
        115                 120                 125

Thr Phe Thr Ile Leu Glu Gln Asn Trp Asn Gly Tyr Ala Asn Lys Lys
    130                 135                 140

Pro Thr Lys Arg Val Asp Asn Tyr Tyr Gly Leu Thr His Phe Ile Glu
145                 150                 155                 160

Ile Pro Val Lys Ala Gly Thr Val Lys Lys Glu Thr Ala Lys Lys
                165                 170                 175

Ser Ala Ser Lys Thr Pro Ala Pro Lys Lys Ala Thr Leu Lys Val
            180                 185                 190

Ser Lys Asn His Ile Asn Tyr Thr Met Asp Lys Arg Gly Lys Lys Pro
        195                 200                 205
```

Glu Gly Met Val Ile His Asn Asp Ala Gly Arg Ser Ser Gly Gln Gln
    210                 215                 220

Tyr Glu Asn Ser Leu Ala Asn Ala Gly Tyr Ala Arg Tyr Ala Asn Gly
225                 230                 235                 240

Ile Ala His Tyr Tyr Gly Ser Glu Gly Tyr Val Trp Glu Ala Ile Asp
                245                 250                 255

Ala Lys Asn Gln Ile Ala Trp His Thr Gly Asp Gly Thr Gly Ala Asn
                260                 265                 270

Ser Gly Asn Phe Arg Phe Ala Gly Ile Glu Val Cys Gln Ser Met Ser
            275                 280                 285

Ala Ser Asp Ala Gln Phe Leu Lys Asn Glu Gln Ala Val Phe Gln Phe
        290                 295                 300

Thr Ala Glu Lys Phe Lys Glu Trp Gly Leu Thr Pro Asn Arg Lys Thr
305                 310                 315                 320

Val Arg Leu His Met Glu Phe Val Pro Thr Ala Cys Pro His Arg Ser
                325                 330                 335

Met Val Leu His Thr Gly Phe Asn Pro Val Thr Gln Gly Arg Pro Ser
                340                 345                 350

Gln Ala Ile Met Asn Lys Leu Lys Asp Tyr Phe Ile Lys Gln Ile Lys
            355                 360                 365

Asn Tyr Met Asp Lys Gly Thr Ser Ser Ser Thr Val Val Lys Asp Gly
        370                 375                 380

Lys Thr Ser Ser Ala Ser Thr Pro Ala Thr Arg Pro Val Thr Gly Ser
385                 390                 395                 400

Trp Lys Lys Asn Gln Tyr Gly Thr Trp Tyr Lys Pro Glu Asn Ala Thr
                405                 410                 415

Phe Val Asn Gly Asn Gln Pro Ile Val Thr Arg Ile Gly Ser Pro Phe
                420                 425                 430

Leu Asn Ala Pro Val Gly Gly Asn Leu Pro Ala Gly Ala Thr Ile Val
            435                 440                 445

Tyr Asp Glu Val Cys Ile Gln Ala Gly His Ile Trp Ile Gly Tyr Asn
        450                 455                 460

Ala Tyr Asn Gly Asn Arg Val Tyr Cys Pro Val Arg Thr Cys Gln Gly
465                 470                 475                 480

Val Pro Pro Asn Gln Ile Pro Gly Val Ala Trp Gly Val Phe Lys
                485                 490                 495

<210> SEQ ID NO 24
<211> LENGTH: 281
<212> TYPE: PRT
<213> ORGANISM: Listeria phage A118

<400> SEQUENCE: 24

Met Thr Ser Tyr Tyr Tyr Ser Arg Ser Leu Ala Asn Val Asn Lys Leu
1               5                   10                  15

Ala Asp Asn Thr Lys Ala Ala Arg Lys Leu Leu Asp Trp Ser Glu
            20                  25                  30

Ser Asn Gly Ile Glu Val Leu Ile Tyr Glu Thr Ile Arg Thr Lys Glu
        35                  40                  45

Gln Gln Ala Ala Asn Val Asn Ser Gly Ala Ser Gln Thr Met Arg Ser
    50                  55                  60

Tyr His Leu Val Gly Gln Ala Leu Asp Phe Val Met Ala Lys Gly Lys
65                  70                  75                  80

Thr Val Asp Trp Gly Ala Tyr Arg Ser Asp Lys Gly Lys Lys Phe Val

```
            85                  90                  95
Ala Lys Ala Lys Ser Leu Gly Phe Glu Trp Gly Gly Asp Trp Ser Gly
            100                 105                 110

Phe Val Asp Asn Pro His Leu Gln Phe Asn Tyr Lys Gly Tyr Gly Thr
            115                 120                 125

Asp Thr Phe Gly Lys Gly Ala Ser Thr Ser Asn Ser Ser Lys Pro Ser
            130                 135                 140

Ala Asp Thr Asn Thr Asn Ser Leu Gly Leu Val Asp Tyr Met Asn Leu
145                 150                 155                 160

Asn Lys Leu Asp Ser Ser Phe Ala Asn Arg Lys Lys Leu Ala Thr Ser
                165                 170                 175

Tyr Gly Ile Lys Asn Tyr Ser Gly Thr Ala Thr Gln Asn Thr Thr Leu
                180                 185                 190

Leu Ala Lys Leu Lys Ala Gly Lys Pro His Thr Pro Ala Ser Lys Asn
                195                 200                 205

Thr Tyr Tyr Thr Glu Asn Pro Arg Lys Val Lys Thr Leu Val Gln Cys
                210                 215                 220

Asp Leu Tyr Lys Ser Val Asp Phe Thr Thr Lys Asn Gln Thr Gly Gly
225                 230                 235                 240

Thr Phe Pro Pro Gly Thr Val Phe Thr Ile Ser Gly Met Gly Lys Thr
                245                 250                 255

Lys Gly Gly Thr Pro Arg Leu Lys Thr Lys Ser Gly Tyr Tyr Leu Thr
                260                 265                 270

Ala Asn Thr Lys Phe Val Lys Lys Ile
                275                 280

<210> SEQ ID NO 25
<211> LENGTH: 341
<212> TYPE: PRT
<213> ORGANISM: Listeria phage A511

<400> SEQUENCE: 25

Met Val Lys Tyr Thr Val Glu Asn Lys Ile Ile Ala Gly Leu Pro Lys
1               5                   10                  15

Gly Lys Leu Lys Gly Ala Asn Phe Val Ile Ala His Glu Thr Ala Asn
                20                  25                  30

Ser Lys Ser Thr Ile Asp Asn Glu Val Ser Tyr Met Thr Arg Asn Trp
                35                  40                  45

Lys Asn Ala Phe Val Thr His Phe Val Gly Gly Gly Arg Val Val
    50                  55                  60

Gln Val Ala Asn Val Asn Tyr Val Ser Trp Gly Ala Gly Gln Tyr Ala
65                  70                  75                  80

Asn Ser Tyr Ser Tyr Ala Gln Val Glu Leu Cys Arg Thr Ser Asn Ala
                85                  90                  95

Thr Thr Phe Lys Lys Asp Tyr Glu Val Tyr Cys Gln Leu Leu Val Asp
                100                 105                 110

Leu Ala Lys Lys Ala Gly Ile Pro Ile Thr Leu Asp Ser Gly Ser Lys
                115                 120                 125

Thr Ser Asp Lys Gly Ile Lys Ser His Lys Trp Val Ala Asp Lys Leu
                130                 135                 140

Gly Gly Thr Thr His Gln Asp Pro Tyr Ala Tyr Leu Ser Ser Trp Gly
145                 150                 155                 160

Ile Ser Lys Ala Gln Phe Ala Ser Asp Leu Ala Lys Val Ser Gly Gly
                165                 170                 175
```

```
Gly Asn Thr Gly Thr Ala Pro Ala Lys Pro Ser Thr Pro Ala Pro Lys
            180                 185                 190

Pro Ser Thr Pro Ser Thr Asn Leu Asp Lys Leu Gly Leu Val Asp Tyr
        195                 200                 205

Met Asn Ala Lys Lys Met Asp Ser Ser Tyr Ser Asn Arg Asp Lys Leu
    210                 215                 220

Ala Lys Gln Tyr Gly Ile Ala Asn Tyr Ser Gly Thr Ala Ser Gln Asn
225                 230                 235                 240

Thr Thr Leu Leu Ser Lys Ile Lys Gly Gly Ala Pro Lys Pro Ser Thr
                245                 250                 255

Pro Ala Pro Lys Pro Ser Thr Ser Thr Ala Lys Lys Ile Tyr Phe Pro
            260                 265                 270

Pro Asn Lys Gly Asn Trp Ser Val Tyr Pro Thr Asn Lys Ala Pro Val
        275                 280                 285

Lys Ala Asn Ala Ile Gly Ala Ile Asn Pro Thr Lys Phe Gly Gly Leu
    290                 295                 300

Thr Tyr Thr Ile Gln Lys Asp Arg Gly Asn Gly Val Tyr Glu Ile Gln
305                 310                 315                 320

Thr Asp Gln Phe Gly Arg Val Gln Val Tyr Gly Ala Pro Ser Thr Gly
                325                 330                 335

Ala Val Ile Lys Lys
            340

<210> SEQ ID NO 26
<211> LENGTH: 289
<212> TYPE: PRT
<213> ORGANISM: Listeria phage A500

<400> SEQUENCE: 26

Met Ala Leu Thr Glu Ala Trp Leu Ile Glu Lys Ala Asn Arg Lys Leu
1               5                   10                  15

Asn Ala Gly Gly Met Tyr Lys Ile Thr Ser Asp Lys Thr Arg Asn Val
            20                  25                  30

Ile Lys Lys Met Ala Lys Glu Gly Ile Tyr Leu Cys Val Ala Gln Gly
        35                  40                  45

Tyr Arg Ser Thr Ala Glu Gln Asn Ala Leu Tyr Ala Gln Gly Arg Thr
    50                  55                  60

Lys Pro Gly Ala Ile Val Thr Asn Ala Lys Gly Gly Gln Ser Asn His
65                  70                  75                  80

Asn Tyr Gly Val Ala Val Asp Leu Cys Leu Tyr Thr Asn Asp Gly Lys
                85                  90                  95

Asp Val Ile Trp Glu Ser Thr Thr Ser Arg Trp Lys Lys Val Val Ala
            100                 105                 110

Ala Met Lys Ala Glu Gly Phe Lys Trp Gly Gly Asp Trp Lys Ser Phe
        115                 120                 125

Lys Asp Tyr Pro His Phe Glu Leu Cys Asp Ala Val Ser Gly Glu Lys
    130                 135                 140

Ile Pro Ala Ala Thr Gln Asn Thr Asn Thr Asn Ser Asn Arg Tyr Glu
145                 150                 155                 160

Gly Lys Val Ile Asp Ser Ala Pro Leu Leu Pro Lys Met Asp Phe Lys
                165                 170                 175

Ser Ser Pro Phe Arg Met Tyr Lys Val Gly Thr Glu Phe Leu Val Tyr
            180                 185                 190

Asp His Asn Gln Tyr Trp Tyr Lys Thr Tyr Ile Asp Asp Lys Leu Tyr
        195                 200                 205
```

```
Tyr Met Tyr Lys Ser Phe Cys Asp Val Val Ala Lys Lys Asp Ala Lys
        210                 215                 220

Gly Arg Ile Lys Val Arg Ile Lys Ser Ala Lys Asp Leu Arg Ile Pro
225                 230                 235                 240

Val Trp Asn Asn Ile Lys Leu Asn Ser Gly Lys Ile Lys Trp Tyr Ala
                245                 250                 255

Pro Asn Val Lys Leu Ala Trp Tyr Asn Tyr Arg Arg Gly Tyr Leu Glu
                260                 265                 270

Leu Trp Tyr Pro Asn Asp Gly Trp Tyr Tyr Thr Ala Glu Tyr Phe Leu
                275                 280                 285

Lys
```

<210> SEQ ID NO 27
<211> LENGTH: 239
<212> TYPE: PRT
<213> ORGANISM: Streptococcus prophage LambdaSa1

<400> SEQUENCE: 27

```
Met Val Ile Asn Ile Glu Gln Ala Ile Ala Trp Met Ala Ser Arg Lys
1               5                   10                  15

Gly Lys Val Thr Tyr Ser Met Asp Tyr Arg Asn Gly Pro Ser Ser Tyr
                20                  25                  30

Asp Cys Ser Ser Ser Val Tyr Phe Ala Leu Arg Ser Ala Gly Ala Ser
                35                  40                  45

Asp Asn Gly Trp Ala Val Asn Thr Glu Tyr Glu His Asp Trp Leu Ile
            50                  55                  60

Lys Asn Gly Tyr Val Leu Ile Ala Glu Asn Thr Asn Trp Asn Ala Gln
65                  70                  75                  80

Arg Gly Asp Ile Phe Ile Trp Gly Lys Arg Gly Ala Ser Ala Gly Ala
                85                  90                  95

Phe Gly His Thr Gly Met Phe Val Asp Pro Asp Asn Ile Ile His Cys
                100                 105                 110

Asn Tyr Gly Tyr Asn Ser Ile Thr Val Asn Asn His Asp Glu Ile Trp
            115                 120                 125

Gly Tyr Asn Gly Gln Pro Tyr Val Tyr Ala Tyr Arg Tyr Ala Arg Lys
        130                 135                 140

Gln Ser Asn Ala Lys Val Asp Asn Gln Ser Val Val Ser Lys Phe Glu
145                 150                 155                 160

Lys Glu Leu Asp Val Asn Thr Pro Leu Ser Asn Ser Asn Met Pro Tyr
                165                 170                 175

Tyr Glu Ala Thr Ile Ser Glu Asp Tyr Tyr Val Glu Ser Lys Pro Asp
                180                 185                 190

Val Asn Ser Thr Asp Lys Glu Leu Leu Val Ala Gly Thr Arg Val Arg
            195                 200                 205

Val Tyr Glu Lys Val Lys Gly Trp Ala Arg Ile Gly Ala Pro Gln Ser
        210                 215                 220

Asn Gln Trp Val Glu Asp Ala Tyr Leu Ile Asp Ala Thr Asp Met
225                 230                 235
```

<210> SEQ ID NO 28
<211> LENGTH: 468
<212> TYPE: PRT
<213> ORGANISM: Streptococcus prophage LambdaSa2

<400> SEQUENCE: 28

-continued

```
Met Glu Ile Asn Thr Glu Ile Ala Ile Ala Trp Met Ser Ala Arg Gln
1               5                   10                  15

Gly Lys Val Ser Tyr Ser Met Asp Tyr Arg Asp Gly Pro Asn Ser Tyr
            20                  25                  30

Asp Cys Ser Ser Ser Val Tyr Tyr Ala Leu Arg Ser Ala Gly Ala Ser
                35                  40                  45

Ser Ala Gly Trp Ala Val Asn Thr Glu Tyr Met His Asp Trp Leu Ile
50                  55                  60

Lys Asn Gly Tyr Glu Leu Ile Ala Glu Asn Val Asp Trp Asn Ala Val
65                      70                  75                  80

Arg Gly Asp Ile Ala Ile Trp Gly Met Arg Gly His Ser Ser Gly Ala
                85                  90                  95

Gly Gly His Val Val Met Phe Ile Asp Pro Glu Asn Ile Ile His Cys
                100                 105                 110

Asn Trp Ala Asn Asn Gly Ile Thr Val Asn Asn Tyr Asn Gln Thr Ala
            115                 120                 125

Ala Ala Ser Gly Trp Met Tyr Cys Tyr Val Tyr Arg Leu Lys Ser Gly
130                 135                 140

Ala Ser Thr Gln Gly Lys Ser Leu Asp Thr Leu Val Lys Glu Thr Leu
145                 150                 155                 160

Ala Gly Asn Tyr Gly Asn Gly Glu Ala Arg Lys Ala Val Leu Gly Asn
                165                 170                 175

Gln Tyr Glu Ala Val Met Ser Val Ile Asn Gly Lys Thr Thr Thr Asn
            180                 185                 190

Gln Lys Thr Val Asp Gln Leu Val Gln Glu Val Ile Ala Gly Lys His
            195                 200                 205

Gly Asn Gly Glu Ala Arg Lys Lys Ser Leu Gly Ser Gln Tyr Asp Ala
210                 215                 220

Val Gln Lys Arg Val Thr Glu Leu Leu Lys Lys Gln Pro Ser Glu Pro
225                 230                 235                 240

Phe Lys Ala Gln Glu Val Asn Lys Pro Thr Glu Thr Lys Thr Ser Gln
                245                 250                 255

Thr Glu Leu Thr Gly Gln Ala Thr Ala Thr Lys Glu Glu Gly Asp Leu
            260                 265                 270

Ser Phe Asn Gly Thr Ile Leu Lys Lys Ala Val Leu Asp Lys Ile Leu
        275                 280                 285

Gly Asn Cys Lys Lys His Asp Ile Leu Pro Ser Tyr Ala Leu Thr Ile
290                 295                 300

Leu His Tyr Glu Gly Leu Trp Gly Thr Ser Ala Val Gly Lys Ala Asp
305                 310                 315                 320

Asn Asn Trp Gly Gly Met Thr Trp Thr Gly Gln Gly Asn Arg Pro Ser
                325                 330                 335

Gly Val Thr Val Thr Gln Gly Ser Ala Arg Pro Ser Asn Glu Gly Gly
            340                 345                 350

His Tyr Met His Tyr Ala Ser Val Asp Asp Phe Leu Thr Asp Trp Phe
        355                 360                 365

Tyr Leu Leu Arg Ala Gly Gly Ser Tyr Lys Val Ser Gly Ala Lys Thr
370                 375                 380

Phe Ser Glu Ala Ile Lys Gly Met Phe Lys Val Gly Gly Ala Val Tyr
385                 390                 395                 400

Asp Tyr Ala Ala Ser Gly Phe Asp Ser Tyr Ile Val Gly Ala Ser Ser
                405                 410                 415

Arg Leu Lys Ala Ile Glu Ala Glu Asn Gly Ser Leu Asp Lys Phe Asp
```

```
                    420             425             430
Lys Ala Thr Asp Ile Gly Asp Gly Ser Lys Asp Lys Ile Asp Ile Thr
                435                 440                 445
Ile Glu Gly Ile Glu Val Thr Ile Asn Gly Ile Thr Tyr Glu Leu Thr
        450                 455                 460
Lys Lys Pro Val
465

<210> SEQ ID NO 29
<211> LENGTH: 236
<212> TYPE: PRT
<213> ORGANISM: Artificial Sequence
<220> FEATURE:
<223> OTHER INFORMATION: Prophage identified in Streptococcus uberis
      (ATCC 700407)

<400> SEQUENCE: 29

Met Thr Asp Ser Ile Gln Glu Met Arg Lys Leu Gln Ser Ile Pro Val
1               5                   10                  15

Arg Tyr Asp Met Gly Asp Arg Tyr Gly Asn Asp Ala Asp Arg Asp Gly
                20                  25                  30

Arg Ile Glu Met Asp Cys Ser Ser Ala Val Ser Lys Ala Leu Gly Ile
            35                  40                  45

Ser Met Thr Asn Asn Thr Glu Thr Leu Gln Gln Ala Leu Pro Ala Ile
    50                  55                  60

Gly Tyr Gly Lys Ile His Asp Ala Val Asp Gly Thr Phe Asp Met Gln
65                  70                  75                  80

Ala Tyr Asp Val Ile Ile Trp Ala Pro Arg Asp Gly Ser Ser Ser Leu
                85                  90                  95

Gly Ala Phe Gly His Val Leu Ile Ala Thr Ser Pro Thr Thr Ala Ile
                100                 105                 110

His Cys Asn Tyr Gly Ser Asp Gly Ile Thr Glu Asn Asp Tyr Asn Tyr
            115                 120                 125

Ile Trp Glu Ile Asn Gly Arg Pro Arg Glu Ile Val Phe Arg Lys Gly
    130                 135                 140

Val Thr Gln Thr Gln Ala Thr Val Thr Ser Gln Phe Glu Arg Glu Leu
145                 150                 155                 160

Asp Val Asn Ala Arg Leu Thr Val Ser Asp Lys Pro Tyr Tyr Glu Ala
                165                 170                 175

Thr Leu Ser Glu Asp Tyr Tyr Val Glu Ala Gly Pro Arg Ile Asp Ser
            180                 185                 190

Gln Asp Lys Glu Leu Ile Lys Ala Gly Thr Arg Val Arg Val Tyr Glu
    195                 200                 205

Lys Leu Asn Gly Trp Ser Arg Ile Asn His Pro Glu Ser Ala Gln Trp
210                 215                 220

Val Glu Asp Ser Tyr Leu Val Asp Ala Thr Glu Met
225                 230                 235

<210> SEQ ID NO 30
<211> LENGTH: 481
<212> TYPE: PRT
<213> ORGANISM: Staphylococcus phage Phi11

<400> SEQUENCE: 30

Met Gln Ala Lys Leu Thr Lys Asn Glu Phe Ile Glu Trp Leu Lys Thr
1               5                   10                  15

Ser Glu Gly Lys Gln Phe Asn Val Asp Leu Trp Tyr Gly Phe Gln Cys
```

-continued

```
               20                  25                  30
Phe Asp Tyr Ala Asn Ala Gly Trp Lys Val Leu Phe Gly Leu Leu Leu
            35                  40                  45
Lys Gly Leu Gly Ala Lys Asp Ile Pro Phe Ala Asn Asn Phe Asp Gly
        50                  55                  60
Leu Ala Thr Val Tyr Gln Asn Thr Pro Asp Phe Leu Ala Gln Pro Gly
65                  70                  75                  80
Asp Met Val Val Phe Gly Ser Asn Tyr Gly Ala Gly Tyr Gly His Val
                85                  90                  95
Ala Trp Val Ile Glu Ala Thr Leu Asp Tyr Ile Ile Val Tyr Glu Gln
            100                 105                 110
Asn Trp Leu Gly Gly Trp Thr Asp Gly Ile Glu Gln Pro Gly Trp
        115                 120                 125
Gly Trp Glu Lys Val Thr Arg Arg Gln His Ala Tyr Asp Phe Pro Met
    130                 135                 140
Trp Phe Ile Arg Pro Asn Phe Lys Ser Glu Thr Ala Pro Arg Ser Val
145                 150                 155                 160
Gln Ser Pro Thr Gln Ala Pro Lys Lys Glu Thr Ala Lys Pro Gln Pro
                165                 170                 175
Lys Ala Val Glu Leu Lys Ile Ile Lys Asp Val Val Lys Gly Tyr Asp
            180                 185                 190
Leu Pro Lys Arg Gly Ser Asn Pro Lys Gly Ile Val Ile His Asn Asp
        195                 200                 205
Ala Gly Ser Lys Gly Ala Thr Ala Glu Ala Tyr Arg Asn Gly Leu Val
    210                 215                 220
Asn Ala Pro Leu Ser Arg Leu Glu Ala Gly Ile Ala His Ser Tyr Val
225                 230                 235                 240
Ser Gly Asn Thr Val Trp Gln Ala Leu Asp Glu Ser Gln Val Gly Trp
                245                 250                 255
His Thr Ala Asn Gln Ile Gly Asn Lys Tyr Tyr Tyr Gly Ile Glu Val
            260                 265                 270
Cys Gln Ser Met Gly Ala Asp Asn Ala Thr Phe Leu Lys Asn Glu Gln
        275                 280                 285
Ala Thr Phe Gln Glu Cys Ala Arg Leu Leu Lys Lys Trp Gly Leu Pro
    290                 295                 300
Ala Asn Arg Asn Thr Ile Arg Leu His Asn Glu Phe Thr Ser Thr Ser
305                 310                 315                 320
Cys Pro His Arg Ser Ser Val Leu His Thr Gly Phe Asp Pro Val Thr
                325                 330                 335
Arg Gly Leu Leu Pro Glu Asp Lys Arg Leu Gln Leu Lys Asp Tyr Phe
            340                 345                 350
Ile Lys Gln Ile Arg Ala Tyr Met Asp Gly Lys Ile Pro Val Ala Thr
        355                 360                 365
Val Ser Asn Glu Ser Ser Ala Ser Ser Asn Thr Val Lys Pro Val Ala
    370                 375                 380
Ser Ala Trp Lys Arg Asn Lys Tyr Gly Thr Tyr Tyr Met Glu Glu Ser
385                 390                 395                 400
Ala Arg Phe Thr Asn Gly Asn Gln Pro Ile Thr Val Arg Lys Val Gly
                405                 410                 415
Pro Phe Leu Ser Cys Pro Val Gly Tyr Gln Phe Gln Pro Gly Gly Tyr
            420                 425                 430
Cys Asp Tyr Thr Glu Val Met Leu Gln Asp Gly His Val Trp Val Gly
        435                 440                 445
```

```
Tyr Thr Trp Glu Gly Gln Arg Tyr Tyr Leu Pro Ile Arg Thr Trp Asn
            450                 455                 460

Gly Ser Ala Pro Pro Asn Gln Ile Leu Gly Asp Leu Trp Gly Glu Ile
465                 470                 475                 480

Ser

<210> SEQ ID NO 31
<211> LENGTH: 481
<212> TYPE: PRT
<213> ORGANISM: Staphylococcus phage PhiH5

<400> SEQUENCE: 31

Met Gln Ala Lys Leu Thr Lys Lys Glu Phe Ile Glu Trp Leu Lys Thr
1               5                   10                  15

Ser Glu Gly Lys Gln Tyr Asn Ala Asp Gly Trp Tyr Gly Phe Gln Cys
            20                  25                  30

Phe Asp Tyr Ala Asn Ala Gly Trp Lys Ala Leu Phe Gly Leu Leu Leu
        35                  40                  45

Lys Gly Val Gly Ala Lys Asp Ile Pro Phe Ala Asn Asn Phe Asp Gly
50                  55                  60

Leu Ala Thr Val Tyr Gln Asn Thr Pro Asp Phe Leu Ala Gln Pro Gly
65                  70                  75                  80

Asp Met Val Val Phe Gly Ser Asn Tyr Gly Ala Gly Tyr Gly His Val
                85                  90                  95

Ala Trp Val Ile Glu Ala Thr Leu Asp Tyr Ile Ile Val Tyr Glu Gln
            100                 105                 110

Asn Trp Leu Gly Gly Gly Trp Thr Asp Gly Val Gln Gln Pro Gly Ser
        115                 120                 125

Gly Trp Glu Lys Val Thr Arg Arg Gln His Ala Tyr Asp Phe Pro Met
130                 135                 140

Trp Phe Ile Arg Pro Asn Phe Lys Ser Glu Thr Ala Pro Arg Ser Val
145                 150                 155                 160

Gln Ser Pro Thr Gln Ala Ser Lys Lys Glu Thr Ala Lys Pro Gln Pro
                165                 170                 175

Lys Ala Val Glu Leu Lys Ile Ile Lys Asp Val Val Lys Gly Tyr Asp
            180                 185                 190

Leu Pro Lys Arg Gly Ser Asn Pro Asn Phe Ile Val Ile His Asn Asp
        195                 200                 205

Ala Gly Ser Lys Gly Ala Thr Ala Glu Ala Tyr Arg Asn Gly Leu Val
210                 215                 220

Asn Ala Pro Leu Ser Arg Leu Glu Ala Gly Ile Ala His Ser Tyr Val
225                 230                 235                 240

Ser Gly Asn Thr Val Trp Gln Ala Leu Asp Glu Ser Gln Val Gly Trp
                245                 250                 255

His Thr Ala Asn Gln Ile Gly Asn Lys Tyr Gly Tyr Gly Ile Glu Val
            260                 265                 270

Cys Gln Ser Met Gly Ala Asp Asn Ala Thr Phe Leu Lys Asn Glu Gln
        275                 280                 285

Ala Thr Phe Gln Glu Cys Ala Arg Leu Leu Lys Lys Trp Gly Leu Pro
290                 295                 300

Ala Asn Arg Asn Thr Ile Arg Leu His Asn Glu Phe Thr Ser Thr Ser
305                 310                 315                 320

Cys Pro His Arg Ser Ser Val Leu His Thr Gly Phe Asp Pro Val Thr
                325                 330                 335
```

-continued

```
Arg Gly Leu Leu Pro Glu Asp Lys Arg Leu Gln Leu Lys Asp Tyr Phe
            340                 345                 350

Ile Lys Gln Ile Arg Ala Tyr Met Asp Gly Lys Ile Pro Val Ala Thr
            355                 360                 365

Val Ser Asn Asp Ser Ser Ala Ser Ser Asn Thr Val Lys Pro Val Ala
            370                 375                 380

Ser Ala Trp Lys Arg Asn Lys Tyr Gly Thr Tyr Tyr Met Glu Glu Ser
385                 390                 395                 400

Ala Arg Phe Thr Asn Gly Asn Gln Pro Ile Thr Val Arg Lys Val Gly
            405                 410                 415

Pro Phe Leu Ser Cys Pro Val Gly Tyr Gln Phe Gln Pro Gly Gly Tyr
            420                 425                 430

Cys Asp Tyr Thr Glu Val Met Leu Gln Asp Gly His Val Trp Val Gly
            435                 440                 445

Tyr Thr Trp Glu Gly Gln Arg Tyr Tyr Leu Pro Ile Arg Thr Trp Asn
450                 455                 460

Gly Ser Ala Pro Pro Asn Gln Ile Leu Gly Asp Leu Trp Gly Glu Ile
465                 470                 475                 480

Ser

<210> SEQ ID NO 32
<211> LENGTH: 477
<212> TYPE: PRT
<213> ORGANISM: Staphylococcus phage phiWMY

<400> SEQUENCE: 32

Met Lys Thr Lys Ala Gln Ala Lys Ser Trp Ile Asn Ser Lys Ile Gly
1               5                   10                  15

Lys Gly Ile Asp Trp Asp Gly Met Tyr Gly Tyr Gln Cys Met Asp Glu
            20                  25                  30

Ala Val Asp Tyr Ile His His Val Thr Asp Gly Lys Val Thr Met Trp
        35                  40                  45

Gly Asn Ala Ile Asp Ala Pro Lys Asn Asn Phe Gln Gly Leu Cys Thr
50                  55                  60

Val Tyr Thr Asn Thr Pro Glu Phe Arg Pro Ala Tyr Gly Asp Val Ile
65                  70                  75                  80

Val Trp Ser Tyr Gly Thr Phe Ala Thr Tyr Gly His Ile Ala Ile Val
            85                  90                  95

Val Asn Pro Asp Pro Tyr Gly Asp Leu Gln Tyr Ile Thr Val Leu Glu
            100                 105                 110

Gln Asn Trp Asn Gly Asn Gly Ile Tyr Lys Thr Glu Phe Ala Thr Ile
        115                 120                 125

Arg Thr His Asp Tyr Thr Gly Val Ser His Phe Arg Pro Lys Phe
            130                 135                 140

Ala Asp Glu Val Lys Glu Thr Ala Lys Thr Val Asn Lys Leu Ser Val
145                 150                 155                 160

Gln Lys Lys Ile Val Thr Pro Lys Asn Ser Val Glu Arg Ile Lys Asn
            165                 170                 175

Tyr Val Lys Thr Ser Gly Tyr Ile Asn Gly Glu His Tyr Glu Leu Tyr
            180                 185                 190

Asn Arg Gly His Lys Pro Lys Gly Val Val Ile His Asn Thr Ala Gly
        195                 200                 205

Thr Ala Ser Ala Thr Gln Glu Gly Gln Arg Leu Thr Asn Met Thr Phe
    210                 215                 220
```

Gln Gln Leu Ala Asn Gly Val Ala His Val Tyr Ile Asp Lys Asn Thr
225                 230                 235                 240

Ile Tyr Glu Thr Leu Pro Glu Asp Arg Ile Ala Trp His Val Ala Gln
            245                 250                 255

Gln Tyr Gly Asn Thr Glu Phe Tyr Gly Ile Glu Val Cys Gly Ser Arg
        260                 265                 270

Asn Thr Asp Lys Glu Gln Phe Leu Ala Asn Glu Gln Val Ala Phe Gln
    275                 280                 285

Glu Ala Ala Arg Arg Leu Lys Ser Trp Gly Met Arg Ala Asn Arg Asn
290                 295                 300

Thr Val Arg Leu His His Thr Phe Ser Ser Thr Glu Cys Pro Asp Met
305                 310                 315                 320

Ser Met Leu Leu His Thr Gly Tyr Ser Met Lys Asn Gly Lys Pro Thr
                325                 330                 335

Gln Asp Ile Thr Asn Lys Cys Ala Asp Tyr Phe Met Lys Gln Ile Asn
            340                 345                 350

Ala Tyr Ile Asp Gly Lys Gln Pro Thr Ser Thr Val Val Gly Ser Ser
        355                 360                 365

Ser Ser Asn Lys Leu Lys Ala Lys Asn Lys Asp Lys Ser Thr Gly Trp
    370                 375                 380

Asn Thr Asn Glu Tyr Gly Thr Leu Trp Lys Lys Glu His Ala Thr Phe
385                 390                 395                 400

Thr Cys Gly Val Arg Gln Gly Ile Val Thr Arg Thr Gly Pro Phe
                405                 410                 415

Thr Ser Cys Pro Gln Ala Gly Val Leu Tyr Tyr Gly Gln Ser Val Asn
            420                 425                 430

Tyr Asp Thr Val Cys Lys Gln Asp Gly Tyr Val Trp Ile Ser Trp Thr
        435                 440                 445

Thr Ser Asp Gly Tyr Asp Val Trp Met Pro Ile Arg Thr Trp Asp Arg
    450                 455                 460

Ser Thr Asp Lys Val Ser Glu Ile Trp Gly Thr Ile Ser
465                 470                 475

<210> SEQ ID NO 33
<211> LENGTH: 443
<212> TYPE: PRT
<213> ORGANISM: Streptococcus phage NCTC 11261

<400> SEQUENCE: 33

Met Ala Thr Tyr Gln Glu Tyr Lys Ser Arg Ser Asn Gly Asn Ala Tyr
1               5                   10                  15

Asp Ile Asp Gly Ser Phe Gly Ala Gln Cys Trp Asp Gly Tyr Ala Asp
            20                  25                  30

Tyr Cys Lys Tyr Leu Gly Leu Pro Tyr Ala Asn Cys Thr Asn Thr Gly
        35                  40                  45

Tyr Ala Arg Asp Ile Trp Glu Gln Arg His Glu Asn Gly Ile Leu Asn
    50                  55                  60

Tyr Phe Asp Glu Val Glu Val Met Gln Ala Gly Asp Val Ala Ile Phe
65                  70                  75                  80

Met Val Val Asp Gly Val Thr Pro Tyr Ser His Val Ala Ile Phe Asp
                85                  90                  95

Ser Asp Ala Gly Gly Gly Tyr Gly Trp Phe Leu Gly Gln Asn Gln Gly
            100                 105                 110

Gly Ala Asn Gly Ala Tyr Asn Ile Val Lys Ile Pro Tyr Ser Ala Thr

```
            115                 120                 125
Tyr Pro Thr Ala Phe Arg Pro Lys Val Phe Lys Asn Ala Val Thr Val
    130                 135                 140

Thr Gly Asn Ile Gly Leu Asn Lys Gly Asp Tyr Phe Ile Asp Val Ser
145                 150                 155                 160

Ala Tyr Gln Gln Ala Asp Leu Thr Thr Thr Cys Gln Gln Ala Gly Thr
                165                 170                 175

Thr Lys Thr Ile Ile Lys Val Ser Glu Ser Ile Ala Trp Leu Ser Asp
            180                 185                 190

Arg His Gln Gln Gln Ala Asn Thr Ser Asp Pro Ile Gly Tyr Tyr His
        195                 200                 205

Phe Gly Arg Phe Gly Gly Asp Ser Ala Leu Ala Gln Arg Glu Ala Asp
    210                 215                 220

Leu Phe Leu Ser Asn Leu Pro Ser Lys Lys Val Ser Tyr Leu Val Ile
225                 230                 235                 240

Asp Tyr Glu Asp Ser Ala Ser Ala Asp Lys Gln Ala Asn Thr Asn Ala
                245                 250                 255

Val Ile Ala Phe Met Asp Lys Ile Ala Ser Ala Gly Tyr Lys Pro Ile
            260                 265                 270

Tyr Tyr Ser Tyr Lys Pro Phe Thr Leu Asn Asn Ile Asp Tyr Gln Lys
        275                 280                 285

Ile Ile Ala Lys Tyr Pro Asn Ser Ile Trp Ile Ala Gly Tyr Pro Asp
    290                 295                 300

Tyr Glu Val Arg Thr Glu Pro Leu Trp Glu Phe Phe Pro Ser Met Asp
305                 310                 315                 320

Gly Val Arg Trp Trp Gln Phe Thr Ser Val Gly Val Ala Gly Gly Leu
                325                 330                 335

Asp Lys Asn Ile Val Leu Leu Ala Asp Asp Ser Ser Lys Met Asp Ile
            340                 345                 350

Pro Lys Val Asp Lys Pro Gln Glu Leu Thr Phe Tyr Gln Lys Leu Ala
        355                 360                 365

Thr Asn Thr Lys Leu Asp Asn Ser Asn Val Pro Tyr Tyr Glu Ala Thr
    370                 375                 380

Leu Ser Thr Asp Tyr Tyr Val Glu Ser Lys Pro Asn Ala Ser Ser Ala
385                 390                 395                 400

Asp Lys Glu Phe Ile Lys Ala Gly Thr Arg Val Arg Val Tyr Glu Lys
                405                 410                 415

Val Asn Gly Trp Ser Arg Ile Asn His Pro Glu Ser Ala Gln Trp Val
            420                 425                 430

Glu Asp Ser Tyr Leu Val Asn Ala Thr Asp Met
        435                 440

<210> SEQ ID NO 34
<211> LENGTH: 334
<212> TYPE: PRT
<213> ORGANISM: Listeria phage FWLLm3

<400> SEQUENCE: 34

Met Val Lys Tyr Thr Val Glu Asn Lys Ile Ile Ala Gly Leu Pro Lys
1               5                   10                  15

Gly Lys Leu Lys Gly Ala Asn Phe Val Ile Ala His Glu Thr Ala Asn
            20                  25                  30

Ser Lys Ser Thr Ile Asp Asn Glu Val Ser Tyr Met Thr Arg Asn Trp
        35                  40                  45
```

```
Gln Asn Ala Phe Val Thr His Phe Val Gly Gly Gly Arg Val Val
 50                  55                  60

Gln Val Ala Asn Val Asn Tyr Val Ser Trp Gly Ala Gly Gln Tyr Ala
 65                  70                  75                  80

Asn Ser Tyr Ser Tyr Ala Gln Val Glu Leu Cys Arg Thr Ser Asn Ala
                 85                  90                  95

Thr Thr Phe Lys Lys Asp Tyr Glu Val Tyr Cys Gln Leu Leu Val Asp
            100                 105                 110

Leu Ala Lys Lys Ala Gly Ile Pro Ile Thr Leu Asp Ser Gly Ser Lys
        115                 120                 125

Thr Ser Asp Lys Gly Ile Lys Ser His Lys Trp Val Ala Asp Lys Leu
130                 135                 140

Gly Gly Thr Thr His Gln Asp Pro Tyr Ala Tyr Leu Ser Ser Trp Gly
145                 150                 155                 160

Ile Ser Lys Ala Gln Phe Ala Ser Asp Leu Ala Lys Val Ser Gly Gly
                165                 170                 175

Gly Asn Thr Gly Thr Ala Pro Ala Lys Pro Ser Thr Pro Ser Thr Asn
            180                 185                 190

Leu Asp Lys Leu Gly Leu Val Asp Tyr Met Asn Ala Lys Lys Met Asp
        195                 200                 205

Ser Ser Tyr Ser Asn Arg Ala Lys Leu Ala Lys Gln Tyr Gly Ile Ala
210                 215                 220

Asn Tyr Ser Gly Thr Ala Ser Gln Asn Thr Thr Leu Leu Ser Lys Ile
225                 230                 235                 240

Lys Gly Gly Ala Pro Lys Pro Ser Thr Pro Ala Pro Lys Pro Ser Thr
                245                 250                 255

Ser Thr Ala Lys Lys Ile Tyr Phe Pro Pro Asn Lys Gly Asn Trp Ser
            260                 265                 270

Val Tyr Pro Thr Asn Lys Ala Pro Val Lys Ala Asn Ala Ile Gly Ala
        275                 280                 285

Ile Asn Pro Thr Lys Phe Gly Gly Leu Thr Tyr Thr Ile Gln Lys Asp
290                 295                 300

Arg Gly Asn Gly Val Tyr Glu Ile Gln Thr Asp Gln Phe Gly Arg Val
305                 310                 315                 320

Gln Val Tyr Gly Ala Pro Ser Thr Gly Ala Val Ile Lys Lys
                325                 330

<210> SEQ ID NO 35
<211> LENGTH: 1278
<212> TYPE: PRT
<213> ORGANISM: Bacillus phage BPS13

<400> SEQUENCE: 35

Met Ala Lys Arg Glu Lys Tyr Ile Phe Asp Val Glu Ala Glu Val Gly
 1               5                  10                  15

Lys Ala Ala Lys Ser Ile Lys Ser Leu Glu Ala Glu Leu Ser Lys Leu
                 20                  25                  30

Gln Lys Leu Asn Lys Glu Ile Asp Ala Thr Gly Gly Asp Arg Thr Glu
             35                  40                  45

Lys Glu Met Leu Ala Thr Leu Lys Ala Lys Glu Val Asn Ala Glu
 50                  55                  60

Tyr Gln Lys Met Gln Arg Ile Leu Lys Asp Leu Ser Lys Tyr Ser Gly
 65                  70                  75                  80

Lys Val Ser Arg Lys Glu Phe Asn Asp Ser Lys Val Ile Asn Asn Ala
                 85                  90                  95
```

-continued

```
Lys Thr Ser Val Gln Gly Gly Lys Val Thr Asp Ser Phe Gly Gln Met
                100                 105                 110
Leu Lys Asn Met Glu Arg Gln Ile Asn Ser Val Asn Lys Gln Phe Asp
            115                 120                 125
Asn His Arg Lys Ala Met Val Asp Arg Gly Gln Gln Tyr Thr Pro His
        130                 135                 140
Leu Lys Thr Asn Arg Lys Asp Ser Gln Gly Asn Ser Asn Pro Ser Met
145                 150                 155                 160
Met Gly Arg Asn Lys Ser Thr Thr Gln Asp Met Glu Lys Ala Val Asp
                165                 170                 175
Lys Phe Leu Asn Gly Gln Asn Glu Ala Thr Thr Gly Leu Asn Gln Ala
            180                 185                 190
Leu Tyr Gln Leu Lys Glu Ile Ser Lys Leu Asn Arg Arg Ser Glu Ser
        195                 200                 205
Leu Ser Arg Arg Ala Ser Ala Ser Gly Tyr Met Ser Phe Gln Gln Tyr
210                 215                 220
Ser Asn Phe Thr Gly Asp Arg Arg Thr Val Gln Gln Thr Tyr Gly Gly
225                 230                 235                 240
Leu Lys Thr Ala Asn Arg Glu Arg Val Leu Glu Leu Ser Gly Gln Ala
                245                 250                 255
Thr Gly Ile Ser Lys Glu Leu Asp Arg Leu Asn Ser Lys Lys Gly Leu
            260                 265                 270
Thr Ala Arg Glu Gly Glu Glu Arg Lys Lys Leu Met Arg Gln Leu Glu
        275                 280                 285
Gly Ile Asp Ala Glu Leu Thr Ala Arg Lys Lys Leu Asn Ser Ser Leu
    290                 295                 300
Asp Glu Thr Thr Ser Asn Met Glu Lys Phe Asn Gln Ser Leu Val Asp
305                 310                 315                 320
Ala Gln Val Ser Val Lys Pro Glu Arg Gly Thr Met Arg Gly Met Met
                325                 330                 335
Tyr Glu Arg Ala Pro Ala Ile Ala Leu Ala Ile Gly Gly Ala Ile Thr
            340                 345                 350
Ala Thr Ile Gly Lys Leu Tyr Ser Glu Gly Gly Asn His Ser Lys Ala
        355                 360                 365
Met Arg Pro Asp Glu Met Tyr Val Gly Gln Gln Thr Gly Ala Val Gly
    370                 375                 380
Ala Asn Trp Arg Pro Asn Arg Thr Ala Thr Met Arg Ser Gly Leu Gly
385                 390                 395                 400
Asn His Leu Gly Phe Thr Gly Gln Glu Met Met Glu Phe Gln Ser Asn
                405                 410                 415
Tyr Leu Ser Ala Asn Gly Tyr His Gly Ala Glu Asp Met Lys Ala Ala
            420                 425                 430
Thr Thr Gly Gln Ala Thr Phe Ala Arg Ala Thr Gly Leu Gly Ser Asp
        435                 440                 445
Glu Val Lys Asp Phe Phe Asn Thr Ala Tyr Arg Ser Gly Gly Ile Asp
    450                 455                 460
Gly Asn Gln Thr Lys Gln Phe Gln Asn Ala Phe Leu Gly Ala Met Lys
465                 470                 475                 480
Gln Ser Gly Ala Val Gly Arg Glu Lys Asp Gln Leu Lys Ala Leu Asn
                485                 490                 495
Gly Ile Leu Ser Ser Met Ser Gly Asn Arg Thr Val Ser Asn Gln Asp
            500                 505                 510
```

```
Met Met Arg Thr Val Gly Leu Gln Ser Ala Ile Ser Ser Ser Gly Val
            515                 520                 525

Ala Ser Leu Gln Gly Thr Lys Gly Gly Ala Leu Met Glu Gln Leu Asp
530                 535                 540

Asn Gly Ile Arg Glu Gly Phe Asn Asp Pro Gln Met Arg Val Leu Phe
545                 550                 555                 560

Gly Gln Gly Thr Lys Tyr Gln Gly Met Gly Gly Arg Ala Ala Leu Arg
                565                 570                 575

Lys Gln Met Glu Lys Gly Ile Ser Asp Pro Asp Asn Leu Asn Thr Leu
            580                 585                 590

Ile Asp Ala Ser Lys Ala Ser Ala Gly Gln Asp Pro Ala Glu Gln Ala
        595                 600                 605

Glu Val Leu Ala Thr Leu Ala Ser Lys Met Gly Val Asn Met Ser Ser
    610                 615                 620

Asp Gln Ala Arg Gly Leu Ile Asp Leu Gln Pro Ser Gly Lys Leu Thr
625                 630                 635                 640

Lys Glu Asn Ile Asp Lys Val Met Lys Glu Gly Leu Lys Glu Gly Ser
                645                 650                 655

Ile Glu Ser Ala Lys Arg Asp Lys Ala Tyr Ser Glu Ser Lys Ala Ser
            660                 665                 670

Ile Asp Asn Ser Ser Glu Ala Ala Thr Ala Lys Gln Ala Thr Glu Leu
        675                 680                 685

Asn Asp Met Gly Ser Lys Leu Arg Gln Ala Asn Ala Ala Leu Gly Gly
    690                 695                 700

Leu Pro Ala Pro Leu Tyr Thr Ala Ile Ala Ala Val Ala Phe Thr
705                 710                 715                 720

Ala Ala Val Ala Gly Ser Ala Leu Met Phe Lys Gly Ala Ser Trp Leu
                725                 730                 735

Lys Gly Gly Met Ala Ser Lys Tyr Gly Gly Lys Gly Gly Lys Gly Gly
            740                 745                 750

Lys Gly Gly Gly Thr Gly Gly Gly Gly Ala Gly Ala Ala Ala
        755                 760                 765

Thr Gly Ala Gly Ala Ala Ala Gly Ala Gly Val Gly Ala Ala Ala
    770                 775                 780

Ala Gly Glu Val Gly Ala Gly Val Ala Ala Gly Gly Ala Ala Ala Gly
785                 790                 795                 800

Ala Ala Ala Gly Gly Ser Lys Leu Ala Gly Val Gly Lys Gly Phe Met
                805                 810                 815

Lys Gly Ala Gly Lys Leu Met Leu Pro Leu Gly Ile Leu Met Gly Ala
            820                 825                 830

Ser Glu Ile Met Gln Ala Pro Glu Glu Ala Lys Gly Ser Ala Ile Gly
        835                 840                 845

Ser Ala Val Gly Gly Ile Gly Gly Ile Ala Gly Ala Ala Thr
    850                 855                 860

Gly Ala Ile Ala Gly Ser Phe Leu Gly Pro Ile Gly Thr Ala Val Gly
865                 870                 875                 880

Gly Ile Ala Gly Gly Ile Ala Gly Gly Phe Ala Gly Ser Ser Leu Gly
                885                 890                 895

Glu Thr Ile Gly Gly Trp Phe Asp Ser Gly Pro Lys Glu Asp Ala Ser
            900                 905                 910

Ala Ala Asp Lys Ala Lys Ala Asp Ala Ser Ala Ala Leu Ala Ala
        915                 920                 925

Ala Ala Gly Thr Ser Gly Ala Val Gly Ser Ser Ala Leu Gln Ser Gln
```

```
                930             935             940
Met Ala Gln Gly Ile Thr Gly Ala Pro Asn Met Ser Gln Val Gly Ser
945             950             955             960

Met Ala Ser Ala Leu Gly Ile Ser Ser Gly Ala Met Ala Ser Ala Leu
            965             970             975

Gly Ile Ser Ser Gly Gln Glu Asn Gln Ile Gln Thr Met Thr Asp Lys
            980             985             990

Glu Asn Thr Asn Thr Lys Lys Ala Asn Glu Ala Lys Lys Gly Asp Asn
            995             1000            1005

Leu Ser Tyr Glu Arg Glu Asn Ile Ser Met Tyr Glu Arg Val Leu
        1010            1015            1020

Thr Arg Ala Glu Gln Ile Leu Ala Gln Ala Arg Ala Gln Asn Gly
        1025            1030            1035

Ile Met Gly Val Gly Gly Gly Thr Ala Gly Ala Gly Gly Gly
        1040            1045            1050

Ile Asn Gly Phe Thr Gly Gly Gly Lys Leu Gln Phe Leu Ala Ala
        1055            1060            1065

Gly Gln Lys Trp Ser Ser Ser Asn Leu Gln Gln His Asp Leu Gly
        1070            1075            1080

Phe Thr Asp Gln Asn Leu Thr Ala Glu Asp Leu Asp Lys Trp Ile
        1085            1090            1095

Asp Ser Lys Ala Pro Gln Gly Ser Met Met Arg Gly Met Gly Ala
        1100            1105            1110

Thr Phe Leu Lys Ala Gly Gln Glu Tyr Gly Leu Asp Pro Arg Tyr
        1115            1120            1125

Leu Ile Ala His Ala Ala Glu Glu Ser Gly Trp Gly Thr Ser Lys
        1130            1135            1140

Ile Ala Arg Asp Lys Gly Asn Phe Phe Gly Ile Gly Ala Phe Asp
        1145            1150            1155

Asp Ser Pro Tyr Ser Ser Ala Tyr Glu Phe Lys Asp Gly Thr Gly
        1160            1165            1170

Ser Ala Ala Glu Arg Gly Ile Met Gly Gly Ala Lys Trp Ile Ser
        1175            1180            1185

Glu Lys Tyr Tyr Gly Lys Gly Asn Thr Thr Leu Asp Lys Met Lys
        1190            1195            1200

Ala Ala Gly Tyr Ala Thr Asn Ala Ser Trp Ala Pro Asn Ile Ala
        1205            1210            1215

Ser Ile Met Ala Gly Ala Pro Thr Gly Ser Gly Ser Gly Asn Val
        1220            1225            1230

Thr Ala Thr Ile Asn Val Asn Val Lys Gly Asp Glu Lys Val Ser
        1235            1240            1245

Asp Lys Leu Lys Asn Ser Ser Asp Met Lys Lys Ala Gly Lys Asp
        1250            1255            1260

Ile Gly Ser Leu Leu Gly Phe Tyr Ser Arg Glu Met Thr Ile Ala
        1265            1270            1275

<210> SEQ ID NO 36
<211> LENGTH: 495
<212> TYPE: PRT
<213> ORGANISM: Staphylococcus phage GH15

<400> SEQUENCE: 36

Met Ala Lys Thr Gln Ala Glu Ile Asn Lys Arg Leu Asp Ala Tyr Ala
1               5                   10                  15
```

Lys Gly Thr Val Asp Ser Pro Tyr Arg Ile Lys Lys Ala Thr Ser Tyr
            20                  25                  30

Asp Pro Ser Phe Gly Val Met Glu Ala Gly Ala Ile Asp Ala Asp Gly
        35                  40                  45

Tyr Tyr His Ala Gln Cys Gln Asp Leu Ile Thr Asp Tyr Val Leu Trp
    50                  55                  60

Leu Thr Asp Asn Lys Val Arg Thr Trp Gly Asn Ala Lys Asp Gln Ile
65                  70                  75                  80

Lys Gln Ser Tyr Gly Thr Gly Phe Lys Ile His Glu Asn Lys Pro Ser
                85                  90                  95

Thr Val Pro Lys Lys Gly Trp Ile Ala Val Phe Thr Ser Gly Ser Tyr
            100                 105                 110

Gln Gln Trp Gly His Ile Gly Ile Val Tyr Asp Gly Gly Asn Thr Ser
        115                 120                 125

Thr Phe Thr Ile Leu Glu Gln Asn Trp Asn Gly Tyr Ala Asn Lys Lys
    130                 135                 140

Pro Thr Lys Arg Val Asp Asn Tyr Tyr Gly Leu Thr His Phe Ile Glu
145                 150                 155                 160

Ile Pro Val Lys Ala Gly Thr Thr Val Lys Lys Glu Thr Ala Lys Lys
                165                 170                 175

Ser Ala Ser Lys Thr Pro Ala Pro Lys Lys Lys Ala Thr Leu Lys Val
            180                 185                 190

Ser Lys Asn His Ile Asn Tyr Thr Met Asp Lys Arg Gly Lys Lys Pro
        195                 200                 205

Glu Gly Met Val Ile His Asn Asp Ala Gly Arg Ser Ser Gly Gln Gln
    210                 215                 220

Tyr Glu Asn Ser Leu Ala Asn Ala Gly Tyr Ala Arg Tyr Ala Asn Gly
225                 230                 235                 240

Ile Ala His Tyr Tyr Gly Ser Glu Gly Tyr Val Trp Glu Ala Ile Asp
                245                 250                 255

Ala Lys Asn Gln Ile Ala Trp His Thr Gly Asp Gly Thr Gly Ala Asn
            260                 265                 270

Ser Gly Asn Phe Arg Phe Ala Gly Ile Glu Val Cys Gln Ser Met Ser
        275                 280                 285

Ala Ser Asp Ala Gln Phe Leu Lys Asn Glu Gln Ala Val Phe Gln Phe
    290                 295                 300

Thr Ala Glu Lys Phe Lys Glu Trp Gly Leu Thr Pro Asn Arg Lys Thr
305                 310                 315                 320

Val Arg Leu His Met Glu Phe Val Pro Thr Ala Cys Pro His Arg Ser
                325                 330                 335

Met Val Leu His Thr Gly Phe Asn Pro Val Thr Gln Gly Arg Pro Ser
            340                 345                 350

Gln Ala Ile Met Asn Lys Leu Lys Asp Tyr Phe Ile Lys Gln Ile Lys
        355                 360                 365

Asn Tyr Met Asp Lys Gly Thr Ser Ser Thr Val Lys Asp Gly
    370                 375                 380

Lys Thr Ser Ser Ala Ser Thr Pro Ala Thr Arg Pro Val Thr Gly Ser
385                 390                 395                 400

Trp Lys Lys Asn Gln Tyr Gly Thr Trp Tyr Lys Pro Glu Asn Ala Thr
                405                 410                 415

Phe Val Asn Gly Asn Gln Pro Ile Val Thr Arg Ile Gly Ser Pro Phe
            420                 425                 430

Leu Asn Ala Pro Val Gly Gly Asn Leu Pro Ala Gly Ala Thr Ile Val

```
            435                 440                 445
Tyr Asp Glu Val Cys Ile Gln Ala Gly His Ile Trp Ile Gly Tyr Asn
450                 455                 460

Ala Tyr Asn Gly Asp Arg Val Tyr Cys Pro Val Arg Thr Cys Gln Gly
465                 470                 475                 480

Val Pro Pro Asn His Ile Pro Gly Val Ala Trp Gly Val Phe Lys
                485                 490                 495

<210> SEQ ID NO 37
<211> LENGTH: 264
<212> TYPE: PRT
<213> ORGANISM: Clostridium phage phi8074-B1

<400> SEQUENCE: 37

Met Lys Ile Gly Ile Asp Met Gly His Thr Leu Ser Gly Ala Asp Tyr
1               5                   10                  15

Gly Val Val Gly Leu Arg Pro Glu Ser Val Leu Thr Arg Glu Val Gly
                20                  25                  30

Thr Lys Val Ile Tyr Lys Leu Gln Lys Leu Gly His Val Val Val Asn
            35                  40                  45

Cys Thr Val Asp Lys Ala Ser Ser Val Ser Glu Ser Leu Tyr Thr Arg
        50                  55                  60

Tyr Tyr Arg Ala Asn Gln Ala Asn Val Asp Leu Phe Ile Ser Ile His
65                  70                  75                  80

Phe Asn Ala Thr Pro Gly Gly Thr Gly Thr Glu Val Tyr Thr Tyr Ala
                85                  90                  95

Gly Arg Gln Leu Gly Glu Ala Thr Arg Ile Arg Gln Glu Phe Lys Ser
            100                 105                 110

Leu Gly Leu Arg Asp Arg Gly Thr Lys Asp Gly Ser Gly Leu Ala Val
        115                 120                 125

Ile Arg Asn Thr Lys Ala Lys Ala Met Leu Val Glu Cys Cys Phe Cys
130                 135                 140

Asp Asn Pro Asn Asp Met Lys Leu Tyr Asn Ser Glu Ser Phe Ser Asn
145                 150                 155                 160

Ala Ile Val Lys Gly Ile Thr Gly Lys Leu Pro Asn Gly Glu Ser Gly
                165                 170                 175

Asn Asn Asn Gln Gly Gly Asn Lys Val Lys Ala Val Ile Tyr Asn
            180                 185                 190

Glu Gly Ala Asp Arg Arg Gly Ala Glu Tyr Leu Ala Asp Tyr Leu Asn
        195                 200                 205

Cys Pro Thr Ile Ser Asn Ser Arg Thr Phe Asp Tyr Ser Cys Val Glu
210                 215                 220

His Val Tyr Ala Val Gly Gly Lys Lys Glu Gln Tyr Thr Lys Tyr Leu
225                 230                 235                 240

Lys Thr Leu Leu Ser Gly Ala Asn Arg Tyr Asp Thr Met Gln Gln Ile
                245                 250                 255

Leu Asn Phe Ile Asn Gly Gly Lys
            260

<210> SEQ ID NO 38
<211> LENGTH: 209
<212> TYPE: PRT
<213> ORGANISM: Salmonella phage SPN1S

<400> SEQUENCE: 38

Met Asp Ile Asn Gln Phe Arg Arg Ala Ser Gly Ile Asn Glu Gln Leu
```

-continued

```
1               5                   10                  15
Ala Ala Arg Trp Phe Pro His Ile Thr Thr Ala Met Asn Glu Phe Gly
                20                  25                  30

Ile Thr Lys Pro Asp Asp Gln Ala Met Phe Ile Ala Gln Val Gly His
                35                  40                  45

Glu Ser Gly Gly Phe Thr Arg Leu Gln Glu Asn Phe Asn Tyr Ser Val
        50                  55                  60

Asn Gly Leu Ser Gly Phe Ile Arg Ala Gly Arg Ile Thr Pro Asp Gln
65                  70                  75                  80

Ala Asn Ala Leu Gly Arg Lys Thr Tyr Glu Lys Ser Leu Pro Leu Glu
                85                  90                  95

Arg Gln Arg Ala Ile Ala Asn Leu Val Tyr Ser Lys Arg Met Gly Asn
                100                 105                 110

Asn Gly Pro Gly Asp Gly Trp Asn Tyr Arg Gly Arg Gly Leu Ile Gln
                115                 120                 125

Ile Thr Gly Leu Asn Asn Tyr Arg Asp Cys Gly Asn Gly Leu Lys Val
            130                 135                 140

Asp Leu Val Ala Gln Pro Glu Leu Leu Ala Gln Asp Glu Tyr Ala Ala
145                 150                 155                 160

Arg Ser Ala Ala Trp Phe Phe Ser Ser Lys Gly Cys Met Lys Tyr Thr
                165                 170                 175

Gly Asp Leu Val Arg Val Thr Gln Ile Ile Asn Gly Gly Gln Asn Gly
            180                 185                 190

Ile Asp Asp Arg Arg Thr Arg Tyr Ala Ala Arg Lys Val Leu Ala
                195                 200                 205

Leu
```

<210> SEQ ID NO 39
<211> LENGTH: 290
<212> TYPE: PRT
<213> ORGANISM: Clavibacter phage CN77

<400> SEQUENCE: 39

```
Met Gly Tyr Trp Gly Tyr Pro Asn Gly Gln Ile Pro Asn Asp Lys Met
1               5                   10                  15

Ala Leu Tyr Arg Gly Cys Leu Leu Arg Ala Asp Ala Ala Gln Ala
                20                  25                  30

Tyr Ala Leu Gln Asp Ala Tyr Thr Arg Ala Thr Gly Lys Pro Leu Val
            35                  40                  45

Ile Leu Glu Gly Tyr Arg Asp Leu Thr Arg Gln Lys Tyr Leu Arg Asn
        50                  55                  60

Leu Tyr Leu Ser Gly Arg Gly Asn Ile Ala Ala Val Pro Gly Leu Ser
65                  70                  75                  80

Asn His Gly Trp Gly Leu Ala Cys Asp Phe Ala Ala Pro Leu Asn Ser
                85                  90                  95

Ser Gly Ser Glu Glu His Arg Trp Met Arg Gln Asn Ala Pro Leu Phe
                100                 105                 110

Gly Phe Asp Trp Ala Arg Gly Lys Ala Asp Asn Glu Pro Trp His Trp
            115                 120                 125

Glu Tyr Gly Asn Val Pro Val Ser Arg Trp Ala Ser Leu Asp Val Thr
        130                 135                 140

Pro Ile Asp Arg Asn Asp Met Ala Asp Ile Thr Glu Gly Gln Met Gln
145                 150                 155                 160

Arg Ile Ala Val Ile Leu Leu Asp Thr Glu Ile Gln Thr Pro Leu Gly
```

```
              165                 170                 175

Pro Arg Leu Val Lys His Ala Leu Gly Asp Ala Leu Leu Gly Gln
        180                 185                 190

Ala Asn Ala Asn Ser Ile Ala Glu Val Pro Asp Lys Thr Trp Asp Val
    195                 200                 205

Leu Val Asp His Pro Leu Ala Lys Asn Glu Asp Gly Thr Pro Leu Lys
    210                 215                 220

Val Arg Leu Gly Asp Val Ala Lys Tyr Glu Pro Leu Glu His Gln Asn
225                 230                 235                 240

Thr Arg Asp Ala Ile Ala Lys Leu Gly Thr Leu Gln Phe Thr Asp Lys
            245                 250                 255

Gln Leu Ala Thr Ile Gly Ala Gly Val Lys Pro Ile Asp Glu Ala Ser
            260                 265                 270

Leu Val Lys Lys Ile Val Asp Gly Val Arg Ala Leu Phe Gly Arg Ala
        275                 280                 285

Ala Ala
    290

<210> SEQ ID NO 40
<211> LENGTH: 185
<212> TYPE: PRT
<213> ORGANISM: Acinetobacter phage phiAB2

<400> SEQUENCE: 40

Met Ile Leu Thr Lys Asp Gly Phe Ser Ile Ile Arg Asn Glu Leu Phe
1               5                   10                  15

Gly Gly Lys Leu Asp Gln Thr Gln Val Asp Ala Ile Asn Phe Ile Val
            20                  25                  30

Ala Lys Ala Thr Glu Ser Gly Leu Thr Tyr Pro Glu Ala Ala Tyr Leu
        35                  40                  45

Leu Ala Thr Ile Tyr His Glu Thr Gly Leu Pro Ser Gly Tyr Arg Thr
    50                  55                  60

Met Gln Pro Ile Lys Glu Ala Gly Ser Asp Ser Tyr Leu Arg Ser Lys
65                  70                  75                  80

Lys Tyr Tyr Pro Tyr Ile Gly Tyr Gly Tyr Val Gln Leu Thr Trp Lys
                85                  90                  95

Glu Asn Tyr Glu Arg Ile Gly Lys Leu Ile Gly Val Asp Leu Ile Lys
            100                 105                 110

Asn Pro Glu Lys Ala Leu Glu Pro Leu Ile Ala Ile Gln Ile Ala Ile
        115                 120                 125

Lys Gly Met Leu Asn Gly Trp Phe Thr Gly Val Gly Phe Arg Arg Lys
    130                 135                 140

Arg Pro Val Ser Lys Tyr Asn Lys Gln Gln Tyr Val Ala Ala Arg Asn
145                 150                 155                 160

Ile Ile Asn Gly Lys Asp Lys Ala Glu Leu Ile Ala Lys Tyr Ala Ile
                165                 170                 175

Ile Phe Glu Arg Ala Leu Arg Ser Leu
            180                 185

<210> SEQ ID NO 41
<211> LENGTH: 262
<212> TYPE: PRT
<213> ORGANISM: Bacillus phage B4

<400> SEQUENCE: 41

Met Ala Met Ala Leu Gln Thr Leu Ile Asp Lys Ala Asn Arg Lys Leu
```

```
            1               5                  10                 15
          Asn Val Ser Gly Met Arg Lys Asp Val Ala Asp Arg Thr Arg Ala Val
                       20                  25                 30

Ile Thr Gln Met His Ala Gln Gly Ile Tyr Ile Cys Val Ala Gln Gly
                       35                  40                 45

Phe Arg Ser Phe Ala Glu Gln Asn Ala Leu Tyr Ala Gln Gly Arg Thr
                       50                  55                 60

Lys Pro Gly Ser Ile Val Thr Asn Ala Arg Gly Gly Gln Ser Asn His
           65              70                  75                 80

Asn Tyr Gly Val Ala Val Asp Leu Cys Leu Tyr Thr Gln Asp Gly Ser
                           85                  90                 95

Asp Val Ile Trp Thr Val Glu Gly Asn Phe Arg Lys Val Ile Ala Ala
                          100                 105                110

Met Lys Ala Gln Gly Phe Lys Trp Gly Asp Trp Val Ser Phe Lys
                          115                 120                125

Asp Tyr Pro His Phe Glu Leu Tyr Asp Val Val Gly Gly Gln Lys Pro
                          130                 135                140

Pro Ala Asp Asn Gly Gly Ala Val Asp Asn Gly Gly Ser Gly Ser
          145                 150                 155                160

Thr Gly Gly Ser Gly Gly Ser Thr Gly Gly Ser Thr Gly Gly
                              165                 170                175

Gly Tyr Asp Ser Ser Trp Phe Thr Lys Glu Thr Gly Thr Phe Val Thr
                          180                 185                190

Asn Thr Ser Ile Lys Leu Arg Thr Ala Pro Phe Thr Ser Ala Asp Val
                          195                 200                205

Ile Ala Thr Leu Pro Ala Gly Ser Pro Val Asn Tyr Asn Gly Phe Gly
                          210                 215                220

Ile Glu Tyr Asp Gly Tyr Val Trp Ile Arg Gln Pro Arg Ser Asn Gly
          225                 230                 235                240

Tyr Gly Tyr Leu Ala Thr Gly Glu Ser Lys Gly Gly Lys Arg Gln Asn
                          245                 250                255

Tyr Trp Gly Thr Phe Lys
                          260

<210> SEQ ID NO 42
<211> LENGTH: 274
<212> TYPE: PRT
<213> ORGANISM: Clostridium phage phiCTP1

<400> SEQUENCE: 42

Met Lys Lys Ile Ala Asp Ile Ser Asn Leu Asn Gly Asn Val Asp Val
           1               5                  10                 15

Lys Leu Leu Phe Asn Leu Gly Tyr Ile Gly Ile Ala Lys Ala Ser
                       20                  25                 30

Glu Gly Gly Thr Phe Val Asp Lys Tyr Tyr Lys Gln Asn Tyr Thr Asn
                       35                  40                 45

Thr Lys Ala Gln Gly Lys Ile Thr Gly Ala Tyr His Phe Ala Asn Phe
                       50                  55                 60

Ser Thr Ile Ala Lys Ala Gln Gln Glu Ala Asn Phe Phe Leu Asn Cys
           65              70                  75                 80

Ile Ala Gly Thr Thr Pro Asp Phe Val Val Leu Asp Leu Glu Gln Gln
                           85                  90                 95

Cys Thr Gly Asp Ile Thr Asp Ala Cys Leu Ala Phe Leu Asn Ile Val
                          100                 105                110
```

```
Ala Lys Lys Phe Lys Cys Val Val Tyr Cys Asn Ser Ser Phe Ile Lys
            115                 120                 125

Glu His Leu Asn Ser Lys Ile Cys Ala Tyr Pro Leu Trp Ile Ala Asn
    130                 135                 140

Tyr Gly Val Ala Thr Pro Ala Phe Thr Leu Trp Thr Lys Tyr Ala Met
145                 150                 155                 160

Trp Gln Phe Thr Glu Lys Gly Gln Val Ser Gly Ile Ser Gly Tyr Ile
                165                 170                 175

Asp Phe Ser Tyr Ile Thr Asp Glu Phe Ile Lys Tyr Ile Lys Gly Glu
                180                 185                 190

Asp Glu Val Glu Asn Leu Val Val Tyr Asn Asp Gly Ala Asp Gln Arg
            195                 200                 205

Ala Ala Glu Tyr Leu Ala Asp Arg Leu Ala Cys Pro Thr Ile Asn Asn
        210                 215                 220

Ala Arg Lys Phe Asp Tyr Ser Asn Val Lys Asn Val Tyr Ala Val Gly
225                 230                 235                 240

Gly Asn Lys Glu Gln Tyr Thr Ser Tyr Leu Thr Thr Leu Ile Ala Gly
                245                 250                 255

Ser Thr Arg Tyr Thr Thr Met Gln Ala Val Leu Asp Tyr Ile Lys Asn
                260                 265                 270

Leu Lys

<210> SEQ ID NO 43
<211> LENGTH: 628
<212> TYPE: PRT
<213> ORGANISM: Staphylococcus virus 187

<400> SEQUENCE: 43

Met Ala Leu Pro Lys Thr Gly Lys Pro Thr Ala Lys Gln Val Val Asp
1               5                   10                  15

Trp Ala Ile Asn Leu Ile Gly Ser Gly Val Asp Val Asp Gly Tyr Tyr
                20                  25                  30

Gly Arg Gln Cys Trp Asp Leu Pro Asn Tyr Ile Phe Asn Arg Tyr Trp
            35                  40                  45

Asn Phe Lys Thr Pro Gly Asn Ala Arg Asp Met Ala Trp Tyr Arg Tyr
        50                  55                  60

Pro Glu Gly Phe Lys Val Phe Arg Asn Thr Ser Asp Phe Val Pro Lys
65                  70                  75                  80

Pro Gly Asp Ile Ala Val Trp Thr Gly Gly Asn Tyr Asn Trp Asn Thr
                85                  90                  95

Trp Gly His Thr Gly Ile Val Val Gly Pro Ser Thr Lys Ser Tyr Phe
            100                 105                 110

Tyr Ser Val Asp Gln Asn Trp Asn Asn Ser Asn Ser Tyr Val Gly Ser
        115                 120                 125

Pro Ala Ala Lys Ile Lys His Ser Tyr Phe Gly Val Thr His Phe Val
    130                 135                 140

Arg Pro Ala Tyr Lys Ala Glu Pro Lys Pro Thr Pro Ala Gln Asn
145                 150                 155                 160

Asn Pro Ala Pro Lys Asp Pro Glu Pro Ser Lys Lys Pro Glu Ser Asn
                165                 170                 175

Lys Pro Ile Tyr Lys Val Val Thr Lys Ile Leu Phe Thr Thr Ala His
                180                 185                 190

Ile Glu His Val Lys Ala Asn Arg Phe Val His Tyr Ile Thr Lys Ser
            195                 200                 205
```

```
Asp Asn His Asn Asn Lys Pro Asn Lys Ile Val Ile Lys Asn Thr Asn
    210                 215                 220

Thr Ala Leu Ser Thr Ile Asp Val Tyr Arg Tyr Arg Asp Glu Leu Asp
225                 230                 235                 240

Lys Asp Glu Ile Pro His Phe Phe Val Asp Arg Leu Asn Val Trp Ala
                245                 250                 255

Cys Arg Pro Ile Glu Asp Ser Ile Asn Gly Tyr His Asp Ser Val Val
                260                 265                 270

Leu Ser Ile Thr Glu Thr Arg Thr Ala Leu Ser Asp Asn Phe Lys Met
            275                 280                 285

Asn Glu Ile Glu Cys Leu Ser Leu Ala Glu Ser Ile Leu Lys Ala Asn
        290                 295                 300

Asn Lys Lys Met Ser Ala Ser Asn Ile Ile Val Asp Asn Lys Ala Trp
305                 310                 315                 320

Arg Thr Phe Lys Leu His Thr Gly Lys Asp Ser Leu Lys Ser Ser Ser
                325                 330                 335

Phe Thr Ser Lys Asp Tyr Gln Lys Ala Val Asn Glu Leu Ile Lys Leu
                340                 345                 350

Phe Asn Asp Lys Asp Lys Leu Leu Asn Asn Lys Pro Lys Asp Val Val
            355                 360                 365

Glu Arg Ile Arg Ile Arg Thr Ile Val Lys Glu Asn Thr Lys Phe Val
        370                 375                 380

Pro Ser Glu Leu Lys Pro Arg Asn Asn Ile Arg Asp Lys Gln Asp Ser
385                 390                 395                 400

Lys Ile Asp Arg Val Ile Asn Asn Tyr Thr Leu Lys Gln Ala Leu Asn
                405                 410                 415

Ile Gln Tyr Lys Leu Asn Pro Lys Pro Gln Thr Ser Asn Gly Val Ser
                420                 425                 430

Trp Tyr Asn Ala Ser Val Asn Gln Ile Lys Ser Ala Met Asp Thr Thr
            435                 440                 445

Lys Ile Phe Asn Asn Val Gln Val Tyr Gln Phe Leu Lys Leu Asn
        450                 455                 460

Gln Tyr Gln Gly Ile Pro Val Asp Lys Leu Asn Lys Leu Leu Val Gly
465                 470                 475                 480

Lys Gly Thr Leu Ala Asn Gln Gly His Ala Phe Ala Asp Gly Cys Lys
                485                 490                 495

Lys Tyr Asn Ile Asn Glu Ile Tyr Leu Ile Ala His Arg Phe Leu Glu
                500                 505                 510

Ser Ala Asn Gly Thr Ser Phe Phe Ala Ser Gly Lys Thr Gly Val Tyr
            515                 520                 525

Asn Tyr Phe Gly Ile Gly Ala Phe Asp Asn Asn Pro Asn Asn Ala Met
        530                 535                 540

Ala Phe Ala Arg Ser His Gly Trp Thr Ser Pro Thr Lys Ala Ile Ile
545                 550                 555                 560

Gly Gly Ala Glu Phe Val Gly Lys Gly Tyr Phe Asn Val Gly Gln Asn
                565                 570                 575

Thr Leu Tyr Arg Met Arg Trp Asn Pro Gln Lys Pro Gly Thr His Gln
                580                 585                 590

Tyr Ala Thr Asp Ile Ser Trp Ala Lys Val Gln Ala Gln Met Ile Ser
            595                 600                 605

Ala Met Tyr Lys Glu Ile Gly Leu Thr Gly Asp Tyr Phe Ile Tyr Asp
610                 615                 620

Gln Tyr Lys Lys
```

-continued

```
<210> SEQ ID NO 44
<211> LENGTH: 291
<212> TYPE: PRT
<213> ORGANISM: Listeria phage phiP35

<400> SEQUENCE: 44

Met Ala Arg Lys Phe Thr Lys Ala Glu Leu Val Ala Lys Ala Glu Lys
1               5                   10                  15

Lys Val Gly Gly Leu Lys Pro Asp Val Lys Ala Val Leu Ser Ala
            20                  25                  30

Val Lys Glu Ala Tyr Asp Arg Tyr Gly Ile Gly Ile Val Ser Gln
        35                  40                  45

Gly Tyr Arg Ser Ile Ala Glu Gln Asn Gly Leu Tyr Ala Gln Gly Arg
    50                  55                  60

Thr Lys Pro Gly Asn Ile Val Thr Asn Ala Lys Gly Gly Gln Ser Asn
65                  70                  75                  80

His Asn Phe Gly Val Ala Val Asp Phe Ala Ile Asp Leu Ile Asp Asp
                85                  90                  95

Gly Lys Ile Asp Ser Trp Gln Pro Ser Ala Thr Ile Val Asn Met Met
            100                 105                 110

Lys Arg Arg Gly Phe Lys Trp Gly Gly Asp Trp Lys Ser Phe Thr Asp
        115                 120                 125

Leu Pro His Phe Glu Ala Cys Asp Trp Tyr Arg Gly Glu Arg Lys Tyr
    130                 135                 140

Lys Val Asp Thr Ser Glu Trp Lys Lys Lys Glu Asn Ile Asn Ile Val
145                 150                 155                 160

Ile Lys Asp Val Gly Tyr Phe Gln Asp Lys Pro Gln Phe Leu Asn Ser
                165                 170                 175

Lys Ser Val Arg Gln Trp Lys His Gly Thr Lys Val Lys Leu Thr Lys
            180                 185                 190

His Asn Ser His Trp Tyr Thr Gly Val Val Lys Asp Gly Asn Lys Ser
        195                 200                 205

Val Arg Gly Tyr Ile Tyr His Ser Met Ala Lys Val Thr Ser Lys Asn
    210                 215                 220

Ser Asp Gly Ser Val Asn Ala Thr Ile Asn Ala His Ala Phe Cys Trp
225                 230                 235                 240

Asp Asn Lys Lys Leu Asn Gly Gly Asp Phe Ile Asn Leu Lys Arg Gly
                245                 250                 255

Phe Lys Gly Ile Thr His Pro Ala Ser Asp Gly Phe Tyr Pro Leu Tyr
            260                 265                 270

Phe Ala Ser Arg Lys Lys Thr Phe Tyr Ile Pro Arg Tyr Met Phe Asp
        275                 280                 285

Ile Lys Lys
    290

<210> SEQ ID NO 45
<211> LENGTH: 342
<212> TYPE: PRT
<213> ORGANISM: Streptococcus phage CP-7

<400> SEQUENCE: 45

Met Val Lys Lys Asn Asp Leu Phe Val Asp Val Ala Ser His Gln Gly
1               5                   10                  15

Tyr Asp Ile Ser Gly Ile Leu Glu Glu Ala Gly Thr Thr Asn Thr Ile
```

```
            20                  25                  30
Ile Lys Val Ser Glu Ser Thr Ser Tyr Leu Asn Pro Cys Leu Ser Ala
            35                  40                  45

Gln Val Ser Gln Ser Asn Pro Ile Gly Phe Tyr His Phe Ala Trp Phe
        50                  55                  60

Gly Gly Asn Glu Glu Glu Ala Glu Ala Glu Ala Arg Tyr Phe Leu Asp
65                  70                  75                  80

Asn Val Pro Thr Gln Val Lys Tyr Leu Val Leu Asp Tyr Glu Asp His
                85                  90                  95

Ala Ser Ala Ser Val Gln Arg Asn Thr Thr Ala Cys Leu Arg Phe Met
            100                 105                 110

Gln Ile Ile Ala Glu Ala Gly Tyr Thr Pro Ile Tyr Tyr Ser Tyr Lys
            115                 120                 125

Pro Phe Thr Leu Asp Asn Val Asp Tyr Gln Gln Ile Leu Ala Gln Phe
        130                 135                 140

Pro Asn Ser Leu Trp Ile Ala Gly Tyr Gly Leu Asn Asp Gly Thr Ala
145                 150                 155                 160

Asn Phe Glu Tyr Phe Pro Ser Met Asp Gly Ile Arg Trp Trp Gln Tyr
                165                 170                 175

Ser Ser Asn Pro Phe Asp Lys Asn Ile Val Leu Leu Asp Asp Glu Lys
            180                 185                 190

Glu Asp Asn Ile Asn Asn Glu Asn Thr Leu Lys Ser Leu Thr Thr Val
            195                 200                 205

Ala Asn Glu Val Ile Gln Gly Leu Trp Gly Asn Gly Gln Glu Arg Tyr
        210                 215                 220

Asp Ser Leu Ala Asn Ala Gly Tyr Asp Pro Gln Ala Val Gln Asp Lys
225                 230                 235                 240

Val Asn Glu Ile Leu Asn Ala Arg Glu Ile Ala Asp Leu Thr Thr Val
                245                 250                 255

Ala Asn Glu Val Ile Gln Gly Leu Trp Gly Asn Gly Gln Glu Arg Tyr
            260                 265                 270

Asp Ser Leu Ala Asn Ala Gly Tyr Asp Pro Gln Ala Val Gln Asp Lys
            275                 280                 285

Val Asn Glu Ile Leu Asn Ala Arg Glu Ile Ala Asp Leu Thr Thr Val
        290                 295                 300

Ala Asn Glu Val Ile Gln Gly Leu Trp Gly Asn Gly Gln Glu Arg Tyr
305                 310                 315                 320

Asp Ser Leu Ala Asn Ala Gly Tyr Asp Pro Gln Ala Val Gln Asp Lys
                325                 330                 335

Val Asn Glu Leu Leu Ser
            340

<210> SEQ ID NO 46
<211> LENGTH: 328
<212> TYPE: PRT
<213> ORGANISM: Enterococcus phage EFAP-1

<400> SEQUENCE: 46

Met Lys Leu Lys Gly Ile Leu Leu Ser Val Val Thr Thr Phe Gly Leu
1               5                   10                  15

Leu Phe Gly Ala Thr Asn Val Gln Ala Tyr Glu Val Asn Asn Glu Phe
            20                  25                  30

Asn Leu Gln Pro Trp Glu Gly Ser Gln Gln Leu Ala Tyr Pro Asn Lys
        35                  40                  45
```

Ile Ile Leu His Glu Thr Ala Asn Pro Arg Ala Thr Gly Arg Asn Glu
        50                  55                  60

Ala Thr Tyr Met Lys Asn Asn Trp Phe Asn Ala His Thr Thr Ala Ile
65                  70                  75                  80

Val Gly Asp Gly Gly Ile Val Tyr Lys Val Ala Pro Glu Gly Asn Val
                85                  90                  95

Ser Trp Gly Ala Gly Asn Ala Asn Pro Tyr Ala Pro Val Gln Ile Glu
            100                 105                 110

Leu Gln His Thr Asn Asp Pro Glu Leu Phe Lys Ala Asn Tyr Lys Ala
            115                 120                 125

Tyr Val Asp Tyr Thr Arg Asp Met Gly Lys Lys Phe Gly Ile Pro Met
130                 135                 140

Thr Leu Asp Gln Gly Gly Ser Leu Trp Glu Lys Gly Val Val Ser His
145                 150                 155                 160

Gln Trp Val Thr Asp Phe Val Trp Gly Asp His Thr Asp Pro Tyr Gly
                165                 170                 175

Tyr Leu Ala Lys Met Gly Ile Ser Lys Ala Gln Leu Ala His Asp Leu
            180                 185                 190

Ala Asn Gly Val Ser Gly Asn Thr Ala Thr Pro Thr Pro Lys Pro Asp
            195                 200                 205

Lys Pro Lys Pro Thr Gln Pro Ser Lys Pro Ser Asn Lys Lys Arg Phe
210                 215                 220

Asn Tyr Arg Val Asp Gly Leu Glu Tyr Val Asn Gly Met Trp Gln Ile
225                 230                 235                 240

Tyr Asn Glu His Leu Gly Lys Ile Asp Phe Asn Trp Thr Glu Asn Gly
                245                 250                 255

Ile Pro Val Glu Val Val Asp Lys Val Asn Pro Ala Thr Gly Gln Pro
            260                 265                 270

Thr Lys Asp Gln Val Leu Lys Val Gly Asp Tyr Phe Asn Phe Gln Glu
            275                 280                 285

Asn Ser Thr Gly Val Val Gln Glu Gln Thr Pro Tyr Met Gly Tyr Thr
            290                 295                 300

Leu Ser His Val Gln Leu Pro Asn Glu Phe Ile Trp Leu Phe Thr Asp
305                 310                 315                 320

Ser Lys Gln Ala Leu Met Tyr Gln
                325

<210> SEQ ID NO 47
<211> LENGTH: 48
<212> TYPE: PRT
<213> ORGANISM: Homo sapiens

<400> SEQUENCE: 47

Ser Ser Leu Leu Glu Lys Gly Leu Asp Gly Ala Lys Lys Ala Val Gly
1               5                   10                  15

Gly Leu Gly Lys Leu Gly Lys Asp Ala Val Glu Asp Leu Glu Ser Val
            20                  25                  30

Gly Lys Gly Ala Val His Asp Val Lys Asp Val Leu Asp Ser Val Leu
        35                  40                  45

<210> SEQ ID NO 48
<211> LENGTH: 37
<212> TYPE: PRT
<213> ORGANISM: Hyalophora cecropia

<400> SEQUENCE: 48

```
Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Val Val Gly Gln Ala
            20                  25                  30

Thr Gln Ile Ala Lys
            35

<210> SEQ ID NO 49
<211> LENGTH: 62
<212> TYPE: PRT
<213> ORGANISM: Drosophila teissieri

<400> SEQUENCE: 49

Met Lys Tyr Phe Ser Val Leu Val Val Leu Thr Leu Ile Leu Ala Ile
1               5                   10                  15

Val Asp Gln Ser Asp Ala Phe Ile Asn Leu Leu Asp Lys Val Glu Asp
            20                  25                  30

Ala Leu His Thr Gly Ala Gln Ala Gly Phe Lys Leu Ile Arg Pro Val
            35                  40                  45

Glu Arg Gly Ala Thr Pro Lys Lys Ser Glu Lys Pro Glu Lys
50                  55                  60

<210> SEQ ID NO 50
<211> LENGTH: 66
<212> TYPE: PRT
<213> ORGANISM: Bombyz mori

<400> SEQUENCE: 50

Met Asn Ile Leu Lys Phe Phe Val Phe Ile Val Ala Met Ser Leu
1               5                   10                  15

Val Ser Cys Ser Thr Ala Ala Pro Ala Lys Ile Pro Ile Lys Ala Ile
            20                  25                  30

Lys Thr Val Gly Lys Ala Val Gly Lys Gly Leu Arg Ala Ile Asn Ile
            35                  40                  45

Ala Ser Thr Ala Asn Asp Val Phe Asn Phe Leu Lys Pro Lys Lys Arg
50                  55                  60

Lys His
65

<210> SEQ ID NO 51
<211> LENGTH: 71
<212> TYPE: PRT
<213> ORGANISM: Ceratitis capitata

<400> SEQUENCE: 51

Met Ala Asn Leu Lys Ala Val Phe Leu Ile Cys Ile Val Ala Phe Ile
1               5                   10                  15

Ala Leu Gln Cys Val Val Ala Glu Pro Ala Ala Glu Asp Ser Val Val
            20                  25                  30

Val Lys Arg Ser Ile Gly Ser Ala Leu Lys Lys Ala Leu Pro Val Ala
            35                  40                  45

Lys Lys Ile Gly Lys Ile Ala Leu Pro Ile Ala Lys Ala Ala Leu Pro
50                  55                  60

Val Ala Ala Gly Leu Val Gly
65                  70

<210> SEQ ID NO 52
<211> LENGTH: 53
<212> TYPE: PRT
```

<213> ORGANISM: Apis mellifera

<400> SEQUENCE: 52

```
Met Lys Val Val Ile Phe Ile Phe Ala Leu Leu Ala Thr Ile Cys Ala
1               5                   10                  15

Ala Phe Ala Tyr Val Pro Leu Pro Asn Val Pro Gln Pro Gly Arg Arg
            20                  25                  30

Pro Phe Pro Thr Phe Pro Gly Gln Gly Pro Phe Asn Pro Lys Ile Lys
        35                  40                  45

Trp Pro Gln Gly Tyr
        50
```

<210> SEQ ID NO 53
<211> LENGTH: 283
<212> TYPE: PRT
<213> ORGANISM: Apis mellifera

<400> SEQUENCE: 53

```
Lys Asn Phe Ala Leu Ala Ile Leu Val Val Thr Phe Val Val Ala Val
1               5                   10                  15

Phe Gly Asn Thr Asn Leu Asp Pro Pro Thr Arg Pro Thr Arg Leu Arg
            20                  25                  30

Arg Glu Ala Lys Pro Glu Ala Glu Pro Gly Asn Asn Arg Pro Val Tyr
        35                  40                  45

Ile Pro Gln Pro Arg Pro His Pro Arg Leu Arg Arg Glu Ala Glu
    50                  55                  60

Pro Glu Ala Glu Pro Gly Asn Asn Arg Pro Val Tyr Ile Pro Gln Pro
65                  70                  75                  80

Arg Pro Pro His Pro Arg Leu Arg Arg Glu Ala Glu Leu Glu Ala Glu
            85                  90                  95

Pro Gly Asn Asn Arg Pro Val Tyr Ile Ser Gln Pro Arg Pro Pro His
        100                 105                 110

Pro Arg Leu Arg Arg Glu Ala Glu Pro Glu Ala Glu Pro Gly Asn Asn
    115                 120                 125

Arg Pro Val Tyr Ile Pro Gln Pro Arg Pro Pro His Pro Arg Leu Arg
130                 135                 140

Arg Glu Ala Glu Leu Glu Ala Glu Pro Gly Asn Asn Arg Pro Val Tyr
145                 150                 155                 160

Ile Ser Gln Pro Arg Pro Pro His Pro Arg Leu Arg Arg Glu Ala Glu
            165                 170                 175

Pro Glu Ala Glu Pro Gly Asn Asn Arg Pro Val Tyr Ile Pro Gln Pro
        180                 185                 190

Arg Pro Pro His Pro Arg Leu Arg Arg Glu Ala Glu Pro Glu Ala Glu
    195                 200                 205

Pro Gly Asn Asn Arg Pro Val Tyr Ile Pro Gln Pro Arg Pro Pro His
210                 215                 220

Pro Arg Leu Arg Arg Glu Ala Glu Pro Glu Ala Glu Pro Gly Asn Asn
225                 230                 235                 240

Arg Pro Val Tyr Ile Pro Gln Pro Arg Pro Pro His Pro Arg Leu Arg
            245                 250                 255

Arg Glu Ala Lys Pro Glu Ala Lys Pro Gly Asn Asn Arg Pro Val Tyr
        260                 265                 270

Ile Pro Gln Pro Arg Pro Pro His Pro Arg Ile
    275                 280
```

<210> SEQ ID NO 54
<211> LENGTH: 228
<212> TYPE: PRT
<213> ORGANISM: Sus scrofa

<400> SEQUENCE: 54

```
Met Glu Thr Gln Arg Ala Ser Leu Cys Leu Gly Arg Trp Ser Leu Trp
1               5                   10                  15

Leu Leu Leu Leu Ala Leu Val Val Pro Ser Ala Ser Ala Gln Ala Leu
            20                  25                  30

Ser Tyr Arg Glu Ala Val Leu Arg Ala Val Asp Arg Leu Asn Glu Gln
        35                  40                  45

Ser Ser Glu Ala Asn Leu Tyr Arg Leu Leu Glu Leu Asp Gln Pro Pro
    50                  55                  60

Lys Ala Asp Glu Asp Pro Gly Thr Pro Lys Pro Val Ser Phe Thr Val
65                  70                  75                  80

Lys Glu Thr Val Cys Pro Arg Pro Thr Arg Arg Pro Glu Leu Cys
                85                  90                  95

Asp Phe Lys Glu Asn Gly Arg Val Lys Gln Cys Val Gly Thr Val Thr
                100                 105                 110

Leu Asp Gln Ile Lys Asp Pro Leu Asp Ile Thr Cys Asn Glu Gly Val
            115                 120                 125

Arg Arg Phe Pro Trp Trp Trp Pro Phe Leu Arg Arg Pro Arg Leu Arg
130                 135                 140

Arg Gln Ala Phe Pro Pro Asn Val Pro Gly Pro Arg Phe Pro Pro
145                 150                 155                 160

Pro Asn Val Pro Gly Pro Arg Phe Pro Pro Asn Phe Pro Gly Pro
                165                 170                 175

Arg Phe Pro Pro Pro Asn Phe Pro Gly Pro Arg Phe Pro Pro Pro Asn
            180                 185                 190

Phe Pro Gly Pro Pro Phe Pro Pro Ile Phe Pro Gly Pro Trp Phe
        195                 200                 205

Pro Pro Pro Pro Phe Arg Pro Pro Phe Gly Pro Pro Arg Phe
    210                 215                 220

Pro Gly Arg Arg
225
```

<210> SEQ ID NO 55
<211> LENGTH: 144
<212> TYPE: PRT
<213> ORGANISM: Bos taurus

<400> SEQUENCE: 55

```
Met Gln Thr Gln Arg Ala Ser Leu Ser Leu Gly Arg Trp Ser Leu Trp
1               5                   10                  15

Leu Leu Leu Leu Gly Leu Val Val Pro Ser Ala Ser Ala Gln Ala Leu
            20                  25                  30

Ser Tyr Arg Glu Ala Val Leu Arg Ala Val Asp Gln Leu Asn Glu Leu
        35                  40                  45

Ser Ser Glu Ala Asn Leu Tyr Arg Leu Leu Glu Leu Asp Pro Pro Pro
    50                  55                  60

Lys Asp Asn Glu Asp Leu Gly Thr Arg Lys Pro Val Ser Phe Thr Val
65                  70                  75                  80

Lys Glu Thr Val Cys Pro Arg Thr Ile Gln Gln Pro Ala Glu Gln Cys
                85                  90                  95

Asp Phe Lys Glu Lys Gly Arg Val Lys Gln Cys Val Gly Thr Val Thr
```

```
                    100                 105                 110
Leu Asp Pro Ser Asn Asp Gln Phe Asp Leu Asn Cys Asn Glu Leu Gln
            115                 120                 125

Ser Val Ile Leu Pro Trp Lys Trp Pro Trp Trp Pro Trp Arg Arg Gly
            130                 135                 140

<210> SEQ ID NO 56
<211> LENGTH: 149
<212> TYPE: PRT
<213> ORGANISM: Sus scrofa

<400> SEQUENCE: 56

Met Glu Thr Gln Arg Ala Ser Leu Cys Leu Gly Arg Trp Ser Leu Trp
1               5                   10                  15

Leu Leu Leu Leu Ala Leu Val Val Pro Ser Ala Ser Ala Gln Ala Leu
            20                  25                  30

Ser Tyr Arg Glu Ala Val Leu Arg Ala Val Asp Arg Leu Asn Glu Gln
            35                  40                  45

Ser Ser Glu Ala Asn Leu Tyr Arg Leu Leu Glu Leu Asp Gln Pro Pro
50                  55                  60

Lys Ala Asp Glu Asp Pro Gly Thr Pro Lys Pro Val Ser Phe Thr Val
65                  70                  75                  80

Lys Glu Thr Val Cys Pro Arg Pro Thr Arg Gln Pro Pro Glu Leu Cys
                85                  90                  95

Asp Phe Lys Glu Asn Gly Arg Val Lys Gln Cys Val Gly Thr Val Thr
            100                 105                 110

Leu Asp Gln Ile Lys Asp Pro Leu Asp Ile Thr Cys Asn Glu Val Gln
            115                 120                 125

Gly Val Arg Gly Gly Arg Leu Cys Tyr Cys Arg Arg Arg Phe Cys Val
            130                 135                 140

Cys Val Gly Arg Gly
145

<210> SEQ ID NO 57
<211> LENGTH: 17
<212> TYPE: PRT
<213> ORGANISM: Tachypleus gigas

<400> SEQUENCE: 57

Lys Trp Cys Phe Arg Val Cys Tyr Arg Gly Ile Cys Tyr Arg Arg Cys
1               5                   10                  15

Arg

<210> SEQ ID NO 58
<211> LENGTH: 102
<212> TYPE: PRT
<213> ORGANISM: Anopheles gambiae

<400> SEQUENCE: 58

Met Lys Cys Ala Thr Ile Val Cys Thr Ile Ala Val Val Leu Ala Ala
1               5                   10                  15

Thr Leu Leu Asn Gly Ser Val Gln Ala Ala Pro Gln Glu Glu Ala Ala
            20                  25                  30

Leu Ser Gly Gly Ala Asn Leu Asn Thr Leu Asp Glu Leu Pro Glu
            35                  40                  45

Glu Thr His His Ala Ala Leu Glu Asn Tyr Arg Ala Lys Arg Ala Thr
50                  55                  60
```

Cys Asp Leu Ala Ser Gly Phe Gly Val Gly Ser Leu Cys Ala Ala
65                  70                  75                  80

His Cys Ile Ala Arg Arg Tyr Arg Gly Gly Tyr Cys Asn Ser Lys Ala
                85                  90                  95

Val Cys Val Cys Arg Asn
            100

<210> SEQ ID NO 59
<211> LENGTH: 70
<212> TYPE: PRT
<213> ORGANISM: Drosophila melanogaster

<400> SEQUENCE: 59

Met Met Gln Ile Lys Tyr Leu Phe Ala Leu Phe Ala Val Leu Met Leu
1               5                   10                  15

Val Val Leu Gly Ala Asn Glu Ala Asp Ala Asp Cys Leu Ser Gly Arg
                20                  25                  30

Tyr Lys Gly Pro Cys Ala Val Trp Asp Asn Glu Thr Cys Arg Arg Val
            35                  40                  45

Cys Lys Glu Glu Gly Arg Ser Ser Gly His Cys Ser Pro Ser Leu Lys
        50                  55                  60

Cys Trp Cys Glu Gly Cys
65                  70

<210> SEQ ID NO 60
<211> LENGTH: 63
<212> TYPE: PRT
<213> ORGANISM: Medicago truncatula

<400> SEQUENCE: 60

Met Thr Lys Ile Val Val Phe Ile Tyr Val Val Ile Leu Leu Leu Thr
1               5                   10                  15

Ile Phe His Val Ser Ala Lys Lys Arg Tyr Ile Glu Cys Glu Thr
                20                  25                  30

His Glu Asp Cys Ser Gln Val Phe Met Pro Pro Phe Val Met Arg Cys
            35                  40                  45

Val Ile His Glu Cys Lys Ile Phe Asn Gly His Leu Arg Tyr
        50                  55                  60

<210> SEQ ID NO 61
<211> LENGTH: 76
<212> TYPE: PRT
<213> ORGANISM: Medicago truncatula

<400> SEQUENCE: 61

Met Ala Lys Ile Met Lys Phe Val Tyr Asn Met Ile Pro Phe Leu Ser
1               5                   10                  15

Ile Phe Ile Ile Thr Leu Gln Val Asn Val Val Cys Glu Ile Asp
                20                  25                  30

Ala Asp Cys Pro Gln Ile Cys Met Pro Pro Tyr Glu Val Arg Cys Val
            35                  40                  45

Asn His Arg Cys Gly Trp Val Asn Thr Asp Asp Ser Leu Phe Leu Thr
        50                  55                  60

Gln Glu Phe Thr Arg Ser Lys Gln Tyr Ile Ile Ser
65                  70                  75

<210> SEQ ID NO 62
<211> LENGTH: 76
<212> TYPE: PRT

<213> ORGANISM: Medicago truncatula

<400> SEQUENCE: 62

Met Tyr Lys Val Val Glu Ser Ile Phe Ile Arg Tyr Met His Arg Lys
1               5                   10                  15

Pro Asn Met Thr Lys Phe Phe Lys Phe Val Tyr Thr Met Phe Ile Leu
            20                  25                  30

Ile Ser Leu Phe Leu Val Val Thr Asn Ala Asn Ala His Asn Cys Thr
        35                  40                  45

Asp Ile Ser Asp Cys Ser Ser Asn His Cys Ser Tyr Glu Gly Val Ser
    50                  55                  60

Leu Cys Met Asn Gly Gln Cys Ile Cys Ile Tyr Glu
65                  70                  75

<210> SEQ ID NO 63
<211> LENGTH: 64
<212> TYPE: PRT
<213> ORGANISM: Medicago truncatula

<400> SEQUENCE: 63

Met Val Glu Thr Leu Arg Leu Phe Tyr Ile Met Ile Leu Phe Val Ser
1               5                   10                  15

Leu Cys Leu Val Val Asp Gly Glu Ser Lys Leu Glu Gln Thr Cys
            20                  25                  30

Ser Glu Asp Phe Glu Cys Tyr Ile Lys Asn Pro His Val Pro Phe Gly
        35                  40                  45

His Leu Arg Cys Phe Gly Phe Cys Gln Gln Leu Asn Gly Pro Ala
    50                  55                  60

<210> SEQ ID NO 64
<211> LENGTH: 67
<212> TYPE: PRT
<213> ORGANISM: Medicago truncatula

<400> SEQUENCE: 64

Met Ala Lys Ile Val Asn Phe Val Tyr Ser Met Ile Val Phe Leu Phe
1               5                   10                  15

Leu Phe Leu Val Ala Thr Lys Ala Ala Arg Gly Tyr Leu Cys Val Thr
            20                  25                  30

Asp Ser His Cys Pro Pro His Met Cys Pro Gly Met Glu Pro Arg
        35                  40                  45

Cys Val Arg Arg Met Cys Lys Cys Leu Pro Ile Gly Trp Arg Lys Tyr
    50                  55                  60

Phe Val Pro
65

<210> SEQ ID NO 65
<211> LENGTH: 96
<212> TYPE: PRT
<213> ORGANISM: Medicago truncatula

<400> SEQUENCE: 65

Met Gln Ile Gly Lys Asn Met Val Glu Thr Pro Lys Leu Asp Tyr Val
1               5                   10                  15

Ile Ile Phe Phe Phe Leu Tyr Phe Phe Arg Gln Met Ile Ile Leu
            20                  25                  30

Arg Leu Asn Thr Thr Phe Arg Pro Leu Asn Phe Lys Met Leu Arg Phe
        35                  40                  45

Trp Gly Gln Asn Arg Asn Ile Met Lys His Arg Gly Gln Lys Val His
    50                  55                  60

Phe Ser Leu Ile Leu Ser Asp Cys Lys Thr Asn Lys Asp Cys Pro Lys
65                  70                  75                  80

Leu Arg Arg Ala Asn Val Arg Cys Arg Lys Ser Tyr Cys Val Pro Ile
                85                  90                  95

<210> SEQ ID NO 66
<211> LENGTH: 65
<212> TYPE: PRT
<213> ORGANISM: Medicago truncatula

<400> SEQUENCE: 66

Met Leu Arg Leu Tyr Leu Val Ser Tyr Phe Leu Leu Lys Arg Thr Leu
1               5                   10                  15

Leu Val Ser Tyr Phe Ser Tyr Phe Ser Thr Tyr Ile Ile Glu Cys Lys
                20                  25                  30

Thr Asp Asn Asp Cys Pro Ile Ser Gln Leu Lys Ile Tyr Ala Trp Lys
            35                  40                  45

Cys Val Lys Asn Gly Cys His Leu Phe Asp Val Ile Pro Met Met Tyr
    50                  55                  60

Glu
65

<210> SEQ ID NO 67
<211> LENGTH: 79
<212> TYPE: PRT
<213> ORGANISM: Medicago truncatula

<400> SEQUENCE: 67

Met Ala Glu Ile Leu Lys Phe Val Tyr Ile Val Ile Leu Phe Val Ser
1               5                   10                  15

Leu Leu Leu Ile Val Val Ala Ser Glu Arg Glu Cys Val Thr Asp Asp
                20                  25                  30

Asp Cys Glu Lys Leu Tyr Pro Thr Asn Glu Tyr Arg Met Met Cys Asp
            35                  40                  45

Ser Gly Tyr Cys Met Asn Leu Leu Asn Gly Lys Ile Ile Tyr Leu Leu
    50                  55                  60

Cys Leu Lys Lys Lys Lys Phe Leu Ile Ile Ser Val Leu Leu
65                  70                  75

<210> SEQ ID NO 68
<211> LENGTH: 95
<212> TYPE: PRT
<213> ORGANISM: Medicago truncatula

<400> SEQUENCE: 68

Met Ala Glu Ile Ile Lys Phe Val Tyr Ile Met Ile Leu Cys Val Ser
1               5                   10                  15

Leu Leu Leu Ile Glu Val Ala Gly Glu Glu Cys Val Thr Asp Ala Asp
                20                  25                  30

Cys Asp Lys Leu Tyr Pro Asp Ile Arg Lys Pro Leu Met Cys Ser Ile
            35                  40                  45

Gly Glu Cys Tyr Ser Leu Tyr Lys Gly Lys Phe Ser Leu Ser Ile Ile
    50                  55                  60

Ser Lys Thr Ser Phe Ser Leu Met Val Tyr Asn Val Val Thr Leu Val
65                  70                  75                  80

Ile Cys Leu Arg Leu Ala Tyr Ile Ser Leu Leu Leu Lys Phe Leu

<210> SEQ ID NO 69
<211> LENGTH: 100
<212> TYPE: PRT
<213> ORGANISM: Medicago truncatula

<400> SEQUENCE: 69

Met Ala Glu Ile Leu Lys Asp Phe Tyr Ala Met Asn Leu Phe Ile Phe
1               5                   10                  15
Leu Ile Ile Leu Pro Ala Lys Ile Arg Gly Glu Thr Leu Ser Leu Thr
            20                  25                  30
His Pro Lys Cys His His Ile Met Leu Pro Ser Leu Phe Ile Thr Glu
        35                  40                  45
Val Phe Gln Arg Val Thr Asp Asp Gly Cys Pro Lys Pro Val Asn His
    50                  55                  60
Leu Arg Val Val Lys Cys Ile Glu His Ile Cys Glu Tyr Gly Tyr Asn
65                  70                  75                  80
Tyr Arg Pro Asp Phe Ala Ser Gln Ile Pro Glu Ser Thr Lys Met Pro
                85                  90                  95
Arg Lys Arg Glu
            100

<210> SEQ ID NO 70
<211> LENGTH: 78
<212> TYPE: PRT
<213> ORGANISM: Medicago truncatula

<400> SEQUENCE: 70

Met Val Glu Ile Leu Lys Asn Phe Tyr Ala Met Asn Leu Phe Ile Phe
1               5                   10                  15
Leu Ile Ile Leu Ala Val Lys Ile Arg Gly Ala His Phe Pro Cys Val
            20                  25                  30
Thr Asp Asp Cys Pro Lys Pro Val Asn Lys Leu Arg Val Ile Lys
        35                  40                  45
Cys Ile Asp His Ile Cys Gln Tyr Ala Arg Asn Leu Pro Asp Phe Ala
    50                  55                  60
Ser Glu Ile Ser Glu Ser Thr Lys Met Pro Cys Lys Gly Glu
65                  70                  75

<210> SEQ ID NO 71
<211> LENGTH: 72
<212> TYPE: PRT
<213> ORGANISM: Medicago truncatula

<400> SEQUENCE: 71

Met Phe His Ala Gln Ala Glu Asn Met Ala Lys Val Ser Asn Phe Val
1               5                   10                  15
Cys Ile Met Ile Leu Phe Leu Ala Leu Phe Phe Ile Thr Met Asn Asp
            20                  25                  30
Ala Ala Arg Phe Glu Cys Arg Glu Asp Ser His Cys Val Thr Arg Ile
        35                  40                  45
Lys Cys Val Leu Pro Arg Lys Pro Glu Cys Arg Asn Tyr Ala Cys Gly
    50                  55                  60
Cys Tyr Asp Ser Asn Lys Tyr Arg
65                  70

<210> SEQ ID NO 72

```
<211> LENGTH: 78
<212> TYPE: PRT
<213> ORGANISM: Medicago truncatula

<400> SEQUENCE: 72

Met Gln Met Arg Gln Asn Met Ala Thr Ile Leu Asn Phe Val Phe Val
1               5                   10                  15

Ile Ile Leu Phe Ile Ser Leu Leu Val Val Thr Lys Gly Tyr Arg
            20                  25                  30

Glu Pro Phe Ser Ser Phe Thr Glu Gly Pro Thr Cys Lys Glu Asp Ile
            35                  40                  45

Asp Cys Pro Ser Ile Ser Cys Val Asn Pro Gln Val Pro Lys Cys Ile
50                  55                  60

Met Phe Glu Cys His Cys Lys Tyr Ile Pro Thr Thr Leu Lys
65                  70                  75

<210> SEQ ID NO 73
<211> LENGTH: 71
<212> TYPE: PRT
<213> ORGANISM: Medicago truncatula

<400> SEQUENCE: 73

Met Ala Thr Ile Leu Met Tyr Val Tyr Ile Thr Ile Leu Phe Ile Ser
1               5                   10                  15

Ile Leu Thr Val Leu Thr Glu Gly Leu Tyr Glu Pro Leu Tyr Asn Phe
            20                  25                  30

Arg Arg Asp Pro Asp Cys Arg Arg Asn Ile Asp Cys Pro Ser Tyr Leu
            35                  40                  45

Cys Val Ala Pro Lys Val Pro Arg Cys Ile Met Phe Glu Cys His Cys
50                  55                  60

Lys Asp Ile Pro Ser Asp His
65                  70

<210> SEQ ID NO 74
<211> LENGTH: 57
<212> TYPE: PRT
<213> ORGANISM: Medicago truncatula

<400> SEQUENCE: 74

Met Thr Thr Ser Leu Lys Phe Val Tyr Val Ala Ile Leu Phe Leu Ser
1               5                   10                  15

Leu Leu Leu Val Val Met Gly Gly Ile Arg Arg Phe Glu Cys Arg Gln
            20                  25                  30

Asp Ser Asp Cys Pro Ser Tyr Phe Cys Glu Lys Leu Thr Val Pro Lys
            35                  40                  45

Cys Phe Trp Ser Lys Cys Tyr Cys Lys
50                  55

<210> SEQ ID NO 75
<211> LENGTH: 57
<212> TYPE: PRT
<213> ORGANISM: Medicago truncatula

<400> SEQUENCE: 75

Met Thr Thr Ser Leu Lys Phe Val Tyr Val Ala Ile Leu Phe Leu Ser
1               5                   10                  15

Leu Leu Leu Val Val Met Gly Gly Ile Arg Lys Lys Glu Cys Arg Gln
            20                  25                  30

Asp Ser Asp Cys Pro Ser Tyr Phe Cys Glu Lys Leu Thr Ile Ala Lys
```

```
                35                  40                  45

Cys Ile His Ser Thr Cys Leu Cys Lys
    50                  55

<210> SEQ ID NO 76
<211> LENGTH: 66
<212> TYPE: PRT
<213> ORGANISM: Medicago truncatula

<400> SEQUENCE: 76

Met Gln Ile Gly Lys Asn Met Val Glu Thr Pro Lys Leu Val Tyr Phe
1               5                   10                  15

Ile Ile Leu Phe Leu Ser Ile Phe Leu Cys Ile Thr Val Ser Asn Ser
                20                  25                  30

Ser Phe Ser Gln Ile Phe Asn Ser Ala Cys Lys Thr Asp Lys Asp Cys
            35                  40                  45

Pro Lys Phe Gly Arg Val Asn Val Arg Cys Arg Lys Gly Asn Cys Val
    50                  55                  60

Pro Ile
65

<210> SEQ ID NO 77
<211> LENGTH: 57
<212> TYPE: PRT
<213> ORGANISM: Medicago truncatula

<400> SEQUENCE: 77

Met Thr Ala Ile Leu Lys Lys Phe Ile Asn Ala Val Phe Leu Phe Ile
1               5                   10                  15

Val Leu Phe Leu Ala Thr Thr Asn Val Glu Asp Phe Val Gly Gly Ser
                20                  25                  30

Asn Asp Glu Cys Val Tyr Pro Asp Val Phe Gln Cys Ile Asn Asn Ile
            35                  40                  45

Cys Lys Cys Val Ser His His Arg Thr
    50                  55

<210> SEQ ID NO 78
<211> LENGTH: 74
<212> TYPE: PRT
<213> ORGANISM: Medicago truncatula

<400> SEQUENCE: 78

Met Gln Lys Arg Lys Asn Met Ala Gln Ile Ile Phe Tyr Val Tyr Ala
1               5                   10                  15

Leu Ile Ile Leu Phe Ser Pro Phe Leu Ala Ala Arg Leu Val Phe Val
                20                  25                  30

Asn Pro Glu Lys Pro Cys Val Thr Asp Ala Asp Cys Asp Arg Tyr Arg
            35                  40                  45

His Glu Ser Ala Ile Tyr Ser Asp Met Phe Cys Lys Asp Gly Tyr Cys
    50                  55                  60

Phe Ile Asp Tyr His His Asp Pro Tyr Pro
65                  70

<210> SEQ ID NO 79
<211> LENGTH: 76
<212> TYPE: PRT
<213> ORGANISM: Medicago truncatula

<400> SEQUENCE: 79
```

Met Gln Met Arg Lys Asn Met Ala Gln Ile Leu Phe Tyr Val Tyr Ala
1               5                   10                  15

Leu Leu Ile Leu Phe Thr Pro Phe Leu Val Ala Arg Ile Met Val Val
            20                  25                  30

Asn Pro Asn Asn Pro Cys Val Thr Asp Ala Asp Cys Gln Arg Tyr Arg
        35                  40                  45

His Lys Leu Ala Thr Arg Met Ile Cys Asn Gln Gly Phe Cys Leu Met
    50                  55                  60

Asp Phe Thr His Asp Pro Tyr Ala Pro Ser Leu Pro
65                  70                  75

<210> SEQ ID NO 80
<211> LENGTH: 64
<212> TYPE: PRT
<213> ORGANISM: Medicago truncatula

<400> SEQUENCE: 80

Met Asn His Ile Ser Lys Phe Val Tyr Ala Leu Ile Ile Phe Leu Ser
1               5                   10                  15

Ile Tyr Leu Val Val Leu Asp Gly Leu Pro Ile Ser Cys Lys Asp His
            20                  25                  30

Phe Glu Cys Arg Arg Lys Ile Asn Ile Leu Arg Cys Ile Tyr Arg Gln
        35                  40                  45

Glu Lys Pro Met Cys Ile Asn Ser Ile Cys Thr Cys Val Lys Leu Leu
    50                  55                  60

<210> SEQ ID NO 81
<211> LENGTH: 67
<212> TYPE: PRT
<213> ORGANISM: Medicago truncatula

<400> SEQUENCE: 81

Met Gln Arg Glu Lys Asn Met Ala Lys Ile Phe Glu Phe Val Tyr Ala
1               5                   10                  15

Met Ile Ile Phe Ile Leu Leu Phe Leu Val Glu Lys Asn Val Val Ala
            20                  25                  30

Tyr Leu Lys Phe Glu Cys Lys Thr Asp Asp Cys Gln Lys Ser Leu
        35                  40                  45

Leu Lys Thr Tyr Val Trp Lys Cys Val Lys Asn Glu Cys Tyr Phe Phe
    50                  55                  60

Ala Lys Lys
65

<210> SEQ ID NO 82
<211> LENGTH: 61
<212> TYPE: PRT
<213> ORGANISM: Medicago truncatula

<400> SEQUENCE: 82

Met Ala Gly Ile Ile Lys Phe Val His Val Leu Ile Ile Phe Leu Ser
1               5                   10                  15

Leu Phe His Val Val Lys Asn Asp Asp Gly Ser Phe Cys Phe Lys Asp
            20                  25                  30

Ser Asp Cys Pro Asp Glu Met Cys Pro Ser Pro Leu Lys Glu Met Cys
        35                  40                  45

Tyr Phe Leu Gln Cys Lys Cys Gly Val Asp Thr Ile Ala
    50                  55                  60

-continued

```
<210> SEQ ID NO 83
<211> LENGTH: 59
<212> TYPE: PRT
<213> ORGANISM: Medicago truncatula

<400> SEQUENCE: 83

Met Ala Asn Thr His Lys Leu Val Ser Met Ile Leu Phe Ile Phe Leu
1               5                   10                  15

Phe Leu Ala Ser Asn Asn Val Glu Gly Tyr Val Asn Cys Glu Thr Asp
            20                  25                  30

Ala Asp Cys Pro Pro Ser Thr Arg Val Lys Arg Phe Lys Cys Val Lys
        35                  40                  45

Gly Glu Cys Arg Trp Thr Arg Met Ser Tyr Ala
    50                  55

<210> SEQ ID NO 84
<211> LENGTH: 63
<212> TYPE: PRT
<213> ORGANISM: Medicago truncatula

<400> SEQUENCE: 84

Met Gln Arg Arg Lys Lys Lys Ala Gln Val Val Met Phe Val His Asp
1               5                   10                  15

Leu Ile Ile Cys Ile Tyr Leu Phe Ile Val Ile Thr Thr Arg Lys Thr
            20                  25                  30

Asp Ile Arg Cys Arg Phe Tyr Tyr Asp Cys Pro Arg Leu Glu Tyr His
        35                  40                  45

Phe Cys Glu Cys Ile Glu Asp Phe Cys Ala Tyr Ile Arg Leu Asn
    50                  55                  60

<210> SEQ ID NO 85
<211> LENGTH: 57
<212> TYPE: PRT
<213> ORGANISM: Medicago truncatula

<400> SEQUENCE: 85

Met Ala Lys Val Tyr Met Phe Val Tyr Ala Leu Ile Ile Phe Val Ser
1               5                   10                  15

Pro Phe Leu Leu Ala Thr Phe Arg Thr Arg Leu Pro Cys Glu Lys Asp
            20                  25                  30

Asp Asp Cys Pro Glu Ala Phe Leu Pro Pro Val Met Lys Cys Val Asn
        35                  40                  45

Arg Phe Cys Gln Tyr Glu Ile Leu Glu
    50                  55

<210> SEQ ID NO 86
<211> LENGTH: 77
<212> TYPE: PRT
<213> ORGANISM: Medicago truncatula

<400> SEQUENCE: 86

Met Ile Lys Gln Phe Ser Val Cys Tyr Ile Gln Met Arg Arg Asn Met
1               5                   10                  15

Thr Thr Ile Leu Lys Phe Pro Tyr Ile Met Val Ile Cys Leu Leu Leu
            20                  25                  30

Leu His Val Ala Ala Tyr Glu Asp Phe Glu Lys Glu Ile Phe Asp Cys
        35                  40                  45

Lys Lys Asp Gly Asp Cys Asp His Met Cys Val Thr Pro Gly Ile Pro
    50                  55                  60
```

```
Lys Cys Thr Gly Tyr Val Cys Phe Cys Phe Glu Asn Leu
 65                  70                  75
```

<210> SEQ ID NO 87
<211> LENGTH: 73
<212> TYPE: PRT
<213> ORGANISM: Medicago truncatula

<400> SEQUENCE: 87

```
Met Gln Arg Ser Arg Asn Met Thr Thr Ile Phe Lys Phe Ala Tyr Ile
 1               5                  10                  15

Met Ile Ile Cys Val Phe Leu Leu Asn Ile Ala Ala Gln Glu Ile Glu
            20                  25                  30

Asn Gly Ile His Pro Cys Lys Lys Asn Glu Asp Cys Asn His Met Cys
        35                  40                  45

Val Met Pro Gly Leu Pro Trp Cys His Glu Asn Asn Leu Cys Phe Cys
    50                  55                  60

Tyr Glu Asn Ala Tyr Gly Asn Thr Arg
 65                  70
```

<210> SEQ ID NO 88
<211> LENGTH: 85
<212> TYPE: PRT
<213> ORGANISM: Medicago truncatula

<400> SEQUENCE: 88

```
Met Thr Ile Ile Ile Lys Phe Val Asn Val Leu Ile Ile Phe Leu Ser
 1               5                  10                  15

Leu Phe His Val Ala Lys Asn Asp Asp Asn Lys Leu Leu Leu Ser Phe
            20                  25                  30

Ile Glu Glu Gly Phe Leu Cys Phe Lys Asp Ser Asp Cys Pro Tyr Asn
        35                  40                  45

Met Cys Pro Ser Pro Leu Lys Glu Met Cys Tyr Phe Ile Lys Cys Val
    50                  55                  60

Cys Gly Val Tyr Gly Pro Ile Arg Glu Arg Arg Leu Tyr Gln Ser His
 65                  70                  75                  80

Asn Pro Met Ile Gln
            85
```

<210> SEQ ID NO 89
<211> LENGTH: 69
<212> TYPE: PRT
<213> ORGANISM: Medicago truncatula

<400> SEQUENCE: 89

```
Met Arg Lys Asn Met Thr Lys Ile Leu Met Ile Gly Tyr Ala Leu Met
 1               5                  10                  15

Ile Phe Ile Phe Leu Ser Ile Ala Val Ser Ile Thr Gly Asn Leu Ala
            20                  25                  30

Arg Ala Ser Arg Lys Lys Pro Val Asp Val Ile Pro Cys Ile Tyr Asp
        35                  40                  45

His Asp Cys Pro Arg Lys Leu Tyr Phe Leu Glu Arg Cys Val Gly Arg
    50                  55                  60

Val Cys Lys Tyr Leu
 65
```

<210> SEQ ID NO 90
<211> LENGTH: 58
<212> TYPE: PRT

<213> ORGANISM: Medicago truncatula

<400> SEQUENCE: 90

Met Ala His Lys Leu Val Tyr Ala Ile Thr Leu Phe Ile Phe Leu Phe
1               5                   10                  15

Leu Ile Ala Asn Asn Ile Glu Asp Asp Ile Phe Cys Ile Thr Asp Asn
            20                  25                  30

Asp Cys Pro Pro Asn Thr Leu Val Gln Arg Tyr Arg Cys Ile Asn Gly
        35                  40                  45

Lys Cys Asn Leu Ser Phe Val Ser Tyr Gly
    50                  55

<210> SEQ ID NO 91
<211> LENGTH: 61
<212> TYPE: PRT
<213> ORGANISM: Medicago truncatula

<400> SEQUENCE: 91

Met Asp Glu Thr Leu Lys Phe Val Tyr Ile Leu Ile Leu Phe Val Ser
1               5                   10                  15

Leu Cys Leu Val Val Ala Asp Gly Val Lys Asn Ile Asn Arg Glu Cys
            20                  25                  30

Thr Gln Thr Ser Asp Cys Tyr Lys Lys Tyr Pro Phe Ile Pro Trp Gly
        35                  40                  45

Lys Val Arg Cys Val Lys Gly Arg Cys Arg Leu Asp Met
    50                  55                  60

<210> SEQ ID NO 92
<211> LENGTH: 62
<212> TYPE: PRT
<213> ORGANISM: Medicago truncatula

<400> SEQUENCE: 92

Met Ala Lys Ile Ile Lys Phe Val Tyr Val Leu Ala Ile Phe Phe Ser
1               5                   10                  15

Leu Phe Leu Val Ala Lys Asn Val Asn Gly Trp Thr Cys Val Glu Asp
            20                  25                  30

Ser Asp Cys Pro Ala Asn Ile Cys Gln Pro Pro Met Gln Arg Met Cys
        35                  40                  45

Phe Tyr Gly Glu Cys Ala Cys Val Arg Ser Lys Phe Cys Thr
    50                  55                  60

<210> SEQ ID NO 93
<211> LENGTH: 61
<212> TYPE: PRT
<213> ORGANISM: Medicago truncatula

<400> SEQUENCE: 93

Met Val Lys Ile Ile Lys Phe Val Tyr Phe Met Thr Leu Phe Leu Ser
1               5                   10                  15

Met Leu Leu Val Thr Thr Lys Glu Asp Gly Ser Val Glu Cys Ile Ala
            20                  25                  30

Asn Ile Asp Cys Pro Gln Ile Phe Met Leu Pro Phe Val Met Arg Cys
        35                  40                  45

Ile Asn Phe Arg Cys Gln Ile Val Asn Ser Glu Asp Thr
    50                  55                  60

<210> SEQ ID NO 94
<211> LENGTH: 67

```
<212> TYPE: PRT
<213> ORGANISM: Medicago truncatula

<400> SEQUENCE: 94

Met Asp Glu Ile Leu Lys Phe Val Tyr Thr Leu Ile Ile Phe Phe Ser
1               5                   10                  15

Leu Phe Phe Ala Ala Asn Asn Val Asp Ala Asn Ile Met Asn Cys Gln
            20                  25                  30

Ser Thr Phe Asp Cys Pro Arg Asp Met Cys Ser His Ile Arg Asp Val
        35                  40                  45

Ile Cys Ile Phe Lys Lys Cys Lys Cys Ala Gly Gly Arg Tyr Met Pro
    50                  55                  60

Gln Val Pro
65

<210> SEQ ID NO 95
<211> LENGTH: 62
<212> TYPE: PRT
<213> ORGANISM: Medicago truncatula

<400> SEQUENCE: 95

Met Gln Arg Arg Lys Asn Met Ala Asn Asn His Met Leu Ile Tyr Ala
1               5                   10                  15

Met Ile Ile Cys Leu Phe Pro Tyr Leu Val Val Thr Phe Lys Thr Ala
            20                  25                  30

Ile Thr Cys Asp Cys Asn Glu Asp Cys Leu Asn Phe Phe Thr Pro Leu
        35                  40                  45

Asp Asn Leu Lys Cys Ile Asp Asn Val Cys Glu Val Phe Met
    50                  55                  60

<210> SEQ ID NO 96
<211> LENGTH: 65
<212> TYPE: PRT
<213> ORGANISM: Medicago truncatula

<400> SEQUENCE: 96

Met Val Asn Ile Leu Lys Phe Ile Tyr Val Ile Ile Phe Phe Ile Leu
1               5                   10                  15

Met Phe Phe Val Leu Ile Asp Val Asp Gly His Val Leu Val Glu Cys
            20                  25                  30

Ile Glu Asn Arg Asp Cys Glu Lys Gly Met Cys Lys Phe Pro Phe Ile
        35                  40                  45

Val Arg Cys Leu Met Asp Gln Cys Lys Cys Val Arg Ile His Asn Leu
    50                  55                  60

Ile
65

<210> SEQ ID NO 97
<211> LENGTH: 74
<212> TYPE: PRT
<213> ORGANISM: Medicago truncatula

<400> SEQUENCE: 97

Met Ile Ile Gln Phe Ser Ile Tyr Met Gln Arg Arg Lys Leu Asn
1               5                   10                  15

Met Val Glu Ile Leu Lys Phe Ser His Ala Leu Ile Ile Phe Leu Phe
            20                  25                  30

Leu Ser Ala Leu Val Thr Asn Ala Asn Ile Phe Phe Cys Ser Thr Asp
        35                  40                  45
```

```
Glu Asp Cys Thr Trp Asn Leu Cys Arg Gln Pro Trp Val Gln Lys Cys
 50                  55                  60

Arg Leu His Met Cys Ser Cys Glu Lys Asn
 65                  70
```

<210> SEQ ID NO 98
<211> LENGTH: 58
<212> TYPE: PRT
<213> ORGANISM: Medicago truncatula

<400> SEQUENCE: 98

```
Met Asp Glu Val Phe Lys Phe Val Tyr Val Met Ile Ile Phe Pro Phe
 1               5                  10                  15

Leu Ile Leu Asp Val Ala Thr Asn Ala Glu Lys Ile Arg Arg Cys Phe
            20                  25                  30

Asn Asp Ala His Cys Pro Pro Asp Met Cys Thr Leu Gly Val Ile Pro
        35                  40                  45

Lys Cys Ser Arg Phe Thr Ile Cys Ile Cys
 50                  55
```

<210> SEQ ID NO 99
<211> LENGTH: 64
<212> TYPE: PRT
<213> ORGANISM: Medicago truncatula

<400> SEQUENCE: 99

```
Met His Arg Lys Pro Asn Met Thr Lys Phe Phe Lys Phe Val Tyr Thr
 1               5                  10                  15

Met Phe Ile Leu Ile Ser Leu Phe Leu Val Val Thr Asn Ala Asn Ala
            20                  25                  30

Asn Asn Cys Thr Asp Thr Ser Asp Cys Ser Ser Asn His Cys Ser Tyr
        35                  40                  45

Glu Gly Val Ser Leu Cys Met Asn Gly Gln Cys Ile Cys Ile Tyr Glu
 50                  55                  60
```

<210> SEQ ID NO 100
<211> LENGTH: 69
<212> TYPE: PRT
<213> ORGANISM: Medicago truncatula

<400> SEQUENCE: 100

```
Met Gln Met Lys Lys Met Ala Thr Ile Leu Lys Phe Val Tyr Leu Ile
 1               5                  10                  15

Ile Leu Leu Ile Tyr Pro Leu Leu Val Val Thr Glu Glu Ser His Tyr
            20                  25                  30

Met Lys Phe Ser Ile Cys Lys Asp Asp Thr Asp Cys Pro Thr Leu Phe
        35                  40                  45

Cys Val Leu Pro Asn Val Pro Lys Cys Ile Gly Ser Lys Cys His Cys
 50                  55                  60

Lys Leu Met Val Asn
 65
```

<210> SEQ ID NO 101
<211> LENGTH: 64
<212> TYPE: PRT
<213> ORGANISM: Medicago truncatula

<400> SEQUENCE: 101

```
Met Val Glu Thr Leu Arg Leu Phe Tyr Ile Met Ile Leu Phe Val Ser
```

```
1               5                   10                  15
Leu Tyr Leu Val Val Asp Gly Val Ser Lys Leu Ala Gln Ser Cys
                20                  25                  30

Ser Glu Asp Phe Glu Cys Tyr Ile Lys Asn Pro His Ala Pro Phe Gly
        35                  40                  45

Gln Leu Arg Cys Phe Glu Gly Tyr Cys Gln Arg Leu Asp Lys Pro Thr
    50                  55                  60
```

<210> SEQ ID NO 102
<211> LENGTH: 63
<212> TYPE: PRT
<213> ORGANISM: Medicago truncatula

<400> SEQUENCE: 102

```
Met Thr Thr Phe Leu Lys Val Ala Tyr Ile Met Ile Cys Val Phe
1               5                   10                  15

Val Leu His Leu Ala Ala Gln Val Asp Ser Gln Lys Arg Leu His Gly
                20                  25                  30

Cys Lys Glu Asp Arg Asp Cys Asp Asn Ile Cys Ser Val His Ala Val
        35                  40                  45

Thr Lys Cys Ile Gly Asn Met Cys Arg Cys Leu Ala Asn Val Lys
    50                  55                  60
```

<210> SEQ ID NO 103
<211> LENGTH: 61
<212> TYPE: PRT
<213> ORGANISM: Medicago truncatula

<400> SEQUENCE: 103

```
Met Arg Ile Asn Arg Thr Pro Ala Ile Phe Lys Phe Val Tyr Thr Ile
1               5                   10                  15

Ile Ile Tyr Leu Phe Leu Leu Arg Val Val Ala Lys Asp Leu Pro Phe
                20                  25                  30

Asn Ile Cys Glu Lys Asp Glu Asp Cys Leu Glu Phe Cys Ala His Asp
        35                  40                  45

Lys Val Ala Lys Cys Met Leu Asn Ile Cys Phe Cys Phe
    50                  55                  60
```

<210> SEQ ID NO 104
<211> LENGTH: 54
<212> TYPE: PRT
<213> ORGANISM: Medicago truncatula

<400> SEQUENCE: 104

```
Met Ala Glu Ile Leu Lys Ile Leu Tyr Val Phe Ile Ile Phe Leu Ser
1               5                   10                  15

Leu Ile Leu Ala Val Ile Ser Gln His Pro Phe Thr Pro Cys Glu Thr
                20                  25                  30

Asn Ala Asp Cys Lys Cys Arg Asn His Lys Arg Pro Asp Cys Leu Trp
        35                  40                  45

His Lys Cys Tyr Cys Tyr
    50
```

<210> SEQ ID NO 105
<211> LENGTH: 65
<212> TYPE: PRT
<213> ORGANISM: Medicago truncatula

<400> SEQUENCE: 105

Met Arg Lys Ser Met Ala Thr Ile Leu Lys Phe Val Tyr Val Ile Met
1               5                   10                  15

Leu Phe Ile Tyr Ser Leu Phe Val Ile Glu Ser Phe Gly His Arg Phe
            20                  25                  30

Leu Ile Tyr Asn Asn Cys Lys Asn Asp Thr Glu Cys Pro Asn Asp Cys
            35                  40                  45

Gly Pro His Glu Gln Ala Lys Cys Ile Leu Tyr Ala Cys Tyr Cys Val
        50                  55                  60

Glu
65

<210> SEQ ID NO 106
<211> LENGTH: 58
<212> TYPE: PRT
<213> ORGANISM: Medicago truncatula

<400> SEQUENCE: 106

Met Asn Thr Ile Leu Lys Phe Ile Phe Val Val Phe Leu Phe Leu Ser
1               5                   10                  15

Ile Phe Leu Ser Ala Gly Asn Ser Lys Ser Tyr Gly Pro Cys Thr Thr
            20                  25                  30

Leu Gln Asp Cys Glu Thr His Asn Trp Phe Glu Val Cys Ser Cys Ile
            35                  40                  45

Asp Phe Glu Cys Lys Cys Trp Ser Leu Leu
        50                  55

<210> SEQ ID NO 107
<211> LENGTH: 64
<212> TYPE: PRT
<213> ORGANISM: Medicago truncatula

<400> SEQUENCE: 107

Met Ala Glu Ile Ile Lys Phe Val Tyr Ile Met Ile Leu Cys Val Ser
1               5                   10                  15

Leu Leu Leu Ile Ala Glu Ala Ser Gly Lys Glu Cys Val Thr Asp Ala
            20                  25                  30

Asp Cys Glu Asn Leu Tyr Pro Gly Asn Lys Lys Pro Met Phe Cys Asn
            35                  40                  45

Asn Thr Gly Tyr Cys Met Ser Leu Tyr Lys Glu Pro Ser Arg Tyr Met
        50                  55                  60

<210> SEQ ID NO 108
<211> LENGTH: 64
<212> TYPE: PRT
<213> ORGANISM: Medicago truncatula

<400> SEQUENCE: 108

Met Ala Lys Ile Ile Lys Phe Val Tyr Ile Met Ile Leu Cys Val Ser
1               5                   10                  15

Leu Leu Leu Ile Val Glu Ala Gly Gly Lys Glu Cys Val Thr Asp Val
            20                  25                  30

Asp Cys Glu Lys Ile Tyr Pro Gly Asn Lys Lys Pro Leu Ile Cys Ser
            35                  40                  45

Thr Gly Tyr Cys Tyr Ser Leu Tyr Glu Glu Pro Pro Arg Tyr His Lys
        50                  55                  60

<210> SEQ ID NO 109
<211> LENGTH: 64
<212> TYPE: PRT

```
<213> ORGANISM: Medicago truncatula

<400> SEQUENCE: 109

Met Ala Lys Val Thr Lys Phe Gly Tyr Ile Ile His Phe Leu Ser
1               5                   10                  15

Leu Phe Phe Leu Ala Met Asn Val Ala Gly Gly Arg Glu Cys His Ala
                20                  25                  30

Asn Ser His Cys Val Gly Lys Ile Thr Cys Val Leu Pro Gln Lys Pro
            35                  40                  45

Glu Cys Trp Asn Tyr Ala Cys Val Cys Tyr Asp Ser Asn Lys Tyr Arg
        50                  55                  60

<210> SEQ ID NO 110
<211> LENGTH: 55
<212> TYPE: PRT
<213> ORGANISM: Medicago truncatula

<400> SEQUENCE: 110

Met Ala Lys Ile Phe Asn Tyr Val Tyr Ala Leu Ile Met Phe Leu Ser
1               5                   10                  15

Leu Phe Leu Met Gly Thr Ser Gly Met Lys Asn Gly Cys Lys His Thr
                20                  25                  30

Gly His Cys Pro Arg Lys Met Cys Gly Ala Lys Thr Thr Lys Cys Arg
            35                  40                  45

Asn Asn Lys Cys Gln Cys Val
        50                  55

<210> SEQ ID NO 111
<211> LENGTH: 69
<212> TYPE: PRT
<213> ORGANISM: Medicago truncatula

<400> SEQUENCE: 111

Met Thr Glu Ile Leu Lys Phe Val Cys Val Met Ile Ile Phe Ile Ser
1               5                   10                  15

Ser Phe Ile Val Ser Lys Ser Leu Asn Gly Gly Gly Lys Asp Lys Cys
                20                  25                  30

Phe Arg Asp Ser Asp Cys Pro Lys His Met Cys Pro Ser Ser Leu Val
            35                  40                  45

Ala Lys Cys Ile Asn Arg Leu Cys Arg Cys Arg Arg Pro Glu Leu Gln
        50                  55                  60

Val Gln Leu Asn Pro
65

<210> SEQ ID NO 112
<211> LENGTH: 69
<212> TYPE: PRT
<213> ORGANISM: Medicago truncatula

<400> SEQUENCE: 112

Met Ala His Ile Ile Met Phe Val Tyr Ala Leu Ile Tyr Ala Leu Ile
1               5                   10                  15

Ile Phe Ser Ser Leu Phe Val Arg Asp Gly Ile Pro Cys Leu Ser Asp
                20                  25                  30

Asp Glu Cys Pro Glu Met Ser His Tyr Ser Phe Lys Cys Asn Asn Lys
            35                  40                  45

Ile Cys Glu Tyr Asp Leu Gly Glu Met Ser Asp Asp Tyr Tyr Leu
        50                  55                  60
```

Glu Met Ser Arg Glu
65

<210> SEQ ID NO 113
<211> LENGTH: 77
<212> TYPE: PRT
<213> ORGANISM: Medicago truncatula

<400> SEQUENCE: 113

Met Tyr Arg Glu Lys Asn Met Ala Lys Thr Leu Lys Phe Val Tyr Val
1               5                   10                  15

Ile Val Leu Phe Leu Ser Leu Phe Leu Ala Ala Lys Asn Ile Asp Gly
            20                  25                  30

Arg Val Ser Tyr Asn Ser Phe Ile Ala Leu Pro Val Cys Gln Thr Ala
        35                  40                  45

Ala Asp Cys Pro Glu Gly Thr Arg Gly Arg Thr Tyr Lys Cys Ile Asn
    50                  55                  60

Asn Lys Cys Arg Tyr Pro Lys Leu Leu Lys Pro Ile Gln
65                  70                  75

<210> SEQ ID NO 114
<211> LENGTH: 56
<212> TYPE: PRT
<213> ORGANISM: Medicago truncatula

<400> SEQUENCE: 114

Met Ala His Ile Phe Asn Tyr Val Tyr Ala Leu Leu Val Phe Leu Ser
1               5                   10                  15

Leu Phe Leu Met Val Thr Asn Gly Ile His Ile Gly Cys Asp Lys Asp
            20                  25                  30

Arg Asp Cys Pro Lys Gln Met Cys His Leu Asn Gln Thr Pro Lys Cys
        35                  40                  45

Leu Lys Asn Ile Cys Lys Cys Val
    50                  55

<210> SEQ ID NO 115
<211> LENGTH: 77
<212> TYPE: PRT
<213> ORGANISM: Medicago truncatula

<400> SEQUENCE: 115

Met Ala Glu Ile Leu Lys Cys Phe Tyr Thr Met Asn Leu Phe Ile Phe
1               5                   10                  15

Leu Ile Ile Leu Pro Ala Lys Ile Arg Glu His Ile Gln Cys Val Ile
            20                  25                  30

Asp Asp Asp Cys Pro Lys Ser Leu Asn Lys Leu Leu Ile Ile Lys Cys
        35                  40                  45

Ile Asn His Val Cys Gln Tyr Val Gly Asn Leu Pro Asp Phe Ala Ser
    50                  55                  60

Gln Ile Pro Lys Ser Thr Lys Met Pro Tyr Lys Gly Glu
65                  70                  75

<210> SEQ ID NO 116
<211> LENGTH: 70
<212> TYPE: PRT
<213> ORGANISM: Medicago truncatula

<400> SEQUENCE: 116

Met Ala Tyr Ile Ser Arg Ile Phe Tyr Val Leu Ile Ile Phe Leu Ser
1               5                   10                  15

-continued

```
Leu Phe Phe Val Val Ile Asn Gly Val Lys Ser Leu Leu Ile Lys
             20                  25                  30

Val Arg Ser Phe Ile Pro Cys Gln Arg Ser Asp Cys Pro Arg Asn
         35                  40                  45

Leu Cys Val Asp Gln Ile Ile Pro Thr Cys Val Trp Ala Lys Cys Lys
 50                  55                  60

Cys Lys Asn Tyr Asn Asp
 65                  70

<210> SEQ ID NO 117
<211> LENGTH: 64
<212> TYPE: PRT
<213> ORGANISM: Medicago truncatula

<400> SEQUENCE: 117

Met Ala Asn Val Thr Lys Phe Val Tyr Ile Ala Ile Tyr Phe Leu Ser
 1               5                  10                  15

Leu Phe Phe Ile Ala Lys Asn Asp Ala Thr Ala Thr Phe Cys His Asp
             20                  25                  30

Asp Ser His Cys Val Thr Lys Ile Lys Cys Val Leu Pro Arg Thr Pro
         35                  40                  45

Gln Cys Arg Asn Glu Ala Cys Gly Cys Tyr His Ser Asn Lys Phe Arg
 50                  55                  60

<210> SEQ ID NO 118
<211> LENGTH: 62
<212> TYPE: PRT
<213> ORGANISM: Medicago truncatula

<400> SEQUENCE: 118

Met Gly Glu Ile Met Lys Phe Val Tyr Val Met Ile Ile Tyr Leu Phe
 1               5                  10                  15

Met Phe Asn Val Ala Thr Gly Ser Glu Phe Ile Phe Thr Lys Lys Leu
             20                  25                  30

Thr Ser Cys Asp Ser Ser Lys Asp Cys Arg Ser Phe Leu Cys Tyr Ser
         35                  40                  45

Pro Lys Phe Pro Val Cys Lys Arg Gly Ile Cys Glu Cys Ile
 50                  55                  60

<210> SEQ ID NO 119
<211> LENGTH: 61
<212> TYPE: PRT
<213> ORGANISM: Medicago truncatula

<400> SEQUENCE: 119

Met Gly Glu Met Phe Lys Phe Ile Tyr Thr Phe Ile Leu Phe Val His
 1               5                  10                  15

Leu Phe Leu Val Val Ile Phe Glu Asp Ile Gly His Ile Lys Tyr Cys
             20                  25                  30

Gly Ile Val Asp Asp Cys Tyr Lys Ser Lys Lys Pro Leu Phe Lys Ile
         35                  40                  45

Trp Lys Cys Val Glu Asn Val Cys Val Leu Trp Tyr Lys
 50                  55                  60

<210> SEQ ID NO 120
<211> LENGTH: 63
<212> TYPE: PRT
<213> ORGANISM: Medicago truncatula
```

```
<400> SEQUENCE: 120

Met Ala Arg Thr Leu Lys Phe Val Tyr Ser Met Ile Leu Phe Leu Ser
1               5                   10                  15

Leu Phe Leu Val Ala Asn Gly Leu Lys Ile Phe Cys Ile Asp Val Ala
                20                  25                  30

Asp Cys Pro Lys Asp Leu Tyr Pro Leu Leu Tyr Lys Cys Ile Tyr Asn
            35                  40                  45

Lys Cys Ile Val Phe Thr Arg Ile Pro Phe Pro Phe Asp Trp Ile
    50                  55                  60

<210> SEQ ID NO 121
<211> LENGTH: 66
<212> TYPE: PRT
<213> ORGANISM: Medicago truncatula

<400> SEQUENCE: 121

Met Ala Asn Ile Thr Lys Phe Val Tyr Ile Ala Ile Leu Phe Leu Ser
1               5                   10                  15

Leu Phe Phe Ile Gly Met Asn Asp Ala Ala Ile Leu Glu Cys Arg Glu
                20                  25                  30

Asp Ser His Cys Val Thr Lys Ile Lys Cys Val Leu Pro Arg Lys Pro
            35                  40                  45

Glu Cys Arg Asn Asn Ala Cys Thr Cys Tyr Lys Gly Gly Phe Ser Phe
    50                  55                  60

His His
65

<210> SEQ ID NO 122
<211> LENGTH: 68
<212> TYPE: PRT
<213> ORGANISM: Medicago truncatula

<400> SEQUENCE: 122

Met Gln Arg Val Lys Lys Met Ser Glu Thr Leu Lys Phe Val Tyr Val
1               5                   10                  15

Leu Ile Leu Phe Ile Ser Ile Phe His Val Val Ile Val Cys Asp Ser
                20                  25                  30

Ile Tyr Phe Pro Val Ser Arg Pro Cys Ile Thr Asp Lys Asp Cys Pro
            35                  40                  45

Asn Met Lys His Tyr Lys Ala Lys Cys Arg Lys Gly Phe Cys Ile Ser
    50                  55                  60

Ser Arg Val Arg
65

<210> SEQ ID NO 123
<211> LENGTH: 72
<212> TYPE: PRT
<213> ORGANISM: Medicago truncatula

<400> SEQUENCE: 123

Met Gln Ile Arg Lys Ile Met Ser Gly Val Leu Lys Phe Val Tyr Ala
1               5                   10                  15

Ile Ile Leu Phe Leu Phe Leu Phe Leu Val Ala Arg Glu Val Gly Gly
                20                  25                  30

Leu Glu Thr Ile Glu Cys Glu Thr Asp Gly Asp Cys Pro Arg Ser Met
            35                  40                  45

Ile Lys Met Trp Asn Lys Asn Tyr Arg His Lys Cys Ile Asp Gly Lys
    50                  55                  60
```

```
Cys Glu Trp Ile Lys Lys Leu Pro
 65                  70
```

<210> SEQ ID NO 124
<211> LENGTH: 54
<212> TYPE: PRT
<213> ORGANISM: Medicago truncatula

<400> SEQUENCE: 124

```
Met Phe Val Tyr Asp Leu Ile Leu Phe Ile Ser Leu Ile Leu Val Val
 1               5                  10                  15

Thr Gly Ile Asn Ala Glu Ala Asp Thr Ser Cys His Ser Phe Asp Asp
             20                  25                  30

Cys Pro Trp Val Ala His His Tyr Arg Glu Cys Ile Glu Gly Leu Cys
         35                  40                  45

Ala Tyr Arg Ile Leu Tyr
         50
```

<210> SEQ ID NO 125
<211> LENGTH: 69
<212> TYPE: PRT
<213> ORGANISM: Medicago truncatula

<400> SEQUENCE: 125

```
Met Gln Arg Arg Lys Lys Ser Met Ala Lys Met Leu Lys Phe Phe Phe
 1               5                  10                  15

Ala Ile Ile Leu Leu Leu Ser Leu Phe Leu Val Ala Thr Glu Val Gly
             20                  25                  30

Gly Ala Tyr Ile Glu Cys Glu Val Asp Asp Asp Cys Pro Lys Pro Met
         35                  40                  45

Lys Asn Ser His Pro Asp Thr Tyr Tyr Lys Cys Val Leu His Arg Cys
     50                  55                  60

Gln Trp Ala Trp Lys
 65
```

<210> SEQ ID NO 126
<211> LENGTH: 140
<212> TYPE: PRT
<213> ORGANISM: Medicago truncatula

<400> SEQUENCE: 126

```
Met Phe Val Tyr Thr Leu Ile Ile Phe Leu Phe Pro Ser His Val Ile
 1               5                  10                  15

Thr Asn Lys Ile Ala Ile Tyr Cys Val Ser Asp Asp Cys Leu Lys
             20                  25                  30

Thr Phe Thr Pro Leu Asp Leu Lys Cys Val Asp Asn Val Cys Glu Phe
         35                  40                  45

Asn Leu Arg Cys Lys Gly Lys Cys Gly Glu Arg Asp Glu Lys Phe Val
     50                  55                  60

Phe Leu Lys Ala Leu Lys Lys Met Asp Gln Lys Leu Val Leu Glu Glu
 65                  70                  75                  80

Gln Gly Asn Ala Arg Glu Val Lys Ile Pro Lys Lys Leu Leu Phe Asp
             85                  90                  95

Arg Ile Gln Val Pro Thr Pro Ala Thr Lys Asp Gln Val Glu Glu Asp
             100                 105                 110

Asp Tyr Asp Asp Asp Glu Glu Glu Glu Glu Glu Asp Asp Val
             115                 120                 125
```

```
Asp Met Trp Phe His Leu Pro Asp Val Val Cys His
    130                 135                 140
```

<210> SEQ ID NO 127
<211> LENGTH: 60
<212> TYPE: PRT
<213> ORGANISM: Medicago truncatula

<400> SEQUENCE: 127

```
Met Ala Lys Phe Ser Met Phe Val Tyr Ala Leu Ile Asn Phe Leu Ser
1               5                   10                  15

Leu Phe Leu Val Glu Thr Ala Ile Thr Asn Ile Arg Cys Val Ser Asp
            20                  25                  30

Asp Asp Cys Pro Lys Val Ile Lys Pro Leu Val Met Lys Cys Ile Gly
        35                  40                  45

Asn Tyr Cys Tyr Phe Phe Met Ile Tyr Glu Gly Pro
    50                  55                  60
```

<210> SEQ ID NO 128
<211> LENGTH: 58
<212> TYPE: PRT
<213> ORGANISM: Medicago truncatula

<400> SEQUENCE: 128

```
Met Ala His Lys Phe Val Tyr Ala Ile Ile Leu Phe Ile Phe Leu Phe
1               5                   10                  15

Leu Val Ala Lys Asn Val Lys Gly Tyr Val Val Cys Arg Thr Val Asp
            20                  25                  30

Asp Cys Pro Pro Asp Thr Arg Asp Leu Arg Tyr Arg Cys Leu Asn Gly
        35                  40                  45

Lys Cys Lys Ser Tyr Arg Leu Ser Tyr Gly
    50                  55
```

<210> SEQ ID NO 129
<211> LENGTH: 61
<212> TYPE: PRT
<213> ORGANISM: Medicago truncatula

<400> SEQUENCE: 129

```
Met Gln Arg Lys Lys Asn Met Gly Gln Ile Leu Ile Phe Val Phe Ala
1               5                   10                  15

Leu Ile Asn Phe Leu Ser Pro Ile Leu Val Glu Met Thr Thr Thr Thr
            20                  25                  30

Ile Pro Cys Thr Phe Ile Asp Asp Cys Pro Lys Met Pro Leu Val Val
        35                  40                  45

Lys Cys Ile Asp Asn Phe Cys Asn Tyr Phe Glu Ile Lys
    50                  55                  60
```

<210> SEQ ID NO 130
<211> LENGTH: 57
<212> TYPE: PRT
<213> ORGANISM: Medicago truncatula

<400> SEQUENCE: 130

```
Met Ala Gln Thr Leu Met Leu Val Tyr Ala Leu Ile Ile Phe Thr Ser
1               5                   10                  15

Leu Phe Leu Val Val Ile Ser Arg Gln Thr Asp Ile Pro Cys Lys Ser
            20                  25                  30

Asp Asp Ala Cys Pro Arg Val Ser Ser His His Ile Glu Cys Val Lys
        35                  40                  45
```

Gly Phe Cys Thr Tyr Trp Lys Leu Asp
        50                  55

<210> SEQ ID NO 131
<211> LENGTH: 77
<212> TYPE: PRT
<213> ORGANISM: Medicago truncatula

<400> SEQUENCE: 131

Met Leu Arg Arg Lys Asn Thr Val Gln Ile Leu Met Phe Val Ser Ala
1               5                   10                  15

Leu Leu Ile Tyr Ile Phe Leu Phe Leu Val Ile Thr Ser Ser Ala Asn
            20                  25                  30

Ile Pro Cys Asn Ser Asp Ser Asp Cys Pro Trp Lys Ile Tyr Tyr Thr
        35                  40                  45

Tyr Arg Cys Asn Asp Gly Phe Cys Val Tyr Lys Ser Ile Asp Pro Ser
    50                  55                  60

Thr Ile Pro Gln Tyr Met Thr Asp Leu Ile Phe Pro Arg
65                  70                  75

<210> SEQ ID NO 132
<211> LENGTH: 59
<212> TYPE: PRT
<213> ORGANISM: Medicago truncatula

<400> SEQUENCE: 132

Met Ala Val Ile Leu Lys Phe Val Tyr Ile Met Ile Ile Phe Leu Phe
1               5                   10                  15

Leu Leu Tyr Val Val Asn Gly Thr Arg Cys Asn Arg Asp Glu Asp Cys
            20                  25                  30

Pro Phe Ile Cys Thr Gly Pro Gln Ile Pro Lys Cys Val Ser His Ile
        35                  40                  45

Cys Phe Cys Leu Ser Ser Gly Lys Glu Ala Tyr
    50                  55

<210> SEQ ID NO 133
<211> LENGTH: 62
<212> TYPE: PRT
<213> ORGANISM: Medicago truncatula

<400> SEQUENCE: 133

Met Asp Ala Ile Leu Lys Phe Ile Tyr Ala Met Phe Leu Phe Leu Phe
1               5                   10                  15

Leu Phe Val Thr Thr Arg Asn Val Glu Ala Leu Phe Glu Cys Asn Arg
            20                  25                  30

Asp Phe Val Cys Gly Asn Asp Asp Glu Cys Val Tyr Pro Tyr Ala Val
        35                  40                  45

Gln Cys Ile His Arg Tyr Cys Lys Cys Leu Lys Ser Arg Asn
    50                  55                  60

<210> SEQ ID NO 134
<211> LENGTH: 67
<212> TYPE: PRT
<213> ORGANISM: Medicago truncatula

<400> SEQUENCE: 134

Met Gln Ile Gly Arg Lys Lys Met Gly Glu Thr Pro Lys Leu Val Tyr
1               5                   10                  15

Val Ile Ile Leu Phe Leu Ser Ile Phe Leu Cys Thr Asn Ser Ser Phe

```
                    20                  25                  30

Ser Gln Met Ile Asn Phe Arg Gly Cys Lys Arg Asp Lys Asp Cys Pro
                35                  40                  45

Gln Phe Arg Gly Val Asn Ile Arg Cys Arg Ser Gly Phe Cys Thr Pro
            50                  55                  60

Ile Asp Ser
65

<210> SEQ ID NO 135
<211> LENGTH: 76
<212> TYPE: PRT
<213> ORGANISM: Medicago truncatula

<400> SEQUENCE: 135

Met Gln Met Arg Lys Asn Met Ala Gln Ile Leu Phe Tyr Val Tyr Ala
1               5                   10                  15

Leu Leu Ile Leu Phe Ser Pro Phe Leu Val Ala Arg Ile Met Val Val
                20                  25                  30

Asn Pro Asn Asn Pro Cys Val Thr Asp Ala Asp Cys Gln Arg Tyr Arg
            35                  40                  45

His Lys Leu Ala Thr Arg Met Val Cys Asn Ile Gly Phe Cys Leu Met
        50                  55                  60

Asp Phe Thr His Asp Pro Tyr Ala Pro Ser Leu Pro
65                  70                  75

<210> SEQ ID NO 136
<211> LENGTH: 77
<212> TYPE: PRT
<213> ORGANISM: Medicago truncatula

<400> SEQUENCE: 136

Met Tyr Val Tyr Tyr Ile Gln Met Gly Lys Asn Met Ala Gln Arg Phe
1               5                   10                  15

Met Phe Ile Tyr Ala Leu Ile Ile Phe Leu Ser Gln Phe Phe Val Val
                20                  25                  30

Ile Asn Thr Ser Asp Ile Pro Asn Asn Ser Asn Arg Asn Ser Pro Lys
            35                  40                  45

Glu Asp Val Phe Cys Asn Ser Asn Asp Cys Pro Thr Ile Leu Tyr
        50                  55                  60

Tyr Val Ser Lys Cys Val Tyr Asn Phe Cys Glu Tyr Trp
65                  70                  75

<210> SEQ ID NO 137
<211> LENGTH: 67
<212> TYPE: PRT
<213> ORGANISM: Medicago truncatula

<400> SEQUENCE: 137

Met Ala Lys Ile Val Asn Phe Val Tyr Ser Met Ile Ile Phe Val Ser
1               5                   10                  15

Leu Phe Leu Val Ala Thr Lys Gly Gly Ser Lys Pro Phe Leu Thr Arg
                20                  25                  30

Pro Tyr Pro Cys Asn Thr Gly Ser Asp Cys Pro Gln Asn Met Cys Pro
            35                  40                  45

Pro Gly Tyr Lys Pro Gly Cys Glu Asp Gly Tyr Cys Asn His Cys Tyr
        50                  55                  60

Lys Arg Trp
65
```

<210> SEQ ID NO 138
<211> LENGTH: 62
<212> TYPE: PRT
<213> ORGANISM: Medicago truncatula

<400> SEQUENCE: 138

Met Val Arg Thr Leu Lys Phe Val Tyr Val Ile Ile Leu Ile Leu Ser
1               5                   10                  15

Leu Phe Leu Val Ala Lys Gly Gly Gly Lys Lys Ile Tyr Cys Glu Asn
            20                  25                  30

Ala Ala Ser Cys Pro Arg Leu Met Tyr Pro Leu Val Tyr Lys Cys Leu
        35                  40                  45

Asp Asn Lys Cys Val Lys Phe Met Met Lys Ser Arg Phe Val
    50                  55                  60

<210> SEQ ID NO 139
<211> LENGTH: 62
<212> TYPE: PRT
<213> ORGANISM: Medicago truncatula

<400> SEQUENCE: 139

Met Ala Arg Thr Leu Lys Phe Val Tyr Ala Val Ile Leu Phe Leu Ser
1               5                   10                  15

Leu Phe Leu Val Ala Lys Gly Asp Asp Val Lys Ile Lys Cys Val Val
            20                  25                  30

Ala Ala Asn Cys Pro Asp Leu Met Tyr Pro Leu Val Tyr Lys Cys Leu
        35                  40                  45

Asn Gly Ile Cys Val Gln Phe Thr Leu Thr Phe Pro Phe Val
    50                  55                  60

<210> SEQ ID NO 140
<211> LENGTH: 65
<212> TYPE: PRT
<213> ORGANISM: Medicago truncatula

<400> SEQUENCE: 140

Met Ser Asn Thr Leu Met Phe Val Ile Thr Phe Ile Val Leu Val Thr
1               5                   10                  15

Leu Phe Leu Gly Pro Lys Asn Val Tyr Ala Phe Gln Pro Cys Val Thr
            20                  25                  30

Thr Ala Asp Cys Met Lys Thr Leu Lys Thr Asp Glu Asn Ile Trp Tyr
        35                  40                  45

Glu Cys Ile Asn Asp Phe Cys Ile Pro Phe Pro Ile Pro Lys Gly Arg
    50                  55                  60

Lys
65

<210> SEQ ID NO 141
<211> LENGTH: 76
<212> TYPE: PRT
<213> ORGANISM: Medicago truncatula

<400> SEQUENCE: 141

Met Lys Arg Val Val Asn Met Ala Lys Ile Val Lys Tyr Val Tyr Val
1               5                   10                  15

Ile Ile Ile Phe Leu Ser Leu Phe Leu Val Ala Thr Lys Ile Glu Gly
            20                  25                  30

Tyr Tyr Tyr Lys Cys Phe Lys Asp Ser Asp Cys Val Lys Leu Leu Cys

```
                35                  40                  45

Arg Ile Pro Leu Arg Pro Lys Cys Met Tyr Arg His Ile Cys Lys Cys
    50                  55                  60

Lys Val Val Leu Thr Gln Asn Asn Tyr Val Leu Thr
65                  70                  75

<210> SEQ ID NO 142
<211> LENGTH: 66
<212> TYPE: PRT
<213> ORGANISM: Medicago truncatula

<400> SEQUENCE: 142

Met Lys Arg Gly Lys Asn Met Ser Lys Ile Leu Lys Phe Ile Tyr Ala
1               5                   10                  15

Thr Leu Val Leu Tyr Leu Phe Leu Val Val Thr Lys Ala Ser Asp Asp
                20                  25                  30

Glu Cys Lys Ile Asp Gly Asp Cys Pro Ile Ser Trp Gln Lys Phe His
            35                  40                  45

Thr Tyr Lys Cys Ile Asn Gln Lys Cys Lys Trp Val Leu Arg Phe His
    50                  55                  60

Glu Tyr
65

<210> SEQ ID NO 143
<211> LENGTH: 64
<212> TYPE: PRT
<213> ORGANISM: Medicago truncatula

<400> SEQUENCE: 143

Met Ala Lys Thr Leu Asn Phe Met Phe Ala Leu Ile Leu Phe Ile Ser
1               5                   10                  15

Leu Phe Leu Val Ser Lys Asn Val Ala Ile Asp Ile Phe Val Cys Gln
                20                  25                  30

Thr Asp Ala Asp Cys Pro Lys Ser Glu Leu Ser Met Tyr Thr Trp Lys
            35                  40                  45

Cys Ile Asp Asn Glu Cys Asn Leu Phe Lys Val Met Gln Gln Met Val
    50                  55                  60

<210> SEQ ID NO 144
<211> LENGTH: 59
<212> TYPE: PRT
<213> ORGANISM: Medicago truncatula

<400> SEQUENCE: 144

Met Ala Asn Thr His Lys Leu Val Ser Met Ile Leu Phe Ile Phe Leu
1               5                   10                  15

Phe Leu Val Ala Asn Asn Val Glu Gly Tyr Val Asn Cys Glu Thr Asp
                20                  25                  30

Ala Asp Cys Pro Pro Ser Thr Arg Val Lys Arg Phe Lys Cys Val Lys
            35                  40                  45

Gly Glu Cys Arg Trp Thr Arg Met Ser Tyr Ala
    50                  55

<210> SEQ ID NO 145
<211> LENGTH: 59
<212> TYPE: PRT
<213> ORGANISM: Medicago truncatula

<400> SEQUENCE: 145
```

Met Ala His Phe Leu Met Phe Val Tyr Ala Leu Ile Thr Cys Leu Ser
1               5                   10                  15

Leu Phe Leu Val Glu Met Gly His Leu Ser Ile His Cys Val Ser Val
                20                  25                  30

Asp Asp Cys Pro Lys Val Glu Lys Pro Ile Thr Met Lys Cys Ile Asn
            35                  40                  45

Asn Tyr Cys Lys Tyr Phe Val Asp His Lys Leu
    50                  55

<210> SEQ ID NO 146
<211> LENGTH: 66
<212> TYPE: PRT
<213> ORGANISM: Medicago truncatula

<400> SEQUENCE: 146

Met Asn Gln Ile Pro Met Phe Gly Tyr Thr Leu Ile Ile Phe Phe Ser
1               5                   10                  15

Leu Phe Pro Val Ile Thr Asn Gly Asp Arg Ile Pro Cys Val Thr Asn
                20                  25                  30

Gly Asp Cys Pro Val Met Arg Leu Pro Leu Tyr Met Arg Cys Ile Thr
            35                  40                  45

Tyr Ser Cys Glu Leu Phe Phe Asp Gly Pro Asn Leu Cys Ala Val Glu
    50                  55                  60

Arg Ile
65

<210> SEQ ID NO 147
<211> LENGTH: 61
<212> TYPE: PRT
<213> ORGANISM: Medicago truncatula

<400> SEQUENCE: 147

Met Arg Lys Asp Met Ala Arg Ile Ser Leu Phe Val Tyr Ala Leu Ile
1               5                   10                  15

Ile Phe Phe Ser Leu Phe Phe Val Leu Thr Asn Gly Glu Leu Glu Ile
                20                  25                  30

Arg Cys Val Ser Asp Ala Asp Cys Pro Leu Phe Pro Leu Pro Leu His
            35                  40                  45

Asn Arg Cys Ile Asp Asp Val Cys His Leu Phe Thr Ser
    50                  55                  60

<210> SEQ ID NO 148
<211> LENGTH: 60
<212> TYPE: PRT
<213> ORGANISM: Medicago truncatula

<400> SEQUENCE: 148

Met Ala Gln Ile Leu Met Phe Val Tyr Phe Leu Ile Ile Phe Leu Ser
1               5                   10                  15

Leu Phe Leu Val Glu Ser Ile Lys Ile Phe Thr Glu His Arg Cys Arg
                20                  25                  30

Thr Asp Ala Asp Cys Pro Ala Arg Glu Leu Pro Glu Tyr Leu Lys Cys
            35                  40                  45

Gln Gly Gly Met Cys Arg Leu Leu Ile Lys Lys Asp
    50                  55                  60

<210> SEQ ID NO 149
<211> LENGTH: 56
<212> TYPE: PRT

<213> ORGANISM: Medicago truncatula

<400> SEQUENCE: 149

Met Ala Arg Val Ile Ser Leu Phe Tyr Ala Leu Ile Ile Phe Leu Phe
1               5                   10                  15

Leu Phe Leu Val Ala Thr Asn Gly Asp Leu Ser Pro Cys Leu Arg Ser
            20                  25                  30

Gly Asp Cys Ser Lys Asp Glu Cys Pro Ser His Leu Val Pro Lys Cys
        35                  40                  45

Ile Gly Leu Thr Cys Tyr Cys Ile
    50                  55

<210> SEQ ID NO 150
<211> LENGTH: 62
<212> TYPE: PRT
<213> ORGANISM: Medicago truncatula

<400> SEQUENCE: 150

Met Gln Arg Arg Lys Asn Met Ala Gln Ile Leu Leu Phe Ala Tyr Val
1               5                   10                  15

Phe Ile Ile Ser Ile Ser Leu Phe Leu Val Val Thr Asn Gly Val Lys
            20                  25                  30

Ile Pro Cys Val Lys Asp Thr Asp Cys Pro Thr Leu Pro Cys Pro Leu
        35                  40                  45

Tyr Ser Lys Cys Val Asp Gly Phe Cys Lys Met Leu Ser Ile
    50                  55                  60

<210> SEQ ID NO 151
<211> LENGTH: 66
<212> TYPE: PRT
<213> ORGANISM: Medicago truncatula

<400> SEQUENCE: 151

Met Asn His Ile Ser Lys Phe Val Tyr Ala Leu Ile Ile Phe Leu Ser
1               5                   10                  15

Val Tyr Leu Val Val Leu Asp Gly Arg Pro Val Ser Cys Lys Asp His
            20                  25                  30

Tyr Asp Cys Arg Arg Lys Val Lys Ile Val Gly Cys Ile Phe Pro Gln
        35                  40                  45

Glu Lys Pro Met Cys Ile Asn Ser Met Cys Thr Cys Ile Arg Glu Ile
    50                  55                  60

Val Pro
65

<210> SEQ ID NO 152
<211> LENGTH: 86
<212> TYPE: PRT
<213> ORGANISM: Medicago truncatula

<400> SEQUENCE: 152

Met Lys Ser Gln Asn His Ala Lys Phe Ile Ser Phe Tyr Lys Asn Asp
1               5                   10                  15

Leu Phe Lys Ile Phe Gln Asn Asn Asp Ser His Phe Lys Val Phe Phe
            20                  25                  30

Ala Leu Ile Ile Phe Leu Tyr Thr Tyr Leu His Val Thr Asn Gly Val
        35                  40                  45

Phe Val Ser Cys Asn Ser His Ile His Cys Arg Val Asn Asn His Lys
    50                  55                  60

```
Ile Gly Cys Asn Ile Pro Glu Gln Tyr Leu Leu Cys Val Asn Leu Phe
 65                  70                  75                  80

Cys Leu Trp Leu Asp Tyr
                85

<210> SEQ ID NO 153
<211> LENGTH: 62
<212> TYPE: PRT
<213> ORGANISM: Medicago truncatula

<400> SEQUENCE: 153

Met Thr Tyr Ile Ser Lys Val Val Tyr Ala Leu Ile Ile Phe Leu Ser
  1               5                  10                  15

Ile Tyr Val Gly Val Asn Asp Cys Met Leu Val Thr Cys Glu Asp His
                 20                  25                  30

Phe Asp Cys Arg Gln Asn Val Gln Gln Val Gly Cys Ser Phe Arg Glu
             35                  40                  45

Ile Pro Gln Cys Ile Asn Ser Ile Cys Lys Cys Met Lys Gly
         50                  55                  60

<210> SEQ ID NO 154
<211> LENGTH: 63
<212> TYPE: PRT
<213> ORGANISM: Medicago truncatula

<400> SEQUENCE: 154

Met Thr His Ile Ser Lys Phe Val Phe Ala Leu Ile Ile Phe Leu Ser
  1               5                  10                  15

Ile Tyr Val Gly Val Asn Asp Cys Lys Arg Ile Pro Cys Lys Asp Asn
                 20                  25                  30

Asn Asp Cys Asn Asn Asn Trp Gln Leu Leu Ala Cys Arg Phe Glu Arg
             35                  40                  45

Glu Val Pro Arg Cys Ile Asn Ser Ile Cys Lys Cys Met Pro Met
         50                  55                  60

<210> SEQ ID NO 155
<211> LENGTH: 60
<212> TYPE: PRT
<213> ORGANISM: Medicago truncatula

<400> SEQUENCE: 155

Met Val Gln Thr Pro Lys Leu Val Tyr Val Ile Val Leu Leu Leu Ser
  1               5                  10                  15

Ile Phe Leu Gly Met Thr Ile Cys Asn Ser Ser Phe Ser His Phe Phe
                 20                  25                  30

Glu Gly Ala Cys Lys Ser Asp Lys Asp Cys Pro Lys Leu His Arg Ser
             35                  40                  45

Asn Val Arg Cys Arg Lys Gly Gln Cys Val Gln Ile
         50                  55                  60

<210> SEQ ID NO 156
<211> LENGTH: 77
<212> TYPE: PRT
<213> ORGANISM: Medicago truncatula

<400> SEQUENCE: 156

Met Thr Lys Ile Leu Met Leu Phe Tyr Ala Met Ile Val Phe His Ser
  1               5                  10                  15

Ile Phe Leu Val Ala Ser Tyr Thr Asp Glu Cys Ser Thr Asp Ala Asp
                 20                  25                  30
```

Cys Glu Tyr Ile Leu Cys Leu Phe Pro Ile Ile Lys Arg Cys Ile His
            35                  40                  45

Asn His Cys Lys Cys Val Pro Met Gly Ser Ile Glu Pro Met Ser Thr
 50                  55                  60

Ile Pro Asn Gly Val His Lys Phe His Ile Ile Asn Asn
 65                  70                  75

<210> SEQ ID NO 157
<211> LENGTH: 64
<212> TYPE: PRT
<213> ORGANISM: Medicago truncatula

<400> SEQUENCE: 157

Met Ala Lys Thr Leu Asn Phe Val Cys Ala Met Ile Leu Phe Ile Ser
 1               5                  10                  15

Leu Phe Leu Val Ser Lys Asn Val Ala Leu Tyr Ile Ile Glu Cys Lys
            20                  25                  30

Thr Asp Ala Asp Cys Pro Ile Ser Lys Leu Asn Met Tyr Asn Trp Arg
        35                  40                  45

Cys Ile Lys Ser Ser Cys His Leu Tyr Lys Val Ile Gln Phe Met Val
 50                  55                  60

<210> SEQ ID NO 158
<211> LENGTH: 72
<212> TYPE: PRT
<213> ORGANISM: Medicago truncatula

<400> SEQUENCE: 158

Met Gln Lys Glu Lys Asn Met Ala Lys Thr Phe Glu Phe Val Tyr Ala
 1               5                  10                  15

Met Ile Ile Phe Ile Leu Leu Phe Leu Val Glu Asn Asn Phe Ala Ala
            20                  25                  30

Tyr Ile Ile Glu Cys Gln Thr Asp Asp Cys Pro Lys Ser Gln Leu
        35                  40                  45

Glu Met Phe Ala Trp Lys Cys Val Lys Asn Gly Cys His Leu Phe Gly
 50                  55                  60

Met Tyr Glu Asp Asp Asp Asp Pro
 65                  70

<210> SEQ ID NO 159
<211> LENGTH: 57
<212> TYPE: PRT
<213> ORGANISM: Medicago truncatula

<400> SEQUENCE: 159

Met Ala Ala Thr Arg Lys Phe Ile Tyr Val Leu Ser His Phe Leu Phe
 1               5                  10                  15

Leu Phe Leu Val Thr Lys Ile Thr Asp Ala Arg Val Cys Lys Ser Asp
            20                  25                  30

Lys Asp Cys Lys Asp Ile Ile Tyr Arg Tyr Ile Leu Lys Cys Arg
        35                  40                  45

Asn Gly Glu Cys Val Lys Ile Lys Ile
 50                  55

<210> SEQ ID NO 160
<211> LENGTH: 75
<212> TYPE: PRT
<213> ORGANISM: Medicago truncatula

```
<400> SEQUENCE: 160

Met Gln Arg Leu Asp Asn Met Ala Lys Asn Val Lys Phe Ile Tyr Val
1               5                   10                  15

Ile Ile Leu Leu Leu Phe Ile Phe Leu Val Ile Val Cys Asp Ser
                20                  25                  30

Ala Phe Val Pro Asn Ser Gly Pro Cys Thr Thr Asp Lys Asp Cys Lys
            35                  40                  45

Gln Val Lys Gly Tyr Ile Ala Arg Cys Arg Lys Gly Tyr Cys Met Gln
    50                  55                  60

Ser Val Lys Arg Thr Trp Ser Ser Tyr Ser Arg
65                  70                  75

<210> SEQ ID NO 161
<211> LENGTH: 102
<212> TYPE: PRT
<213> ORGANISM: Medicago truncatula

<400> SEQUENCE: 161

Met Lys Phe Ile Tyr Ile Met Ile Leu Phe Leu Ser Leu Phe Leu Val
1               5                   10                  15

Gln Phe Leu Thr Cys Lys Gly Leu Thr Val Pro Cys Glu Asn Pro Thr
                20                  25                  30

Thr Cys Pro Glu Asp Phe Cys Thr Pro Pro Met Ile Thr Arg Cys Ile
            35                  40                  45

Asn Phe Ile Cys Leu Cys Asp Gly Pro Glu Tyr Ala Glu Pro Glu Tyr
    50                  55                  60

Asp Gly Pro Glu Pro Glu Tyr Asp His Lys Gly Asp Phe Leu Ser Val
65                  70                  75                  80

Lys Pro Lys Ile Ile Asn Glu Asn Met Met Met Arg Glu Arg His Met
                85                  90                  95

Met Lys Glu Ile Glu Val
            100

<210> SEQ ID NO 162
<211> LENGTH: 59
<212> TYPE: PRT
<213> ORGANISM: Medicago truncatula

<400> SEQUENCE: 162

Met Ala Gln Phe Leu Met Phe Ile Tyr Val Leu Ile Ile Phe Leu Tyr
1               5                   10                  15

Leu Phe Tyr Val Glu Ala Ala Met Phe Glu Leu Thr Lys Ser Thr Ile
                20                  25                  30

Arg Cys Val Thr Asp Ala Asp Cys Pro Asn Val Val Lys Pro Leu Lys
            35                  40                  45

Pro Lys Cys Val Asp Gly Phe Cys Glu Tyr Thr
    50                  55

<210> SEQ ID NO 163
<211> LENGTH: 70
<212> TYPE: PRT
<213> ORGANISM: Medicago truncatula

<400> SEQUENCE: 163

Met Lys Met Arg Ile His Met Ala Gln Ile Ile Met Phe Phe Tyr Ala
1               5                   10                  15

Leu Ile Ile Phe Leu Ser Pro Phe Leu Val Asp Arg Arg Ser Phe Pro
                20                  25                  30
```

```
Ser Ser Phe Val Ser Pro Lys Ser Tyr Thr Ser Glu Ile Pro Cys Lys
        35                  40                  45

Ala Thr Arg Asp Cys Pro Tyr Glu Leu Tyr Tyr Glu Thr Lys Cys Val
 50                  55                  60

Asp Ser Leu Cys Thr Tyr
 65                  70

<210> SEQ ID NO 164
<211> LENGTH: 41
<212> TYPE: PRT
<213> ORGANISM: Medicago truncatula

<400> SEQUENCE: 164

Thr Arg Met Leu Thr Ile Pro Cys Thr Ser Asp Asp Asn Cys Pro Lys
 1               5                  10                  15

Val Ile Ser Pro Cys His Thr Lys Cys Phe Asp Gly Phe Cys Gly Trp
                20                  25                  30

Tyr Ile Glu Gly Ser Tyr Glu Gly Pro
            35                  40

<210> SEQ ID NO 165
<211> LENGTH: 69
<212> TYPE: PRT
<213> ORGANISM: Medicago truncatula

<400> SEQUENCE: 165

Met Ala Gln Phe Leu Leu Phe Val Tyr Ser Leu Ile Ile Phe Leu Ser
 1               5                  10                  15

Leu Phe Phe Gly Glu Ala Ala Phe Glu Arg Thr Glu Thr Arg Met Leu
                20                  25                  30

Thr Ile Pro Cys Thr Ser Asp Asp Asn Cys Pro Lys Val Ile Ser Pro
            35                  40                  45

Cys His Thr Lys Cys Phe Asp Gly Phe Cys Gly Trp Tyr Ile Glu Gly
        50                  55                  60

Ser Tyr Glu Gly Pro
 65

<210> SEQ ID NO 166
<211> LENGTH: 78
<212> TYPE: PRT
<213> ORGANISM: Buchnera aphidicola

<400> SEQUENCE: 166

Met Lys Leu Leu His Gly Phe Leu Ile Ile Met Leu Thr Met His Leu
 1               5                  10                  15

Ser Ile Gln Tyr Ala Tyr Gly Gly Pro Phe Leu Thr Lys Tyr Leu Cys
                20                  25                  30

Asp Arg Val Cys His Lys Leu Cys Gly Asp Glu Phe Val Cys Ser Cys
            35                  40                  45

Ile Gln Tyr Lys Ser Leu Lys Gly Leu Trp Phe Pro His Cys Pro Thr
        50                  55                  60

Gly Lys Ala Ser Val Val Leu His Asn Phe Leu Thr Ser Pro
 65                  70                  75

<210> SEQ ID NO 167
<211> LENGTH: 77
<212> TYPE: PRT
<213> ORGANISM: Buchnera aphidicola
```

<400> SEQUENCE: 167

Met Lys Leu Leu Tyr Gly Phe Leu Ile Ile Met Leu Thr Ile His Leu
1               5                   10                  15

Ser Val Gln Tyr Phe Glu Ser Pro Phe Glu Thr Lys Tyr Asn Cys Asp
            20                  25                  30

Thr His Cys Asn Lys Leu Cys Gly Lys Ile Asp His Cys Ser Cys Ile
        35                  40                  45

Gln Tyr His Ser Met Glu Gly Leu Trp Phe Pro His Cys Arg Thr Gly
    50                  55                  60

Ser Ala Ala Gln Met Leu His Asp Phe Leu Ser Asn Pro
65                  70                  75

<210> SEQ ID NO 168
<211> LENGTH: 86
<212> TYPE: PRT
<213> ORGANISM: Buchnera aphidicola

<400> SEQUENCE: 168

Met Ser Val Arg Lys Asn Val Leu Pro Thr Met Phe Val Val Leu Leu
1               5                   10                  15

Ile Met Ser Pro Val Thr Pro Thr Ser Val Phe Ile Ser Ala Val Cys
            20                  25                  30

Tyr Ser Gly Cys Gly Ser Leu Ala Leu Val Cys Phe Val Ser Asn Gly
        35                  40                  45

Ile Thr Asn Gly Leu Asp Tyr Phe Lys Ser Ser Ala Pro Leu Ser Thr
    50                  55                  60

Ser Glu Thr Ser Cys Gly Glu Ala Phe Asp Thr Cys Thr Asp His Cys
65                  70                  75                  80

Leu Ala Asn Phe Lys Phe
                85

<210> SEQ ID NO 169
<211> LENGTH: 69
<212> TYPE: PRT
<213> ORGANISM: Buchnera aphidicola

<400> SEQUENCE: 169

Met Arg Leu Leu Tyr Gly Phe Leu Ile Ile Met Leu Thr Ile Tyr Leu
1               5                   10                  15

Ser Val Gln Asp Phe Asp Pro Thr Glu Phe Lys Gly Pro Phe Pro Thr
            20                  25                  30

Ile Glu Ile Cys Ser Lys Tyr Cys Ala Val Val Cys Asn Tyr Thr Ser
        35                  40                  45

Arg Pro Cys Tyr Cys Val Glu Ala Ala Lys Glu Arg Asp Gln Trp Phe
    50                  55                  60

Pro Tyr Cys Tyr Asp
65

<210> SEQ ID NO 170
<211> LENGTH: 77
<212> TYPE: PRT
<213> ORGANISM: Buchnera aphidicola

<400> SEQUENCE: 170

Met Arg Leu Leu Tyr Gly Phe Leu Ile Ile Met Leu Thr Ile His Leu
1               5                   10                  15

Ser Val Gln Asp Ile Asp Pro Asn Thr Leu Arg Gly Pro Tyr Pro Thr
            20                  25                  30

```
Lys Glu Ile Cys Ser Lys Tyr Cys Glu Tyr Asn Val Val Cys Gly Ala
        35                  40                  45

Ser Leu Pro Cys Ile Cys Val Gln Asp Ala Arg Gln Leu Asp His Trp
    50                  55                  60

Phe Ala Cys Cys Tyr Asp Gly Gly Pro Glu Met Leu Met
65                  70                  75

<210> SEQ ID NO 171
<211> LENGTH: 108
<212> TYPE: PRT
<213> ORGANISM: Buchnera aphidicola

<400> SEQUENCE: 171

Met Lys Leu Phe Val Val Val Val Leu Val Ala Val Gly Ile Met Phe
1               5                   10                  15

Val Phe Ala Ser Asp Thr Ala Ala Ala Pro Thr Asp Tyr Glu Asp Thr
            20                  25                  30

Asn Asp Met Ile Ser Leu Ser Ser Leu Val Gly Asp Asn Ser Pro Tyr
        35                  40                  45

Val Arg Val Ser Ser Ala Asp Ser Gly Gly Ser Ser Lys Thr Ser Ser
    50                  55                  60

Lys Asn Pro Ile Leu Gly Leu Leu Lys Ser Val Ile Lys Leu Leu Thr
65                  70                  75                  80

Lys Ile Phe Gly Thr Tyr Ser Asp Ala Ala Pro Ala Met Pro Pro Ile
                85                  90                  95

Pro Pro Ala Leu Arg Lys Asn Arg Gly Met Leu Ala
            100                 105

<210> SEQ ID NO 172
<211> LENGTH: 178
<212> TYPE: PRT
<213> ORGANISM: Buchnera aphidicola

<400> SEQUENCE: 172

Met Val Ala Cys Lys Val Ile Leu Ala Val Ala Val Val Phe Val Ala
1               5                   10                  15

Ala Val Gln Gly Arg Pro Gly Gly Glu Pro Glu Trp Ala Ala Pro Ile
            20                  25                  30

Phe Ala Glu Leu Lys Ser Val Ser Asp Asn Ile Thr Asn Leu Val Gly
        35                  40                  45

Leu Asp Asn Ala Gly Glu Tyr Ala Thr Ala Ala Lys Asn Asn Leu Asn
    50                  55                  60

Ala Phe Ala Glu Ser Leu Lys Thr Glu Ala Ala Val Phe Ser Lys Ser
65                  70                  75                  80

Phe Glu Gly Lys Ala Ser Ala Ser Asp Val Phe Lys Glu Ser Thr Lys
                85                  90                  95

Asn Phe Gln Ala Val Val Asp Thr Tyr Ile Lys Asn Leu Pro Lys Asp
            100                 105                 110

Leu Thr Leu Lys Asp Phe Thr Glu Lys Ser Glu Gln Ala Leu Lys Tyr
        115                 120                 125

Met Val Glu His Gly Thr Glu Ile Thr Lys Lys Ala Gln Gly Asn Thr
    130                 135                 140

Glu Thr Glu Lys Glu Ile Lys Glu Phe Phe Lys Lys Gln Ile Glu Asn
145                 150                 155                 160

Leu Ile Gly Gln Gly Lys Ala Leu Gln Ala Lys Ile Ala Glu Ala Lys
                165                 170                 175
```

Lys Ala

<210> SEQ ID NO 173
<211> LENGTH: 311
<212> TYPE: PRT
<213> ORGANISM: Buchnera aphidicola

<400> SEQUENCE: 173

```
Met Lys Thr Ser Ser Ser Lys Val Phe Ala Ser Cys Val Ala Ile Val
1               5                   10                  15

Cys Leu Ala Ser Val Ala Asn Ala Leu Pro Val Gln Lys Ser Val Ala
            20                  25                  30

Ala Thr Thr Glu Asn Pro Ile Val Glu Lys His Gly Cys Arg Ala His
        35                  40                  45

Lys Asn Leu Val Arg Gln Asn Val Val Asp Leu Lys Thr Tyr Asp Ser
    50                  55                  60

Met Leu Ile Thr Asn Glu Val Val Gln Lys Gln Ser Asn Glu Val Gln
65                  70                  75                  80

Ser Ser Glu Gln Ser Asn Glu Gly Gln Asn Ser Glu Gln Ser Asn Glu
                85                  90                  95

Gly Gln Asn Ser Glu Gln Ser Asn Glu Val Gln Ser Ser Glu His Ser
            100                 105                 110

Asn Glu Gly Gln Asn Ser Lys Gln Ser Asn Glu Gly Gln Asn Ser Glu
        115                 120                 125

Gln Ser Asn Glu Val Gln Ser Ser Glu His Ser Asn Glu Gly Gln Asn
    130                 135                 140

Ser Glu Gln Ser Asn Glu Val Gln Ser Ser Glu His Ser Asn Glu Gly
145                 150                 155                 160

Gln Asn Ser Lys Gln Ser Asn Glu Gly Gln Asn Ser Lys Gln Ser Asn
                165                 170                 175

Glu Val Gln Ser Ser Glu His Trp Asn Glu Gly Gln Asn Ser Lys Gln
            180                 185                 190

Ser Asn Glu Asp Gln Asn Ser Glu Gln Ser Asn Glu Gly Gln Asn Ser
        195                 200                 205

Lys Gln Ser Asn Glu Gly Gln Asn Ser Lys Gln Ser Asn Glu Asp Gln
    210                 215                 220

Asn Ser Glu Gln Ser Asn Glu Gly Gln Asn Ser Lys Gln Ser Asn Glu
225                 230                 235                 240

Val Gln Ser Ser Glu Gln Ser Asn Glu Gly Gln Asn Ser Lys Gln Ser
                245                 250                 255

Asn Glu Gly Gln Ser Ser Glu Gln Ser Asn Glu Gly Gln Asn Ser Lys
            260                 265                 270

Gln Ser Asn Glu Val Gln Ser Pro Glu Glu His Tyr Asp Leu Pro Asp
        275                 280                 285

Pro Glu Ser Ser Tyr Glu Ser Glu Glu Thr Lys Gly Ser His Glu Ser
    290                 295                 300

Gly Asp Asp Ser Glu His Arg
305                 310
```

<210> SEQ ID NO 174
<211> LENGTH: 431
<212> TYPE: PRT
<213> ORGANISM: Buchnera aphidicola

<400> SEQUENCE: 174

```
Met Lys Thr Ile Ile Leu Gly Leu Cys Leu Phe Gly Ala Leu Phe Trp
1               5                   10                  15
Ser Thr Gln Ser Met Pro Val Gly Glu Val Ala Pro Ala Val Pro Ala
            20                  25                  30
Val Pro Ser Glu Ala Val Pro Gln Lys Gln Val Glu Ala Lys Pro Glu
        35                  40                  45
Thr Asn Ala Ala Ser Pro Val Ser Asp Ala Lys Pro Glu Ser Asp Ser
    50                  55                  60
Lys Pro Val Asp Ala Glu Val Lys Pro Thr Val Ser Glu Val Lys Ala
65                  70                  75                  80
Glu Ser Glu Gln Lys Pro Ser Gly Glu Pro Lys Pro Glu Ser Asp Ala
            85                  90                  95
Lys Pro Val Val Ala Ser Glu Ser Lys Pro Glu Ser Asp Pro Lys Pro
        100                 105                 110
Ala Ala Val Val Glu Ser Lys Pro Glu Asn Asp Ala Val Ala Pro Glu
    115                 120                 125
Thr Asn Asn Asp Ala Lys Pro Glu Asn Ala Ala Ala Pro Val Ser Glu
    130                 135                 140
Asn Lys Pro Ala Thr Asp Ala Lys Ala Glu Thr Glu Leu Ile Ala Gln
145                 150                 155                 160
Ala Lys Pro Glu Ser Lys Pro Ala Ser Asp Leu Lys Ala Glu Pro Glu
            165                 170                 175
Ala Ala Lys Pro Asn Ser Glu Val Pro Val Ala Leu Pro Leu Asn Pro
        180                 185                 190
Thr Glu Thr Lys Ala Thr Gln Gln Ser Val Glu Thr Asn Gln Val Glu
    195                 200                 205
Gln Ala Ala Pro Ala Ala Gln Ala Asp Pro Ala Ala Ala Pro Ala
    210                 215                 220
Ala Asp Pro Ala Pro Ala Pro Ala Ala Pro Val Ala Ala Glu Glu
225                 230                 235                 240
Ala Lys Leu Ser Glu Ser Ala Pro Ser Thr Glu Asn Lys Ala Ala Glu
            245                 250                 255
Glu Pro Ser Lys Pro Ala Glu Gln Gln Ser Ala Lys Pro Val Glu Asp
        260                 265                 270
Ala Val Pro Ala Ala Ser Glu Ile Ser Glu Thr Lys Val Ser Pro Ala
    275                 280                 285
Val Pro Ala Val Pro Glu Val Pro Ala Ser Pro Ser Ala Pro Ala Val
    290                 295                 300
Ala Asp Pro Val Ser Ala Pro Glu Ala Glu Lys Asn Ala Glu Pro Ala
305                 310                 315                 320
Lys Ala Ala Asn Ser Ala Glu Pro Ala Val Gln Ser Glu Ala Lys Pro
            325                 330                 335
Ala Glu Asp Ile Gln Lys Ser Gly Ala Val Val Ser Ala Glu Asn Pro
        340                 345                 350
Lys Pro Val Glu Glu Gln Lys Pro Ala Glu Val Ala Lys Pro Ala Glu
    355                 360                 365
Gln Ser Lys Ser Glu Ala Pro Ala Glu Ala Pro Lys Pro Thr Glu Gln
    370                 375                 380
Ser Ala Ala Glu Glu Pro Lys Lys Pro Glu Ser Ala Asn Asp Glu Lys
385                 390                 395                 400
Lys Glu Gln His Ser Val Asn Lys Arg Asp Ala Thr Lys Glu Lys Lys
            405                 410                 415
Pro Thr Asp Ser Ile Met Lys Lys Gln Lys Gln Lys Lys Ala Asn
```

<210> SEQ ID NO 175
<211> LENGTH: 160
<212> TYPE: PRT
<213> ORGANISM: Buchnera aphidicola

<400> SEQUENCE: 175

Met Asn Gly Lys Ile Val Leu Cys Phe Ala Val Val Phe Ile Gly Gln
1               5                   10                  15

Ala Met Ser Ala Ala Thr Gly Thr Thr Pro Glu Val Glu Asp Ile Lys
            20                  25                  30

Lys Val Ala Glu Gln Met Ser Gln Thr Phe Met Ser Val Ala Asn His
        35                  40                  45

Leu Val Gly Ile Thr Pro Asn Ser Ala Asp Ala Gln Lys Ser Ile Glu
    50                  55                  60

Lys Ile Arg Thr Ile Met Asn Lys Gly Phe Thr Asp Met Glu Thr Glu
65                  70                  75                  80

Ala Asn Lys Met Lys Asp Ile Val Arg Lys Asn Ala Asp Pro Lys Leu
                85                  90                  95

Val Glu Lys Tyr Asp Glu Leu Glu Lys Glu Leu Lys Lys His Leu Ser
            100                 105                 110

Thr Ala Lys Asp Met Phe Glu Asp Lys Val Val Lys Pro Ile Gly Glu
        115                 120                 125

Lys Val Glu Leu Lys Lys Ile Thr Glu Asn Val Ile Lys Thr Thr Lys
    130                 135                 140

Asp Met Glu Ala Thr Met Asn Lys Ala Ile Asp Gly Phe Lys Lys Gln
145                 150                 155                 160

<210> SEQ ID NO 176
<211> LENGTH: 415
<212> TYPE: PRT
<213> ORGANISM: Buchnera aphidicola

<400> SEQUENCE: 176

Met His Leu Phe Leu Ala Leu Gly Leu Phe Ile Val Cys Gly Met Val
1               5                   10                  15

Asp Ala Thr Phe Tyr Asn Pro Arg Ser Gln Thr Phe Asn Gln Leu Met
            20                  25                  30

Glu Arg Arg Gln Arg Ser Ile Pro Ile Pro Tyr Ser Tyr Gly Tyr His
        35                  40                  45

Tyr Asn Pro Ile Glu Pro Ser Ile Asn Val Leu Asp Ser Leu Ser Glu
    50                  55                  60

Gly Leu Asp Ser Arg Ile Asn Thr Phe Lys Pro Ile Tyr Gln Asn Val
65                  70                  75                  80

Lys Met Ser Thr Gln Asp Val Asn Ser Val Pro Arg Thr Gln Tyr Gln
                85                  90                  95

Pro Lys Asn Ser Leu Tyr Asp Ser Glu Tyr Ile Ser Ala Lys Asp Ile
            100                 105                 110

Pro Ser Leu Phe Pro Glu Glu Asp Ser Tyr Asp Tyr Lys Tyr Leu Gly
        115                 120                 125

Ser Pro Leu Asn Lys Tyr Leu Thr Arg Pro Ser Thr Gln Glu Ser Gly
    130                 135                 140

Ile Ala Ile Asn Leu Val Ala Ile Lys Glu Thr Ser Val Phe Asp Tyr
145                 150                 155                 160

Gly Phe Pro Thr Tyr Lys Ser Pro Tyr Ser Ser Asp Ser Val Trp Asn

```
            165                 170                 175
Phe Gly Ser Lys Ile Pro Asn Thr Val Phe Glu Asp Pro Gln Ser Val
            180                 185                 190

Glu Ser Asp Pro Asn Thr Phe Lys Val Ser Ser Pro Thr Ile Lys Ile
            195                 200                 205

Val Lys Leu Leu Pro Glu Thr Pro Glu Gln Glu Ser Ile Ile Thr Thr
        210                 215                 220

Thr Lys Asn Tyr Glu Leu Asn Tyr Lys Thr Thr Gln Glu Thr Pro Thr
225                 230                 235                 240

Glu Ala Glu Leu Tyr Pro Ile Thr Ser Glu Glu Phe Gln Thr Glu Asp
                245                 250                 255

Glu Trp His Pro Met Val Pro Lys Glu Asn Thr Thr Lys Asp Glu Ser
                260                 265                 270

Ser Phe Ile Thr Thr Glu Glu Pro Leu Thr Glu Asp Lys Ser Asn Ser
                275                 280                 285

Ile Thr Ile Glu Lys Thr Gln Thr Glu Asp Glu Ser Asn Ser Ile Glu
            290                 295                 300

Phe Asn Ser Ile Arg Thr Glu Glu Lys Ser Asn Ser Ile Thr Thr Glu
305                 310                 315                 320

Glu Asn Gln Lys Glu Asp Asp Glu Ser Met Ser Thr Thr Ser Gln Glu
                325                 330                 335

Thr Thr Thr Ala Phe Asn Leu Asn Asp Thr Phe Asp Thr Asn Arg Tyr
                340                 345                 350

Ser Ser Ser His Glu Ser Leu Met Leu Arg Ile Arg Glu Leu Met Lys
                355                 360                 365

Asn Ile Ala Asp Gln Gln Asn Lys Ser Gln Phe Arg Thr Val Asp Asn
                370                 375                 380

Ile Pro Ala Lys Ser Gln Ser Asn Leu Ser Ser Asp Glu Ser Thr Asn
385                 390                 395                 400

Gln Gln Phe Glu Pro Gln Leu Val Asn Gly Ala Asp Thr Tyr Lys
                405                 410                 415

<210> SEQ ID NO 177
<211> LENGTH: 126
<212> TYPE: PRT
<213> ORGANISM: Sitophilus zeamais

<400> SEQUENCE: 177

Met Thr Arg Thr Met Leu Phe Leu Ala Cys Val Ala Ala Leu Tyr Val
1               5                   10                  15

Cys Ile Ser Ala Thr Ala Gly Lys Pro Glu Glu Phe Ala Lys Leu Ser
            20                  25                  30

Asp Glu Ala Pro Ser Asn Asp Gln Ala Met Tyr Glu Ser Ile Gln Arg
        35                  40                  45

Tyr Arg Arg Phe Val Asp Gly Asn Arg Tyr Asn Gly Gln Gln Gln
    50                  55                  60

Gln Gln Gln Pro Lys Gln Trp Glu Val Arg Pro Asp Leu Ser Arg Asp
65                  70                  75                  80

Gln Arg Gly Asn Thr Lys Ala Gln Val Glu Ile Asn Lys Lys Gly Asp
                85                  90                  95

Asn His Asp Ile Asn Ala Gly Trp Gly Lys Asn Ile Asn Gly Pro Asp
            100                 105                 110

Ser His Lys Asp Thr Trp His Val Gly Gly Ser Val Arg Trp
        115                 120                 125
```

<210> SEQ ID NO 178
<211> LENGTH: 16
<212> TYPE: PRT
<213> ORGANISM: Acyrthosiphon pisum

<400> SEQUENCE: 178

Arg Gln Ile Lys Ile Trp Phe Gln Asn Arg Arg Met Lys Trp Lys Lys
1               5                   10                  15

<210> SEQ ID NO 179
<211> LENGTH: 13
<212> TYPE: PRT
<213> ORGANISM: Artificial Sequence
<220> FEATURE:
<223> OTHER INFORMATION: Tat peptide

<400> SEQUENCE: 179

Gly Arg Lys Lys Arg Arg Gln Arg Arg Arg Pro Pro Gln
1               5                   10

<210> SEQ ID NO 180
<211> LENGTH: 18
<212> TYPE: PRT
<213> ORGANISM: Human immunodeficiency virus 1

<400> SEQUENCE: 180

Leu Leu Ile Ile Leu Arg Arg Arg Ile Arg Lys Gln Ala His Ala His
1               5                   10                  15

Ser Lys

<210> SEQ ID NO 181
<211> LENGTH: 27
<212> TYPE: PRT
<213> ORGANISM: Artificial Sequence
<220> FEATURE:
<223> OTHER INFORMATION: Transportan

<400> SEQUENCE: 181

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 182
<211> LENGTH: 27
<212> TYPE: PRT
<213> ORGANISM: Artificial Sequence
<220> FEATURE:
<223> OTHER INFORMATION: MPG

<400> SEQUENCE: 182

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 183
<211> LENGTH: 21
<212> TYPE: PRT
<213> ORGANISM: Artificial Sequence
<220> FEATURE:
<223> OTHER INFORMATION: Pep-1

<400> SEQUENCE: 183

-continued

```
Lys Glu Thr Trp Trp Glu Thr Trp Trp Thr Glu Trp Ser Gln Pro Lys
1               5                   10                  15
Lys Lys Arg Lys Val
            20

<210> SEQ ID NO 184
<211> LENGTH: 18
<212> TYPE: PRT
<213> ORGANISM: Artificial Sequence
<220> FEATURE:
<223> OTHER INFORMATION: MAP

<400> SEQUENCE: 184

Lys Leu Ala Leu Lys Leu Ala Leu Lys Ala Leu Lys Ala Ala Leu Lys
1               5                   10                  15
Leu Ala

<210> SEQ ID NO 185
<211> LENGTH: 9
<212> TYPE: PRT
<213> ORGANISM: Artificial Sequence
<220> FEATURE:
<223> OTHER INFORMATION: R6W3

<400> SEQUENCE: 185

Arg Arg Trp Trp Arg Arg Trp Arg Arg
1               5

<210> SEQ ID NO 186
<211> LENGTH: 20
<212> TYPE: DNA
<213> ORGANISM: Artificial Sequence
<220> FEATURE:
<223> OTHER INFORMATION: Bacillus, forward primer

<400> SEQUENCE: 186
gaggtagacg aagcgacctg                                              20

<210> SEQ ID NO 187
<211> LENGTH: 20
<212> TYPE: DNA
<213> ORGANISM: Artificial Sequence
<220> FEATURE:
<223> OTHER INFORMATION: Bacillus, reverse primer

<400> SEQUENCE: 187
ttccctcacg gtactggttc                                              20

<210> SEQ ID NO 188
<211> LENGTH: 20
<212> TYPE: DNA
<213> ORGANISM: Artificial Sequence
<220> FEATURE:
<223> OTHER INFORMATION: Universal bacterial primer 27F

<400> SEQUENCE: 188
agagtttgat cmtggctcag                                              20

<210> SEQ ID NO 189
<211> LENGTH: 16
<212> TYPE: DNA
<213> ORGANISM: Artificial Sequence
<220> FEATURE:
<223> OTHER INFORMATION: Universal bacterial primer 1492R

<400> SEQUENCE: 189
```

```
taccttgtta cgactt                                               16
```

<210> SEQ ID NO 190
<211> LENGTH: 1583
<212> TYPE: DNA
<213> ORGANISM: Lactobacillus kunkeei

<400> SEQUENCE: 190

```
ttccttagaa aggaggtgat ccagccgcag gttctcctac ggctaccttg ttacgacttc    60
accctaatca tctgtcccac cttagacgac tagctcctaa aaggttaccc catcgtcttt   120
gggtgttaca aactctcatg gtgtgacggg cggtgtgtac aaggcccggg aacgtattca   180
ccgtggcatg ctgatccacg attactagtg attccaactt catgcaggcg agttgcagcc   240
tgcaatccga actgagaatg gctttaagag attagcttga cctcgcggtt tcgcgactcg   300
ttgtaccatc cattgtagca cgtgtgtagc ccagctcata ggggcatga tgatttgacg   360
tcgtccccac cttcctccgg tttatcaccg gcagtctcac tagagtgccc aactaaatgc   420
tggcaactaa taataagggt tgcgctcgtt gcgggactta acccaacatc tcacgacacg   480
agctgacgac aaccatgcac cacctgtcat tctgtccccg aagggaacgc ccaatctctt   540
gggttggcag aagatgtcaa gagctggtaa ggttcttcgc gtagcatcga attaaaccac   600
atgctccacc acttgtgcgg gccccgtca attcctttga gtttcaacct tgcggtcgta   660
ctccccaggc ggaatactta atgcgttagc tgcggcactg aagggcggaa accctccaac   720
acctagtatt catcgtttac ggcatggact accagggtat ctaatcctgt tcgctaccca   780
tgctttcgag cctcagcgtc agtaacagac cagaaagccg ccttcgccac tggtgttctt   840
ccatatatct acgcatttca ccgctacaca tggagttcca cttttcctctt ctgtactcaa   900
gttttgtagt ttccactgca cttcctcagt tgagctgagg gctttcacag cagacttaca   960
aaaccgcctg cgctcgcttt acgcccaata aatccggaca acgcttgcca cctacgtatt  1020
accgcggctg ctggcacgta gttagccgtg gctttctggt aaataccgt caaagtgtta  1080
acagttactc taaacttgt tcttctttaa caacagagtt ttacgatccg aaaaccttca  1140
tcactcacgc ggcgttgctc catcagactt tcgtccattg tggaagattc cctactgctg  1200
cctcccgtag gagtctgggc cgtgtctcag tcccaatgtg gccgattacc ctctcaggtc  1260
ggctacgtat catcgtcttg gtgggctttt atctcaccaa ctaactaata cggcgcgggt  1320
ccatcccaaa gtgatagcaa agccatcttt caagttggaa ccatgcggtt ccaactaatt  1380
atgcggtatt agcacttgtt tccaaatgtt atccccgct tcggggcagg ttacccacgt  1440
gttactcacc agttcgccac tcgctccgaa tccaaaaatc atttatgcaa gcataaaatc  1500
aatttgggag aactcgttcg acttgcatgt attaggcacg ccgccagcgt tcgtcctgag  1560
ccaggatcaa actctcatct taa                                          1583
```

<210> SEQ ID NO 191
<211> LENGTH: 1395
<212> TYPE: DNA
<213> ORGANISM: Lactobacillus Firm-4

<400> SEQUENCE: 191

```
acgaacgctg gcggcgtgcc taatacatgc aagtcgagcg cgggaagtca gggaagcctt    60
cgggtggaac tggtggaacg agcggcggat gggtgagtaa cacgtaggta acctgcccta   120
aagcggggga taccatctgg aaacaggtgc taataccgca taaacccagc agtcacatga   180
```

-continued

```
gtgctggttg aaagacggct tcggctgtca ctttaggatg gacctgcggc gtattagcta     240
gttggtggag taacggttca ccaaggcaat gatacgtagc cgacctgaga gggtaatcgg     300
ccacattggg actgagacac ggcccaaact cctacgggag gcagcagtag ggaatcttcc     360
acaatggacg caagtctgat ggagcaacgc cgcgtggatg aagaaggtct tcggatcgta     420
aaatcctgtt gttgaagaag aacggttgtg agagtaactg ctcataacgt gacggtaatc     480
aaccagaaag tcacggctaa ctacgtgcca gcagccgcgg taatacgtag gtggcaagcg     540
ttgtccggat ttattgggcg taagggagc gcaggcggtc ttttaagtct gaatgtgaaa      600
gccctcagct taactgagga agagcatcgg aaactgagag acttgagtgc agaagaggag     660
agtggaactc catgtgtagc ggtgaaatgc gtagatatat ggaagaacac cagtggcgaa     720
ggcggctctc tggtctgtta ctgacgctga ggctcgaaag catgggtagc gaacaggatt     780
agataccctg gtagtccatg ccgtaaacga tgagtgctaa gtgttgggag gtttccgcct     840
ctcagtgctg cagctaacgc attaagcact ccgcctgggg agtacgaccg caaggttgaa     900
actcaaagga attgacgggg gcccgcacaa gcggtggagc atgtggttta attcgaagca     960
acgcgaagaa ccttaccagg tcttgacatc tcctgcaagc ctaagagatt agggggttccc     1020 ttcggggaca ggaagacagg tggtgcatgg ttgtcgtcag ctcgtgtcgt gagatgttgg     1080
gttaagtccc gcaacgagcg caaccccttgt tactagttgc cagcattaag ttgggcactc     1140
tagtgagact gccggtgaca aaccggagga aggtggggac gacgtcaaat catcatgccc     1200
cttatgacct gggctacaca cgtgctacaa tggatggtac aatgagaagc gaactcgcga     1260
ggggaagctg atctctgaaa accattctca gttcggattg caggctgcaa ctcgcctgca     1320
tgaagctgga atcgctagta atcgcggatc agcatgccgc ggtgaatacg ttcccgggcc     1380
ttgtacacac cgccc                                                    1395
```

<210> SEQ ID NO 192
<211> LENGTH: 220
<212> TYPE: PRT
<213> ORGANISM: Sitophilus zeamais

<400> SEQUENCE: 192

```
Met Lys Glu Thr Thr Val Val Trp Ala Lys Leu Phe Leu Ile Leu Ile
1               5                   10                  15

Ile Leu Ala Lys Pro Leu Gly Leu Lys Ala Val Asn Glu Cys Lys Arg
            20                  25                  30

Leu Gly Asn Asn Ser Cys Arg Ser His Gly Glu Cys Cys Ser Gly Phe
        35                  40                  45

Cys Phe Ile Glu Pro Gly Trp Ala Leu Gly Val Cys Lys Arg Leu Gly
    50                  55                  60

Thr Pro Lys Lys Ser Asp Asp Ser Asn Asn Gly Lys Asn Ile Glu Lys
65                  70                  75                  80

Asn Asn Gly Val His Glu Arg Ile Asp Asp Val Phe Glu Arg Gly Val
                85                  90                  95

Cys Ser Tyr Tyr Lys Gly Pro Ser Ile Thr Ala Asn Gly Asp Val Phe
            100                 105                 110

Asp Glu Asn Glu Met Thr Ala Ala His Arg Thr Leu Pro Phe Asn Thr
        115                 120                 125

Met Val Lys Val Glu Gly Met Gly Thr Ser Val Val Lys Ile Asn
    130                 135                 140

Asp Arg Lys Thr Ala Ala Asp Gly Lys Val Met Leu Leu Ser Arg Ala
145                 150                 155                 160
```

```
Ala Ala Glu Ser Leu Asn Ile Asp Glu Asn Thr Gly Pro Val Gln Cys
            165                 170                 175

Gln Leu Lys Phe Val Leu Asp Gly Ser Gly Cys Thr Pro Asp Tyr Gly
        180                 185                 190

Asp Thr Cys Val Leu His His Glu Cys Cys Ser Gln Asn Cys Phe Arg
            195                 200                 205

Glu Met Phe Ser Asp Lys Gly Phe Cys Leu Pro Lys
    210                 215                 220

<210> SEQ ID NO 193
<211> LENGTH: 13
<212> TYPE: PRT
<213> ORGANISM: Pandinum imperator

<400> SEQUENCE: 193

Phe Leu Ser Thr Ile Trp Asn Gly Ile Lys Gly Leu Leu
1               5                   10

<210> SEQ ID NO 194
<211> LENGTH: 13
<212> TYPE: PRT
<213> ORGANISM: Urodacus yaschenkoi

<400> SEQUENCE: 194

Ile Leu Ser Ala Ile Trp Ser Gly Ile Lys Ser Leu Phe
1               5                   10

<210> SEQ ID NO 195
<211> LENGTH: 13
<212> TYPE: PRT
<213> ORGANISM: Scorpiops tibetanus

<400> SEQUENCE: 195

Leu Trp Gly Lys Leu Trp Glu Gly Val Lys Ser Leu Ile
1               5                   10

<210> SEQ ID NO 196
<211> LENGTH: 22
<212> TYPE: PRT
<213> ORGANISM: Apostichopus japonicus

<400> SEQUENCE: 196

Phe Pro Phe Leu Lys Leu Ser Leu Lys Ile Pro Lys Ser Ala Ile Lys
1               5                   10                  15

Ser Ala Ile Lys Arg Leu
            20

<210> SEQ ID NO 197
<211> LENGTH: 13
<212> TYPE: PRT
<213> ORGANISM: Urodacus yaschenkoi

<400> SEQUENCE: 197

Ile Leu Ser Ala Ile Trp Ser Gly Ile Lys Gly Leu Leu
1               5                   10

<210> SEQ ID NO 198
<211> LENGTH: 27
<212> TYPE: PRT
<213> ORGANISM: Artificial Sequence
<220> FEATURE:
<223> OTHER INFORMATION: Uy192 + cell penetrating peptide
```

```
<400> SEQUENCE: 198

Tyr Gly Arg Lys Lys Arg Arg Gln Arg Arg Arg Phe Leu Ser Thr Ile
1               5                   10                  15

Trp Asn Gly Ile Lys Gly Leu Leu Phe Ala Met
            20              25
```

COMPOSITIONS AND RELATED METHODS FOR AGRICULTURE

CROSS-REFERENCE TO RELATED APPLICATIONS

This application claims priority to U.S. Provisional Application No. 62/450,017, filed on Jan. 24, 2017, and U.S. Provisional Application No. 62/583,736, filed on Nov. 9, 2017, the contents of which are hereby incorporated herein by reference in their entireties.

SEQUENCE LISTING

The instant application contains a Sequence Listing which has been submitted electronically in ASCII format and is hereby incorporated by reference in its entirety. Said ASCII copy, created Aug. 22, 2019, is named 51215-002003_Sequence_Listing_08.22.19_ST25 and is 227,509 bytes in size.

BACKGROUND

Certain invertebrates, such as nematodes and arthropods (e.g., insects, e.g., European honey bees (*Apis melliferia*) or silkworms (*Bombyx mori*)), are utilized in agriculture for pollination efforts and pest control as well as in commerce for the production of commercial products, such as honey or silk. To cultivate beneficial nematodes and arthropods for use in agricultural or commercial industries, there is a need in the art for ways to promote the growth and fitness of beneficial invertebrates.

SUMMARY OF THE INVENTION

Disclosed herein are compositions and methods for modulating the fitness of invertebrates for agriculture or commerce. The composition includes an agent that alters a level, activity, or metabolism of one or more microorganisms resident in a host, the alteration resulting in a modulation in the host's fitness.

In one aspect, provided herein is a method for increasing the fitness of a honeybee, the method including administering to the honeybee a composition including an effective amount of an organophosphorus insecticide-metabolizing bacteria formulated with an insect comestible carrier.

In some embodiments, the administration involves delivering the composition to a honeybee hive or at least one habitat where the honeybee grows, lives, reproduces, or feeds.

In some embodiments, the composition may be a liquid, a solid, an aerosol, a paste, a gel, or a gas.

In some embodiments, the organophosphorus insecticide may be fenitrothion.

In some embodiments, the carrier may be a seed coating.

In some embodiments, the honeybee may be in a honeybee colony.

In another aspect, provided herein is a composition including an effective amount of an organophosphorus insecticide-metabolizing bacteria formulated with an insect comestible carrier as a liquid, a solid, an aerosol, a paste, a gel, or a gas.

In some embodiments of the second aspect, the organophosphorus insecticide-metabolizing bacteria metabolize fenitrothion.

In some embodiments of the second aspect, the carrier is a seed coating.

In some embodiments of the second aspect, the organophosphorus insecticide-metabolizing bacteria are at a concentration of at least 100,000 cells/ml (e.g., at least about 100,000 cells/ml, at least about 150,000 cells/ml, at least about 200,000 cells/ml, at least about 250,000 cells/ml, at least about 300,000 cells/ml, at least about 350,000 cells/ml, at least about 400,000 cells/ml, at least about 450,000 cells/ml, or at least about 500,000 cells/ml).

In yet another aspect, the composition includes an agent that alters a level, activity, or metabolism of one or more microorganisms resident in an insect host, the alteration resulting in an increase in the insect host's fitness.

In another instance, the composition includes an agent that alters a level, activity, or metabolism of one or more microorganisms resident in a nematode host, the alteration resulting in an increase in the nematode host's fitness.

In some embodiments of any of the above compositions, the one or more microorganisms may be a bacterium or fungus resident in the host. In some embodiments, the bacterium resident in the host is at least one selected from the group consisting of *Candidatus* spp, *Buchenera* spp, *Blattabacterium* spp, *Baumania* spp, *Wigglesworthia* spp, *Wolbachia* spp, *Rickettsia* spp, *Orientia* spp, *Sodalis* spp, *Burkholderia* spp, *Cupriavidus* spp, *Frankia* spp, *Snirhizobium* spp, *Streptococcus* spp, *Wolinella* spp, *Xylella* spp, *Erwinia* spp, *Agrobacterium* spp, *Bacillus* spp, *Paenibacillus* spp, *Streptomyces* spp, *Micrococcus* spp, *Corynebacterium* spp, *Acetobacter* spp, *Cyanobacteria* spp, *Salmonella* spp, *Rhodococcus* spp, *Pseudomonas* spp, *Lactobacillus* spp, *Enterococcus* spp, *Alcaligenes* spp, *Klebsiella* spp, *Paenibacillus* spp, *Arthrobacter* spp, *Corynebacterium* spp, *Brevibacterium* spp, *Thermus* spp, *Pseudomonas* spp, *Clostridium* spp, and *Escherichia* spp. In some embodiments, the fungus resident in the host is at least one selected from the group consisting of *Candida, Metschnikowia, Debaromyces, Starmerella, Pichia, Cryptococcus, Pseudozyma, Symbiotaphrina bucneri, Symbiotaphrina Scheffersomyces shehatae, Scheffersomyces stipites, Cryptococcus, Trichosporon, Amylostereum areolatum, Epichloe* spp, *Pichia pinus, Hansenula capsulate, Daldinia decipien, Ceratocytis* spp, *Ophiostoma* spp, and *Attamyces bromatificus*.

In any of the above compositions, the agent, which hereinafter may also be referred to as a modulating agent, may alter the growth, division, viability, metabolism, and/or longevity of the microorganism resident in the host. In any of the above embodiments, the modulating agent may decrease the viability of the one or more microorganisms resident in the host. In some embodiments, the modulating agent increases growth or viability of the one or more microorganisms resident in the host.

In any of the above embodiments, the modulating agent is a phage, a polypeptide, a small molecule, an antibiotic, a bacterium, or any combination thereof.

In some embodiments, the phage binds a cell surface protein on a bacterium resident in the host. In some embodiments, the phage is virulent to a bacterium resident in the host. In some embodiments, the phage is at least one selected from the group consisting of Myoviridae, Siphoviridae, Podoviridae, Lipothrixviridae, Rudiviridae, Ampullaviridae, Bicaudaviridae, Clavaviridae, Corticoviridae, Cystoviridae, Fuselloviridae, Globuloviridae, Guttaviridae, Inoviridae, Leviviridae, Microviridae, Plasmaviridae, and Tectiviridae.

In some embodiments, the polypeptide is at least one of a bacteriocin, R-type bacteriocin, nodule C-rich peptide, antimicrobial peptide, lysin, or bacteriocyte regulatory peptide.

In some embodiments, the small molecule is a metabolite.

In some embodiments, the antibiotic is a broad-spectrum antibiotic.

In some embodiments, the modulating agent is a naturally occurring bacteria. In some embodiments, the bacteria is at least one selected from the group consisting of *Bartonella apis, Parasaccharibacter apium, Frischella perrara, Snodgrassella alvi, Gilliamela apicola, Bifidobacterium* spp, and *Lactobacillus* spp. In some embodiments, the bacterium is at least one selected from the group consisting of *Candidatus* spp, *Buchenera* spp, *Blattabacterium* spp, *Baumania* spp, *Wigglesworthia* spp, *Wolbachia* spp, *Rickettsia* spp, *Orientia* spp, *Sodalis* spp, *Burkholderia* spp, *Cupriavidus* spp, *Frankia* spp, *Snirhizobium* spp, *Streptococcus* spp, *Wolinella* spp, *Xylella* spp, *Erwinia* spp, *Agrobacterium* spp, *Bacillus* spp, *Paenibacillus* spp, *Streptomyces* spp, *Micrococcus* spp, *Corynebacterium* spp, *Acetobacter* spp, *Cyanobacteria* spp, *Salmonella* spp, *Rhodococcus* spp, *Pseudomonas* spp, *Lactobacillus* spp, *Enterococcus* spp, *Alcaligenes* spp, *Klebsiella* spp, *Paenibacillus* spp, *Arthrobacter* spp, *Corynebacterium* spp, *Brevibacterium* spp, *Thermus* spp, *Pseudomonas* spp, *Clostridium* spp, and *Escherichia* spp. In certain instances, the bacterium is a naturally occurring bacterium that is capable of degrading pesticides such as organophosphorus insecticides (e.g., phosphorothioate, e.g., fenitrothion).

In any of the above compositions, host fitness may be measured by survival, reproduction, or metabolism of the host. In some embodiments, the modulating agent modulates the host's fitness by decreasing pesticidal susceptibility of the host (e.g., susceptibility to a pesticide listed in Table 12). In some embodiments, the pesticidal susceptibility is bactericidal or fungicidal susceptibility. In some embodiments, the pesticidal susceptibility is insecticidal or nematicidal susceptibility.

In any of the above compositions, the composition may include a plurality of different modulating agents. In some embodiments, the composition includes a modulating agent and a pesticidal agent (e.g., a pesticide listed in Table 12). In some embodiments, the pesticidal agent is a bactericidal or fungicidal agent. In some embodiments, the pesticidal agent is an insecticidal or nematicidal agent.

In any of the above compositions, the composition may include a modulating agent and an agent that increases crop growth.

In any of the above compositions, modulating agent may be linked to a second moiety. In some embodiments, the second moiety is a modulating agent.

In any of the above compositions, the modulating agent may be linked to a targeting domain. In some embodiments, the targeting domain targets the modulating agent to a target site in the host. In some embodiments, the targeting domain targets the modulating agent to the one or more microorganisms resident in the host.

In any of the above compositions, the modulating agent may include an inactivating pre- or pro-sequence, thereby forming a precursor modulating agent. In some embodiments, the precursor modulating agent is converted to an active form in the host.

In any of the above compositions, the modulating agent may include a linker. In some embodiments, the linker is a cleavable linker.

In any of the above compositions, the composition may further include a carrier. In some instances, the carrier may be an agriculturally acceptable carrier.

In any of the above compositions, the composition may further include a host bait, a sticky agent, or a combination thereof. In some embodiments, the host bait is a comestible agent and/or a chemoattractant.

In any of the above compositions, the composition may be at a dose effective to modulate host fitness.

In any of the above compositions, the composition may be formulated for delivery to a microorganism inhabiting the gut of the host.

In any of the above compositions, the composition may be formulated for delivery to a microorganism inhabiting a bacteriocyte of the host and/or the gut of the host. In some embodiments, the composition may be formulated for delivery to a plant. In some embodiments, the composition may be formulated for use in a host feeding station.

In any of the above compositions, the composition may be formulated as a liquid, a powder, granules, or nanoparticles. In some embodiments, the composition is formulated as one selected from the group consisting of a liposome, polymer, bacteria secreting peptide, and synthetic nanocapsule. In some embodiments, the synthetic nanocapsule delivers the composition to a target site in the host. In some embodiments, the target site is the gut of the host. In some embodiments, the target site is a bacteriocyte in the host.

In a further aspect, also provided herein are hosts that include any of the above compositions. In some embodiments, the host is an insect. In some embodiments, the insect aids in pest control, pollination, generation of a commercial product, or a combination thereof. In some embodiments, the insect is a species belonging to *Coccinellidae*, Carabidae, Mantidae, *Syrphidae*, Lampyridae, Myrmeliontidase, Chrysopidae, Hemerobiidae, Brachonidae, Ichneumonidae, or *Odonata*. In some embodiments, the insect is a species belonging to Andrenidae, Apidae, Colletidae, Halicitdae, or Megahlidae. In some embodiments, the insect is a species belonging to Bombycidae or Saturniidae. In certain embodiments, the insect is a honey bee or silkworm.

In some embodiments, the host is a nematode. In some embodiments, the nematode is a species belonging to Heterorhabditis or Steinernema.

In yet a further aspect, also provided herein is a system for modulating a host's fitness comprising a modulating agent that targets a microorganism that is required for a host's fitness, wherein the system is effective to modulate the host's fitness, and wherein the host is an insect or nematode. The modulating agent may include any of the compositions described herein. In some embodiments, the modulating agent is formulated as a powder. In some embodiments, the modulating agent is formulated as a solvent. In some embodiments, the modulating agent is formulated as a concentrate. In some embodiments, the modulating agent is formulated as a diluent. In some embodiments, the modulating agent is prepared for delivery by combining any of the previous compositions with a carrier.

In another aspect, also provided herein are methods for modulating the fitness of an insect or nematode using any of the compositions described herein. In one instance, the method of modulating the fitness of an insect or nematode host includes delivering the composition of any one of the previous claims to the host, wherein the modulating agent targets the one or more microorganisms resident in the host, and thereby modulates the host's fitness. In another instance, the method of modulating microbial diversity in an insect or nematode host includes delivering the composition of any one of the previous claims to the host, wherein the modulating agent targets the one or more microorganisms resident in the host, and thereby modulates microbial diversity in the host.

In some embodiments of any of the above methods, the modulating agent may alter the levels of the one or more microorganisms resident in the host. In some embodiments of any of the above methods, the modulating agent may alter the function of the one or more microorganisms resident in the host. In some embodiments, the one or more microorganisms may be a bacterium and/or fungus. In some embodiments, the one or more microorganisms are required for host fitness. In some embodiments, the one or more microorganisms are required for host survival.

In some embodiments of any of the above methods, the delivering step may include providing the modulating agent at a dose and time sufficient to effect the one or more microorganisms, thereby modulating microbial diversity in the host. In some embodiments, the delivering step includes topical application of any of the previous compositions to a plant. In some embodiments, the delivering step includes providing the modulating agent through a genetically engineered plant. In some embodiments, the delivering step includes providing the modulating agent to the host as a comestible. In some embodiments, the delivering step includes providing a host carrying the modulating agent. In some embodiments the host carrying the modulating agent can transmit the modulating agent to one or more additional hosts.

In some embodiments of any of the above methods, the composition is effective to increase health and/or survival of the host. In some embodiments, the composition is effective to increase host fitness, increase host lifespan, increase effective pollination, increase generation of a host product, increase host reproduction, or a combination thereof. In some embodiments, the composition is effective to decrease the host's sensitivity to a pesticidal agent (e.g., a pesticide listed in Table 12). In certain embodiments, the pesticidal agent is a neonicotinoid (e.g., imidacloprid). In certain embodiments, the pesticidal agent is an organophosphorus insecticide (e.g., a phosphorothioate, e.g., fenitrothion). In some embodiments, the composition is effective to increase the host's resistance to an allelochemical agent produced by a plant. In some embodiments, the allelochemical agent is toxic to the host prior to delivery of the composition. In some embodiments, the allelochemical agent is caffeine, soyacystatin N, monoterpenes, diterpene acids, or phenolic compounds.

In some embodiments of any of the above methods, the host is an insect. In some embodiments, the insect aids in pest control, pollination, generation of a commercial product, waste degradation, or a combination thereof. In some embodiments, the insect is a species belonging to *Coccinellidae*, Carabidae, Mantidae, *Syrphidae*, Lampyridae, Myrmeliontidase, Chrysopidae, Hemerobiidae, Brachonidae, Ichneumonidae, or *Odonata*. In some embodiments, the insect is a species belonging to Andrenidae, Apidae, Colletidae, Halicitdae, or Megahlidae. In some embodiments, the insect is a species belonging to Bombycidae or Saturniidae. In certain embodiments, the insect is a honey bee or silkworm.

In some embodiments, the host is a nematode. In some embodiments, the nematode is a species belonging to Heterorhabditis or Steinernema.

In some embodiments of any of the above methods, the delivering step includes delivering any of the previous compositions to a plant. In some embodiments, the plant is an agricultural crop. In some embodiments, the crop is an unharvested crop at the time of delivery. In some embodiments, the crop is a harvested crop at the time of delivery. The some embodiments, the crop comprises harvested fruits or vegetables. In some embodiments, the composition is delivered in an amount and for a duration effective to increase growth of the crop. In some embodiments, the crop includes corn, soybean, or wheat plants.

In another aspect, also provided herein are screening assays to identify modulating agent that modulate the fitness of a host. In one instance, the screening assay to identify a modulating agent that modulates the fitness of a host, includes the steps of (a) exposing a microorganism that can be resident in the host to one or more candidate modulating agents and (b) identifying a modulating agent that increases the fitness of the host.

In some embodiments of the screening assay, the modulating agent is a microorganism resident in the host. In some embodiments, the microorganism is a bacterium. In some embodiments, the bacterium, when resident in the host, increases host fitness. In some embodiments, the bacterium degrades a pesticide (e.g., a pesticide listed in Table 12). In certain embodiments, the pesticide is a neonicotinoid (e.g., imidacloprid) or an organophosphorus insecticide (e.g., a phosphorothioate, e.g., fenitrothion). In some embodiments, the bacterium secretes an amino acid. In certain embodiments, wherein the amino acid is methionine.

In some embodiments of the screening assay, the modulating agent affects an allelochemical-degrading microorganism. In some embodiments, the modulating agent is a phage, an antibiotic, or a test compound. In certain embodiments, the antibiotic is timentin or azithromycin.

In some embodiments of the screening assay, the host may be an invertebrate. In some embodiments, the invertebrate is an insect or a nematode. In certain embodiments, the insect is a honey bee. In other particular embodiments, the insect is a silkworm.

In any of the above embodiments of the screening assay, host fitness may be modulated by altering the host microbiota.

Definitions

As used herein, the term "bacteriocin" refers to a peptide or polypeptide that possesses anti-microbial properties. Naturally occurring bacteriocins are produced by certain prokaryotes and act against organisms related to the producer strain, but not against the producer strain itself. Bacteriocins contemplated herein include, but are not limited to, naturally occurring bacteriocins, such as bacteriocins produced by bacteria, or derivatives thereof, such as engineered bacteriocins, recombinantly expressed bacteriocins, or chemically synthesized bacteriocins. In some instances, the bacteriocin is a functionally active variant of the bacteriocins described herein. In some instances, the variant of the bacteriocin has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region or over the entire sequence, to a sequence of a bacteriocin described herein or a naturally occurring bacteriocin.

As used herein, the term "bacteriocyte" refers to a specialized cell found in certain insects where intracellular bacteria reside with symbiotic bacterial properties.

As used herein, the term "effective amount" refers to an amount of a modulating agent (e.g., a phage, lysin, bacteriocin, small molecule, or antibiotic) or composition including said agent sufficient to effect the recited result, e.g., to increase or promote the fitness of a host organism (e.g., insect); to reach a target level (e.g., a predetermined or threshold level) of a modulating agent concentration inside a target host; to reach a target level (e.g., a predetermined or threshold level) of a modulating agent concentration inside a target host gut; to reach a target level (e.g., a predetermined or threshold level) of a modulating agent concentration inside a target host bacteriocyte; to modulate the level, or an activity, of one or more microorganism (e.g., endosymbiont) in the target host.

As used herein, the term "fitness" refers to the ability of a host organism to survive, grow, and/or to produce surviving offspring. Fitness of an organism may be measured by one or more parameters, including, but not limited to, life span, reproductive rate, mobility, body weight, and/or metabolic rate. Fitness may additionally be measured based on measures of activity (e.g., pollination) or product output (e.g., honey or silk).

As used herein, the term "gut" refers to any portion of a host's gut, including, the foregut, midgut, or hindgut of the host.

As used herein, the term "host" refers to an organism (e.g., insect) carrying resident microorganisms (e.g., endogenous microorganisms, endosymbiotic microorganisms (e.g., primary or secondary endosymbionts), commensal organisms, and/or pathogenic microorganisms.

As used herein "increasing host fitness" or "promoting host fitness" refers to any favorable alteration in host physiology, or any activity carried out by said host, as a consequence of administration of a modulating agent, including, but not limited to, any one or more of the following desired effects: (1) increasing a population of a host by about 10%, 20%, 30%, 40%, 50%, 60%, 70%, 80%, 90%, 95%, 99%, 100% or more; (2) increasing the reproductive rate of a host (e.g., insect, e.g., bee or silkworm) by about 10%, 20%, 30%, 40%, 50%, 60%, 70%, 80%, 90%, 95%, 99%, 100% or more; (3) increasing the mobility of a host (e.g., insect, e.g., bee or silkworm) by about 10%, 20%, 30%, 40%, 50%, 60%, 70%, 80%, 90%, 95%, 99%, 100% or more; (4) increasing the body weight of a host (e.g., insect, e.g., bee or silkworm) by about 10%, 20%, 30%, 40%, 50%, 60%, 70%, 80%, 90%, 95%, 99%, 100% or more; (5) increasing the metabolic rate or activity of a host (e.g., insect, e.g., bee or silkworm) by about 10%, 20%, 30%, 40%, 50%, 60%, 70%, 80%, 90%, 95%, 99%, 100% or more; (6) increasing pollination (e.g., number of plants pollinated in a given amount of time) by a host (e.g., insect, e.g., bee or silkworm) by about 10%, 20%, 30%, 40%, 50%, 60%, 70%, 80%, 90%, 95%, 99%, 100% or more; (7) increasing production of host (e.g., insect, e.g., bee or silkworm) byproducts (e.g., honey from a honeybee or silk from a silkworm) by about 10%, 20%, 30%, 40%, 50%, 60%, 70%, 80%, 90%, 95%, 99%, 100% or more; (8) increasing nutrient content of the host (e.g., insect) (e.g., protein, fatty acids, or amino acids) by about 10%, 20%, 30%, 40%, 50%, 60%, 70%, 80%, 90%, 95%, 99%, 100% or more; or (9) increasing host resistance to pesticides (e.g., a neonicotinoid (e.g., imidacloprid) or an organophosphorus insecticide (e.g., a phosphorothioate, e.g., fenitrothion)) by about 10%, 20%, 30%, 40%, 50%, 60%, 70%, 80%, 90%, 95%, 99%, 100% or more. An increase in host fitness can be determined in comparison to a host organism to which the modulating agent has not been administered.

The term "insect" includes any organism belonging to the phylum *Arthropoda* and to the class *Insecta* or the class Arachnida, in any stage of development, i.e., immature or adult insects.

As used herein, "lysin" also known as endolysin, autolysin, murein hydrolase, peptidoglycan hydrolase, or cell wall hydrolase refers to a hydrolytic enzyme that can lyse a bacterium by cleaving peptidoglycan in the cell wall of the bacterium. Lysins contemplated herein include, but are not limited to, naturally occurring lysins, such as lysins produced by phages, lysins produced by bacteria, or derivatives thereof, such as engineered lysins, recombinantly expressed lysins, or chemically synthesized lysins. A functionally active variant of the bacteriocin may have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region or over the entire sequence, to a sequence of a synthetic, recombinant, or naturally derived bacteriocin, including any described herein.

As used herein, the term "microorganism" refers to bacteria or fungi. Microorganisms may refer to microorganisms resident in a host organism (e.g., endogenous microorganisms, endosymbiotic microorganisms (e.g., primary or secondary endosymbionts)) or microorganisms exogenous to the host, including those that may act as modulating agents. As used herein, the term "target microorganism" refers to a microorganism that is resident in the host and impacted by a modulating agent, either directly or indirectly.

As used herein, the term "agent" or "modulating agent" refers to an agent that is capable of altering the levels and/or functioning of microorganisms resident in a host organism (e.g., insect), and thereby modulate (e.g., increase) the fitness of the host organism (e.g., insect).

As used herein, the term "pesticide" or "pesticidal agent" refers to a substance that can be used in the control of agricultural, environmental, or domestic/household pests, such as insects, fungi, bacteria, or viruses. The term "pesticide" is understood to encompass naturally occurring or synthetic insecticides (larvicides or adulticides), insect growth regulators, acaricides (miticides), nematicides, ectoparasiticides, bactericides, fungicides, or herbicides (substance which can be used in agriculture to control or modify plant growth). Further examples of pesticides or pesticidal agents are listed in Table 12. In some instances, the pesticide is an allelochemical. As used herein, "allelochemical" or "allelochemical agent" is a substance produced by an organism that can effect a physiological function (e.g., the germination, growth, survival, or reproduction) of another organism (e.g., a host insect or nematode).

As used herein, the term "peptide," "protein," or "polypeptide" encompasses any chain of naturally or non-naturally occurring amino acids (either D- or L-amino acids), regardless of length (e.g., at least 2, 3, 4, 5, 6, 7, 10, 12, 14, 16, 18, 20, 25, 30, 40, 50, 100, or more amino acids), the presence or absence of post-translational modifications (e.g., glycosylation or phosphorylation), or the presence of, e.g., one or more non-amino acyl groups (for example, sugar, lipid, etc.) covalently linked to the peptide, and includes, for example, natural proteins, synthetic, or recombinant polypeptides and peptides, hybrid molecules, peptoids, or peptidomimetics.

As used herein, "percent identity" between two sequences is determined by the BLAST 2.0 algorithm, which is described in Altschul et al. (*J. Mol. Biol.* 215:403-410, 1990). Software for performing BLAST analyses is publicly available through the National Center for Biotechnology Information.

As used herein, the term "phage" or "bacteriophage" refers to a virus that infects and replicates in bacteria. Bacteriophages replicate within bacteria following the injection of their genome into the cytoplasm and do so using either a lytic cycle, which results in bacterial cell lysis, or a lysogenic (non-lytic) cycle, which leaves the bacterial cell intact. The phage may be a naturally occurring phage isolate, or an engineered phage, including vectors, or nucleic acids that encode either a partial phage genome (e.g., including at least all essential genes necessary to carry out the life cycle of the phage inside a host bacterium) or the full phage genome.

As used herein, the term "plant" refers to whole plants, plant organs, plant tissues, seeds, plant cells, seeds, and progeny of the same. Plant cells include, without limitation, cells from seeds, suspension cultures, embryos, meristematic regions, callus tissue, leaves, roots, shoots, gametophytes, sporophytes, pollen, or microspores. Plant parts include differentiated or undifferentiated tissues including, but not limited to the following: roots, stems, shoots, leaves, pollen, seeds, tumor tissue, and various forms of cells and culture (e.g., single cells, protoplasts, embryos, or callus tissue). The plant tissue may be in a plant or in a plant organ, tissue, or cell culture. In addition, a plant may be genetically engineered to produce a heterologous protein or RNA, for example, of any of the modulating agents in the methods or compositions described herein.

The terms "obtainable by", "producible by" or the like are used to indicate that a claim or embodiment refers to compound, composition, product, etc. per se, i.e. that the compound, composition, product, etc. can be obtained or produced by a method which is described for manufacture of the compound, composition, product, etc., but that the compound, composition, product, etc. may be obtained or produced by other methods than the described one as well. The terms "obtained by," "produced by," or the like indicate that the compound, composition, product, is obtained or produced by a recited specific method. It is to be understood that the terms "obtainable by," "producible by" and the like also disclose the terms "obtained by", "produced by" and the like as a preferred embodiment of "obtainable by", "producible by" and the like.

Other features and advantages of the invention will be apparent from the following Detailed Description and the Claims.

BRIEF DESCRIPTION OF THE FIGURES

The figures are meant to be illustrative of one or more features, aspects, or embodiments of the invention and are not intended to be limiting.

DETAILED DESCRIPTION

Figure 1:
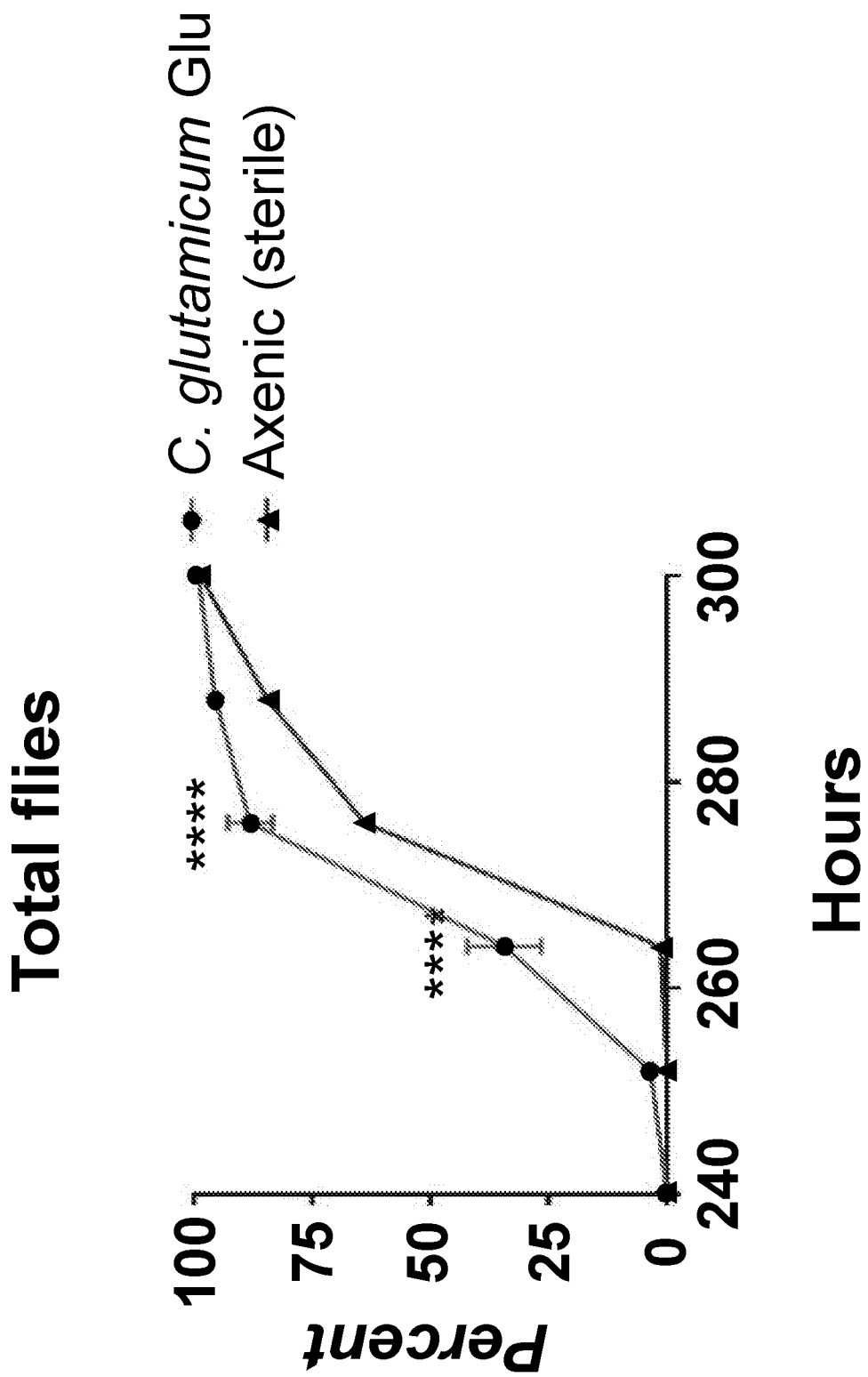
FIG. 1 is a graph showing the time to reach adulthood from embryos in *Drosophila melanogaster*. Embryos of *Drosophila melanogaster* were either raised on diet seeded with *Corynebacterium glutamicum* (a strain that produces glutamate—*C. glutamicum* Glu) or on axenic diet without any bacteria. The percentage of adults emerging from their pupa was measured every 12 hours from the time of the emergence of the first adult. The organisms raised on bacteria supplemented diet reach adulthood faster than their bacteria free counterparts.

Provided herein are methods and compositions for agricultural use, e.g., for altering a level, activity, or metabolism of one or more microorganisms resident in a host nematode or arthropod (e.g., honeybee or silkworm), the alteration resulting in an increase in the fitness of the host. The invention features a composition that includes a modulating agent (e.g., phage, peptide, small molecule, antibiotic, or combinations thereof) that can alter the host's microbiota in a manner that is beneficial to the host. By promoting favorable microbial levels, microbial activity, microbial metabolism, and/or microbial diversity, the modulating agent described herein may be used to increase the fitness of a variety of beneficial nematodes or arthropods, such as bees and silkworms, utilized in agriculture and commerce.

The methods and compositions described herein are based in part on the examples which illustrate how different agents, for example imidacloprid-degrading microorganisms, fenitrothion-degrading microorganisms, and different phages can be used in insect hosts such as honeybees or *Drosophila* to indirectly improve the health of these hosts by altering the level, activity or metabolism of microorganisms within these hosts. Imidacloprid-degrading microorganisms are a representative example of neonicotinoid-degrading microorganisms and more generally are representative of insecticide- or pesticide-degrading microorganisms. Similarly, fenitrothion-degrading microorganisms are a representative example of organophosphorus insecticide-degrading microorganisms and more generally are representative of insecticide- or pesticide-degrading microorganisms. On this basis the present disclosure describes a variety of different approaches to the use of agents that alter a level, activity, or metabolism of one or more microorganisms resident in a host, the alteration resulting in a modulation in the host's fitness.

I. Hosts i. Hosts

The host of any of the compositions or methods described herein may be any organism belonging to the phyla Nematoda (e.g., nematodes, e.g., beneficial nematodes) or *Arthropoda* (e.g., insects, e.g., beneficial insects), including any arthropods described herein. In some instances, the host is a beneficial insect or nematode (e.g., a pollinator, a natural competitor of a pest, or a producer of useful substances for humans). The term "beneficial insect" or "beneficial nematode," as used herein, refers to an insect or nematode that confers a benefit (e.g., economical and/or ecological) to humans, animals, an ecosystem, and/or the environment. For example, the host may be an insect that is involved in the production of a commercial product, including, but not limited to, insects cultivated to produce food (e.g., honey from honey bees, e.g., *Apis mellifera*), materials (such as silk from *Bombyx mori*), and/or substances (e.g., lac from *Laccifer lacca* or pigments from *Dactylopius coccus* and *Cynipidae*). Additionally, the host may include insects or nematodes that are used in agricultural applications, including insects that aid in the pollination of crops, spreading seeds, or pest control. Further, in some instances, the host may be an insect that is useful for waste disposal and/or organic recycling (e.g., earthworms, termites, or *Diptera* larvae).

In some instances, the host produces a usable product (e.g., honey, silk, beeswax, or shellac). In some instances, the host is a bee. Exemplary bee genera include, but are not limited to *Apis, Bombus, Trigona*, and *Osmia*. In some instances, the bee is a honeybee (e.g., an insect belonging to the genus *Apis*). In some instances, the honeybee is the species *Apis mellifera* (the European or Western honey bee), *Apis cerana* (the Asiatic, Eastern, or Himalayan honey bee), *Apis dorsata* (the "giant" honey bee), *Apis florea* (the "red dwarf" honey bee), *Apis andreniformis* (the "black dwarf" honey bee), or *Apis nigrocincta*. In some instances, the host is a silkworm. The silkworm may be a species in the family Bombycidae or Saturniidae. In some instances, the silkworm is *Bombyx mori*. In some instances, the host is a lac bug. The lac bug may be a species in the family Kerriidae. In some instances, the lac bug is *Kerria lacca*.

In some instances, the host aids in pollination of a plant (e.g., bees, beetles, wasps, flies, butterflies, or moths). In some examples, the host aiding in pollination of a plant is beetle. In some instances, the beetle is a species in the family Buprestidae, Cantharidae, Cerambycidae, Chrysomelidae, Cleridae, Coccinellidae, Elateridae, Melandryidae, Meloidae, Melyridae, Mordellidae, Nitidulidae, Oedemeridae, Scarabaeidae, or Staphyllinidae. In some instances, the host aiding in pollination of a plant is a butterfly or moth (e.g., *Lepidoptera*). In some instances, the butterfly or moth is a species in the family Geometridae, Hesperiidae, Lycaenidae, Noctuidae, Nymphalidae, Papilionidae, Pieridae, or Sphingidae. In some instances, the host aiding in pollination of a plant is a fly (e.g., *Diptera*). In some instances, the fly is in the family Anthomyiidae, Bibionidae, Bombyliidae, Calliphoridae, Cecidomiidae, Certopogonidae, Chrionomidae, Conopidae, Culicidae, Dolichopodidae, Empididae, Ephydridae, Lonchopteridae, Muscidae, Mycetophilidae, Phoridae, Simuliidae, Stratiomyidae, or Syrphidae. In some instances, the host aiding in pollination is an ant (e.g., Formicidae), sawfly (e.g., Tenthredinidae), or wasp (e.g., Sphecidae or Vespidae). In some instances, the host aiding in pollination of a plant is a bee. In some instances, the bee is in the family Andrenidae, Apidae, Colletidae, Halictidae, or Megachilidae.

In some instances, the host aids in pest control. In some instances, the host aiding in pest control is a predatory nematode. In particular examples, the nematode is a species of Heterorhabditis or Steinernema. In some instances, the host aiding in pest control is an insect. For example, the host aiding in pest control may be a species belonging to the family Braconidae (e.g., parasitoid wasps), Carabidae (e.g., ground beetles), Chrysopidae (e.g., green lacewings), Coccinellidae (e.g., ladybugs), Hemerobiidae (e.g., brown lacewings), Ichneumonidae (e.g., ichneumon wasps), Lampyridae (e.g., fireflies), Mantidae (e.g., praying mantises), Myrmeleontidae (e.g., antlions), Odonata (e.g., dragonflies and damselflies), or Syrphidae (e.g., hoverfly). In other instances, the host aiding in pest control is an insect that competes with an insect that is considered a pest (e.g., an agricultural pest). For example, the Mediterranean fruit fly, *Ceratitis capitata* is a common pest of fruits and vegetables worldwide. One way to control *C. captitata* is to release the sterilized male insect into the environment to compete with wild males to mate the females. In these instances, the host may be a sterilized male belonging to a species that is typically considered a pest.

In some instances, the host aids in degradation of waste or organic material. In some examples, the host aiding in degradation of waste or organic material belongs to *Coleoptera* or *Diptera*. In some instances, the host belonging to *Diptera* is in the family Calliphoridae, Curtonotidae, Drosophilidae, Fanniidae, Heleomyzidae, Milichiidae, Muscidae, Phoridae, Psychodidae, Scatopsidae, Sepsidae, Sphaeroceridae, Stratiomyidae, Syrphidae, Tephritidae, or Ulidiidae. In some instances, the host belonging to Coleoptera is in the family Carabidae, Hydrophilidae, Phalacaridae, Ptiliidae, or Staphylinidae.

In particular instances, the modulating agents disclosed herein may be used to increase the fitness of honeybee or silkworm hosts.

ii. Host Fitness

The methods and compositions provided herein may be used to increase the fitness of any of the hosts described herein. The increase in fitness may arise from any alterations in microorganisms resident in the host, wherein the alterations are a consequence of administration of a modulating agent and have beneficial or advantageous effects on the host.

In some instances, the increase in host fitness may manifest as an improvement in the physiology of the host (e.g., improved health or survival) as a consequence of administration of a modulating agent. In some instances, the fitness of an organism may be measured by one or more parameters, including, but not limited to, reproductive rate, lifespan, mobility, fecundity, body weight, metabolic rate or activity, or survival in comparison to a host organism to which the modulating agent has not been administered. For example, the methods or compositions provided herein may be effective to improve the overall health of the host or to improve the overall survival of the host in comparison to a host organism to which the modulating agent has not been administered. In some instances, the improved survival of the host is about 2%, 5%, 10%, 20%, 30%, 40%, 50%, 60%, 70%, 80%, 90%, 100%, or greater than 100% greater relative to a reference level (e.g., a level found in a host that does not receive a modulating agent). In some instances, the methods and compositions are effective to increase host reproduction (e.g., reproductive rate) in comparison to a host organism to which the modulating agent has not been administered. In some instances, the methods and compositions are effective to increase other physiological parameters, such as mobility, body weight, life span, fecundity, or metabolic rate, by about 2%, 5%, 10%, 20%, 30%, 40%, 50%, 60%, 70%, 80%, 90%, 100%, or greater than 100% relative to a reference level (e.g., a level found in a host that does not receive a modulating agent).

In some instances, the increase in host fitness may manifest as an increased production of a product generated by said host in comparison to a host organism to which the modulating agent has not been administered. In some instances, the methods or compositions provided herein may be effective to increase the production of a product generated by the host, as described herein (e.g., honey, beeswax, beebread, propolis, silk, or lac), by about 2%, 5%, 10%, 20%, 30%, 40%, 50%, 60%, 70%, 80%, 90%, 100%, or greater than 100% relative to a reference level (e.g., a level found in a host that does not receive a modulating agent).

In some instances, the increase in host fitness may manifest as an increase in the frequency or efficacy of a desired activity carried out by the host (e.g., pollination, predation on pests, seed spreading, or breakdown of waste or organic material) in comparison to a host organism to which the modulating agent has not been administered. In some instances, the methods or compositions provided herein may be effective to increase the frequency or efficacy of a desired activity carried out by the host (e.g., pollination, predation on pests, seed spreading, or breakdown of waste or organic material) by about 2%, 5%, 10%, 20%, 30%, 40%, 50%, 60%, 70%, 80%, 90%, 100%, or greater than 100% relative to a reference level (e.g., a level found in a host that does not receive a modulating agent).

In some instances, the increase in host fitness may manifest as an increase in the production of one or more nutrients in the host (e.g., vitamins, carbohydrates, amino acids, or polypeptides) in comparison to a host organism to which the modulating agent has not been administered. In some instances, the methods or compositions provided herein may be effective to increase the production of nutrients in the host (e.g., vitamins, carbohydrates, amino acids, or polypeptides) by about 2%, 5%, 10%, 20%, 30%, 40%, 50%, 60%, 70%, 80%, 90%, 100%, or greater than 100% relative to a reference level (e.g., a level found in a host that does not receive a modulating agent). In some instances, the methods or compositions provided herein may increase nutrients in the host by increasing the production of nutrients by one or more microorganisms (e.g., endosymbiont) in the host.

In some instances, the increase in host fitness may manifest as a decrease in the host's sensitivity to a pesticidal agent (e.g., a pesticide listed in Table 12) and/or an increase in the host's resistance to a pesticidal agent (e.g., a pesticide listed in Table 12) in comparison to a host organism to which the modulating agent has not been administered. In some instances, the methods or compositions provided herein may be effective to decrease the host's sensitivity to a pesticidal agent (e.g., a pesticide listed in Table 12) by about 2%, 5%, 10%, 20%, 30%, 40%, 50%, 60%, 70%, 80%, 90%, 100%, or greater than 100% relative to a reference level (e.g., a level found in a host that does not receive a modulating agent). In some instances, the host's sensitivity to the pesticidal agent is altered by administering a modulating agent that degrades a pesticidal agent (e.g., a pesticidal-degrading bacteria, e.g., a neonicotinoid-degrading bacteria or an organophosphorus insecticide-degrading bacteria). The pesticidal agent may be any pesticidal agent known in the art, including insecticidal agents. In some instances, the pesticidal agent is a neonicotinoid (e.g., imidacloprid) or an organophosphorus insecticide (e.g., a phosphorothioate, e.g., fenitrothion). In some instances, the methods or compositions provided herein may decrease the host's sensitivity to a pesticidal agent (e.g., a pesticide listed in Table 12) by increasing the host's ability to metabolize or degrade the pesticidal agent into usable substrates.

In some instances, the host's sensitivity to the pesticidal agent is altered by administering a modulating agent that detoxifies a xenobiotic.

In some instances, the increase in host fitness may manifest as a decrease in the host's sensitivity to an allelochemical agent and/or an increase in the host's resistance to an allelochemical agent in comparison to a host organism to which the modulating agent has not been administered. In some instances, the methods or compositions provided herein may be effective to increase the host's resistance to an allelochemical agent by about 2%, 5%, 10%, 20%, 30%, 40%, 50%, 60%, 70%, 80%, 90%, 100%, or greater than 100% relative to a reference level (e.g., a level found in a host that does not receive a modulating agent). In some instances, the allelochemical agent is caffeine, soyacystatin N, monoterpenes, diterpene acids, or phenolic compounds. In some instances, the methods or compositions provided herein may decrease the host's sensitivity to an allelochemical agent by increasing the host's ability to metabolize or degrade the allelochemical agent into usable substrates.

In some instances, the methods or compositions provided herein may be effective to increase the host's resistance to parasites or pathogens (e.g., fungal, bacterial, or viral pathogens; or parasitic mites (e.g., *Varroa destructor* mite in honeybees)) in comparison to a host organism to which the modulating agent has not been administered. In some instances, the methods or compositions provided herein may be effective to increase the host's resistance to a pathogen or parasite (e.g., fungal, bacterial, or viral pathogens; or parasitic mites (e.g., *Varroa destructor* mite in honeybees)) by about 2%, 5%, 10%, 20%, 30%, 40%, 50%, 60%, 70%, 80%, 90%, 100%, or greater than 100% relative to a reference level (e.g., a level found in a host that does not receive a modulating agent).

In some instances, the increase in host fitness may manifest as other fitness advantages, such as improved tolerance to certain environmental factors (e.g., a high or low temperature tolerance), improved ability to survive in certain habitats, or an improved ability to sustain a certain diet (e.g., an improved ability to metabolize soy vs corn) in comparison to a host organism to which the modulating agent has not been administered. In some instances, the methods or compositions provided herein may be effective to increase host fitness in any plurality of ways described herein. Further, the modulating agent may increase host fitness in any number of host classes, orders, families, genera, or species (e.g., 1 host species, 2, 3, 4, 5, 6, 7, 8, 9, 10, 15, 20, 30, 40, 50, 60, 70, 80, 90, 100, 150, 200, 200, 250, 500, or more host species). In some instances, the modulating agent acts on a single host class, order, family, genus, or species.

Host fitness may be evaluated using any standard methods in the art. In some instances, host fitness may be evaluated by assessing an individual host. Alternatively, host fitness may be evaluated by assessing a host population. For example, an increase in host fitness may manifest as an increase in successful competition against other insects, thereby leading to an increase in the size of the host population.

iii. Host Invertebrates in Agriculture

By increasing the fitness of beneficial nematodes or insects, the modulating agents provided herein may be effective to promote the growth of plants that benefit from said hosts. The modulating agent may be delivered using any formulations and delivery methods described herein, in an amount and for a duration effective to increase the fitness of the hosts of interest and thereby benefit the plant (e.g., increase crop growth, increase crop yield, decrease pest infestation, and/or decrease damage to plants). This may or may not involve direct application of the modulating agent to the plant. For example, in instances where the primary host habitat is different than the region of plant growth, the modulating agent may be applied to either the primary host habitat, the plants of interest, or a combination of both.

In some instances, the plant may be an agricultural crop, such as a cereal, grain, legume, fruit, or vegetable crop. The compositions described herein may be delivered to the crop any time prior to or after harvesting the cereal, grain, legume, fruit, or vegetable. Crop yield is a measurement often used for, e.g., a cereal, grain, or legume and is normally measured in metric tons per hectare (or kilograms per hectare). Crop yield can also refer to the actual seed generation from the plant. In some instances, the modulating agent may be effective to increase crop yield (e.g., increase metric tons of cereal, grain, legume, fruit, or vegetable per hectare and/or increase seed generation) by about 2%, 5%, 10%, 20%, 30%, 40%, 50%, 60%, 70%, 80%, 90%, 100%, or more in comparison to a reference level (e.g., a crop to which the modulating agent has not been administered.

In some instances, the plant (e.g., crop) may be at risk of developing a pest infestation (e.g., by an insect) or may have already developed a pest infestation. The methods and compositions described herein may be used to reduce or prevent pest infestation in such crops by promoting the fitness of beneficial insects that prey on agricultural pests. In some instances, the modulating agent may be effective to reduce crop infestation (e.g., reduce the number of plants infested, reduce the pest population size, or reduce damage to plants) by about 2%, 5%, 10%, 20%, 30%, 40%, 50%, 60%, 70%, 80%, 90%, 100%, or more in comparison to a reference level (e.g., a crop to which the modulating agent has not been administered). In other instances, the modulating agent may be effective to prevent or reduce the likelihood of crop infestation by about 2%, 5%, 10%, 20%, 30%, 40%, 50%, 60%, 70%, 80%, 90%, 100%, or more in comparison to a reference level (e.g., a crop to which the modulating agent has not been administered).

Any suitable plant tissues may benefit from the compositions and methods described herein, including, but not limited to, somatic embryos, pollen, leaves, stems, calli, stolons, microtubers, and shoots. The methods described herein may include treatment of angiosperm and gymnosperm plants such as acacia, alfalfa, apple, apricot, artichoke, ash tree, asparagus, avocado, banana, barley, beans, beet, birch, beech, blackberry, blueberry, broccoli, brussels sprouts, cabbage, canola, cantaloupe, carrot, cassava, cauliflower, cedar, a cereal, celery, chestnut, cherry, Chinese cabbage, citrus, clementine, clover, coffee, corn, cotton, cowpea, cucumber, cypress, eggplant, elm, endive, eucalyptus, fava beans, fennel, figs, fir, geranium, grape, grapefruit, groundnuts, ground cherry, gum hemlock, hickory, kale, kiwifruit, kohlrabi, larch, lettuce, leek, lemon, lime, locust, pine, maidenhair, maize, mango, maple, melon, millet, mushroom, mustard, nuts, oak, oats, okra, onion, orange, an ornamental plant or flower or tree, papaya, palm, parsley, parsnip, pea, peach, peanut, pear, peat, pepper, persimmon, pigeon pea, pine, pineapple, plantain, plum, pomegranate, potato, pumpkin, radicchio, radish, rapeseed, raspberry, rice, rye, sorghum, sallow, soybean, spinach, spruce, squash, strawberry, sugarbeet, sugarcane, sunflower, sweet potato, sweet corn, tangerine, tea, tobacco, tomato, trees, triticale, turf grasses, turnips, a vine, walnut, watercress, watermelon, wheat, yams, yew, and zucchini.

II. Target Microorganisms

The microorganisms targeted by the modulating agent described herein may include any microorganism resident in or on the host, including, but not limited to, any bacteria and/or fungi described herein. Microorganisms resident in the host may include, for example, symbiotic (e.g., endosymbiotic microorganisms that provide beneficial nutrients or enzymes to the host), commensal, pathogenic, or parasitic microorganisms. A symbiotic microorganism (e.g., bacteria or fungi) may be an obligate symbiont of the host or a facultative symbiont of the host. Microorganisms resident in the host may be acquired by any mode of transmission, including vertical, horizontal, or multiple origins of transmission.

i. Bacteria

Exemplary bacteria that may be targeted in accordance with the methods and compositions provided herein, include, but are not limited to, *Xenorhabdus* spp, *Photorhabdus* spp, *Candidatus* spp, *Buchnera* spp, *Blattabacterium* spp, *Baumania* spp, *Wigglesworthia* spp, *Wolbachia* spp, *Rickettsia* spp, *Orientia* spp, *Sodalis* spp, *Burkholderia* spp, *Cupriavidus* spp, *Frankia* spp, *Snirhizobium* spp, *Streptococcus* spp, *Wolinella* spp, *Xylella* spp, *Erwinia* spp, *Agrobacterium* spp, *Bacillus* spp, *Paenibacillus* spp, *Streptomyces* spp, *Micrococcus* spp, *Corynebacterium* spp, *Acetobacter* spp, *Cyanobacteria* spp, *Salmonella* spp, *Rhodococcus* spp, *Pseudomonas* spp, *Lactobacillus* spp, *Enterococcus* spp, *Alcaligenes* spp, *Klebsiella* spp, *Paenibacillus* spp, *Arthrobacter* spp, *Corynebacterium* spp, *Brevibacterium* spp, *Thermus* spp, *Pseudomonas* spp, *Clostridium* spp, and *Escherichia* spp. Non-limiting examples of bacteria that may be targeted by the methods and compositions provided herein are shown in Table 1.

TABLE 1

Examples of Target Bacteria and Host Insects

| Endosymbiont | Host Insect | Location | 16S rRNA |
|---|---|---|---|
| *Snodgrassella alvi* | honeybee (*Apis mellifera*) and *Bombus* spp. | Ileum | GAGAGTTTGATCCTGGCTCAGATTGAACGC TGGCGGCATGCCTTACACATGCAAGTCGAA CGGCAGCACGGAGAGCTTGCTCTCTGGTG GCGAGTGGCGAACGGGTGAGTAATGCATC GGAACGTACCGAGTAATGGGGGATAACTG TCCGAAAGGATGGCTAATACCGCATACGCC CTGAGGGGGAAAGCGGGGGATCGAAAGAC CTCGCGTTATTTGAGCGGCCGATGTTGGAT |

TABLE 1-continued

Examples of Target Bacteria and Host Insects

| Endosymbiont | Host Insect | Location | 16S rRNA |
|---|---|---|---|
| | | | TAGCTAGTTGGTGGGGTAAAGGCCTACCAA GGCGACGATCCATAGCGGGTCTGAGAGGA TGATCCGCCACATTGGGACTGAGACACGG CCCAAACTCCTACGGGAGGCAGCAGTGGG GAATTTTGGACAATGGGGGGAACCCTGATC CAGCCATGCCGCGTGTCTGAAGAAGGCCT TCGGGTTGTAAAGGACTTTTGTTAGGGAAG AAAAGCCGGGTGTTAATACCATCTGGTGCT GACGGTACCTAAAGAATAAGCACCGGCTAA CTACGTGCCAGCAGCCGCGGTAATACGTA GGGTGCGAGCGTTAATCGGAATTACTGGG CGTAAAGCGAGCGCAGACGGTTAATTAAGT CAGATGTGAAATCCCCGAGCTCAACTTGGG ACGTGCATTTGAAACTGGTTAACTAGAGTG TGTCAGAGGGAGGTAGAATTCCACGTGTAG CAGTGAAATGCGTAGAGATGTGGAGGAATA CCGATGGCGAAGGCAGCCTCCTGGGATAA CACTGACGTTCATGCTCGAAAGCGTGGGTA GCAAACAGGATTAGATACCCTGGTAGTCCA CGCCCTAAACGATGACAATTAGCTGTTGGG ACACTAGATGTCTTAGTAGCGAAGCTAACG CGTGAAATTGTCCGCCTGGGGAGTACGGT CGCAAGATTAAAACTCAAAGGAATTGACGG GGACCCGCACAAGCGGTGGATGATGTGGA TTAATTCGATGCAACGCGAAGAACCTTACC TGGTCTTGACATGTACGGAATCTCTTAGAG ATAGGAGAGTGCCTTCGGGAACCGTAACA CAGGTGCTGCATGGCTGTCGTCAGCTCGT GTCGTGAGATGTTGGGTTAAGTCCCGCAAC GAGCGCAACCCTTGTCATTAGTTGCCATCA TTAAGTTGGGCACTCTAATGAGACTGCCGG TGACAAACCGGAGGAAGGTGGGGATGACG TCAAGTCCTCATGGCCCTTATGACCAGGGC TTCACACGTCATACAATGGTCGGTACAGAG GGTAGCGAAGCCGCGAGGTGAAGCCAATC TCAGAAAGCCGATCGTAGTCCGGATTGCAC TCTGCAACTCGAGTGCATGAAGTCGGAATC GCTAGTAATCGCAGGTCAGCATACTGCGGT GAATACGTTCCCGGGTCTTGTACACACCGC CCGTCACACCATGGGAGTGGGGATACCA GAATTGGGTAGACTAACCGCAAGGAGGTC GCTTAACACGGTATGCTTCATGACTGGGGT GAAGTCGTAACAAGGTAGCCGTAG (SEQ ID NO: 1) |
| *Gilliamella apicola* | honeybee (*Apis mellifera*) and *Bombus* spp. | Ileum | TTAAATTGAAGAGTTTGATCATGGCTCAGAT TGAACGCTGGCGGCAGGCTTAACACATGC AAGTCGAACGGTAACATGAGTGCTTGCACT TGATGACGAGTGGCGGACGGGTGAGTAAA GTATGGGGATCTGCCGAATGGAGGGGGAC AACAGTTGGAAACGACTGCTAATACCGCAT AAAGTTGAGAGACCAAAGCATGGGACCTTC GGGCCATGCGCCATTTGATGAACCCATATG GGATTAGCTAGTTGGTAGGGTAATGGCTTA CCAAGGCGACGATCTCTAGCTGGTCTGAG AGGATGACCAGCCACACTGGAACTGAGAC ACGGTCCAGACTCCTACGGGAGGCAGCAG TGGGGAATATTGCACAATGGGGGAAACCCT GATGCAGCCATGCCGCGTGTATGAAGAAG GCCTTCGGGTTGTAAAGTACTTTCGGTGAT GAGGAAGGTGGTGTATCTAATAGGTGCATC AATTGACGTTAATTACAGAAGAAGCACCGG CTAACTCCGTGCCAGCAGCCGCGGTAATA CGGAGGGTGCGAGCGTTAATCGGAATGAC TGGGCGTAAAGGGCATGTAGGCGGATAAT TAAGTTAGGTGTGAAAGCCCTGGGCTCAAC CTAGGAATTGCACTTAAAACTGGTTAACTA GAGTATTGTAGAGGAAGGTAGAATTCCACG TGTAGCGGTGAAATGCGTAGAGATGTGGA GGAATACCGGTGGCGAAGGCGGCCTTCTG GACAGATACTGACGCTGAGATGCGAAAGC GTGGGGAGCAAACAGGATTAGATACCCTG GTAGTCCACGCTGTAAACGATGTCGATTTG GAGTTTGTTGCCTAGAGTGATGGGCTCCGA AGCTAACGCGATAAATCGACCGCCTGGGG AGTACGGCCGCAAGGTTAAAACTCAAATGA |

TABLE 1-continued

Examples of Target Bacteria and Host Insects

| Endosymbiont | Host Insect | Location | 16S rRNA |
|---|---|---|---|
| | | | ATTGACGGGGGCCCGCACAAGCGGTGGAG<br>CATGTGGTTTAATTCGATGCAACGCGAAGA<br>ACCTTACCTGGTCTTGACATCCACAGAATC<br>TTGCAGAGATGCGGGAGTGCCTTCGGGAA<br>CTGTGAGACAGGTGCTGCATGGCTGTCGT<br>CAGCTCGTGTTGTGAAATGTTGGGTTAAGT<br>CCCGCAACGAGCGCAACCCTTATCCTTTGT<br>TGCCATCGGTTAGGCCGGGAACTCAAAGG<br>AGACTGCCGTTGATAAAGCGGAGGAAGGT<br>GGGGACGACGTCAAGTCATCATGGCCCTT<br>ACGACCAGGGCTACACACGTGCTACAATG<br>GCGTATACAAAGGGAGGCGACCTCGCGAG<br>AGCAAGCGGACCTCATAAAGTACGTCTAAG<br>TCCGGATTGGAGTCTGCAACTCGACTCCAT<br>GAAGTCGGAATCGCTAGTAATCGTGAATCA<br>GAATGTCACGGTGAATACGTTCCCGGGCCT<br>TGTACACACCGCCCGTCACACCATGGGAG<br>TGGGTTGCACCAGAAGTAGATAGCTTAACC<br>TTCGGGAGGGCGTTTACCACGGTGTGGTC<br>CATGACTGGGGTGAAGTCGTAACAAGGTAA<br>CCGTAGGGGAACCTGCGGTTGGATCACCT<br>CCTTAC (SEQ ID NO: 2) |
| Bartonella apis | honeybee (Apis mellifera) | Gut | AAGCCAAAATCAAATTTTCAACTTGAGAGTT<br>TGATCCTGGCTCAGAACGAACGCTGGCGG<br>CAGGCTTAACACATGCAAGTCGAACGCACT<br>TTTCGGAGTGAGTGGCAGACGGGTGAGTA<br>ACGCGTGGGAATCTACCTATTTCTACGGAA<br>TAACGCAGAGAAATTTGTGCTAATACCGTA<br>TACGTCCTTCGGGAGAAAGATTTATCGGAG<br>ATAGATGAGCCCGCGTTGGATTAGCTAGTT<br>GGTGAGGTAATGGCCCACCAAGGCGACGA<br>TCCATAGCTGGTCTGAGAGGATGACCAGC<br>CACATTGGGACTGAGACACGGCCCAGACT<br>CCTACGGGAGGCAGCAGTGGGGAATATTG<br>GACAATGGGCGCAAGCCTGATCCAGCCAT<br>GCCGCGTGAGTGATGAAGGCCCTAGGGTT<br>GTAAAGCTCTTTCACCGGTGAAGATAATGA<br>CGGTAACCGGAGAAGAAGCCCCGGCTAAC<br>TTCGTGCCAGCAGCCGCGGTAATACGAAG<br>GGGGCTAGCGTTGTTCGGATTTACTGGGC<br>GTAAAGCGCACGTAGGCGGATATTTAAGTC<br>AGGGGTGAAATCCCGGGGCTCAACCCCGG<br>AACTGCCTTTGATACTGGATATCTTGAGTAT<br>GGAAGAGGTAAGTGGAATTCCGAGTGTAG<br>AGGTGAAATTCGTAGATATTCGGAGGAACA<br>CCAGTGGCGAAGGCGGCTTACTGGTCCAT<br>TACTGACGCTGAGGTGCGAAAGCGTGGGG<br>AGCAAACAGGATTAGATACCCTGGTAGTCC<br>ACGCTGTAAACGATGAATGTTAGCCGTTGG<br>ACAGTTTACTGTTCGGTGGCGCAGCTAACG<br>CATTAAACATTCCGCCTGGGGAGTACGGTC<br>GCAAGATTAAAACTCAAAGGAATTGACGGG<br>GGCCCGCACAAGCGGTGGAGCATGTGGTT<br>TAATTCGAAGCAACGCGCAGAACCTTACCA<br>GCCCTTGACATCCCGATCGCGGATGGTGG<br>AGACACCGTCTTTCAGTTCGGCTGGATCGG<br>TGACAGGTGCTGCATGGCTGTCGTCAGCT<br>CGTGTCGTGAGATGTTGGGTTAAGTCCCGC<br>AACGAGCGCAACCCTCGCCCTTAGTTGCCA<br>TCATTTAGTTGGGCACTCTAAGGGGACTGC<br>CGGTGATAAGCCGAGAGGAAGGTGGGGAT<br>GACGTCAAGTCCTCATGGCCCTTACGGGCT<br>GGGCTACACACGTGCTACAATGGTGGTGA<br>CAGTGGGCAGCGAGACCGCGAGGTCGAG<br>CTAATCTCCAAAAGCCATCTCAGTTCGGAT<br>TGCACTCTGCAACTCGAGTGCATGAAGTTG<br>GAATCGCTAGTAATCGTGGATCAGCATGCC<br>ACGGTGAATACGTTCCCGGGCCTTGTACAC<br>ACCGCCCGTCACACCATGGGAGTTGGTTTT<br>ACCCGAAGGTGCTGTGCTAACCGCAAGGA<br>GGCAGGCAACCACGGTAGGGTCAGCGACT<br>GGGGTGAAGTCGTAACAAGGTAGCCGTAG<br>GGGAACCTGCGGCTGGATCACCTCCTTTCT<br>AAGGAAGATGAAGAATTGGAA (SEQ ID NO: 3) |

TABLE 1-continued

Examples of Target Bacteria and Host Insects

| Endosymbiont | Host Insect | Location | 16S rRNA |
|---|---|---|---|
| Parasaccharibacter apium | honeybee (Apis mellifera) | Gut | CTACCATGCAAGTCGCACGAAACCTTTCGG GGTTAGTGGCGGACGGGTGAGTAACGCGT TAGGAACCTATCTGGAGGTGGGGGATAAC ATCGGGAAACTGGTGCTAATACCGCATGAT GCCTGAGGGCCAAAGGAGAGATCCGCCAT TGGAGGGGCCTGCGTTCGATTAGCTAGTT GGTTGGGTAAAGGCTGACCAAGGCGATGA TCGATAGCTGGTTTGAGAGGATGATCAGCC ACACTGGGACTGAGACACGGCCCAGACTC CTACGGGAGGCAGCAGTGGGGAATATTGG ACAATGGGGGCAACCCTGATCCAGCAATG CCGCGTGTGTGAAGAAGGTCTTCGGATTGT AAAGCACTTTCACTAGGGAAGATGATGACG GTACCTAGAGAAGAAGCCCCGGCTAACTTC GTGCCAGCAGCCGCGGTAATACGAAGGGG GCTAGCGTTGCTCGGAATGACTGGGCGTA AAGGGCGCGTAGGCTGTTTGTACAGTCAG ATGTGAAATCCCCGGGCTTAACCTGGGAAC TGCATTTGATACGTGCAGACTAGAGTCCGA GAGAGGGTTGTGGAATTCCCAGTGTAGAG GTGAAATTCGTAGATATTGGGAAGAACACC GGTTGCGAAGGCGGCAACCTGGCTNNNNN NNNNNNNNNNNNNNNNNNNNNNNNNNNN NNNNNNNNNNNNNNNNNNNNNNNNNNNN NNNNNNNNNNNNNNNNNNNNNNNNNNNN NNNNNNNNNNNNNNNNNNNNNGAGCTAA CGCGTTAAGCACACCGCCTGGGGAGTACG GCCGCAAGGTTGAAACTCAAAGGAATTGAC GGGGGCCCGCACAAGCGGTGGAGCATGT GGTTTAATTCGAAGCAACGCGCAGAACCTT ACCAGGGCTTGCATGGGGAGGCTGTATTC AGAGATGGATATTTCTTCGGACCTCCCGCA CAGGTGCTGCATGGCTGTCGTCAGCTCGT GTCGTGAGATGTTGGGTTAAGTCCCGCAAC GAGCGCAACCCTTGTCTTTAGTTGCCATCA CGTCTGGGTGGGCACTCTAGAGAGACTGC CGGTGACAAGCCGGAGGAAGGTGGGGATG ACGTCAAGTCCTCATGGCCCTTATGTCCTG GGCTACACACGTGCTACAATGGCGGTGAC AGAGGGATGCTACATGGTGACATGGTGCT GATCTCAAAAAACCGTCTCAGTTCGGATTG TACTCTGCAACTCGAGTGCATGAAGGTGGA ATCGCTAGTAATCGCGGATCAGCATGCCGC GGTGAATACGTTCCCGGGCCTTGTACACAC CGCCCGTCACACCATGGGAGTTGGTTTGA CCTTAAGCCGGTGAGCGAACCGCAAGGAA CGCAGCCGACCACCGGTTCGGGTTCAGCG ACTGGGGGA (SEQ ID NO: 4) |
| Lactobacillus kunkeei | honeybee (Apis mellifera) | Gut | TTCCTTAGAAAGGAGGTGATCCAGCCGCAG GTTCTCCTACGGCTACCTTGTTACGACTTC ACCCTAATCATCTGTCCCACCTTAGACGAC TAGCTCCTAAAAGGTTACCCCATCGTCTTT GGGTGTTACAAACTCTCATGGTGTGACGGG CGGTGTGTACAAGGCCCGGGAACGTATTC ACCGTGGCATGCTGATCCACGATTACTAGT GATTCCAACTTCATGCAGGCGAGTTGCAGC CTGCAATCCGAACTGAGAATGGCTTTAAGA GATTAGCTTGACCTCGCGGTTTCGCGACTC GTTGTACCATCCATTGTAGCACGTGTGTAG CCCAGCTCATAAGGGGCATGATGATTTGAC GTCGTCCCACCTTCCTCCGGTTTATCACC GGCAGTCTCACTAGAGTGCCCAACTAAATG CTGGCAACTAATAATAAGGGTTGCGCTCGT TGCGGGACTTAACCCAACATCTCACGACAC GAGCTGACGACAACCATGCACCACCTGTCA TTCTGTCCCCGAAGGGAACGCCCAATCTCT TGGGTTGGCAGAAGATGTCAAGAGCTGGT AAGGTTCTTCGCGTAGCATCGAATTAAACC ACATGCTCCACCACTTGTGCGGGCCCCCG TCAATTCCTTTGAGTTTCAACCTTGCGGTC GTACTCCCCAGGCGGAATACTTAATGCGTT AGCTGCGGCACTGAAGGGCGGAAACCCTC CAACACCTAGTATTCATCGTTTACGGCATG GACTACCAGGGTATCTAATCCTGTTCGCTA |

TABLE 1-continued

Examples of Target Bacteria and Host Insects

| Endosymbiont | Host Insect | Location | 16S rRNA |
|---|---|---|---|
| | | | CCCATGCTTTCGAGCCTCAGCGTCAGTAAC<br>AGACCAGAAAGCCGCCTTCGCCACTGGTG<br>TTCTTCCATATATCTACGCATTTCACCGCTA<br>CACATGGAGTTCCACTTTCCTCTTCTGTACT<br>CAAGTTTTGTAGTTTCCACTGCACTTCCTCA<br>GTTGAGCTGAGGGCTTTCACAGCAGACTTA<br>CAAAACCGCCTGCGCTCGCTTTACGCCCAA<br>TAAATCCGGACAACGCTTGCCACCTACGTA<br>TTACCGCGGCTGCTGGCACGTAGTTAGCC<br>GTGGCTTTCTGGTTAAATACCGTCAAAGTG<br>TTAACAGTTACTCTAACACTTGTTCTTCTTT<br>AACAACAGAGTTTTACGATCCGAAAACCTT<br>CATCACTCACGCGGCGTTGCTCCATCAGAC<br>TTTCGTCCATTGTGGAAGATTCCCTACTGC<br>TGCCTCCCGTAGGAGTCTGGGCCGTGTCT<br>CAGTCCCAATGTGGCCGATTACCCTCTCAG<br>GTCGGCTACGTATCATCGTCTTGGTGGGCT<br>TTTATCTCACCAACTAACTAATACGGCGCG<br>GGTCCATCCCAAAGTGATAGCAAAGCCATC<br>TTTCAAGTTGGAACCATGCGGTTCCAACTA<br>ATTATGCGGTATTAGCACTTGTTTCCAAATG<br>TTATCCCCCGCTTCGGGGCAGGTTACCCAC<br>GTGTTACTCACCAGTTCGCCACTCGCTCCG<br>AATCCAAAAATCATTTATGCAAGCATAAAAT<br>CAATTTGGGAGAACTCGTTCGACTTGCATG<br>TATTAGGCACGCCGCCAGCGTTCGTCCTGA<br>GCCAGGATCAAACTCTCATCTTAA<br>(SEQ ID NO: 190) |
| Lactobacillus<br>Firm-4 | honeybee<br>(Apis<br>mellifera) | Gut | ACGAACGCTGGCGGCGTGCCTAATACATG<br>CAAGTCGAGCGCGGGAAGTCAGGGAAGCC<br>TTCGGGTGGAACTGGTGGAACGAGCGGCG<br>GATGGGTGAGTAACACGTAGGTAACCTGC<br>CCTAAAGCGGGGGATACCATCTGGAAACA<br>GGTGCTAATACCGCATAAACCCAGCAGTCA<br>CATGAGTGCTGGTTGAAAGACGGCTTCGG<br>CTGTCACTTTAGGATGGACCTGCGGCGTAT<br>TAGCTAGTTGGTGGAGTAACGGTTCACCAA<br>GGCAATGATACGTAGCCGACCTGAGAGGG<br>TAATCGGCCACATTGGGACTGAGACACGG<br>CCCAAACTCCTACGGGAGGCAGCAGTAGG<br>GAATCTTCCACAATGGACGCAAGTCTGATG<br>GAGCAACGCCGCGTGGATGAAGAAGGTCT<br>TCGGATCGTAAAATCCTGTTGTTGAAGAAG<br>AACGGTTGTGAGAGTAACTGCTCATAACGT<br>GACGGTAATCAACCAGAAAGTCACGGCTAA<br>CTACGTGCCAGCAGCCGCGGTAATACGTA<br>GGTGGCAAGCGTTGTCCGGATTTATTGGG<br>CGTAAAGGGAGCGCAGGCGGTCTTTTAAG<br>TCTGAATGTGAAAGCCCTCAGCTTAACTGA<br>GGAAGAGCATCGGAAACTGAGAGACTTGA<br>GTGCAGAAGAGGAGAGTGGAACTCCATGT<br>GTAGCGGTGAAATGCGTAGATATATGGAAG<br>AACACCAGTGGCGAAGGCGGCTCTCTGGT<br>CTGTTACTGACGCTGAGGCTCGAAAGCATG<br>GGTAGCGAACAGGATTAGATACCCTGGTAG<br>TCCATGCCGTAAACGATGAGTGCTAAGTGT<br>TGGGAGGTTTCCGCCTCTCAGTGCTGCAG<br>CTAACGCATTAAGCACTCCGCCTGGGGAGT<br>ACGACCGCAAGGTTGAAACTCAAAGGAATT<br>GACGGGGGCCCGCACAAGCGGTGGAGCA<br>TGTGGTTTAATTCGAAGCAACGCGAAGAAC<br>CTTACCAGGTCTTGACATCTCCTGCAAGCC<br>TAAGAGATTAGGGGTTCCCTTCGGGGACA<br>GGAAGACAGGTGGTGCATGGTTGTCGTCA<br>GCTCGTGTCGTGAGATGTTGGGTTAAGTCC<br>CGCAACGAGCGCAACCCTTGTTACTAGTTG<br>CCAGCATTAAGTTGGGCACTCTAGTGAGAC<br>TGCCGGTGACAAACCGGAGGAAGGTGGGG<br>ACGACGTCAAATCATCATGCCCCTTATGAC<br>CTGGGCTACACACGTGCTACAATGGATGGT<br>ACAATGAGAAGCGAACTCGCGAGGGGAAG<br>CTGATCTCTGAAAACCATTCTCAGTTCGGA<br>TTGCAGGCTGCAACTCGCCTGCATGAAGCT |

TABLE 1-continued

Examples of Target Bacteria and Host Insects

| Endosymbiont | Host Insect | Location | 16S rRNA |
|---|---|---|---|
| | | | GGAATCGCTAGTAATCGCGGATCAGCATGC
CGCGGTGAATACGTTCCCGGGCCTTGTAC
ACACCGCCC
(SEQ ID NO: 191) |
| Enterococcus | Bombyx mori | Gut | AGGTGATCCAGCCGCACCTTCCGATACGG
CTACCTTGTTACGACTTCACCCCAATCATCT
ATCCCACCTTAGGCGGCTGGCTCCAAAAAG
GTTACCTCACCGACTTCGGGTGTTACAAAC
TCTCGTGGTGTGACGGGCGGTGTGTACAA
GGCCCGGGAACGTATTCACCGCGGCGTGC
TGATCCGCGATTACTAGCGATTCCGGCTTC
ATGCAGGCGAGTTGCAGCCTGCAATCCGA
ACTGAGAGAAGCTTTAAGAGATTTGCATGA
CCTCGCGGTCTAGCGACTCGTTGTACTTCC
CATTGTAGCACGTGTGTAGCCCAGGTCATA
AGGGGCATGATGATTTGACGTCATCCCCAC
CTTCCTCCGGTTTGTCACCGGCAGTCTCGC
TAGAGTGCCCAACTAAATGATGGCAACTAA
CAATAAGGGTTGCGCTCGTTGCGGGACTTA
ACCCAACATCTCACGACACGAGCTGACGAC
AACCATGCACCACCTGTCACTTTGTCCCCG
AAGGGAAAGCTCTATCTCTAGAGTGGTCAA
AGGATGTCAAGACCTGGTAAGGTTCTTCGC
GTTGCTTCGAATTAAACCACATGCTCCACC
GCTTGTGCGGGCCCCCGTCAATTCCTTTGA
GTTTCAACCTTGCGGTCGTACTCCCCAGGC
GGAGTGCTTAATGCGTTTGCTGCAGCACTG
AAGGGCGGAAACCCTCCAACACTTAGCACT
CATCGTTTACGGCGTGGACTACCAGGGTAT
CTAATCCTGTTTGCTCCCCACGCTTTCGAG
CCTCAGCGTCAGTTACAGACCAGAGAGCC
GCCTTCGCCACTGGTGTTCCTCCATATATC
TACGCATTTCACCGCTACACATGGAATTCC
ACTCTCCTCTTCTGCACTCAAGTCTCCCAG
TTTCCAATGACCCTCCCCGGTTGAGCCGG
GGGCTTTCACATCAGACTTAAGAAACCGCC
TGCGCTCGCTTTACGCCCAATAAATCCGGA
CAACGCTTGCCACCTACGTATTACCGCGGC
TGCTGGCACGTAGTTAGCCGTGGCTTTCTG
GTTAGATACCGTCAGGGGACGTTCAGTTAC
TAACGTCCTTGTTCTTCTCTAACAACAGAGT
TTTACGATCCGAAAACCTTCTTCACTCACG
CGGCGTTGCTCGGTCAGACTTTCGTCCATT
GCCGAAGATTCCCTACTGCTGCCTCCCGTA
GGAGTCTGGGCCGTGTCTCAGTCCCAGTG
TGGCCGATCACCCTCTCAGGTCGGCTATG
CATCGTGGCCTTGGTGAGCCGTTACCTCAC
CAACTAGCTAATGCACCGCGGGTCCATCCA
TCAGCGACACCCGAAAGCGCCTTTCACTCT
TATGCCATGCGGCATAAACTGTTATGCGGT
ATTAGCACCTGTTTCCAAGTGTTATCCCCCT
CTGATGGGTAGGTTACCCACGTGTTACTCA
CCCGTCCGCCACTCCTCTTTCCAATTGAGT
GCAAGCACTCGGGAGGAAAGAAGCGTTCG
ACTTGCATGTATTAGGCACGCCGCCAGCGT
TCGTCCTGAGCCAGGATCAAACTCT
(SEQ ID NO: 5) |
| Delftia | Bombyx mori | Gut | CAGAAAGGAGGTGATCCAGCCGCACCTTC
CGATACGGCTACCTTGTTACGACTTCACCC
CAGTCACGAACCCGCCGTGGTAAGCGCC
CTCCTTGCGGTTAGGCTACCTACTTCTGGC
GAGACCCGCTCCCATGGTGTGACGGGCGG
TGTGTACAAGACCCGGGAACGTATTCACCG
CGGCATGCTGATCCGCGATTACTAGCGATT
CCGACTTCACGCAGTCGAGTTGCAGACTG
CGATCCGGACTACGACTGGTTTTATGGGAT
TAGCTCCCCCTCGCGGGTTGGCAACCCTC
TGTACCAGCCATTGTATGACGTGTGTAGCC
CCACCTATAAGGGCCATGAGGACTTGACGT
CATCCCCACCTTCCTCCGGTTTGTCACCGG
CAGTCTCATTAGAGTGCTCAACTGAATGTA
GCAACTAATGACAAGGGTTGCGCTCGTTGC
GGGACTTAACCCAACATCTCACGACACGAG
CTGACGACAGCCATGCAGCACCTGTGTGC |

TABLE 1-continued

Examples of Target Bacteria and Host Insects

| Endosymbiont | Host Insect | Location | 16S rRNA |
|---|---|---|---|
| | | | AGGTTCTCTTTCGAGCACGAATCCATCTCT<br>GGAAACTTCCTGCCATGTCAAAGGTGGGTA<br>AGGTTTTTCGCGTTGCATCGAATTAAACCA<br>CATCATCCACCGCTTGTGCGGGTCCCCGT<br>CAATTCCTTTGAGTTTCAACCTTGCGGCCG<br>TACTCCCCAGGCGGTCAACTTCACGCGTTA<br>GCTTCGTTACTGAGAAAACTAATTCCCAAC<br>AACCAGTTGACATCGTTTAGGGCGTGGACT<br>ACCAGGGTATCTAATCCTGTTTGCTCCCCA<br>CGCTTTCGTGCATGAGCGTCAGTACAGGTC<br>CAGGGGATTGCCTTCGCCATCGGTGTTCCT<br>CCGCATATCTACGCATTTCACTGCTACACG<br>CGGAATTCCATCCCCCTCTACCGTACTCTA<br>GCCATGCAGTCACAAATGCAGTTCCCAGGT<br>TGAGCCCGGGGATTTCACATCTGTCTTACA<br>TAACCGCCTGCGCACGCTTTACGCCCAGTA<br>ATTCCGATTAACGCTCGCACCCTACGTATT<br>ACCGCGGCTGCTGGCACGTAGTTAGCCGG<br>TGCTTATTCTTACGGTACCGTCATGGGCCC<br>CCTGTATTAGAAGGAGCTTTTTCGTTCCGT<br>ACAAAAGCAGTTTACAACCCGAAGGCCTTC<br>ATCCTGCACGCGGCATTGCTGGATCAGGC<br>TTTCGCCCATTGTCCAAAATTCCCCACTGC<br>TGCCTCCCGTAGGAGTCTGGGCCGTGTCT<br>CAGTCCCAGTGTGGCTGGTCGTCCTCTCA<br>GACCAGCTACAGATCGTCGGCTTGGTAAG<br>CTTTTATCCCACCAACTACCTAATCTGCCAT<br>CGGCCGCTCCAATCGCGCGAGGCCCGAAG<br>GGCCCCCGCTTTCATCCTCAGATCGTATGC<br>GGTATTAGCTACTCTTTCGAGTAGTTATCCC<br>CCACGACTGGGCACGTTCCGATGTATTACT<br>CACCCGTTCGCCACTCGTCAGCGTCCGAA<br>GACCTGTTACCGTTCGACTTGCATGTGTAA<br>GGCATGCCGCCAGCGTTCAATCTGAGCCA<br>GGATCAAACTCTACAGTTCGATCT<br>(SEQ ID NO: 6) |
| Pelomonas | Bombyx mori | Gut | ATCCTGGCTCAGATTGAACGCTGGCGGCAT<br>GCCTTACACATGCAAGTCGAACGGTAACAG<br>GTTAAGCTGACGAGTGGCGAACGGGTGAG<br>TAATATATCGGAACGTGCCCAGTCGTGGGG<br>GATAACTGCTCGAAAGAGCAGCTAATACCG<br>CATACGACCTGAGGGTGAAAGCGGGGGAT<br>CGCAAGACCTCGCNNGATTGGAGCGGCCG<br>ATATCAGATTAGGTAGTTGGTGGGGTAAAG<br>GCCCACCAAGCCAACGATCTGTAGCTGGT<br>CTGAGAGGACGACCAGCCACACTGGGACT<br>GAGACACGGCCCAGACTCCTACGGGAGGC<br>AGCAGTGGGGAATTTTGGACAATGGGCGC<br>AAGCCTGATCCAGCCATGCCGCGTGCGGG<br>AAGAAGGCCTTCGGGTTGTAAACCGCTTTT<br>GTCAGGGAAGAAAAGGTTCTGGTTAATACC<br>TGGGACTCATGACGGTACCTGAAGAATAAG<br>CACCGGCTAACTACGTGCCAGCAGCCGCG<br>GTAATACGTAGGGTGCAAGCGTTAATCGGA<br>ATTACTGGGCGTAAAGCGTGCGCAGGCGG<br>TTATGCAAGACAGAGGTGAAATCCCCGGG<br>CTCAACCTGGGAACTGCCTTTGTGACTGCA<br>TAGCTAGAGTACGGTAGAGGGGGATGGAA<br>TTCCGCGTGTAGCAGTGAAATGCGTAGATA<br>TGCGGAGGAACACCGATGGCGAAGGCAAT<br>CCCCTGGACCTGTACTGACGCTCATGCAC<br>GAAAGCGTGGGGAGCAAACAGGATTAGAT<br>ACCCTGGTAGTCCACGCCCTAAACGATGTC<br>AACTGGTTGTTGGGAGGGTTTCTTCTCAGT<br>AACGTANNTAACGCGTGAAGTTGACCGCCT<br>GGGGAGTACGGCCGCAAGGTTGAAACTCA<br>AAGGAATTGACGGGGACCCGCACAAGCGG<br>TGGATGATGTGGTTTAATTCGATGCAACGC<br>GAAAAACCTTACCTACCCTTGACATGCCAG<br>GAATCCTGAAGAGATTTGGGAGTGCTCGAA<br>AGAGAACCTGGACACAGGTGCTGCATGGC<br>CGTCGTCAGCTCGTGTCGTGAGATGTTGG<br>GTTAAGTCCCGCAACGAGCGCAACCCTTGT<br>CATTAGTTGCTACGAAAGGGCACTCTAATG<br>AGACTGCCGGTGACAAACCGGAGGAAGGT |

TABLE 1-continued

Examples of Target Bacteria and Host Insects

| Endosymbiont | Host Insect | Location | 16S rRNA |
|---|---|---|---|
| | | | GGGGATGACGTCAGGTCATCATGGCCCTT<br>ATGGGTAGGGCTACACACGTCATACAATGG<br>CCGGGACAGAGGGCTGCCAACCCGCGAG<br>GGGGAGCTAATCCCAGAAACCCGGTCGTA<br>GTCCGGATCGTAGTCTGCAACTCGACTGC<br>GTGAAGTCGGAATCGCTAGTAATCGCGGAT<br>CAGCTTGCCGCGGTGAATACGTTCCCGGG<br>TCTTGTACACACCGCCCGTCACACCATGGG<br>AGCGGGTTCTGCCAGAAGTAGTTAGCCTAA<br>CCGCAAGGAGGGCGATTACCACGGCAGGG<br>TTCGTGACTGGGGTGAAGTCGTAACAAGGT<br>AGCCGTATCGGAAGGTGCGGCTGGATCAC<br>(SEQ ID NO: 7) |

Any number of bacterial species may be targeted by the compositions or methods described herein. For example, in some instances, the modulating agent may target a single bacterial species. In some instances, the modulating agent may target at least about any of 1, 2, 3, 4, 5, 6, 7, 8, 9, 10, 15, 20, 30, 40, 50, 60, 70, 80, 90, 100, 150, 200, 250, 500, or more distinct bacterial species. In some instances, the modulating agent may target any one of about 1 to about 5, about 5 to about 10, about 10 to about 20, about 20 to about 50, about 50 to about 100, about 100 to about 200, about 200 to about 500, about 10 to about 50, about 5 to about 20, or about 10 to about 100 distinct bacterial species. In some instances, the modulating agent may target at least about any of 1, 2, 3, 4, 5, 6, 7, 8, 9, 10, 15, 20, 30, 40, 50, 60, 70, 80, 90, 100, or more phyla, classes, orders, families, or genera of bacteria.

In some instances, the modulating agent may increase a population of one or more bacteria (e.g., symbiotic bacteria) by at least about any of 10%, 20%, 30%, 40%, 50%, 60%, 70%, 80%, 90% or more in the host in comparison to a host organism to which the modulating agent has not been administered. In some instances, the modulating agent may reduce the population of one or more bacteria (e.g., pathogenic or parasitic bacteria) by at least about any of 10%, 20%, 30%, 40%, 50%, 60%, 70%, 80%, 90%, or more in the host in comparison to a host organism to which the modulating agent has not been administered. In some instances, the modulating agent may eradicate the population of a bacterium (e.g., a pathogenic or parasitic bacteria) in the host. In some instances, the modulating agent may increase the level of one or more symbiotic bacteria by at least about any of 10%, 20%, 30%, 40%, 50%, 60%, 70%, 80%, 90% or more in the host and/or decreases the level of one or more pathogenic bacteria by at least about any of 10%, 20%, 30%, 40%, 50%, 60%, 70%, 80%, 90%, or more in the host in comparison to a host organism to which the modulating agent has not been administered.

In some instances, the modulating agent may alter the bacterial diversity and/or bacterial composition of the host. In some instances, the modulating agent may increase the bacterial diversity in the host relative to a starting diversity by at least about any of 10%, 20%, 30%, 40%, 50%, 60%, 70%, 80%, 90%, or more in comparison to a host organism to which the modulating agent has not been administered. In some instances, the modulating agent may decrease the bacterial diversity in the host relative to a starting diversity by at least about any of 10%, 20%, 30%, 40%, 50%, 60%, 70%, 80%, 90%, or more in comparison to a host organism to which the modulating agent has not been administered.

In some instances, the modulating agent may alter the function, activity, growth, and/or division of one or more bacterial cells. For example, the modulating agent may alter the expression of one or genes in the bacteria. In some instances, the modulating agent may alter the function of one or more proteins in the bacteria. In some instances, the modulating agent may alter the function of one or more cellular structures (e.g., the cell wall, the outer or inner membrane) in the bacteria. In some instances, the modulating agent may kill (e.g., lyse) the bacteria.

The target bacterium may reside in one or more parts of the insect. Further, the target bacteria may be intracellular or extracellular. In some instances, the bacteria reside in or on one or more parts of the host gut, including, e.g., the foregut, midgut, and/or hindgut. For example, in honey bees (e.g., *Apis mellifera*), bacterial symbionts confined to the hindguts of adults are acquired in the first few days following emergence of adults from the pupal stage, through social interactions with other adult worker bees in the colony. Honey bee gut inhabitants belong to a small number of distinctive lineages found only in honey bees and also in other *Apis* species and in *Bombus* species (bumble bees). In some instances, the target bacteria are resident in a honeybee. In some instances, one or more bacteria targeted in the honeybee is a *Snodgrassella* spp. (e.g., *Snodgrasella alvi*), a *Gilliamella* spp. (e.g., *Gilliamella apicola*), a *Bartonella* spp. (e.g., *Bartonella apis*), a *Parasaccharibacter* spp. (e.g., *Parasaccharibacter apium*), or a *Lactobacillus* spp. (e.g., *Lactobacillus kunkeei, Lactobacillus* Firm-4).

In some instances, the bacteria reside as an intracellular bacteria within a cell of the host insect. In some instances, the bacteria reside in a bacteriocyte of the host insect.

Changes to the populations of bacteria in the host may be determined by any methods known in the art, such as microarray, polymerase chain reaction (PCR), real-time PCR, flow cytometry, fluorescence microscopy, transmission electron microscopy, fluorescence in situ hybridization (e.g., FISH), spectrophotometry, matrix-assisted laser desorption ionization-mass spectrometry (MALDI-MS), and DNA sequencing. In some instances, a sample of the host treated with a modulating agent is sequenced (e.g., by metagenomics sequencing of 16S rRNA or rDNA) to determine the microbiome of the host after delivery or administration of the modulating agent. In some instances, a sample of a host that did not receive the modulating agent is also sequenced to provide a reference.

ii. Fungi

Exemplary fungi that may be targeted in accordance with the methods and compositions provided herein, include, but are not limited to *Amylostereum areolatum, Epichloe* spp, *Pichia pinus, Hansenula capsulate, Daldinia decipien, Ceratocytis* spp, *Ophiostoma* spp, and *Attamyces bromatificus*. Non-limiting examples of yeast and yeast-like symbionts found in insects include *Candida, Metschnikowia, Debaromyces, Scheffersomyces shehatae* and *Scheffersomyces stipites, Starmerella, Pichia, Trichosporon, Cryptococcus, Pseudozyma*, and yeast-like symbionts from the subphylum *Pezizomycotina* (e.g., *Symbiotaphrina bucneri* and *Symbiotaphrina kochii*). Non-limiting examples of yeast that may be targeted by the methods and compositions herein are listed in Table 2.

TABLE 2

Examples of Yeast in Insects

| Insect Species | Order: Family | Yeast Location (Species) |
|---|---|---|
| *Stegobium paniceum* (=*Sitodrepa panicea*) | Coleoptera: Anobiidae | Mycetomes (*Saccharomyces*) <br> Cecae (*Torulopsis buchnerii*) <br> Mycetome between foregut and midgut <br> Mycetomes (*Symbiotaphrina buchnerii*) <br> Mycetomes and digestive tube (*Torulopsis buchnerii*) <br> Gut cecae (*Symbiotaphrina buchnerii*) |
| *Lasioderma serricorne* | Coleoptera: Anobiidae | Mycetome between foregut and midgut (*Symbiotaphrina kochii*) |
| *Ernobius abietis* | Coleoptera: Anobiidae | Mycetomes (*Torulopsis karawaiewii*) (*Candida karawaiewii*) |
| *Ernobius mollis* | Coleoptera: Anobiidae | Mycetomes (*Torulopsis ernobii*) (*Candida ernobii*) |
| *Hemicoelus gibbicollis* | Coleoptera: Anobiidae | Larval mycetomes |
| *Xestobium plumbeum* | Coleoptera: Anobiidae | Mycetomes (*Torulopsis xestobii*) (*Candida xestobii*) |
| *Criocephalus rusticus* | Coleoptera: Cerambycidae | Mycetomes |
| *Phoracantha semipunctata* | Coleoptera: Cerambycidae | Alimentary canal (*Candida guilliermondii, C. tenuis*) <br> Cecae around midgut (*Candida guilliermondii*) |
| *Harpium inquisitor* | Coleoptera: Cerambycidae | Mycetomes (*Candida rhagii*) |
| *Harpium mordax* <br> *H. sycophanta* | Coleoptera: Cerambycidae | Cecae around midgut (*Candida tenuis*) |
| *Gaurotes virginea* | Coleoptera: Cerambycidae | Cecae around midgut (*Candida rhagii*) |
| *Leptura rubra* | Coleoptera: Cerambycidae | Cecae around midgut (*Candida tenuis*) <br> Cecae around midgut (*Candida parapsilosis*) |
| *Leptura maculicornis* <br> *L. cerambyciformis* | Coleoptera: Cerambycidae | Cecae around midgut (*Candida parapsilosis*) |
| *Leptura sanguinolenta* | Coleoptera: Cerambycidae | Cecae around midgut (*Candida* sp.) |
| *Rhagium bifasciatum* | Coleoptera: Cerambycidae | Cecae around midgut (*Candida tenuis*) |
| *Rhagium inquisitor* | Coleoptera: Cerambycidae | Cecae around midgut (*Candida guilliermondii*) |
| *Rhagium mordax* | Coleoptera: Cerambycidae | Cecae around midgut (*Candida*) |
| *Carpophilus hemipterus* | Coleoptera: Nitidulidae | Intestinal tract (10 yeast species) |
| *Odontotaenius disjunctus* | Coleoptera: Passalidae | Hindgut (*Enteroramus dimorphus*) |
| *Odontotaenius disjunctus* <br> *Verres sternbergianus* | Coleoptera: Passalidae | Gut (*Pichia stipitis, P. segobiensis, Candida shehatae*) <br> (*C. ergatensis*) |
| *Scarabaeus semipunctatus* <br> *Chironitis furcifer* | Coleoptera: Scarabaeidae | Digestive tract (10 yeast species) |
| Unknown species | Coleoptera: Scarabaeidae | Guts (*Trichosporon cutaneum*) |
| *Dendroctonus* and *Ips* spp. | Coleoptera: Scolytidae | Alimentary canal (13 yeast species) |
| *Dendroctonus frontalis* | Coleoptera: Scolytidae | Midgut (*Candida* sp.) |
| *Ips sexdentatus* | Coleoptera: Scolytidae | Digestive tract (*Pichia bovis, P. rhodanensis*) <br> *Hansenula holstii* (*Candida rhagii*) <br> Digestive tract (*Candida pulcherina*) |
| *Ips typographus* | Coleoptera: Scolytidae | Alimentary canal <br> Alimentary tracts (*Hansenula capsulata, Candida parapsilosis*) <br> Guts and beetle homogenates (*Hansenula holstii, H. capsulata, Candida diddensii, C. mohschtana, C. nitratophila, Cryptococcus albidus, C. laurentii*) |
| *Trypodendron lineatum* | Coleoptera: Scolytidae | Not specified |
| *Xyloterinus politus* | Coleoptera: Scolytidae | Head, thorax, abdomen (*Candida, Pichia, Saccharomycopsis*) |

TABLE 2-continued

Examples of Yeast in Insects

| Insect Species | Order: Family | Yeast Location (Species) |
|---|---|---|
| *Periplaneta americana* | Dictyoptera: Blattidae | Hemocoel (*Candida* sp. nov.) |
| *Blatta orientalis* | Dictyoptera: Blattidae | Intestinal tract (*Kluyveromyces blattae*) |
| *Blatella germanica* | Dictyoptera: Blattellidae | Hemocoel |
| *Cryptocercus punctulatus* | Dictyoptera: Cryptocercidae | Hindgut (1 yeast species) |
| *Philophylla heraclei* | Diptera: Tephritidae | Hemocoel |
| *Aedes* (4 species) | Diptera: Culicidae | Internal microflora (9 yeast genera) |
| *Drosophila pseudoobscura* | Diptera: Drosophilidae | Alimentary canal (24 yeast species) |
| *Drosophila* (5 spp.) | Diptera: Drosophilidae | Crop (42 yeast species) |
| *Drosophila melanogaster* | Diptera: Drosophilidae | Crop (8 yeast species) |
| *Drosophila* (4 spp.) | Diptera: Drosophilidae | Crop (7 yeast species) |
| *Drosophila* (6 spp.) | Diptera: Drosophilidae | Larval gut (17 yeast species) |
| *Drosophila* (20 spp.) | Diptera: Drosophilidae | Crop (20 yeast species) |
| *Drosophila* (8 species groups) | Diptera: Drosophilidae | Crop (*Kloeckera, Candida, Kluyveromyces*) |
| *Drosophila serido* | Diptera: Drosophilidae | Crop (18 yeast species) |
| *Drosophila* (6 spp.) | Diptera: Drosophilidae | Intestinal epithelium (*Coccidiascus legeri*) |
| *Protaxymia melanoptera* | Diptera | Unknown (*Candida, Cryptococcus, Sporoblomyces*) |
| *Astegopteryx styraci* | Homoptera: Aphididae | Hemocoel and fat body |
| *Tuberaphis* sp. *Hamiltonaphis styraci Glyphinaphis bambusae Cerataphis* sp. | Homoptera: Aphididae | Tissue sections |
| *Hamiltonaphis styraci* | Homoptera: Aphididae | Abdominal hemocoel |
| *Cofana unimaculata* | Homoptera: Cicadellidae | Fat body |
| *Leofa unicolor* | Homoptera: Cicadellidae | Fat body |
| *Lecaniines*, etc. | Homoptera: Coccoidea d | Hemolymph, fatty tissue, etc. |
| *Lecanium* sp. | Homoptera: Coccidae | Hemolymph, adipose tissue |
| *Ceroplastes* (4 sp.) | Homoptera: Coccidae | Blood smears |
| *Laodelphax striatellus* | Homoptera: Delphacidae | Fat body<br>Eggs<br>Eggs (*Candida*) |
| *Nilaparvata lugens* | Homoptera: Delphacidae | Fat body<br>Eggs (2 unidentified yeast species)<br>Eggs, nymphs (*Candida*)<br>Eggs (7 unidentified yeast species)<br>Eggs (*Candida*) |
| *Nisia nervosa Nisia grandiceps Perkinsiella* spp. *Sardia rostrata Sogatella furcifera* | Homoptera: Delphacidae | Fat body |
| *Sogatodes orizicola* | Homoptera: Delphacidae | Fat body |
| *Amrasca devastans* | Homoptera: Jassidae | Eggs, mycetomes, hemolymph |
| *Tachardina lobata* | Homoptera: Kerriidae | Blood smears (*Torulopsis*) |
| *Laccifer* (=*Lakshadia*) sp. | Homoptera: Kerriidae | Blood smears (*Torula variabilis*) |
| *Comperia merceti* | Hymenoptera: Encyrtidae | Hemolymph, gut, poison gland |
| *Solenopsis invicta S. quinquecuspis* | Hymenoptera: Formicidae | Hemolymph (*Myrmecomyces annellisae*) |
| *Solenopsis invicta* | Hymenoptera: Formicidae | Fourth instar larvae (*Candida parapsilosis, Yarrowia lipolytica*)<br>Gut and hemolymph (*Candida parapsilosis, C. lipolytica, C. guillermondii, C. rugosa, Debaryomyces hansenii*) |
| *Apis mellifera* | Hymenoptera: Apidae | Digestive tracts (*Torulopsis* sp.)<br>Intestinal tract (*Torulopsis apicola*)<br>Digestive tracts (8 yeast species)<br>Intestinal contents (12 yeast species)<br>Intestinal contents (7 yeast species)<br>Intestines (14 yeast species)<br>Intestinal tract (*Pichia melissophila*)<br>Intestinal tracts (7 yeast species)<br>Alimentary canal (*Hansenula silvicola*)<br>Crop and gut (13 yeast species) |
| *Apis mellifera* | Hymenoptera: Apidae | Midguts (9 yeast genera) |
| *Anthophora occidentalis* | Hymenoptera: Anthophoridae | |
| *Nomia melanderi* | Hymenoptera: Halictidae | |

TABLE 2-continued

Examples of Yeast in Insects

| Insect Species | Order: Family | Yeast Location (Species) |
|---|---|---|
| Halictus rubicundus | Hymenoptera: Halictidae | |
| Megachile rotundata | Hymenoptera: Megachilidae | |

Any number of fungal species may be targeted by the compositions or methods described herein. For example, in some instances, the modulating agent may target a single fungal species. In some instances, the modulating agent may target at least about any of 1, 2, 3, 4, 5, 6, 7, 8, 9, 10, 15, 20, 30, 40, 50, 60, 70, 80, 90, 100, 150, 200, 250, 500, or more distinct fungal species. In some instances, the modulating agent may target any one of about 1 to about 5, about 5 to about 10, about 10 to about 20, about 20 to about 50, about 50 to about 100, about 100 to about 200, about 200 to about 500, about 10 to about 50, about 5 to about 20, or about 10 to about 100 distinct fungal species. In some instances, the modulating agent may target at least about any of 1, 2, 3, 4, 5, 6, 7, 8, 9, 10, 15, 20, 30, 40, 50, 60, 70, 80, 90, 100, or more phyla, classes, orders, families, or genera of fungi.

In some instances, the modulating agent may increase a population of one or more fungi (e.g., symbiotic fungi) by at least about any of 10%, 20%, 30%, 40%, 50%, 60%, 70%, 80%, 90% or more in the host in comparison to a host organism to which the modulating agent has not been administered. In some instances, the modulating agent may reduce the population of one or more fungi (e.g., pathogenic or parasitic fungi) by at least about any of 10%, 20%, 30%, 40%, 50%, 60%, 70%, 80%, 90% or more in the host in comparison to a host organism to which the modulating agent has not been administered. In some instances, the modulating agent may eradicate the population of a fungi (e.g., a pathogenic or parasitic fungi) in the host. In some instances, the modulating agent may increase the level of one or more symbiotic fungi by at least about any of 10%, 20%, 30%, 40%, 50%, 60%, 70%, 80%, 90% or more in the host and/or may decrease the level of one or more pathogenic fungi by at least about any of 10%, 20%, 30%, 40%, 50%, 60%, 70%, 80%, 90% or more in the host in comparison to a host organism to which the modulating agent has not been administered.

In some instances, the modulating agent may alter the fungal diversity and/or fungal composition of the host. In some instances, the modulating agent may increase the fungal diversity in the host relative to a starting diversity by at least about any of 10%, 20%, 30%, 40%, 50%, 60%, 70%, 80%, 90%, or more in comparison to a host organism to which the modulating agent has not been administered. In some instances, the modulating agent may decrease the fungal diversity in the host relative to a starting diversity by at least about any of 10%, 20%, 30%, 40%, 50%, 60%, 70%, 80%, 90%, or more in comparison to a host organism to which the modulating agent has not been administered.

In some instances, the modulating agent may alter the function, activity, growth, and/or division of one or more fungi. For example, the modulating agent may alter the expression of one or more genes in the fungus. In some instances, the modulating agent may alter the function of one or more proteins in the fungus. In some instances, the modulating agent may alter the function of one or more cellular components in the fungus. In some instances, the modulating agent may kill the fungus.

Further, the target fungus may reside in one or more parts of the insect. In some instances, the fungus resides in or on one or more parts of the insect gut, including, e.g., the foregut, midgut, and/or hindgut. In some instances, the fungus lives extracellularly in the hemolymph, fat bodies or in specialized structures in the host.

Changes to the population of fungi in the host may be determined by any methods known in the art, such as microarray, polymerase chain reaction (PCR), real-time PCR, flow cytometry, fluorescence microscopy, transmission electron microscopy, fluorescence in situ hybridization (e.g., FISH), spectrophotometry, matrix-assisted laser desorption ionization-mass spectrometry (MALDI-MS), and DNA sequencing. In some instances, a sample of the host treated with modulating agent is sequenced (e.g., by metagenomics sequencing) to determine the microbiome of the host after delivery or administration of the modulating agent. In some instances, a sample of a host that did not receive the modulating agent is also sequenced to provide a reference.

III. Modulating Agents

The modulating agent of the methods and compositions provided herein may include a phage, a polypeptide, a small molecule, an antibiotic, a secondary metabolite, a bacterium, or any combination thereof.

i. Phage

The modulating agent described herein may include a phage (e.g., a lytic phage or a non-lytic phage). In some instances, an effective concentration of any phage described herein may altering a level, activity, or metabolism of one or more microorganisms (as described herein) resident in a host described herein, the alteration resulting in an increase in the host's fitness. In some instances, the modulating agent includes at least one phage selected from the order Tectiviridae, Myoviridae, Siphoviridae, Podoviridae, Caudovirales, Lipothrixviridae, Rudiviridae, or Ligamenvirales. In some instances, the composition includes at least one phage selected from the family Myoviridae, Siphoviridae, Podoviridae, Lipothrixviridae, Rudiviridae, Ampullaviridae, Bicaudaviridae, Clavaviridae, Corticoviridae, Cystoviridae, Fuselloviridae, Globuloviridae, Guttaviridae, Inoviridae, Leviviridae, Microviridae, Plasmaviridae, and Tectiviridae. Further non-limiting examples of phages useful in the methods and compositions are listed in Table 3.

TABLE 3

Examples of Phage and Targeted Bacteria

| Phage and Accession # | Target bacteria | Target host |
|---|---|---|
| SA1(NC_027991), phiP68 (NC_004679) | *Staphylococcus* sp. | Apidae family |
| WO (AB036666.1) | *Wolbachia* sp. | *Aedes aegypt*; *Drosophila melanogaster*, *Plasmodium* sp; *Teleogryllus taiwanemma*; *Bombyx mori* |
| KL1 (NC_018278), BcepNazgul (NC_005091) PhiE125 (NC_003309) | *Burkholderia* sp. | *Riptortus* sp.; *Pyrrhocoris apterus*. |
| Fern (NC_028851), Xenia (NC_028837), HB10c2 (NC_028758) | *Paenibacillus larvae* | bumble bees: *Bombus* sp.; honey bees: *A. mellifera* |
| CP2 (NC_020205), XP10 (NC_004902), XP15 (NC_007024), phiL7 (NC_012742) | *Xanthomonas* sp. | *Plebeina denoiti*; Apidae family; *Apis mellifera*; Drosphilidae family; and Chloropidae family |
| PP1 (NC_019542), PM1 (NC_023865) | *Pectobacterium carotovorum* subsp. *carotovorum* | Apidae family |
| ΦRSA1 (NC_009382), ΦRSB1 (NC_011201), ΦRSL1 (NC.010811), RSM1 (NC_008574) | *Ralstonia solanacearum* | *Bombyx mori* |
| SF1 (NC_028807) | *Streptomyces scabies* | *Philantus* sp.; *Trachypus* sp |
| ECML-4 (NC_025446), ECML-117 (NC_025441), ECML-134 (NC_025449) | *Escherichia coli* | Apidae family; *Varroa destructor* |
| SSP5(JX274646.1), SSP6 (NC_004831), SFP10 (NC_016073), F18SE (NC_028698) | *Salmonella* sp. | Drosphilidae family |
| γ (NC_001416), Bcp1 (NC_024137) | *Bacillus* sp. | Gypsy moth; *Lymantria dispar*, *Varroa destructor* |
| Phi1 (NC_009821) | *Enterococcus* sp. | *Schistocerca gragaria* |
| ΦKMV (NC_005045), ΦEL(AJ697969.1), ΦKZ (NC_004629) | *Pseudomonas* sp. | *Lymantria dispar*; Apidae family |
| A2 (NC_004112), phig1e (NC_004305) | *Lactobacilli* sp. | Apidae family; Drosophila family; *Varroa destructor* |
| KLPN1 (NC_028760) | *Klebsiella* sp | *C. capitata* |
| vB_AbaM_Acibel004 (NC_025462), vB_AbaP_Acibel007 (NC_025457) | *Acinetobacter* sp. | *Schistocerca gragaria* |

In some instances, a modulating agent includes a lytic phage. Thus, after delivery of the lytic phage to a bacterial cell resident in the host, the phage causes lysis in the target bacterial cell. In some instances, the lytic phage targets and kills a bacterium resident in a host insect to increase the fitness of the host. Alternatively or additionally, the phage of the modulating agent may be a non-lytic phage (also referred to as lysogenic or temperate phage). Thus, after delivery of the non-lytic phage to a bacterial cell resident in the host, the bacterial cell may remain viable and able to stably maintain expression of genes encoded in the phage genome. In some instances, a non-lytic phage is used to alter gene expression in a bacterium resident in a host insect to increase the fitness of the host. In some instances, the modulating agent includes a mixture of lytic and non-lytic phage.

The modulating agent described herein may include phage with either a narrow or broad bacterial target range. In some instances, the phage has a narrow bacterial target range. In some instances, the phage is a promiscuous phage with a large bacterial target range. For example, the promiscuous phage may target at least about any of 5, 10, 20, 30, 40, 50, or more bacterium resident in the host. A phage with a narrow bacterial target range may target a specific bacterial strain in the host without affecting another, e.g., non-targeted, bacterium in the host. For example, the phage may target no more than about any of 50, 40, 30, 20, 10, 8, 6, 4, 2, or 1 bacterium resident in the host. For example, the compositions described herein may target the bacterial pathogen *Paenibacillus* larvae in honeybees but may not target other bacteria (e.g., symbiotic bacteria) including *Lactobacillus* Firm4, *Lactobacillus* Firm5, *Bifidobacterium* sp, *Snodgrassella alvi*, *Gilliamella apicola*, *Bartonella apis*, *Parasaccharibacter apium*, or *Lactobacillus kunkeei*. In some instances, the phage infects one or more specific bacteria by binding to a cell surface protein (e.g., OmpF, LamB, BtuB, TolC, etc) or to a different recognition molecule (e.g., glycolipids, LPS, lipoteichoic acid, etc.).

The compositions described herein may include any number of phage, such as at least about any one of 1, 2, 3, 4, 5, 10, 15, 20, 30, 40, 50, 100, or more phage. In some instances, the composition includes phage from one or more (e.g., 2, 3, 4, 5, 6, 7, 8, 9, 10, or more phage) families, one or more orders (e.g., 2, 3, 4, 5, 6, 7, 8, 9, 10, or more phage), or one or more species (e.g., 1, 2, 3, 4, 5, 10, 15, 20, 30, 40, 50, 100, or more phage). Compositions including one or more phage are also referred herein as "phage cocktails." Phage cocktails are useful because they allow for targeting of a wider host range of bacteria. Furthermore, they allow for each bacterial strain (i.e. subspecies) to be targeted by multiple orthogonal phages, thereby preventing or significantly delaying the onset of resistance. In some instances, a cocktail includes multiple phages targeting one bacterial species. In some instances, a cocktail includes multiple phages targeting multiple bacterial species. In some instances, a one-phage "cocktail" includes a single promiscuous phage (i.e. a phage with a large host range) targeting many strains within a species.

Suitable concentrations of the phage in the modulating agent described herein depends on factors such as efficacy, survival rate, transmissibility of the phage, number of distinct phage, and/or lysin types in the compositions, formulation, and methods of application of the composition. In some instances, the phage is in a liquid or a solid formulation. In some instances, the concentration of each phage in any of the compositions described herein is at least about any of $10^2$, $10^3$, $10^4$, $10^5$, $10^6$, $10^7$, $10^8$, $10^9$, $10^{10}$ or more pfu/ml. In some instances, the concentration of each phage in any of the compositions described herein is no more than about any of $10^2$, $10^3$, $10^4$, $10^5$, $10^6$, $10^7$, $10^8$, $10^9$ pfu/ml. In some instances, the concentration of each phage in the composition is any of about $10^2$ to about $10^3$, about $10^3$ to about $10^4$, about $10^4$ to about $10^5$, about $10^5$ to about $10^6$, about $10^7$ to about $10^8$, about $10^8$ to about $10^9$, about $10^2$ to about $10^4$, about $10^4$ to about $10^6$, about $10^6$ to about $10^9$, or about $10^3$ to about $10^8$ pfu/ml. In some instances, wherein the composition includes at least two types of phages, the concentration of each type of the phages may be the same or different. For example, in some instances, the concentration of one phage in the cocktail is about $10^8$ pfu/ml and the concentration of a second phage in the cocktail is about $10^6$ pfu/ml.

A modulating agent including a phage as described herein can be contacted with the target host in an amount and for a time sufficient to: (a) reach a target level (e.g., a predetermined or threshold level) of phage concentration inside a target host; (b) reach a target level (e.g., a predetermined or threshold level) of phage concentration inside a target host gut; (c) reach a target level (e.g., a predetermined or threshold level) of phage concentration inside a target host bacteriocyte; (d) modulate the level, or an activity, of one or more microorganism (e.g., endosymbiont) in the target host; or/and (e) modulate fitness of the target host.

As illustrated by Example 7 and 11, phages can be used as a modulating agents by eliminating bacterial pathogens such as *Serratia marcescens, Erwinia catotovora,* and *Pseudomonas enzomophila* from insect hosts, such as honeybees or silkworms.

ii. Polypeptides

Numerous polypeptides (e.g., a bacteriocin, R-type bacteriocin, nodule C-rich peptide, antimicrobial peptide, lysin, or bacteriocyte regulatory peptide) may be used in the compositions and methods described herein. In some instances, an effective concentration of any peptide or polypeptide described herein may alter a level, activity, or metabolism of one or more microorganisms (as described herein) resident in a host, the alteration resulting in an increase in the host's fitness. Polypeptides included herein may include naturally occurring polypeptides or recombinantly produced variants. For example, the polypeptide may be a functionally active variant of any of the polypeptides described herein with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region or over the entire sequence, to a sequence of a polypeptide described herein or a naturally occurring polypeptide.

A modulating agent comprising a polypeptide as described herein can be contacted with the target host in an amount and for a time sufficient to: (a) reach a target level (e.g., a predetermined or threshold level) of concentration inside a target host; (b) reach a target level (e.g., a predetermined or threshold level) of concentration inside a target host gut; (c) reach a target level (e.g., a predetermined or threshold level) of concentration inside a target host bacteriocyte; (d) modulate the level, or an activity, of one or more microorganism (e.g., endosymbiont) in the target host; or/and (e) modulate fitness of the target host.

The polypeptide modulating agents discussed hereinafter, namely bacteriocins, lysins, antimicrobial peptides, nodule C-rich peptides, and bacteriocyte regulatory peptides, can be used to alter the level, activity, or metabolism of target microorganisms as indicated in the section for increasing the fitness of insects, such as honeybees and silkworms.

(a) Bacteriocins

The modulating agent described herein may include a bacteriocin. In some instances, the bacteriocin is naturally produced by Gram-positive bacteria, such as *Pseudomonas, Streptomyces, Bacillus, Staphylococcus,* or lactic acid bacteria (LAB, such as *Lactococcus lactis*). In some instances, the bacteriocin is naturally produced by Gram-negative bacteria, such as *Hafnia alvei, Citrobacter freundii, Klebsiella oxytoca, Klebsiella pneumonia, Enterobacter cloacae, Serratia plymithicum, Xanthomonas campestris, Erwinia carotovora, Ralstonia solanacearum,* or *Escherichia coli*. Exemplary bacteriocins include, but are not limited to, Class I-IV LAB antibiotics (such as lantibiotics), colicins, microcins, and pyocins. Non-limiting examples of bacteriocins are listed in Table 4.

TABLE 4

Examples of Bacteriocins

| Class | Name | Producer | Targets | Sequence |
|---|---|---|---|---|
| Class I | Nisin | *Lactococcus lactis* | Active on Gram-positive bacteria: *Enterococcus, Lactobacillus, Lactococcus, Leuconostoc, Listeria, Clostridium* | ITSISLCTPGCKT GALMGCNMKTA TCHCSIHVSK (SEQ ID NO: 8) |
| | Epidermin | *Staphylococcus epidermis* | Gram-positive bacteria | IASKFICTPGCA KTGSFNSYCC (SEQ ID NO: 9) |

TABLE 4-continued

Examples of Bacteriocins

| Class | Name | Producer | Targets | Sequence |
|---|---|---|---|---|
| Class II | | | | |
| Class II a | Pediocin PA-1 | *Pediococcus acidilactici* | Pediococci, Lactobacilli, Leuconostoc, Brochothrix thermosphacta, Propionibacteria, Bacilli, Enterococci, Staphylococci, Listeria clostridia, Listeria monocytogenes, Listeria innocua | KYYGNGVTCG KHSCSVDWGK ATTCINNGAMA WATGGHQGNH KC (SEQ ID NO: 10) |
| Class II b | Enterocin P | *Enterococcus faecium* | Lactobacillus sakei, Enterococcus faecium | ATRSYGNGVYC NNSKCWVNWG EAKENIAGIVISG WASGLAGMGH (SEQ ID NO: 11) |
| Class II c | Lactococcin G | *Streptococcus lactis* | Gram-positive bacteria | GTWDDIGQGIG RVAYWVGKAM GNMSDVNQAS RINRKKKH (SEQ ID NO: 12) |
| Class II d | Lactacin-F | *Lactobacillus johnsonii* | Lactobacilli, Enterococcus faecalis | NRWGDTVLSAA SGAGTGIKACK SFGPWGMAICG VGGAAIGGYFG YTHN (SEQ ID NO: 13) |
| Class III | | | | |
| Class III a | Enterocin AS-48 | *Enterococcus faecalis* | Broad spectrum: Gram positive and Gram negative bacteria. | MAKEFGIPAAVA GTVLNVVEAGG WVTTIVSILTAV GSGGLSLLAAA GRESIKAYLKKE IKKKGKRAVIAW (SEQ ID NO: 14) |
| Class III b | Aureocin A70 | *Staphylococcus aureus* | Broad spectrum: Gram positive and Gram negative bacteria. | MSWLNFLKYIAK YGKKAVSAAWK YKGKVLEWLNV GPTLEWVWQKL KKIAGL (SEQ ID NO: 15) |
| Class IV | Garvicin A | *Lactococcus garvieae* | Broad spectrum: Gram positive and Gram negative bacteria. | IGGALGNALNGL GTWANMMNGG GFVNQWQVYA NKGKINQYRPY (SEQ ID NO: 16) |
| Unclassified | Colicin V | *Escherichia coli* | Active against Escherichia coli (also closely related bacteria), Enterobacteriaceae | MRTLTLNELDS VSGGASGRDIA MAIGTLSGQFV AGGIGAAAGGV AGGAIYDYAST HKPNPAMSPSG LGGTIKQKPEGI PSEAWNYAAGR LCNWSPNNLSD VCL (SEQ ID NO: 17) |

In some instances, the bacteriocin is a colicin, a pyocin, or a microcin produced by Gram-negative bacteria. In some instances, the bacteriocin is a colicin. The colicin may be a group A colicin (e.g., uses the Tol system to penetrate the outer membrane of a target bacterium) or a group B colicin (e.g., uses the Ton system to penetrate the outer membrane of a target bacterium). In some instances, the bacteriocin is a microcin. The microcin may be a class I microcin (e.g., <5 kDa, has post-translational modifications) or a class II microcin (e.g., 5-10 kDa, with or without post-translational modifications). In some instances, the class II microcin is a class IIa microcin (e.g., requires more than one genes to synthesize and assemble functional peptides) or a class IIb microcin (e.g., linear peptides with or without post-translational modifications at C-terminus). In some instances, the bacteriocin is a pyocin. In some instances, the pyocin is an R-pyocin, F-pyocin, or S-pyocin.

In some instances, the bacteriocin is a class I, class II, class III, or class IV bacteriocin produced by Gram-positive bacteria. In some instances, the modulating agent includes a Class I bacteriocin (e.g., lanthionine-containing antibiotics (lantibiotics) produced by a Gram-positive bacteria). The class I bacteriocins or lantibiotic may be a low molecular weight peptide (e.g., less than about 5 kDa) and may possess post-translationally modified amino acid residues (e.g., lanthionine, β-methyllanthionine, or dehydrated amino acids).

In some instances, the bacteriocin is a Class II bacteriocin (e.g., non-lantibiotics produced by Gram-positive bacteria). Many are positively charged, non-lanthionine-containing peptides, which unlike lantibiotics, do not undergo extensive post-translational modification. The Class II bacteriocin may belong to one of the following subclasses: "pediocin-like" bacteriocins (e.g., pediocin PA-1 and carnobacteriocin X (Class IIa)); two-peptide bacteriocins (e.g., lactacin F and ABP-118 (Class IIb)); circular bacteriocins (e.g., carnocyclin A and enterocin AS-48 (Class IIc)); or unmodified, linear, non-pediocin-like bacteriocins (e.g., epidermicin NI01 and lactococcin A (Class IId)).

In some instances, the bacteriocin is a Class III bacteriocin (e.g., produced by Gram-positive bacteria). Class III bacteriocins may have a molecular weight greater than 10 kDa and may be heat unstable proteins. The Class III bacteriocins can be further subdivided into Group IIIA and Group IIIB bacteriocins. The Group IIIA bacteriocins include bacteriolytic enzymes which kill sensitive strains by lysis of the cell well, such as Enterolisin A. Group IIIB bacteriocins include non-lytic proteins, such as Caseicin 80, Helveticin J, and lactacin B.

In some instances, the bacteriocin is a Class IV bacteriocin (e.g., produced by Gram-positive bacteria). Class IV bacteriocins are a group of complex proteins, associated with other lipid or carbohydrate moieties, which appear to be required for activity. They are relatively hydrophobic and heat stable. Examples of Class IV bacteriocins leuconocin S, lactocin 27, and lactocin S.

In some instances, the bacteriocin is an R-type bacteriocin. R-type bacteriocins are contractile bacteriocidal protein complexes. Some R-type bacteriocins have a contractile phage-tail-like structure. The C-terminal region of the phage tail fiber protein determines target-binding specificity. They may attach to target cells through a receptor-binding protein, e.g., a tail fiber. Attachment is followed by sheath contraction and insertion of the core through the envelope of the target bacterium. The core penetration results in a rapid depolarization of the cell membrane potential and prompt cell death. Contact with a single R-type bacteriocin particle can result in cell death. An R-type bacteriocin, for example, may be thermolabile, mild acid resistant, trypsin resistant, sedimentable by centrifugation, resolvable by electron microscopy, or a combination thereof. Other R-type bacteriocins may be complex molecules including multiple proteins, polypeptides, or subunits, and may resemble a tail structure of bacteriophages of the myoviridae family. In naturally occurring R-type bacteriocins, the subunit structures may be encoded by a bacterial genome, such as that of C. difficile or P. aeruginosa and form R-type bacteriocins to serve as natural defenses against other bacteria. In some instances, the R-type bacteriocin is a pyocin. In some instances, the pyocin is an R-pyocin, F-pyocin, or S-pyocin.

In some instances, the bacteriocin is a functionally active variant of the bacteriocins described herein. In some instances, the variant of the bacteriocin has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region or over the entire sequence, to a sequence of a bacteriocin described herein or a naturally occurring bacteriocin.

In some instances, the bacteriocin may be bioengineered, according to standard methods, to modulate their bioactivity, e.g., increase or decrease or regulate, or to specify their target microorganisms. In other instances, the bacteriocin is produced by the translational machinery (e.g. a ribosome, etc.) of a microbial cell. In some instances, the bacteriocin is chemically synthesized. Some bacteriocins can be derived from a polypeptide precursor. The polypeptide precursor can undergo cleavage (e.g., processing by a protease) to yield the polypeptide of the bacteriocin itself. As such, in some instances, the bacteriocin is produced from a precursor polypeptide. In some other instances, the bacteriocin includes a polypeptide that has undergone post-translational modifications, for example, cleavage, or the addition of one or more functional groups.

The bacteriocins described herein may be formulated in a composition for any of the uses described herein. The compositions disclosed herein may include any number or type (e.g., classes) of bacteriocins, such as at least about any one of 1 bacteriocin, 2, 3, 4, 5, 10, 15, 20, 30, 40, 50, 100, or more bacteriocins. Suitable concentrations of each bacteriocin in the compositions described herein depends on factors such as efficacy, stability of the bacteriocin, number of distinct bacteriocin types in the compositions, formulation, and methods of application of the composition. In some instances, each bacteriocin in a liquid composition is from about 0.01 ng/ml to about 100 mg/mL. In some instances, each bacteriocin in a solid composition is from about 0.01 ng/g to about 100 mg/g. In some instances, wherein the composition includes at least two types of bacteriocins, the concentration of each type of the bacteriocins may be the same or different. In some instances, the bacteriocin is provided in a composition including a bacterial cell that secretes the bacteriocin. In some instances, the bacteriocin is provided in a composition including a polypeptide (e.g., a polypeptide isolated from a bacterial cell).

Bacteriocins may neutralize (e.g., kill) at least one microorganism other than the individual bacterial cell in which the polypeptide is made, including cells clonally related to the bacterial cell and other microbial cells. As such, a bacterial cell may exert cytotoxic or growth-inhibiting effects on a plurality of microbial organisms by secreting bacteriocins. In some instances, the bacteriocin targets and kills one or more species of bacteria resident in the host via cytoplasmic membrane pore formation, cell wall interference (e.g., peptidoglycanase activity), or nuclease activity (e.g., DNase activity, 16S rRNase activity, or tRNase activity).

In some instances, the bacteriocin has a neutralizing activity. Neutralizing activity of bacteriocins may include, but is not limited to, arrest of microbial reproduction, or cytotoxicity. Some bacteriocins have cytotoxic activity, and thus can kill microbial organisms, for example bacteria, yeast, algae, and the like. Some bacteriocins can inhibit the reproduction of microbial organisms, for example bacteria, yeast, algae, and the like, for example by arresting the cell cycle.

In some instances, the bacteriocin has killing activity. The killing mechanism of bacteriocins is specific to each group of bacteriocins. In some instances, the bacteriocin has narrow-spectrum bioactivity. Bacteriocins are known for their very high potency against their target strains. Some bacteriocin activity is limited to strains that are closely related to the bacteriocin producer strain (narrow-spectrum bioactivity). In some instances, the bacteriocin has broad-spectrum bioactivity against a wide range of genera.

In some instances, bacteriocins interact with a receptor molecule or a docking molecule on the target bacterial cell membrane. For example, nisin is extremely potent against its target bacterial strains, showing antimicrobial activity even at a single-digit nanomolar concentration. The nisin molecule has been shown to bind to lipid II, which is the main transporter of peptidoglycan subunits from the cytoplasm to the cell wall In some instances, the bacteriocin has anti-fungal activity. A number of bacteriocins with anti-yeast or anti-fungal activity have been identified. For example, bacteriocins from *Bacillus* have been shown to have neutralizing activity against some yeast strains (see, for example, Adetunji and Olaoye, *Malaysian Journal of Microbiology* 9:130-13, 2013). In another example, an *Enterococcus faecalis* peptide has been shown to have neutralizing activity against *Candida* species (see, for example, Shekh and Roy, *BMC Microbiology* 12:132, 2012). In another example, bacteriocins from *Pseudomonas* have been shown to have neutralizing activity against fungi, such as *Curvularia lunata*, *Fusarium* species, *Helminthosporium* species, and *Biopolaris* species (see, for example, Shalani and Srivastava, *The Internet Journal of Microbiology* Volume 5 Number 2, 2008). In another example, botrycidin AJ1316 and alirin B1 from *B. subtilis* have been shown to have antifungal activities.

A modulating agent including a bacteriocin as described herein can be contacted with the target host in an amount and for a time sufficient to: (a) reach a target level (e.g., a predetermined or threshold level) of bacteriocin concentration inside a target host; (b) reach a target level (e.g., a predetermined or threshold level) of bacteriocin concentration inside a target host gut; (c) reach a target level (e.g., a predetermined or threshold level) of bacteriocin concentration inside a target host bacteriocyte; (d) modulate the level, or an activity, of one or more microorganism (e.g., endoymbiont) in the target host; or/and (e) modulate fitness of the target host.

(b) Lysins

The modulating agent described herein may include a lysin (e.g., also known as a murein hydrolase or peptidoglycan autolysin). Any lysin suitable for inhibiting a bacterium resident in the host may be used. In some instances, the lysin is one that can be naturally produced by a bacterial cell. In some instances, the lysin is one that can be naturally produced by a bacteriophage. In some instances, the lysin is obtained from a phage that inhibits a bacterium resident in the host. In some instances, the lysin is engineered based on a naturally occurring lysin. In some instances, the lysin is engineered to be secreted by a host bacterium, for example, by introducing a signal peptide to the lysin. In some instances, the lysin is used in combination with a phage holin. In some instances, a lysin is expressed by a recombinant bacterium host that is not sensitive to the lysin. In some instances, the lysin is used to inhibit a Gram-positive or Gram-negative bacterium resident in the host.

The lysin may be any class of lysin and may have one or more substrate specificities. For example, the lysin may be a glycosidase, an endopeptidase, a carboxypeptidase, or a combination thereof. In some instances, the lysin cleaves the β-1-4 glycosidic bond in the sugar moiety of the cell wall, the amide bond connecting the sugar and peptide moieties of the bacterial cell wall, and/or the peptide bonds between the peptide moieties of the cell wall. The lysin may belong to one or more specific lysin groups, depending on the cleavage site within the peptidoglycan. In some instances, the lysin is a N-acetyl-β-D-muramidase (e.g., lysozyme), lytic transglycosylase, N-acetyl-β-D-glucosaminidase, N-acetylmuramyl-L-alanine amidase, L,D-endopeptidase, D,D-endopeptidase, D,D-carboxypeptidase, L,D-carboxypeptidase, or L,D-transpeptidase. Non-limiting examples of lysins and their activities are listed in Table 5.

TABLE 5

Examples of Lysins

| Target Bacteria | Producer | Lysins | Activity | Sequence |
| --- | --- | --- | --- | --- |
| S. pneumoniae | Cpl | Cpl-1 | Muramidase | MVKKNDLFVDVSSHNGY DITGILEQMGTTNTIIKISES TTYLNPCLSAQVEQSNPI GFYHFARFGGDVAEAERE AQFFLDNVPMQVKYLVLD YEDDPSGDAQANTNACL RFMQMIADAGYKPIYYSY KPFTHDNVDYQQILAQFP NSLWIAGYGLNDGTANFE YFPSMDGIRWWQYSSNP FDKNIVLLDDEEDDKPKTA GTWKQDSKGWWFRRNN GSFPYNKWEKIGGVWYY FDSKGYCLTSEWLKDNEK WYYLKDNGAMATGWVLV GSEWYYMDDSGAMVTG WVKYKNNWYYMTNERGN MVSNEFIKSGKGWYFMNT NGELADNPSFTKEPDGLIT VA (SEQ ID NO: 18) |

TABLE 5-continued

Examples of Lysins

| Target Bacteria | Producer | Lysins | Activity | Sequence |
|---|---|---|---|---|
| S. pneumoniae | Dp-1 | Pal | Amidase | MGVDIEKGVAWMQARKG RVSYSMDFRDGPDSYDC SSSMYYALRSAGASSAG WAVNTEYMHAWLIENGY ELISENAPWDAKRGDIFIW GRKGASAGAGGHTGMFI DSDNIIHCNYAYDGISVND HDERWYYAGQPYYVYR LTNANAQPAEKKLGWQK DATGFWYARANGTYPKD EFEYIEENKSWFYFDDQG YMLAEKWLKHTDGNWYW FDRDGYMATSWKRIGES WYYFNRDGSMVTGWIKY YDNWYYCDATNGDMKSN AFIRYNDGWYLLLPDGRL ADKPQFTVEPDGLITAKV (SEQ ID NO: 19) |
| S. pyogenes | C1 | C1 | Amidase | N/A |
| B. anthracis | γ | PlyG | Amidase | MEIQKKLVDPSKYGTKCP YTMKPKYITVHNTYNDAP AENEVSYMISNNNEVSFHI AVDDKKAIQGIPLERNAW ACGDGNGSGNRQSISVEI CYSKSGGDRYYKAEDNA VDVVRQLMSMYNIPIENV RTHQSWSGKYCPHRMLA EGRWGAFIQKVKNGNVAT TSPTKQNIIQSGAFSPYET PDVMGALTSLKMTADFIL QSDGLTYFISKPTSDAQLK AMKEYLDRKGWWYEVK (SEQ ID NO: 20) |
| B. anthracis | Ames prophage | PlyPH | Amidase | N/A |
| E. faecalis and E. faecium | Phi1 | PlyV12 | Amidase | N/A |
| S. aureus | MR11 | MV-L | Endopeptidase and amidase | MQAKLTKKEFIEWLKTSE GKQFNVDLWYGFQCFDY ANAGWKVLFGLLLKGLGA KDIPFANNFDGLATVYQN TPDFLAQPGDMVVFGSNY GAGYGHVAWVIEATLDYII VYEQNWLGGGWTDRIEQ PGWGWEKVTRRQHAYDF PMWFIRPNFKSETAPRSI QSPTQASKKETAKPQPKA VELKIIKDVVKGYDLPKRG GNPKGIVIHNDAGSKGAT AEAYRNGLVNAPLSRLEA GIAHSYVSGNTVWQALDE SQVGWHTANQLGNKYYY GIEVCQSMGADNATFLKN EQATFQECARLLKKWGLP ANRNTIRLHNEFTSTSCPH RSSVLHTGFDPVTRGLLP EDKQLQLKDYFIKQIRVYM DGKIPVATVSNESSASSN TVKPVASAWKRNKYGTYY MEENARFTNGNQPITVRKI GPFLSCPVAYQFQPGGY CDYTEVMLQDGHVWVGY TWEGQRYYLPIRTWNGS APPNQILGDLWGEIS (SEQ ID NO: 21) |
| S. pyogenes | C1 | PlyC | Amidase | N/A |

TABLE 5-continued

Examples of Lysins

| Target Bacteria | Producer | Lysins | Activity | Sequence |
|---|---|---|---|---|
| S. agalactiae | B30 | GBS lysin | Muramidase and endopeptidase | MVINIEQAIAWMASRKGK VTYSMDYRNGPSSYDCS SSVYFALRSAGASDNGW AVNTEYEHDWLIKNGYVLI AENTNWNAQRGDIFIWGK RGASAGAFGHTGMFVDP DNIIHCNYGYNSITVNNHD EIWGYNGQPYVYAYRYS GKQSNAKVDNKSVVSKFE KELDVNTPLSNSNMPYYE ATISEDYYVESKPDVNSTD KELLVAGTRVRVYEKVKG WARIGAPQSNQWVEDAY LIDATDM (SEQ ID NO: 22) |
| S. aureus | P68 | Lys16 | Endopeptidase | N/A |
| S. aureus | K | LysK | Amidase and endopeptidase | MAKTQAEINKRLDAYAKG TVDSPYRVKKATSYDPSF GVMEAGAIDADGYYHAQ CQDLITDYVLWLTDNKVR TWGNAKDQIKQSYGTGFK IHENKPSTVPKKGWIAVFT SGSYEQWGHIGIVYDGGN TSTFTILEQNWNGYANKK PTKRVDNYYGLTHFIEIPV KAGTTVKKETAKKSASKT PAPKKKATLKVSKNHINYT MDKRGKKPEGMVIHNDA GRSSGQQYENSLANAGY ARYANGIAHYYGSEGYVW EAIDAKNQIAWHTGDGTG ANSGNFRFAGIEVCQSMS ASDAQFLKNEQAVFQFTA EKFKEWGLTPNRKTVRLH MEFVPTACPHRSMVLHTG FNPVTQGRPSQAIMNKLK DYFIKQIKNYMDKGTSSST VVKDGKTSSASTPATRPV TGSWKKNQYGTWYKPEN ATFVNGNQPIVTRIGSPFL NAPVGGNLPAGATIVYDE VCIQAGHIWIGYNAYNGN RVYCPVRTCQGVPPNQIP GVAWGVFK (SEQ ID NO: 23) |
| L. monocytogenes | A118 | Ply118 | Amidase | MTSYYYSRSLANVNKLAD NTKAAARKLLDWSESNGI EVLIYETIRTKEQQAANVN SGASQTMRSYHLVGQAL DFVMAKGKTVDWGAYRS DKGKKFVAKAKSLGFEW GGDWSGFVDNPHLQFNY KGYGTDTFGKGASTSNSS KPSADTNTNSLGLVDYMN LNKLDSSFANRKKLATSY GIKNYSGTATQNTTLLAKL KAGKPHTPASKNTYYTEN PRKVKTLVQCDLYKSVDF TTKNQTGGTFPPGTVFTIS GMGKTKGGTPRLKTKSG YYLTANTKFVKKI (SEQ ID NO: 24) |
| L. monocytogenes | A511 | Ply511 | Amidase | MVKYTVENKIIAGLPKGKL KGANFVIAHETANSKSTID NEVSYMTRNWKNAFVTH FVGGGGRVVQVANVNYV SWGAGQYANSYSYAQVE LCRTSNATTFKKDYEVYC QLLVDLAKKAGIPITLDSG SKTSDKGIKSHKWVADKL GGTTHQDPYAYLSSWGIS |

TABLE 5-continued

Examples of Lysins

| Target Bacteria | Producer | Lysins | Activity | Sequence |
|---|---|---|---|---|
| | | | | KAQFASDLAKVSGGGNT GTAPAKPSTPAPKPSTPS TNLDKLGLVDYMNAKKMD SSYSNRDKLAKQYGIANY SGTASQNTTLLSKIKGGAP KPSTPAPKPSTSTAKKIYF PPNKGNWSVYPTNKAPV KANAIGAINPTKFGGLTYTI QKDRGNGVYEIQTDQFG RVQVYGAPSTGAVIKK (SEQ ID NO: 25) |
| L. monocytogenes | A500 | Ply500 | Endopeptidase | MALTEAWLIEKANRKLNA GGMYKITSDKTRNVIKKM AKEGIYLCVAQGYRSTAE QNALYAQGRTKPGAIVTN AKGGQSNHNYGVAVDLC LYTNDGKDVIWESTTSRW KKVVAAMKAEGFKWGGD WKSFKDYPHFELCDAVSG EKIPAATQNTNTNSNRYE GKVIDSAPLLPKMDFKSSP FRMYKVGTEFLVYDHNQY WYKTYIDDKLYYMYKSFC DVVAKKDAKGRIKVRIKSA KDLRIPVWNNIKLNSGKIK WYAPNVKLAWYNYRRGY LELWYPNDGWYYTAEYFL K (SEQ ID NO: 26) |
| S. pneumoniae | ΦDp-1 | Pal, S | Endopeptidase and amidase | N/A |
| S. agalactiae | LambdaSa1 prophage | LambdaSa1 | Glycosidase | MVINIEQAIAWMASRKGK VTYSMDYRNGPSSYDCS SSVYFALRSAGASDNGW AVNTEYEHDWLIKNGYVLI AENTNWNAQRGDIFIWGK RGASAGAFGHTGMFVDP DNIIHCNYGYNSITVNNHD EIWGYNGQPYVYAYRYAR KQSNAKVDNQSVVSKFEK ELDVNTPLSNSNMPYYEA TISEDYYVESKPDVNSTDK ELLVAGTRVRVYEKVKGW ARIGAPQSNQWVEDAYLI DATDM (SEQ ID NO: 27) |
| S. agalactiae | LambdaSa2 prophage | LambdaSa2 | Glycosidase and endopeptidase | MEINTEIAIAWMSARQGKV SYSMDYRDGPNSYDCSS SVYYALRSAGASSAGWA VNTEYMHDWLIKNGYELIA ENVDWNAVRGDIAIWGM RGHSSGAGGHVVMFIDPE NIIHCNWANNGITVNNYN QTAAASGWMYCYVYRLK SGASTQGKSLDTLVKETL AGNYGNGEARKAVLGNQ YEAVMSVINGKTTTNQKT VDQLVQEVIAGKHGNGEA RKKSLGSQYDAVQKRVTE LLKKQPSEPFKAQEVNKP TETKTSQTELTGQATATK EEGDLSFNGTILKKAVLDK ILGNCKKHDILPSYALTILH YEGLWGTSAVGKADNNW GGMTWTGQGNRPSGVTV TQGSARPSNEGGHYMHY ASVDDFLTDWFYLLRAGG SYKVSGAKTFSEAIKGMF KVGGAVYDYAASGFDSYI |

TABLE 5-continued

Examples of Lysins

| Target Bacteria | Producer | Lysins | Activity | Sequence |
|---|---|---|---|---|
| | | | | VGASSRLKAIEAENGSLD<br>KFDKATDIGDGSKDKIDITI<br>EGIEVTINGITYELTKKPV<br>(SEQ ID NO: 28) |
| S. uberis | (AT00700407)<br>prophage | Ply700 | Amidase | MTDSIQEMRKLOSIPVRY<br>DMGDRYGNDADRDGRIE<br>MDCSSAVSKALGISMTNN<br>TETLQQALPAIGYGKIHDA<br>VDGTFDMQAYDVIIWAPR<br>DGSSSLGAFGHVLIATSPT<br>TAIHCNYGSDGITENDYNY<br>IWEINGRPREIVFRKGVTQ<br>TQATVTSQFERELDVNAR<br>LTVSDKPYYEATLSEDYY<br>VEAGPRIDSQDKELIKAGT<br>RVRVYEKLNGWSRINHPE<br>SAQWVEDSYLVDATEM<br>(SEQ ID NO: 29) |
| S. suis | SMP | LySMP | Glycosidase<br>and<br>endopeptidase | N/A |
| B. anthracis | Bcp1 | PlyB | Muramidase | N/A |
| S. aureus | Phi11 and<br>Phi12 | Phi11 lysin | Amidase and<br>endopeptidase | MQAKLTKNEFIEWLKTSE<br>GKQFNVDLWYGFQCFDY<br>ANAGWKVLFGLLLKGLGA<br>KDIPFANNFDGLATVYQN<br>TPDFLAQPGDMVVFGSNY<br>GAGYGHVAWVIEATLDYII<br>VYEQNWLGGGWTDGIEQ<br>PGWGWEKVTRRQHAYDF<br>PMWFIRPNFKSETAPRSV<br>QSPTQAPKKETAKPQPKA<br>VELKIIKDVVKGYDLPKRG<br>SNPKGIVIHNDAGSKGATA<br>EAYRNGLVNAPLSRLEAGI<br>AHSYVSGNTVWQALDES<br>QVGWHTANQIGNKYYYGI<br>EVCQSMGADNATFLKNE<br>QATFQECARLLKKWGLPA<br>NRNTIRLHNEFTSTSCPH<br>RSSVLHTGFDPVTRGLLP<br>EDKRLQLKDYFIKQIRAYM<br>DGKIPVATVSNESSASSN<br>TVKPVASAWKRNKYGTYY<br>MEESARFTNGNQPITVRK<br>VGPFLSCPVGYQFQPGG<br>YCDYTEVMLQDGHVWVG<br>YTWEGQRYYLPIRTWNG<br>SAPPNQILGDLWGEIS<br>(SEQ ID NO: 30) |
| S. aureus | ΦH5 | LysH5 | Amidase and<br>endopeptidase | MQAKLTKKEFIEWLKTSE<br>GKQYNADGWYGFQCFDY<br>ANAGWKALFGLLLKGVGA<br>KDIPFANNFDGLATVYQN<br>TPDFLAQPGDMVVFGSNY<br>GAGYGHVAWVIEATLDYII<br>VYEQNWLGGGWTDGVQ<br>QPGSGWEKVTRRQHAYD<br>FPMWFIRPNFKSETAPRS<br>VQSPTQASKKETAKPQPK<br>AVELKIIKDVVKGYDLPKR<br>GSNPNFIVIHNDAGSKGAT<br>AEAYRNGLVNAPLSRLEA<br>GIAHSYVSGNTVWQALDE<br>SQVGWHTANQIGNKYGY<br>GIEVCQSMGADNATFLKN<br>EQATFQECARLLKKWGLP<br>ANRNTIRLHNEFTSTSCPH<br>RSSVLHTGFDPVTRGLLP<br>EDKRLQLKDYFIKQIRAYM<br>DGKIPVATVSNDSSASSN |

TABLE 5-continued

Examples of Lysins

| Target Bacteria | Producer | Lysins | Activity | Sequence |
|---|---|---|---|---|
| | | | | TVKPVASAWKRNKYGTYY MEESARFTNGNQPITVRK VGPFLSCPVGYQFQPGG YCDYTEVMLQDGHVWVG YTWEGQRYYLPIRTWNG SAPPNQILGDLWGEIS (SEQ ID NO: 31) |
| S. warneri | ΦWMY | LysWMY | Amidase and endopeptidase | MKTKAQAKSWINSKIGKGI DWDGMYGYQCMDEAVD YIHHVTDGKVTMWGNAID APKNNFQGLCTVYTNTPE FRPAYGDVIVWSYGTFAT YGHIAIVVNPDPYGDLQYI TVLEQNWNGNGIYKTEFA TIRTHDYTGVSHFIRPKFA DEVKETAKTVNKLSVQKKI VTPKNSVERIKNYVKTSG YINGEHYELYNRGHKPKG VVIHNTAGTASATQEGQR LTNMTFQQLANGVAHVYI DKNTIYETLPEDRIAWHVA QQYGNTEFYGIEVCGSRN TDKEQFLANEQVAFQEAA RRLKSWGMRANRNTVRL HHTFSSTECPDMSMLLHT GYSMKNGKPTQDITNKCA DYFMKQINAYIDGKQPTST VVGSSSSNKLKAKNKDKS TGWNTNEYGTLWKKEHA TFTCGVRQGIVTRTTGPF TSCPQAGVLYYGQSVNY DTVCKQDGYVWISWTTS DGYDVWMPIRTWDRSTD KVSEIWGTIS (SEQ ID NO: 32) |
| Streptococci (GBS) | ΦNCTC 11261 | PlyGBS | Muramidase and endopeptidase | MATYQEYKSRSNGNAYDI DGSFGAQCWDGYADYCK YLGLPYANCTNTGYARDI WEQRHENGILNYFDEVEV MQAGDVAIFMVVDGVTPY SHVAIFDSDAGGGYGWFL GQNQGGANGAYNIVKIPY SATYPTAFRPKVFKNAVT VTGNIGLNKGDYFIDVSAY QQADLTTTCQQAGTTKTII KVSESIAWLSDRHQQQAN TSDPIGYYHFGRFGGDSA LAQREADLFLSNLPSKKV SYLVIDYEDSASADKQAN TNAVIAFMDKIASAGYKPI YYSYKPFTLNNIDYQKIIAK YPNSIWIAGYPDYEVRTEP LWEFFPSMDGVRWWQFT SVGVAGGLDKNIVLLADD SSKMDIPKVDKPQELTFY QKLATNTKLDNSNVPYYE ATLSTDYYVESKPNASSA DKEFIKAGTRVRVYEKVN GWSRINHPESAQWVEDS YLVNATDM (SEQ ID NO: 33) |
| C. perfringens | Φ3626 | Ply3626 | Amidase | N/A |
| C. difficile | ΦCD27 | CD27 lysin | Amidase | N/A |
| E. faecalis | Φ1 | PlyV12 | Amidase | N/A |
| A. naeslundii | ΦAv-1- | Av-1 lysin | Putative amidase/ muramidase | N/A |
| L. gasseri | ΦgaY | LysgaY | Muramidase | N/A |

TABLE 5-continued

Examples of Lysins

| Target Bacteria | Producer | Lysins | Activity | Sequence |
|---|---|---|---|---|
| S. aureus | ΦSA4 | LysSA4 | Amidase and endopeptidase | N/A |
| S. haemolyticus | ΦSH2 | SH2 | Amidase and endopeptidase | N/A |
| B. thuringiensis | ΦBtCS33 | PlyBt33 | Amidase | N/A |
| L. monocytogenes | ΦP40 | PlyP40 | Amidase | N/A |
| L. monocytogenes | ΦFWLLm3 | LysZ5 | Amidase | MVKYTVENKIIAGLPKGKL KGANFVIAHETANSKSTID NEVSYMTRNWQNAFVTH FVGGGGRVVQVANVNYV SWGAGQYANSYSYAQVE LCRTSNATTFKKDYEVYC QLLVDLAKKAGIPITLDSG SKTSDKGIKSHKWVADKL GGTTHQDPYAYLSSWGIS KAQFASDLAKVSGGGNT GTAPAKPSTPSTNLDKLG LVDYMNAKKMDSSYSNR AKLAKQYGIANYSGTASQ NTTLLSKIKGGAPKPSTPA PKPSTSTAKKIYFPPNKGN WSVYPTNKAPVKANAIGAI NPTKFGGLTYTIQKDRGN GVYEIQTDQFGRVQVYGA PSTGAVIKK (SEQ ID NO: 34) |
| B. cereus | ΦBPS13 | LysBPS13 | Amidase | MAKREKYIFDVEAEVGKA AKSIKSLEAELSKLQKLNK EIDATGGDRTEKEMLATL KAAKEVNAEYQKMQRILK DLSKYSGKVSRKEFNDSK VINNAKTSVQGGKVTDSF GQMLKNMERQINSVNKQ FDNHRKAMVDRGQQYTP HLKTNRKDSQGNSNPSM MGRNKSTTQDMEKAVDK FLNGQNEATTGLNQALYQ LKEISKLNRRSESLSRRAS ASGYMSFQQYSNFTGDR RTVQQTYGGLKTANRERV LELSGQATGISKELDRLNS KKGLTAREGEERKKLMRQ LEGIDAELTARKKLNSSLD ETTSNMEKFNQSLVDAQV SVKPERGTMRGMMYERA PAIALAIGGAITATIGKLYS EGGNHSKAMRPDEMYVG QQTGAVGANWRPNRTAT MRSGLGNHLGFTGQEMM EFQSNYLSANGYHGAED MKAATTGQATFARATGLG SDEVKDFFNTAYRSGGID GNQTKQFQNAFLGAMKQ SGAVGREKDQLKALNGIL SSMSQNRTVSNQDMMRT VGLQSAISSSGVASLQGT KGGALMEQLDNGIREGFN DPQMRVLFGQGTKYQGM GGRAALRKQMEKGISDPD NLNTLIDASKASAGQDPA EQAEVLATLASKMGVNMS SDQARGLIDLQPSGKLTK ENIDKVMKEGLKEGSIESA KRDKAYSESKASIDNSSE AATAKQATELNDMGSKLR QANAALGGLPAPLYTAIAA VVAFTAAVAGSALMFKGA SWLKGGMASKYGGKGGK GGKGGGTGGGGAGGA AATGAGAAAGAGGVGAA |

TABLE 5-continued

Examples of Lysins

| Target Bacteria | Producer | Lysins | Activity | Sequence |
|---|---|---|---|---|
| | | | | AAGEVGAGVAAGGAAAG<br>AAAGGSKLAGVGKGFMK<br>GAGKLMLPLGILMGASEIM<br>QAPEEAKGSAIGSAVGGI<br>GGGIAGGAATGAIAGSFL<br>GPIGTAVGGIAGGIAGGFA<br>GSSLGETIGGWFDSGPKE<br>DASAADKAKADASAAALA<br>AAAGTSGAVGSSALQSQ<br>MAQGITGAPNMSQVGSM<br>ASALGISSGAMASALGISS<br>GQENQIQTMTDKENTNTK<br>KANEAKKGDNLSYERENI<br>SMYERVLTRAEQILAQAR<br>AQNGIMGVGGGTAGAG<br>GGINGFTGGGKLQFLAAG<br>QKWSSSNLQQHDLGFTD<br>QNLTAEDLDKWIDSKAPQ<br>GSMMRGMGATFLKAGQE<br>YGLDPRYLIAHAAEESGW<br>GTSKIARDKGNFFGIGAFD<br>DSPYSSAYEFKDGTGSAA<br>ERGIMGGAKWISEKYYGK<br>GNTTLDKMKAAGYATNAS<br>WAPNIASIMAGAPTGSGS<br>GNVTATINVNVKGDEKVS<br>DKLKNSSDMKKAGKDIGS<br>LLGFYSREMTIA<br>(SEQ ID NO: 35) |
| S. aureus | ΦGH15 | LysGH15 | Amidase and endopeptidase | MAKTQAEINKRLDAYAKG<br>TVDSPYRIKKATSYDPSFG<br>VMEAGAIDADGYYHAQC<br>QDLITDYVLWLTDNKVRT<br>WGNAKDQIKQSYGTGFKI<br>HENKPSTVPKKGWIAVFT<br>SGSYQQWGHIGIVYDGG<br>NTSTFTILEQNWNGYANK<br>KPTKRVDNYYGLTHFIEIP<br>VKAGTTVKKETAKKSASK<br>TPAPKKKATLKVSKNHINY<br>TMDKRGKKPEGMVIHNDA<br>GRSSGQQYENSLANAGY<br>ARYANGIAHYYGSEGYVW<br>EAIDAKNQIAWHTGDGTG<br>ANSGNFRFAGIEVCQSMS<br>ASDAQFLKNEQAVFQFTA<br>EKFKEWGLTPNRKTVRLH<br>MEFVPTACPHRSMVLHTG<br>FNPVTQGRPSQAIMNKLK<br>DYFIKQIKNYMDKGTSSST<br>VVKDGKTSSASTPATRPV<br>TGSWKKNQYGTWYKPEN<br>ATFVNGNQPIVTRIGSPFL<br>NAPVGGNLPAGATIVYDE<br>VCIQAGHIWIGYNAYNGD<br>RVYCPVRTCQGVPPNHIP<br>GVAWGVFK<br>(SEQ ID NO: 36) |
| S. aureus | ΦvB SauS-PLA88 | HydH5 | Endopeptidase and glycosidase | N/A |
| E. faecalis | ΦF168/08 | Lys168 | Endopeptidase | N/A |
| E. faecalis | ΦF170/08 | Lys170 | Amidase | N/A |
| S. aureus | ΦP-27/HP | P-27/HP | Nonspecified | N/A |
| C. perfringens | ΦSM101 | Psm | Muramidase | N/A |
| C. sporogenes | Φ8074-B1 | 0574L | Amidase | MKIGIDMGHTLSGADYGV<br>VGLRPESVLTREVGTKVIY<br>KLQKLGHVVVNCTVDKAS<br>SVSESLYTRYYRANQANV |

TABLE 5-continued

Examples of Lysins

| Target Bacteria | Producer | Lysins | Activity | Sequence |
|---|---|---|---|---|
| | | | | DLFISIHFNATPGGTGTEV YTYAGRQLGEATRIRQEF KSLGLRDRGTKDGSGLAV IRNTKAKAMLVECCFCDN PNDMKLYNSESFSNAIVK GITGKLPNGESGNNNQG GNKVKAVVIYNEGADRRG AEYLADYLNCPTISNSRTF DYSCVEHVYAVGGKKEQ YTKYLKTLLSGANRYDTM QQILNFINGGK (SEQ ID NO: 37) |
| S. typhimurium | ΦSPN1S | SPN1S | Glycosidase | MDINQFRRASGINEQLAA RWFPHITTAMNEFGITKPD DQAMFIAQVGHESGGFTR LQENFNYSVNGLSGFIRA GRITPDQANALGRKTYEK SLPLERQRAIANLVYSKR MGNNGPGDGWNYRGRG LIQITGLNNYRDCGNGLKV DLVAQPELLAQDEYAARS AAWFFSSKGCMKYTGDL VRVTQIINGGQNGIDDRRT RYAAARKVLAL (SEQ ID NO: 38) |
| C. michiganensis | ΦCMP1 | CMP1 | Peptidase | N/A |
| C. michiganensis | ΦCN77 | CN77 | Peptidase | MGYWGYPNGQIPNDKMA LYRGCLLRADAAAQAYAL QDAYTRATGKPLVILEGY RDLTRQKYLRNLYLSGRG NIAAVPGLSNHGWGLACD FAAPLNSSGSEEHRWMR QNAPLFGFDWARGKADN EPWHWEYGNVPVSRWA SLDVTPIDRNDMADITEGQ MQRIAVILLDTEIQTPLGPR LVKHALGDALLLGQANAN SIAEVPDKTWDVLVDHPL AKNEDGTPLKVRLGDVAK YEPLEHQNTRDAIAKLGTL QFTDKQLATIGAGVKPIDE ASLVKKIVDGVRALFGRAA A (SEQ ID NO: 39) |
| A. baumannii | ΦAB2 | LysAB2 | G lycosidase | MILTKDGFSIIRNELFGGKL DQTQVDAINFIVAKATESG LTYPEAAYLLATIYHETGL PSGYRTMQPIKEAGSDSY LRSKKYYPYIGYGYVQLT WKENYERIGKLIGVDLIKN PEKALEPLIAIQIAIKGMLN GWFTGVGFRRKRPVSKY NKQQYVAARNIINGKDKA ELIAKYAIIFERALRSL (SEQ ID NO: 40) |
| B. cereus | ΦB4 | LysB4 | Endopeptidase | MAMALQTLIDKANRKLNV SGMRKDVADRTRAVITQM HAQGIYICVAQGFRSFAE QNALYAQGRTKPGSIVTN ARGGQSNHNYGVAVDLC LYTQDGSDVIWTVEGNFR KVIAAMKAQGFKWGGDW VSFKDYPHFELYDVVGGQ KPPADNGGAVDNGGGSG STGGSGGGSTGGGSTGG GYDSSWFTKETGTFVTNT SIKLRTAPFTSADVIATLPA GSPVNYNGFGIEYDGYV WIRQPRSNGYGYLATGES KGGKRQNYVVGTFK (SEQ ID NO: 41) |

TABLE 5-continued

Examples of Lysins

| Target Bacteria | Producer | Lysins | Activity | Sequence |
|---|---|---|---|---|
| P. aeruginosa | ΦKMV | KMV45 | Nonspecified | N/A |
| C. tyrobutyricum | ΦCTP1 | Ctp1I | Glycosidase | MKKIADISNLNGNVDVKLL FNLGYIGIIAKASEGGTFV DKYYKQNYTNTKAQGKIT GAYHFANFSTIAKAQQEA NFFLNCIAGTTPDFVVLDL EQQCTGDITDACLAFLNIV AKKFKCVVYCNSSFIKEHL NSKICAYPLWIANYGVATP AFTLWTKYAMWQFTEKG QVSGISGYIDFSYITDEFIK YIKGEDEVENLVVYNDGA DQRAAEYLADRLACPTIN NARKFDYSNVKNVYAVG GNKEQYTSYLTTLIAGSTR YTTMQAVLDYIKNLK (SEQ ID NO: 42) |
| P. aeruginosa | ΦEL | EL188 | Transglycosylase | N/A |
| P. aeruginosa | ΦKZ | KZ144 | Transglycosylase | N/A |
| S. aureus | Staphylococcus virus 187 | Ply187 | Cell Wall Hydrolase | MALPKTGKPTAKQVVDW AINLIGSGVDVDGYYGRQ CWDLPNYIFNRYWNFKTP GNARDMAWYRYPEGFKV FRNTSDFVPKPGDIAVWT GGNYNWNTWGHTGIVVG PSTKSYFYSVDQNWNNS NSYVGSPAAKIKHSYFGV THFVRPAYKAEPKPTPPA QNNPAPKDPEPSKKPESN KPIYKVVTKILFTTAHIEHV KANRFVHYITKSDNHNNK PNKIVIKNTNTALSTIDVYR YRDELDKDEIPHFFVDRLN VWACRPIEDSINGYHDSV VLSITETRTALSDNFKMNE IECLSLAESILKANNKKMS ASNIIVDNKAWRTFKLHTG KDSLKSSSFTSKDYQKAV NELIKLFNDKDKLLNNKPK DVVERIRIRTIVKENTKFVP SELKPRNNIRDKQDSKIDR VINNYTLKQALNIQYKLNP KPQTSNGVSWYNASVNQI KSAMDTTKIFNNNVQVYQ FLKLNQYQGIPVDKLNKLL VGKGTLANQGHAFADGC KKYNINEIYLIAHRFLESAN GTSFFASGKTGVYNYFGI GAFDNNPNNAMAFARSH GWTSPTKAIIGGAEFVGK GYFNVGQNTLYRMRWNP QKPGTHQYATDISWAKVQ AQMISAMYKEIGLTGDYFI YDQYKK (SEQ ID NO: 43) |
| P. uorescens | ΦOBP | OBPgp279 | Glycosidase | N/A |
| L. monocytogenes | ΦP35 | PlyP35 | Amidase | MARKFTKAELVAKAEKKV GGLKPDVKKAVLSAVKEA YDRYGIGIIVSQGYRSIAE QNGLYAQGRTKPGNIVTN AKGGQSNHNFGVAVDFAI DLIDDGKIDSWQPSATIVN MMKRRGFKWGGDWKSF TDLPHFEACDWYRGERK YKVDTSEWKKKENINIVIK DVGYFQDKPQFLNSKSVR QWKHGTKVKLTKHNSHW YTGVVKDGNKSVRGYIYH SMAKVTSKNSDGSVNATI |

TABLE 5-continued

Examples of Lysins

| Target Bacteria | Producer | Lysins | Activity | Sequence |
|---|---|---|---|---|
| | | | | NAHAFCWDNKKLNGGDFI NLKRGFKGITHPASDGFY PLYFASRKKTFYIPRYMFD IKK (SEQ ID NO: 44) |
| L. fermentum | ΦPYB5 | Lyb5 | Muramidase | N/A |
| S. pneumoniae | ΦCP-7 | Cpl-7 | Muramidase | MVKKNDLFVDVASHQGY DISGILEEAGTTNTIIKVSE STSYLNPCLSAQVSQSNPI GFYHFAWFGGNEEEAEA EARYFLDNVPTQVKYLVL DYEDHASASVQRNTTACL RFMQIIAEAGYTPIYYSYK PFTLDNVDYQQILAQFPN SLWIAGYGLNDGTANFEY FPSMDGIRWWQYSSNPF DKNIVLLDDEKEDNINNEN TLKSLTTVANEVIQGLWG NGQERYDSLANAGYDPQ AVQDKVNEILNAREIADLT TVANEVIQGLWGNGQER YDSLANAGYDPQAVQDK VNEILNAREIADLTTVANE VIQGLWGNGQERYDSLA NAGYDPQAVQDKVNELLS (SEQ ID NO: 45) |
| P. chlororaphis201 | Φ2-1 | 201φ92-1gp229 | Glycosidase | N/A |
| S. enterica | ΦPVP-SE1) | PVP-SE1gp146 | Glycosidase | N/A |
| Corynebacterium | ΦBFK20 | BKF20 | Amidase | N/A |
| E. faecalis | ΦEFAP-1 | EFAL-1 | Amidase | MKLKGILLSVVTTFGLLFG ATNVQAYEVNNEFNLQP WEGSQQLAYPNKIILHETA NPRATGRNEATYMKNNW FNAHTTAIVGDGGIVYKVA PEGNVSWGAGNANPYAP VQIELQHTNDPELFKANYK AYVDYTRDMGKKFGIPMT LDQGGSLWEKGVVSHQW VTDFVWGDHTDPYGYLA KMGISKAQLAHDLANGVS GNTATPTPKPDKPKPTQP SKPSNKKRFNYRVDGLEY VNGMWQIYNEHLGKIDFN WTENGIPVEVVDKVNPAT GQPTKDQVLKVGDYFNF QENSTGVVQEQTPYMGY TLSHVQLPNEFIWLFTDSK QALMYQ (SEQ ID NO: 46) |
| Lactobacilli | lambdaSA2 | LysA, LysA2, and Lysga Y | Nonspecified | N/A |
| S. aureus | | SAL-1 | Nonspecified | N/A |

In some instances, the lysin is a functionally active variant of the lysins described herein. In some instances, the variant of the lysin has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region or over the entire sequence, to a sequence of a lysin described herein or a naturally occurring lysin.

In some instances, the lysin may be bioengineered to modulate its bioactivity, e.g., increase or decrease or regulate, or to specify a target microorganism. In some instances, the lysin is produced by the translational machinery (e.g. a ribosome, etc.) of a microbial cell. In some instances, the lysin is chemically synthesized. In some instances, the lysin is derived from a polypeptide precursor. The polypeptide precursor can undergo cleavage (for example, processing by a protease) to yield the polypeptide of the lysin itself. As such, in some instances, the lysin is produced from a precursor polypeptide. In some instances, the lysin includes a polypeptide that has undergone post-translational modifications, for example, cleavage, or the addition of one or more functional groups.

The lysins described herein may be formulated in a composition for any of the uses described herein. The compositions disclosed herein may include any number or type (e.g., classes) of lysins, such as at least about any one of 1 lysin, 2, 3, 4, 5, 10, 15, 20, or more lysins. A suitable concentration of each lysin in the composition depends on factors such as efficacy, stability of the lysin, number of distinct lysin, the formulation, and methods of application of the composition. In some instances, each lysin in a liquid composition is from about 0.1 ng/mL to about 100 mg/mL. In some instances, each lysin in a solid composition is from about 0.1 ng/g to about 100 mg/g. In some instances, wherein the composition includes at least two types of lysins, the concentration of each type of lysin may be the same or different.

A modulating agent including a lysin as described herein can be contacted with the target host in an amount and for a time sufficient to: (a) reach a target level (e.g., a predetermined or threshold level) of lysin concentration inside a target host; (b) reach a target level (e.g., a predetermined or threshold level) of lysin concentration inside a target host gut; (c) reach a target level (e.g., a predetermined or threshold level) of lysin concentration inside a target host bacteriocyte; (d) modulate the level, or an activity, of one or more microorganism (e.g., endosymbiont) in the target host; or/and (e) modulate fitness of the target host.

(c) Antimicrobial Peptides

The modulating agent described herein may include an antimicrobial peptide (AMP). Any AMP suitable for inhibiting a microorganism resident in the host may be used. AMPs are a diverse group of molecules, which are divided into subgroups on the basis of their amino acid composition and structure. The AMP may be derived or produced from any organism that naturally produces AMPs, including AMPs derived from plants (e.g., copsin), insects (e.g., drosocin, scorpion peptide (e.g., Uy192, UyCT3, D3, D10, Uy17, Uy192), mastoparan, poneratoxin, cecropin, moricin, melittin), frogs (e.g., magainin, dermaseptin, aurein), and mammals (e.g., cathelicidins, defensins and protegrins). For example, the AMP may be a scorpion peptide, such as Uy192 (5'-FLSTIWNGIKGLL-3'; SEQ ID NO: 193), UyCT3 (5'-LSAIWSGIKSLF-3; SEQ ID NO: 194'), D3 (5'-LWGKLWEGVKSLI-3'; SEQ ID NO: 195), and D10 (5'-FPFLKLSLKIPKSAIKSAIKRL-3'; SEQ ID NO: 196), Uy17 (5'-ILSAIWSGIKGLL-3'; SEQ ID NO: 197). Other non-limiting examples of AMPs are listed in Table 6.

TABLE 6

Examples of Antimicrobial Peptides

| Type | Characteristic | Example AMP | Sequence |
|---|---|---|---|
| Anionic peptides | rich in glutamic and aspartic acid | dermcidin | SSLLEKGLDGAKKAVGGLGKL GKDAVEDLESVGKGAVHDVKD VLDSVL (SEQ ID NO: 47) |
| Linear cationic α-helical peptides | lack cysteine | cecropin A | KWKLFKKIEKVGQNIRDGIIK AGPAVAVVGQATQIAK (SEQ ID NO: 48) |
| | | andropin | MKYFSVLVVLTLILAIVDQSD AFINLLDKVEDALHTGAQAGF KLIRPVERGATPKKSEKPEK (SEQ ID NO: 49) |
| | | moricin | MNILKFFFVFIVAMSLVSCST AAPAKIPIKAIKTVGKAVGKG LRAINIASTANDVFNFLKPKK RKH (SEQ ID NO: 50) |
| | | ceratotoxin | MANLKAVFLICIVAFIALQCV VAEPAAEDSVVVKRSIGSALK KALPVAKKIGKIALPIAKAAL PVAAGLVG (SEQ ID NO: 51) |
| Cationic peptide enriched for specific amino acid | rich in proline, arginine, phenylalanine, glycine, tryptophan | abaecin | MKVVIFIFALLATICAAFAYV PLPNVPQPGRRPFPTFPGQGP FNPKIKWPQGY (SEQ ID NO: 52) |
| | | apidaecins | KNFALAILVVTFVVAVFGNTN LDPPTRPTRLRREAKPEAEPG NNRPVYIPQPRPPHPRLRREA EPEAEPGNNRPVYIPQPRPPH PRLRREAELEAEPGNNRPVYI SQPRPPHPRLRREAEPEAEPG NNRPVYIPQPRPPHPRLRREA ELEAEPGNNRPVYISQPRPPH PRLRREAEPEAEPGNNRPVYI PQPRPPHPRLRREAEPEAEPG |

TABLE 6-continued

Examples of Antimicrobial Peptides

| Type | Characteristic | Example AMP | Sequence |
|---|---|---|---|
| | | | NNRPVYIPQPRPPHPRLRREA<br>EPEAEPGNNRPVYIPQPRPPH<br>PRLRREAKPEAKPGNNRPVYI<br>PQPRPPHPRI<br>(SEQ ID NO: 53) |
| | | prophenin | METQRASLCLGRWSLWLLLLA<br>LVVPSASAQALSYREAVLRAV<br>DRLNEQSSEANLYRLLELDQP<br>PKADEDPGTPKPVSFTVKETV<br>CPRPTRRPPELCDFKENGRVK<br>QCVGTVTLDQIKDPLDITCNE<br>GVRRFPWWWPFLRRPRLRRQA<br>FPPPNVPGPRFPPPNVPGPRF<br>PPPNFPGPRFPPPNFPGPRFP<br>PPNFPGPPFPPPIFPGPWFPP<br>PPPFRPPPFGPPRFPGRR<br>(SEQ ID NO: 54) |
| | | indolicidin | MQTQRASLSLGRWSLWLLLLG<br>LVVPSASAQALSYREAVLRAV<br>DQLNELSSEANLYRLLELDPP<br>PKDNEDLGTRKPVSFTVKETV<br>CPRTIQQPAEQCDFKEKGRVK<br>QCVGTVTLDPSNDQFDLNCNE<br>LQSVILPWKWPWWPWRRG<br>(SEQ ID NO: 55) |
| Anionic and cationic peptides that contain cysteine and form disulfide bonds | contain 1-3 disulfide bond | protegrin | METQRASLCLGRWSLWLLLLA<br>LVVPSASAQALSYREAVLRAV<br>DRLNEQSSEANLYRLLELDQP<br>PKADEDPGTPKPVSFTVKETV<br>CPRPTRQPPELCDFKENGRVK<br>QCVGTVTLDQIKDPLDITCNE<br>VQGVRGGRLCYCRRRFCVCVG<br>RG<br>(SEQ ID NO: 56) |
| | | tachyplesins | KWCFRVCYRGICYRRCR<br>(SEQ ID NO: 57) |
| | | defensin | MKCATIVCTIAVVLAATLLNG<br>SVQAAPQEEAALSGGANLNTL<br>LDELPEETHHAALENYRAKRA<br>TCDLASGFGVGSSLCAAHCIA<br>RRYRGGYCNSKAVCVCRN<br>(SEQ ID NO: 58) |
| | | drosomycin | MMQIKYLFALFAVLMLVVLGA<br>NEADADCLSGRYKGPCAVWDN<br>ETCRRVCKEEGRSSGHCSPSL<br>KCWCEGC<br>(SEQ ID NO: 59) |

The AMP may be active against any number of target microorganisms. In some instances, the AMP may have antibacterial and/or antifungal activities. In some instances, the AMP may have a narrow-spectrum bioactivity or a broad-spectrum bioactivity. For example, some AMPs target and kill only a few species of bacteria or fungi, while others are active against both gram-negative and gram-positive bacteria as well as fungi.

Further, the AMP may function through a number of known mechanisms of action. For example, the cytoplasmic membrane is a frequent target of AMPs, but AMPs may also interfere with DNA and protein synthesis, protein folding, and cell wall synthesis. In some instances, AMPs with net cationic charge and amphipathic nature disrupt bacterial membranes leading to cell lysis. In some instances, AMPs may enter cells and interact with intracellular target to interfere with DNA, RNA, protein, or cell wall synthesis. In addition to killing microorganisms, AMPs have demonstrated a number of immunomodulatory functions that are involved in the clearance of infection, including the ability to alter host gene expression, act as chemokines and/or induce chemokine production, inhibit lipopolysaccharide induced pro-inflammatory cytokine production, promote wound healing, and modulating the responses of dendritic cells and cells of the adaptive immune response.

In some instances, the AMP is a functionally active variant of the AMPs described herein. In some instances, the variant of the AMP has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region or over the entire sequence, to a sequence of an AMP described herein or a naturally derived AMP.

In some instances, the AMP may be bioengineered to modulate its bioactivity, e.g., increase or decrease or regulate, or to specify a target microorganism. In some instances, the AMP is produced by the translational machinery (e.g. a ribosome, etc.) of a cell. In some instances, the AMP is chemically synthesized. In some instances, the AMP is derived from a polypeptide precursor. The polypeptide precursor can undergo cleavage (for example, processing by a protease) to yield the polypeptide of the AMP itself. As such, in some instances, the AMP is produced from a precursor polypeptide. In some instances, the AMP includes a polypeptide that has undergone post-translational modifications, for example, cleavage, or the addition of one or more functional groups.

The AMPs described herein may be formulated in a composition for any of the uses described herein. The compositions disclosed herein may include any number or type (e.g., classes) of AMPs, such as at least about any one of 1 AMP, 2, 3, 4, 5, 10, 15, 20, or more AMPs. A suitable concentration of each AMP in the composition depends on factors such as efficacy, stability of the AMP, number of distinct AMP in the composition, the formulation, and methods of application of the composition. In some instances, each AMP in a liquid composition is from about 0.1 ng/mL to about 100 mg/mL. In some instances, each AMP in a solid composition is from about 0.1 ng/g to about 100 mg/g. In some instances, wherein the composition includes at least two types of AMPs, the concentration of each type of AMP may be the same or different.

A modulating agent including an AMP as described herein can be contacted with the target host in an amount and for a time sufficient to: (a) reach a target level (e.g., a predetermined or threshold level) of AMP concentration inside a target host; (b) reach a target level (e.g., a predetermined or threshold level) of AMP concentration inside a target host gut; (c) reach a target level (e.g., a predetermined or threshold level) of AMP concentration inside a target host bacteriocyte; (d) modulate the level, or an activity, of one or more microorganism (e.g., endosymbiont) in the target host; or/and (e) modulate fitness of the target host.

(d) Nodule C-Rich Peptides

The modulating agent described herein may include a nodule C-rich peptide (NCR peptide). NCR peptides are produced in certain leguminous plants and play an important role in the mutualistic, nitrogen-fixing symbiosis of the plants with bacteria from the *Rhizobiaceae* family (rhizobia), resulting in the formation of root nodules where plant cells contain thousands of intracellular endosymbionts. NCR peptides possess anti-microbial properties that direct an irreversible, terminal differentiation process of bacteria, e.g., to permeabilize the bacterial membrane, disrupt cell division, or inhibit protein synthesis. For example, in *Medicago truncatula* nodule cells infected with *Sinorhizobium meliloti*, hundreds of NCR peptides are produced which direct irreversible differentiation of the bacteria into large polyploid nitrogen-fixing bacteroids). Non-limiting examples of NCR peptides are listed in Table 7.

TABLE 7

Examples of NCR Peptides

| NAME | Peptide sequence | Producer |
|---|---|---|
| >gi\|152218086\|gb\|<br>ABS31477.1\|NCR 340 | MTKIVVFIYVVILLLTIFHVSAKKKR<br>YIECETHEDCSQVFMPPFVMRCVIHE<br>CKIFNGEHLRY<br>(SEQ ID NO: 60) | *Medicago truncatula* |
| >gi\|152218084\|gb\|<br>ABS31476.1\|NCR 339 | MAKIMKFVYNMIPFLSIFIITLQVNV<br>VVCEIDADCPQICMPPYEVRCVNHRC<br>GWVNTDDSLFLTQEFTRSKQYIIS<br>(SEQ ID NO: 61) | *Medicago truncatula* |
| >gi\|152218082\|gb\|<br>ABS31475.1\|NCR 338 | MYKVVESIFIRYMHRKPNMTKFFKFV<br>YTMFILISLFLVVTNANAHNCTDISD<br>CSSNHCSYEGVSLCMNGQCICIYE<br>(SEQ ID NO: 62) | *Medicago truncatula* |
| >gi\|152218080\|gb\|<br>ABS31474.1\|NCR 337 | MVETLRLFYIMILFVSLCLVVVDGES<br>KLEQTCSEDFECYIKNPHVPFGHLRC<br>FEGFCQQLNGPA<br>(SEQ ID NO: 63) | *Medicago truncatula* |
| >gi\|152218078\|gb\|<br>ABS31473.1\|NCR 336 | MAKIVNFVYSMIVFLFLFLVATKAAR<br>GYLCVTDSHCPPHMCPPGMEPRCVRR<br>MCKCLPIGWRKYFVP<br>(SEQ ID NO: 64) | *Medicago truncatula* |
| >gi\|152218076\|gb\|<br>ABS31472.1\|NCR 335 | MQIGKNMVETPKLDYVIIFFFLYFFF<br>RQMIILRLNTTFRPLNFKMLRFWGQN<br>RNIMKHRGQKVHFSLILSDCKTNKDC<br>PKLRRANVRCRKSYCVPI<br>(SEQ ID NO: 65) | *Medicago truncatula* |
| >gi\|152218074\|gb\|<br>ABS31471.1\|NCR 334 | MLRLYLVSYFLLKRTLLVSYFSYFST<br>YIIECKTDNDCPISQLKIYAWKCVKN<br>GCHLFDVIPMMYE<br>(SEQ ID NO: 66) | *Medicago truncatula* |

TABLE 7-continued

Examples of NCR Peptides

| NAME | Peptide sequence | Producer |
|---|---|---|
| >gi\|152218072\|gb\|<br>ABS31470.1\|NCR 333 | MAEILKFVYIVILFVSLLLIVVASER<br>ECVTDDDCEKLYPTNEYRMMCDSGYC<br>MNLLNGKIIYLLCLKKKKFLIIISVL<br>L<br>(SEQ ID NO: 67) | *Medicago truncatula* |
| >gi\|152218070\|gb\|<br>ABS31469.1\|NCR 332 | MAEIIKFVYIMILCVSLLLIEVAGEE<br>CVTDADCDKLYPDIRKPLMCSIGECY<br>SLYKGKFSLSIISKTSFSLMVYNVVT<br>LVICLRLAYISLLLKFL<br>(SEQ ID NO: 68) | *Medicago truncatula* |
| >gi\|152218068\|gb\|<br>ABS31468.1\|NCR 331 | MAEILKDFYAMNLFIFLIILPAKIRG<br>ETLSLTHPKCHHIMLPSLFITEVFQR<br>VTDDGCPKPVNHLRVVKCIEHICEYG<br>YNYRPDFASQIPESTKMPRKRE<br>(SEQ ID NO: 69) | *Medicago truncatula* |
| >gi\|152218066\|gb\|<br>ABS31467.1\|NCR 330 | MVEILKNFYAMNLFIFLIILAVKIRG<br>AHFPCVTDDDCPKPVNKLRVIKCIDH<br>ICQYARNLPDFASEISESTKMPCKGE<br>(SEQ ID NO: 70) | *Medicago truncatula* |
| >gi\|152218064\|gb\|<br>ABS31466.1\|NCR 329 | MFHAQAENMAKVSNFVCIMILFLALF<br>FITMNDAARFECREDSHCVTRIKCVL<br>PRKPECRNYACGCYDSNKYR<br>(SEQ ID NO: 71) | *Medicago truncatula* |
| >gi\|152218062\|gb\|<br>ABS31465.1\|NCR 328 | MQMRQNMATILNFVFVIILFISLLLV<br>VTKGYREPFSSFTEGPTCKEDIDCPS<br>ISCVNPQVPKCIMFECHCKYIPTTLK<br>(SEQ ID NO: 72) | *Medicago truncatula* |
| >gi\|152218060\|gb\|<br>ABS31464.1\|NCR 327 | MATILMYVYITILFISILTVLTEGLY<br>EPLYNFRRDPDCRRNIDCPSYLCVAP<br>KVPRCIMFECHCKDIPSDH<br>(SEQ ID NO: 73) | *Medicago truncatula* |
| >gi\|152218058\|gb\|<br>ABS31463.1\|NCR 326 | MTTSLKFVYVAILFLSLLLVVMGGIR<br>RFECRQDSDCPSYFCEKLTVPKCFWS<br>KCYCK<br>(SEQ ID NO: 74) | *Medicago truncatula* |
| >gi\|152218056\|gb\|<br>ABS31462.1\|NCR 325 | MTTSLKFVYVAILFLSLLLVVMGGIR<br>KKECRQDSDCPSYFCEKLTIAKCIHS<br>TCLCK<br>(SEQ ID NO: 75) | *Medicago truncatula* |
| >gi\|152218054\|gb\|<br>ABS31461.1\|NCR 324 | MQIGKNMVETPKLVYFIILFLSIFLC<br>ITVSNSSFSQIFNSACKTDKDCPKFG<br>RVNVRCRKGNCVPI<br>(SEQ ID NO: 76) | *Medicago truncatula* |
| >gi\|152218046\|gb\|<br>ABS31457.1\|NCR 320 | MTAILKKFINAVFLFIVLFLATTNVE<br>DFVGGSNDECVYPDVFQCINNICKCV<br>SHHRT<br>(SEQ ID NO: 77) | *Medicago truncatula* |
| >gi\|152218044\|gb\|<br>ABS31456.1\|NCR 319 | MQKRKNMAQIIFYVYALIILFSPPLA<br>ARLVFVNPEKPCVTDADCDRYRHESA<br>IYSDMFCKDGYCFIDYHHDPYP<br>(SEQ ID NO: 78) | *Medicago truncatula* |
| >gi\|152218042\|gb\|<br>ABS31455.1\|NCR 318 | MQMRKNMAQILFYVYALLILFTPFLV<br>ARIMVVNPNNPCVTDADCQRYRHKLA<br>TRMICNQGFCLMDFTHDPYAPSLP<br>(SEQ ID NO: 79) | *Medicago truncatula* |
| >gi\|152218040\|gb\|<br>ABS31454.1\|NCR 317 | MNHISKFVYALIIFLSIYLVVLDGLP<br>ISCKDHFECRRKINILRCIYRQEKPM<br>CINSICTCVKLL<br>(SEQ ID NO: 80) | *Medicago truncatula* |

TABLE 7-continued

Examples of NCR Peptides

| NAME | Peptide sequence | Producer |
|---|---|---|
| >gi\|152218038\|gb\|<br>ABS31453.1\|NCR 316 | MQREKNMAKIFEFVYAMIIFILLFLV<br>EKNVVAYLKFECKTDDDCQKSLLKTY<br>VWKCVKNECYFFAKK<br>(SEQ ID NO: 81) | *Medicago truncatula* |
| >gi\|152218036\|gb\|<br>ABS31452.1\|NCR 315 | MAGIIKFVHVLIIFLSLFHVVKNDDG<br>SFCFKDSDCPDEMCPSPLKEMCYFLQ<br>CKCGVDTIA<br>(SEQ ID NO: 82) | *Medicago truncatula* |
| >gi\|152218034\|gb\|<br>ABS31451.1\|NCR 314 | MANTHKLVSMILFIFLFLASNNVEGY<br>VNCETDADCPPSTRVKRFKCVKGECR<br>WTRMSYA<br>(SEQ ID NO: 83) | *Medicago truncatula* |
| >gi\|152218032\|gb\|<br>ABS31450.1\|NCR 313 | MQRRKKKAQVVMFVHDLIICIYLFIV<br>ITTRKTDIRCRFYYDCPRLEYHFCEC<br>IEDFCAYIRLN<br>(SEQ ID NO: 84) | *Medicago truncatula* |
| >gi\|152218030\|gb\|<br>ABS31449.1\|NCR 312 | MAKVYMFVYALIIFVSPFLLATFRTR<br>LPCEKDDDCPEAFLPPVMKCVNRFCQ<br>YEILE<br>(SEQ ID NO: 85) | *Medicago truncatula* |
| >gi\|152218028\|gb\|<br>ABS31448.1\|NCR 310 | MIKQFSVCYIQMRRNMTTILKFPYIM<br>VICLLLLHVAAYEDFEKEIFDCKKDG<br>DCDHMCVTPGIPKCTGYVCFCFENL<br>(SEQ ID NO: 86) | *Medicago truncatula* |
| >gi\|152218026\|gb\|<br>ABS31447.1\|NCR 309 | MQRSRNMTTIFKFAYIMIICVFLLNI<br>AAQEIENGIHPCKKNEDCNHMCVMPG<br>LPWCHENNLCFCYENAYGNTR<br>(SEQ ID NO: 87) | *Medicago truncatula* |
| >gi\|152218024\|gb\|<br>ABS31446.1\|NCR 304 | MTIIIKFVNVLIIFLSLFHVAKNDDN<br>KLLLSFIEEGFLCFKDSDCPYNMCPS<br>PLKEMCYFIKCVCGVYGPIRERRLYQ<br>SHNPMIQ<br>(SEQ ID NO: 88) | *Medicago truncatula* |
| >gi\|152218022\|gb\|<br>ABS31445.1\|NCR 303 | MRKNMTKILMIGYALMIFIFLSIAVS<br>ITGNLARASRKKPVDVIPCIYDHDCP<br>RKLYFLERCVGRVCKYL<br>(SEQ ID NO: 89) | *Medicago truncatula* |
| >gi\|152218020\|gb\|<br>ABS31444.1\|NCR 301 | MAHKLVYAITLFIFLFLIANNIEDDI<br>FCITDNDCPPNTLVQRYRCINGKCNL<br>SFVSYG<br>(SEQ ID NO: 90) | *Medicago truncatula* |
| >gi\|152218018\|gb\|<br>ABS31443.1\|NCR 300 | MDETLKFVYILILFVSLCLVVADGVK<br>NINRECTQTSDCYKKYPFIPWGKVRC<br>VKGRCRLDM<br>(SEQ ID NO: 91) | *Medicago truncatula* |
| >gi\|152218016\|gb\|<br>ABS31442.1\|NCR 290 | MAKIIKFVYVLAIFFSLFLVAKNVNG<br>WTCVEDSDCPANICQPPMQRMCFYGE<br>CACVRSKFCT<br>(SEQ ID NO: 92) | *Medicago truncatula* |
| >gi\|152218014\|gb\|<br>ABS31441.1\|NCR 289 | MVKIIKFVYFMTLFLSMLLVTTKEDG<br>SVECIANIDCPQIFMLPFVMRCINFR<br>CQIVNSEDT<br>(SEQ ID NO: 93) | *Medicago truncatula* |
| >gi\|152218012\|gb\|<br>ABS31440.1\|NCR 286 | MDEILKFVYTLIIFFSLFFAANNVDA<br>NIMNCQSTFDCPRDMCSHIRDVICIF<br>KKCKCAGGRYMPQVP<br>(SEQ ID NO: 94) | *Medicago truncatula* |
| >gi\|152218008\|gb\|<br>ABS31438.1\|NCR 278 | MQRRKNMANNHMLIYAMIICLFPYLV<br>VTFKTAITCDCNEDCLNFFTPLDNLK<br>CIDNVCEVFM<br>(SEQ ID NO: 95) | *Medicago truncatula* |

TABLE 7-continued

Examples of NCR Peptides

| NAME | Peptide sequence | Producer |
|---|---|---|
| >gi\|152218006\|gb\|ABS31437.1\|NCR 266 | MVNILKFIYVIIFFILMFFVLIDVDG HVLVECIENRDCEKGMCKFPFIVRCL MDQCKCVRIHNLI (SEQ ID NO: 96) | *Medicago truncatula* |
| >gi\|152218004\|gb\|ABS31436.1\|NCR 265 | MIIQFSIYYMQRRKLNMVEILKFSHA LIIFLFLSALVTNANIFFCSTDEDCT WNLCRQPWVQKCRLHMCSCEKN (SEQ ID NO: 97) | *Medicago truncatula* |
| >gi\|152218002\|gb\|ABS31435.1\|NCR 263 | MDEVFKFVYVMIIFPFLILDVATNAE KIRRCFNDAHCPPDMCTLGVIPKCSR FTICIC (SEQ ID NO: 98) | *Medicago truncatula* |
| >gi\|152218000\|gb\|ABS31434.1\|NCR 244 | MHRKPNMTKFFKFVYTMFILISLFLV VTNANANNCTDTSDCSSNHCSYEGVS LCMNGQCICIYE (SEQ ID NO: 99) | *Medicago truncatula* |
| >gi\|152217998\|gb\|ABS31433.1\|NCR 239 | MQMKKMATILKFVYLIILLIYPLLVV TEESHYMKFSICKDDTDCPTLFCVLP NVPKCIGSKCHCKLMVN (SEQ ID NO: 100) | *Medicago truncatula* |
| >gi\|152217996\|gb\|ABS31432.1\|NCR 237 | MVETLRLFYIMILFVSLYLVVVDGVS KLAQSCSEDFECYIKNPHAPFGQLRC FEGYCQRLDKPT (SEQ ID NO: 101) | *Medicago truncatula* |
| >gi\|152217994\|gb\|ABS31431.1\|NCR 228 | MTTFLKVAYIMIICVFVLHLAAQVDS QKRLHGCKEDRDCDNICSVHAVTKCI GNMCRCLANVK (SEQ ID NO: 102) | *Medicago truncatula* |
| >gi\|152217992\|gb\|ABS31430.1\|NCR 224 | MRINRTPAIFKFVYTIIIYLFLLRVV AKDLPFNICEKDEDCLEFCAHDKVAK CMLNICFCF (SEQ ID NO: 103) | *Medicago truncatula* |
| >gi\|152217990\|gb\|ABS31429.1\|NCR 221 | MAEILKILYVFIIFLSLILAVISQHP FTPCETNADCKCRNHKRPDCLWHKCY CY (SEQ ID NO: 104) | *Medicago truncatula* |
| >gi\|152217988\|gb\|ABS31428.1\|NCR 217 | MRKSMATILKFVYVIMLFIYSLFVIE SFGHRFLIYNNCKNDTECPNDCGPHE QAKCILYACYCVE (SEQ ID NO: 105) | *Medicago truncatula* |
| >gi\|152217986\|gb\|ABS31427.1\|NCR 209 | MNTILKFIFVVFLFLSIFLSAGNSKS YGPCTTLQDCETHNWFEVCSCIDFEC KCWSLL (SEQ ID NO: 106) | *Medicago truncatula* |
| >gi\|152217984\|gb\|ABS31426.1\|NCR 206 | MAEIIKFVYIMILCVSLLLIAEASGK ECVTDADCENLYPGNKKPMFCNNTGY CMSLYKEPSRYM (SEQ ID NO: 107) | *Medicago truncatula* |
| >gi\|152217982\|gb\|ABS31425.1\|NCR 201 | MAKIIKFVYIMILCVSLLLIVEAGGK ECVTDVDCEKIYPGNKKPLICSTGYC YSLYEEPPRYHK (SEQ ID NO: 108) | *Medicago truncatula* |
| >gi\|152217980\|gb\|ABS31424.1\|NCR 200 | MAKVTKFGYIIIHPFLSLFFLAMNVAG GRECHANSHCVGKITCVLPQKPECWN YACVCYDSNKYR (SEQ ID NO: 109) | *Medicago truncatula* |
| >gi\|152217978\|gb\|ABS31423.1\|NCR 192 | MAKIFNYVYALIMFLSLFLMGTSGMK NGCKHTGHCPRKMCGAKTTKCRNNKC QCV (SEQ ID NO: 110) | *Medicago truncatula* |

TABLE 7-continued

Examples of NCR Peptides

| NAME | Peptide sequence | Producer |
|---|---|---|
| >gi\|152217976\|gb\|ABS31422.1\|NCR 189 | MTEILKFVCVMIIFISSFIVSKSLNGGGKDKCFRDSDCPKHMCPSSLVAKCINRLCRCRRPELQVQLNP (SEQ ID NO: 111) | *Medicago truncatula* |
| >gi\|152217974\|gb\|ABS31421.1\|NCR 187 | MAHIIMFVYALIYALIIFSSLFVRDGIPCLSDDECPEMSHYSFKCNNKICEYDLGEMSDDDYYLEMSRE (SEQ ID NO: 112) | *Medicago truncatula* |
| >gi\|152217972\|gb\|ABS31420.1\|NCR 181 | MYREKNMAKTLKFVYVIVLFLSLFLAAKNIDGRVSYNSFIALPVCQTAADCPEGTRGRTYKCINNKCRYPKLLKPIQ (SEQ ID NO: 113) | *Medicago truncatula* |
| >gi\|152217970\|gb\|ABS31419.1\|NCR 176 | MAHIFNYVYALLVFLSLFLMVTNGIHIGCDKDRDCPKQMCHLNQTPKCLKNICKCV (SEQ ID NO: 114) | *Medicago truncatula* |
| >gi\|152217968\|gb\|ABS31418.1\|NCR 175 | MAEILKCFYTMNLFIFLIILPAKIREHIQCVIDDDCPKSLNKLLIIKCINHVCQYVGNLPDFASQIPKSTKMPYKGE (SEQ ID NO: 115) | *Medicago truncatula* |
| >gi\|152217966\|gb\|ABS31417.1\|NCR 173 | MAYISRIFYVLIIFLSLFFVVINGVKSLLLIKVRSFIPCQRSDDCPRNLCVDQIIPTCVWAKCKCKNYND (SEQ ID NO: 116) | *Medicago truncatula* |
| >gi\|152217964\|gb\|ABS31416.1\|NCR 172 | MANVTKFVYIAIYFLSLFFIAKNDATATFCHDDSHCVTKIKCVLPRTPQCRNEACGCYHSNKFR (SEQ ID NO: 117) | *Medicago truncatula* |
| >gi\|152217962\|gb\|ABS31415.1\|NCR 171 | MGEIMKFVYVMIIYLFMFNVATGSEFIFTKKLTSCDSSKDCRSFLCYSPKFPVCKRGICECI (SEQ ID NO: 118) | *Medicago truncatula* |
| >gi\|152217960\|gb\|ABS31414.1\|NCR 169 | MGEMFKFIYTFILFVHLFLVVIFEDIGHIKYCGIVDDCYKSKKPLFKIWKCVENVCVLWYK (SEQ ID NO: 119) | *Medicago truncatula* |
| >gi\|152217958\|gb\|ABS31413.1\|NCR 165 | MARTLKFVYSMILFLSLFLVANGLKIFCIDVADCPKDLYPLLYKCIYNKCIVFTRIPFPFDWI (SEQ ID NO: 120) | *Medicago truncatula* |
| >gi\|152217956\|gb\|ABS31412.1\|NCR 159 | MANITKFVYIAILFLSLFFIGMNDAAILECREDSHCVTKIKCVLPRKPECRNNACTCYKGGFSFHH (SEQ ID NO: 121) | *Medicago truncatula* |
| >gi\|152217954\|gb\|ABS31411.1\|NCR 147 | MQRVKKMSETLKFVYVLILFISIFHVVIVCDSIYFPVSRPCITDKDCPNMKHYKAKCRKGFCISSRVR (SEQ ID NO: 122) | *Medicago truncatula* |
| >gi\|152217952\|gb\|ABS31410.1\|NCR 146 | MQIRKIMSGVLKFVYAIILFLFLFLVAREVGGLETIECETDGDCPRSMIKMWNKNYRHKCIDGKCEWIKKLP (SEQ ID NO: 123) | *Medicago truncatula* |
| >gi\|152217950\|gb\|ABS31409.1\|NCR 145 | MFVYDLILFISLILVVTGINAEADTSCHSFDDCPWVAHHYRECIEGLCAYRILY (SEQ ID NO: 124) | *Medicago truncatula* |
| >gi\|152217948\|gb\|ABS31408.1\|NCR 144 | MQRRKKSMAKMLKFFFAIILLLSLFLVATEVGGAYIECEVDDDCPKPMKNSHPDTYYKCVKHRCQWAWK (SEQ ID NO: 125) | *Medicago truncatula* |

TABLE 7-continued

Examples of NCR Peptides

| NAME | Peptide sequence | Producer |
| --- | --- | --- |
| >gi\|152217946\|gb\|ABS31407.1\|NCR 140 | MFVYTLIIFLFPSHVITNKIAIYCVS DDDCLKTFTPLDLKCVDNVCEFNLRC KGKCGERDEKFVFLKALKKMDQKLVL EEQGNAREVKIPKKLLFDRIQVPTPA TKDQVEEDDYDDDDEEEEEEEDDVDM WFHLPDVVCH (SEQ ID NO: 126) | *Medicago truncatula* |
| >gi\|152217944\|gb\|ABS31406.1\|NCR 138 | MAKFSMFVYALINFLSLFLVETAITN IRCVSDDDCPKVIKPLVMKCIGNYCY FFMIYEGP (SEQ ID NO: 127) | *Medicago truncatula* |
| >gi\|152217942\|gb\|ABS31405.1\|NCR 136 | MAHKFVYAIILFIFLFLVAKNVKGYV VCRTVDDCPPDTRDLRYRCLNGKCKS YRLSYG (SEQ ID NO: 128) | *Medicago truncatula* |
| >gi\|152217940\|gb\|ABS31404.1\|NCR 129 | MQRKKNMGQILIFVFALINFLSPILV EMTTTTIPCTFIDDCPKMPLVVKCID NFCNYFEIK (SEQ ID NO: 129) | *Medicago truncatula* |
| >gi\|152217938\|gb\|ABS31403.1\|NCR 128 | MAQTLMLVYALIIFTSLFLVVISRQT DIPCKSDDACPRVSSHHIECVKGFCT YWKLD (SEQ ID NO: 130) | *Medicago truncatula* |
| >gi\|152217936\|gb\|ABS31402.1\|NCR 127 | MLRRKNTVQILMFVSALLIYIFLFLV ITSSANIPCNSDSDCPWKIYYTYRCN DGFCVYKSIDPSTIPQYMTDLIFPR (SEQ ID NO: 131) | *Medicago truncatula* |
| >gi\|152217934\|gb\|ABS31401.1\|NCR 122 | MAVILKFVYIMIIFLFLLYVVNGTRC NRDEDCPFICTGPQIPKCVSHICFCL SSGKEAY (SEQ ID NO: 132) | *Medicago truncatula* |
| >gi\|152217932\|gb\|ABS31400.1\|NCR 121 | MDAILKFIYAMFLFLFLFVTTRNVEA LFECNRDFVCGNDDECVYPYAVQCIH RYCKCLKSRN (SEQ ID NO: 133) | *Medicago truncatula* |
| >gi\|152217930\|gb\|ABS31399.1\|NCR 119 | MQIGRKKMGETPKLVYVIILFLSIFL CTNSSFSQMINFRGCKRDKDCPQFRG VNIRCRSGFCTPIDS (SEQ ID NO: 134) | *Medicago truncatula* |
| >gi\|152217928\|gb\|ABS31398.1\|NCR 118 | MQMRKNMAQILFYVYALLILFSPFLV ARIMVVNPNNPCVTDADCQRYRHKLA TRMVCNIGFCLMDFTHDPYAPSLP (SEQ ID NO: 135) | *Medicago truncatula* |
| >gi\|152217926\|gb\|ABS31397.1\|NCR 111 | MYVYYIQMGKNMAQRFMFIYALIIFL SQFFVVINTSDIPNNSNRNSPKEDVF CNSNDDCPTILYYVSKCVYNFCEYW (SEQ ID NO: 136) | *Medicago truncatula* |
| >gi\|152217924\|gb\|ABS31396.1\|NCR 103 | MAKIVNFVYSMIIFVSLFLVATKGGS KPFLTRPYPCNTGSDCPQNMCPPGYK PGCEDGYCNHCYKRW (SEQ ID NO: 137) | *Medicago truncatula* |
| >gi\|152217922\|gb\|ABS31395.1\|NCR 101 | MVRTLKFVYVIILILSLFLVAKGGGK KIYCENAASCPRLMYPLVYKCLDNKC VKFMMKSRFV (SEQ ID NO: 138) | *Medicago truncatula* |
| >gi\|152217920\|gb\|ABS31394.1\|NCR 96 | MARTLKFVYAVILFLSLFLVAKGDDV KIKCVVAANCPDLMYPLVYKCLNGIC VQFTLTFPFV (SEQ ID NO: 139) | *Medicago truncatula* |

TABLE 7-continued

Examples of NCR Peptides

| NAME | Peptide sequence | Producer |
|---|---|---|
| >gi\|152217918\|gb\|ABS31393.1\|NCR 94 | MSNTLMFVITFIVLVTLFLGPKNVYAFQPCVTTADCMKTLKTDENIWYECINDFCIPFPIPKGRK (SEQ ID NO: 140) | *Medicago truncatula* |
| >gi\|152217916\|gb\|ABS31392.1\|NCR 93 | MKRVVNMAKIVKYVYVIIIFLSLFLVATKIEGYYYKCFKDSDCVKLLCRIPLRPKCMYRHICKCKVVLTQNNYVLT (SEQ ID NO: 141) | *Medicago truncatula* |
| >gi\|152217914\|gb\|ABS31391.1\|NCR 90 | MKRGKNMSKILKFIYATLVLYLFLVVTKASDDECKIDGDCPISWQKFHTYKCINQKCKWVLRFHEY (SEQ ID NO: 142) | *Medicago truncatula* |
| >gi\|152217912\|gb\|ABS31390.1\|NCR 88 | MAKTLNFMFALILFISLFLVSKNVAIDIFVCQTDADCPKSELSMYTWKCIDNECNLFKVMQQMV (SEQ ID NO: 143) | *Medicago truncatula* |
| >gi\|152217910\|gb\|ABS31389.1\|NCR 86 | MANTHKLVSMILFIFLFLVANNVEGYVNCETDADCPPSTRVKRFKCVKGECRWTRMSYA (SEQ ID NO: 144) | *Medicago truncatula* |
| >gi\|152217908\|gb\|ABS31388.1\|NCR 77 | MAHFLMFVYALITCLSLFLVEMGHLSIHCVSVDDCPKVEKPITMKCINNYCKYFVDHKL (SEQ ID NO: 145) | *Medicago truncatula* |
| >gi\|152217906\|gb\|ABS31387.1\|NCR 76 | MNQIPMFGYTLIIFFSLFPVITNGDRIPCVTNGDCPVMRLPLYMRCITYSCELFFDGPNLCAVERI (SEQ ID NO: 146) | *Medicago truncatula* |
| >gi\|152217904\|gb\|ABS31386.1\|NCR 74 | MRKDMARISLFVYALIIFFSLFFVLTNGELEIRCVSDADCPLFPLPLHNRCIDDVCHLFTS (SEQ ID NO: 147) | *Medicago truncatula* |
| >gi\|152217902\|gb\|ABS31385.1\|NCR 68 | MAQILMFVYFLIIFLSLFLVESIKIFTEHRCRTDADCPARELPEYLKCQGGMCRLLIKKD (SEQ ID NO: 148) | *Medicago truncatula* |
| >gi\|152217900\|gb\|ABS31384.1\|NCR 65 | MARVISLFYALIIFLFLFLVATNGDLSPCLRSGDCSKDECPSHLVPKCIGLTCYCI (SEQ ID NO: 149) | *Medicago truncatula* |
| >gi\|152217898\|gb\|ABS31383.1\|NCR 62 | MQRRKNMAQILLFAYVFIISISLFLVVTNGVKIPCVKDTDCPTLPCPLYSKCVDGFCKMLSI (SEQ ID NO: 150) | *Medicago truncatula* |
| >gi\|152217896\|gb\|ABS31382.1\|NCR 57 | MNHISKFVYALIIFLSVYLVVLDGRPVSCKDHYDCRRKVKIVGCIFPQEKPMCINSMCTCIREIVP (SEQ ID NO: 151) | *Medicago truncatula* |
| >gi\|152217894\|gb\|ABS31381.1\|NCR 56 | MKSQNHAKFISFYKNDLFKIFQNNDSHFKVFFALIIFLYTYLHVTNGVFVSCNSHIHCRVNNHKIGCNIPEQYLLCVNLFCLWLDY (SEQ ID NO: 152) | *Medicago truncatula* |
| >gi\|152217892\|gb\|ABS31380.1\|NCR 54 | MTYISKVVYALIIFLSIYVGVNDCMLVTCEDHFDCRQNVQQVGCSFREIPQCINSICKCMKG (SEQ ID NO: 153) | *Medicago truncatula* |
| >gi\|152217890\|gb\|ABS31379.1\|NCR 53 | MTHISKFVPALIIFLSIYVGVNDCKRIPCKDNNDCNNNWQLLACRFEREVPRCINSICKCMPM (SEQ ID NO: 154) | *Medicago truncatula* |

TABLE 7-continued

Examples of NCR Peptides

| NAME | Peptide sequence | Producer |
|---|---|---|
| >gi\|152217888\|gb\|<br>ABS31378.1\|NCR 43 | MVQTPKLVYVIVLLLSIFLGMTICNS<br>SFSHFFEGACKSDKDCPKLHRSNVRC<br>RKGQCVQI<br>(SEQ ID NO: 155) | Medicago truncatula |
| >gi\|152217886\|gb\|<br>ABS31377.1\|NCR 28 | MTKILMLFYAMIVFHSIFLVASYTDE<br>CSTDADCEYILCLFPIIKRCIHNHCK<br>CVPMGSIEPMSTIPNGVHKFHIINN<br>(SEQ ID NO: 156) | Medicago truncatula |
| >gi\|152217884\|gb\|<br>ABS31376.1\|NCR 26 | MAKTLNFVCAMILFISLFLVSKNVAL<br>YIIECKTDADCPISKLNMYNWRCIKS<br>SCHLYKVIQFMV<br>(SEQ ID NO: 157) | Medicago truncatula |
| >gi\|152217882\|gb\|<br>ABS31375.1\|NCR 24 | MQKEKNMAKTFEFVYAMIIFILLFLV<br>ENNFAAYIIECQTDDDCPKSQLEMFA<br>WKCVKNGCHLFGMYEDDDDP<br>(SEQ ID NO: 158) | Medicago truncatula |
| >gi\|152217880\|gb\|<br>ABS31374.1\|NCR 21 | MAATRKFIYVLSHFLFLFLVTKITDA<br>RVCKSDKDCKDIIIYRYILKCRNGEC<br>VKIKI<br>(SEQ ID NO: 159) | Medicago truncatula |
| >gi\|152217878\|gb\|<br>ABS31373.1\|NCR 20 | MQRLDNMAKNVKFIYVIILLLFIFLV<br>IIVCDSAFVPNSGPCTTDKDCKQVKG<br>YIARCRKGYCMQSVKRTWSSYSR<br>(SEQ ID NO: 160) | Medicago truncatula |
| >gi\|152217876\|gb\|<br>ABS31372.1\|NCR 19 | MKFIYIMILFLSLFLVQFLTCKGLTV<br>PCENPTTCPEDFCTPPMITRCINPIC<br>LCDGPEYAEPEYDGPEPEYDHKGDFL<br>SVKPKIINENMMMRERHMMKEIEV<br>(SEQ ID NO: 161) | Medicago truncatula |
| >gi\|152217874\|gb\|<br>ABS31371.1\|NCR 12 | MAQFLMFIYVLIIFLYLFYVEAAMFE<br>LTKSTIRCVTDADCPNVVKPLKPKCV<br>DGFCEYT<br>(SEQ ID NO: 162) | Medicago truncatula |
| >gi\|152217872\|gb\|<br>ABS31370.1\|NCR 10 | MKMRIHMAQIIMFFYALIIFLSPFLV<br>DRRSFPSSFVSPKSYTSEIPCKATRD<br>CPYELYYETKCVDSLCTY<br>(SEQ ID NO: 163) | Medicago truncatula |

Any NCR peptide known in the art is suitable for use in the methods or compositions described herein. NCR peptide-producing plants include but are not limited to *Pisum sativum* (pea), *Astragalus sinicus* (IRLC legumes), *Phaseolus vulgaris* (bean), *Vigna unguiculata* (cowpea), *Medicago truncatula* (barrelclover), and *Lotus japonicus*. For example, over 600 potential NCR peptides are predicted from the *M. truncatula* genome sequence and almost 150 different NCR peptides have been detected in cells isolated from root nodules by mass spectrometry.

The NCR peptides described herein may be mature or immature NCR peptides. Immature NCR peptides have a C-terminal signal peptide that is required for translocation into the endoplasmic reticulum and cleaved after translocation. The N-terminus of a NCR peptide includes a signal peptide, which may be cleavable, for targeting to a secretory pathway. NCR peptides are generally small peptides with disulfide bridges that stabilize their structure. Mature NCR peptides have a length in the range of about 20 to about 60 amino acids, about 25 to about 55 amino acids, about 30 to about 50 amino acids, about 35 to about 45 amino acids, or any range therebetween. NCR peptides may include a conserved sequence of cysteine residues with the rest of the peptide sequence highly variable. NCR peptides generally have about four or eight cysteines.

NCR peptides may be anionic, neutral, or cationic. In some instances, synthetic cationic NCR peptides having a pI greater than about eight possess antimicrobial activities. For example, NCR247 (pI=10.15, RNG-CIVDPRCPYQQCRRPLYCRRR; SEQ ID NO: 164) and NCR335 (pI=11.22) are both effective against gram-negative and gram-positive bacteria as well as fungi. In some instances, neutral and/or anionic NCR peptides, such as NCR001 (MAQFLLFVYSLIIFLSLFFGEAAFERTET-RMLTIPCTSDDNCPKVIS-PCHTKCFDGFCGWYIEGSYEGP; SEQ ID NO: 165), do not possess antimicrobial activities at a pI greater than about 8.

In some instances, the NCR peptide is effective to kill bacteria. In some instances, the NCR peptide is effective to kill *S. meliloti*, *Xenorhabdus* spp, *Photorhabdus* spp, *Candidatus* spp, *Buchnera* spp, *Blattabacterium* spp, *Baumania* spp, *Wigglesworthia* spp, *Wolbachia* spp, *Rickettsia* spp, *Orientia* spp, *Sodalis* spp, *Burkholderia* spp, *Cupriavidus* spp, *Frankia* spp, *Snirhizobium* spp, *Streptococcus* spp, *Wolinella* spp, *Xylella* spp, *Erwinia* spp, *Agrobacterium* spp, *Bacillus* spp, *Paenibacillus* spp, *Streptomyces* spp, *Micrococcus* spp, *Corynebacterium* spp, *Acetobacter* spp, *Cyanobacteria* spp, *Salmonella* spp, *Rhodococcus* spp, *Pseudomonas* spp, *Lactobacillus* spp, *Enterococcus* spp, *Alcaligenes* spp, *Klebsiella* spp, *Paenibacillus* spp, *Arthrobacter* spp, *Corynebacterium* spp, *Brevibacterium* spp, *Thermus* spp, *Pseudomonas* spp, *Clostridium* spp, or *Escherichia* spp.

In some instances, the NCR peptide is a functionally active variant of a NCR peptide described herein. In some instances, the variant of the NCR peptide has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region or over the entire sequence, to a sequence of a NCR peptide described herein or naturally derived NCR peptide.

In some instances, the NCR peptide may be bioengineered to modulate its bioactivity, e.g., increase or decrease or regulate, or to specify a target microorganism. In some instances, the NCR peptide is produced by the translational machinery (e.g. a ribosome, etc.) of a cell. In some instances, the NCR peptide is chemically synthesized. In some instances, the NCR peptide is derived from a polypeptide precursor. The polypeptide precursor can undergo cleavage (for example, processing by a protease) to yield the NCR peptide itself. As such, in some instances, the NCR peptide is produced from a precursor polypeptide. In some instances, the NCR peptide includes a polypeptide that has undergone post-translational modifications, for example, cleavage, or the addition of one or more functional groups.

The NCR peptide described herein may be formulated in a composition for any of the uses described herein. The compositions disclosed herein may include any number or type of NCR peptides, such as at least about any one of 1 NCR peptide, 2, 3, 4, 5, 10, 15, 20, 30, 40, 50, 100, or more NCR peptides. A suitable concentration of each NCR peptide in the composition depends on factors such as efficacy, stability of the NCR peptide, number of distinct NCR peptide, the formulation, and methods of application of the composition. In some instances, each NCR peptide in a liquid composition is from about 0.1 ng/mL to about 100 mg/mL. In some instances, each NCR peptide in a solid composition is from about 0.1 ng/g to about 100 mg/g. In some instances, wherein the composition includes at least two types of NCR peptides, the concentration of each type of NCR peptide may be the same or different.

A modulating agent including a NCR peptide as described herein can be contacted with the target host in an amount and for a time sufficient to: (a) reach a target level (e.g., a predetermined or threshold level) of NCR peptide concentration inside a target host; (b) reach a target level (e.g., a predetermined or threshold level) of NCR peptide concentration inside a target host gut; (c) reach a target level (e.g., a predetermined or threshold level) of NCR peptide concentration inside a target host bacteriocyte; (d) modulate the level, or an activity, of one or more microorganism (e.g., endosymbiont) in the target host; or/and (e) modulate fitness of the target host.

(e) Bacteriocyte Regulatory Peptides

The modulating agent described herein may include a bacteriocyte regulatory peptide (BRP). BRPs are peptides expressed in the bacteriocytes of insects. These genes are expressed first at a developmental time point coincident with the incorporation of symbionts and their bacteriocyte-specific expression is maintained throughout the insect's life. In some instances, the BRP has a hydrophobic amino terminal domain, which is predicted to be a signal peptide. In addition, some BRPs have a cysteine-rich domain. In some instances, the bacteriocyte regulatory peptide is a bacteriocyte-specific cysteine rich (BCR) protein. Bacteriocyte regulatory peptides have a length between about 40 and 150 amino acids. In some instances, the bacteriocyte regulatory peptide has a length in the range of about 45 to about 145, about 50 to about 140, about 55 to about 135, about 60 to about 130, about 65 to about 125, about 70 to about 120, about 75 to about 115, about 80 to about 110, about 85 to about 105, or any range therebetween. Non-limiting examples of BRPs and their activities are listed in Table 8.

TABLE 8

Examples of Bacteriocyte Regulatory Peptides

| Name | Peptide Sequence |
|---|---|
| Bacteriocyte-specific cysteine rich proteins BCR family, peptide BCR1 | MKLLHGFLIIMLTMHLSIQYAYGGPFLTKYLCDRV CHKLCGDEFVCSCIQYKSLKGLWFPHCPTGKASVV LHNFLTSP (SEQ ID NO: 166) |
| Bacteriocyte-specific cysteine rich proteins BCR family, peptide BCR2 | MKLLYGFLIIMLTIHLSVQYFESPFETKYNCDTHC NKLCGKIDHCSCIQYHSMEGLWFPHCRTGSAAQML HDFLSNP (SEQ ID NO: 167) |
| Bacteriocyte-specific cysteine rich proteins BCR family, peptide BCR3 | MSVRKNVLPTMFVVLLIMSPVTPTSVFISAVCYSG CGSLALVCFVSNGITNGLDYFKSSAPLSTSETSCG EAFDTCTDHCLANFKF (SEQ ID NO: 168) |
| Bacteriocyte-specific cysteine rich proteins BCR family, peptide BCR4 | MRLLYGFLIIMLTIYLSVQDFDPTEFKGPFPTIEI CSKYCAVVCNYTSRPCYCVEAAKERDQWFPYCYD (SEQ ID NO: 169) |
| Bacteriocyte-specific cysteine rich proteins BCR family, peptide BCR5 | MRLLYGFLIIMLTIHLSVQDIDPNTLRGPYPTKEI CSKYCEYNVVCGASLPCICVQDARQLDHWFACCYD GGPEMLM (SEQ ID NO: 170) |
| Secreted proteins SP family, peptide SP1 | MKLFVVVVLVAVGIMFVFASDTAAAPTDYEDTNDM ISLSSLVGDNSPYVRVSSADSGGSSKTSSKNPILG LLKSVIKLLTKIFGTYSDAAPAMPPIPPALRKNRG MLA (SEQ ID NO: 171) |

TABLE 8-continued

Examples of Bacteriocyte Regulatory Peptides

| Name | Peptide Sequence |
| --- | --- |
| Secreted proteins SP family, peptide SP2 | MVACKVILAVAVVFVAAVQGRPGGEPEWAAPIFAE LKSVSDNITNLVGLDNAGEYATAAKNNLNAFAESL KTEAAVFSKSFEGKASASDVFKESTKNFQAVVDTY IKNLPKDLTLKDFTEKSEQALKYMVEHGTEITKKA QGNTETEKEIKEFFKKQIENLIGQGKALQAKIAEA KKA (SEQ ID NO: 172) |
| Secreted proteins SP family, peptide SP3 | MKTSSSKVFASCVAIVCLASVANALPVQKSVAATT ENPIVEKHGCRAHKNLVRQNVVDLKTYDSMLITNE VVQKQSNEVQSSEQSNEGQNSEQSNEGQNSEQSNE VQSSEHSNEGQNSKQSNEGQNSEQSNEVQSSEHSN EGQNSEQSNEVQSSEHSNEGQNSKQSNEGQNSKQS NEVQSSEHWNEGQNSKQSNEDQNSEQSNEGQNSKQ SNEGQNSKQSNEDQNSEQSNEGQNSKQSNEVQSSE QSNEGQNSKQSNEGQSSEQSNEGQNSKQSNEVQSP EEHYDLPDPESSYESEETKGSHESGDDSEHR (SEQ ID NO: 173) |
| Secreted proteins SP family, peptide SP4 | MKTIILGLCLFGALFWSTQSMPVGEVAPAVPAVPS EAVPQKQVEAKPETNAASPVSDAKPESDSKPVDAE VKPTVSEVKAESEQKPSGEPKPESDAKPVVASESK PESDPKPAAVVESKPENDAVAPETNNDAKPENAAA PVSENKPATDAKAETELIAQAKPESKPASDLKAEP EAAKPNSEVPVALPLNPTETKATQQSVETNQVEQA APAAAQADPAAAPAADPAPAPAAAPVAAEEAKLSE SAPSTENKAAEEPSKPAEQQSAKPVEDAVPAASEI SETKVSPAVPAVPEVPASPSAPAVADPVSAPEAEK NAEPAKAANSAEPAVQSEAKPAEDIQKSGAVVSAE NPKPVEEQKPAEVAKPAEQSKSEAPAEAPKPTEQS AAEEPKKPESANDEKKEQHSVNKRDATKEKKPTDS IMKKQKQKKAN (SEQ ID NO: 174) |
| Secreted proteins SP family, peptide SP5a | MNGKIVLCFAVVFIGQAMSAATGTTPEVEDIKKVA EQMSQTFMSVANHLVGITPNSADAQKSIEKIRTIM NKGFTDMETEANKMKDIVRKNADPKLVEKYDELEK ELKKHLSTAKDMFEDKVVKPIGEKVELKKITENVI KTTKDMEATMNKAIDGFKKQ (SEQ ID NO: 175) |
| Secreted proteins SP family, peptide SP6 | MHLFLALGLFIVCGMVDATFYNPRSQTFNQLMERR QRSIPIPYSYGYHYNPIEPSINVLDSLSEGLDSRI NTFKPIYQNVKMSTQDVNSVPRTQYQPKNSLYDSE YISAKDIPSLFPEEDSYDYKYLGSPLNKYLTRPST QESGIAINLVAIKETSVFDYGFPTYKSPYSSDSVW NFGSKIPNTVFEDPQSVESDPNTFKVSSPTIKIVK LLPETPEQESIITTTKNYELNYKTTQETPTEAELY PITSEEFQTEDEWHPMVPKENTTKDESSFITTEEP LTEDKSNSITIEKTQTEDESNSIEFNSIRTEEKSN SITTEENQKEDDESMSTTSQETTTAFNLNDTFDTN RYSSSHESLMLRIRELMKNIADQQNKSQFRTVDNI PAKSQSNLSSDESTNQQFEPQLVNGADTYK (SEQ ID NO: 176) |
| Colepotericin A, ColA peptide | MTRTMLFLACVAALYVCISATAGKPEEFAKLSDEA PSNDQAMYESIQRYRRFVDGNRYNGGQQQQQQPKQ WEVRPDLSRDQRGNTKAQVEINKKGDNHDINAGWG KNINGPDSHKDTWHVGGSVRW (SEQ ID NO: 177) |
| RIpA type I | MKETTVVWAKLFLILIILAKPLGLKAVNECKRLGN NSCRSHGECCSGFCFIEPGWALGVCKRLGTPKKSD DSNNGKNIEKNNGVHERIDDVFERGVCSYYKGPSI TANGDVFDENEMTAAHRTLPFNTMVKVEGMGTSVV VKINDRKTAADGKVMLLSRAAAESLNIDENTGPVQ CQLKFVLDGSGCTPDYGDTCVLHHECCSQNCFREM FSDKGFCLPK (SEQ ID NO: 192) |

In some instances, the BRP alters the growth and/or activity of one or more bacteria resident in the bacteriocyte of the host. In some instances, the BRP may be bioengineered to modulate its bioactivity (e.g., increase, decrease, or regulate) or to specify a target microorganism. In some instances, the BRP is produced by the translational machinery (e.g. a ribosome, etc.) of a cell. In some instances, the BRP is chemically synthesized. In some instances, the BRP is derived from a polypeptide precursor. The polypeptide precursor can undergo cleavage (for example, processing by a protease) to yield the polypeptide of the BRP itself. As such, in some instances, the BRP is produced from a precursor polypeptide. In some instances, the BRP includes a polypeptide that has undergone post-translational modifications, for example, cleavage, or the addition of one or more functional groups.

Functionally active variants of the BRPs as described herein are also useful in the compositions and methods described herein. In some instances, the variant of the BRP has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region or over the entire sequence, to a sequence of a BRP described herein or naturally derived BRP.

The BRP described herein may be formulated in a composition for any of the uses described herein. The compositions disclosed herein may include any number or type (e.g., classes) of BRPs, such as at least about any one of 1 BRP, 2, 3, 4, 5, 10, 15, 20, or more BRPs. A suitable concentration of each BRP in the composition depends on factors such as efficacy, stability of the BRP, number of distinct BRP, the formulation, and methods of application of the composition. In some instances, each BRP in a liquid composition is from about 0.1 ng/mL to about 100 mg/mL. In some instances, each BRP in a solid composition is from about 0.1 ng/g to about 100 mg/g. In some instances, wherein the composition includes at least two types of BRPs, the concentration of each type of BRP may be the same or different.

A modulating agent including a BRP as described herein can be contacted with the target host in an amount and for a time sufficient to: (a) reach a target level (e.g., a predetermined or threshold level) of BRP concentration inside a target host; (b) reach a target level (e.g., a predetermined or threshold level) of BRP concentration inside a target host gut; (c) reach a target level (e.g., a predetermined or threshold level) of BRP concentration inside a target host bacteriocyte; (d) modulate the level, or an activity, of one or more microorganism (e.g., endosymbiont) in the target host; or/and (e) modulate fitness of the target host.

iii. Small Molecules

Numerous small molecules (e.g., an antibiotic or a metabolite) may be used in the compositions and methods described herein. In some instances, an effective concentration of any small molecule described herein may alter the level, activity, or metabolism of one or more microorganisms (as described herein) resident in a host, the alteration resulting in an increase in the host's fitness.

A modulating agent comprising a small molecule as described herein can be contacted with the target host in an amount and for a time sufficient to: (a) reach a target level (e.g., a predetermined or threshold level) of a small molecule concentration inside a target host; (b) reach a target level (e.g., a predetermined or threshold level) of small molecule concentration inside a target host gut; (c) reach a target level (e.g., a predetermined or threshold level) of a small molecule concentration inside a target host bacteriocyte; (d) modulate the level, or an activity, of one or more microorganism (e.g., endosymbiont) in the target host; or/and (e) modulate fitness of the target host.

The small molecules discussed hereinafter, namely antibiotics and secondary metabolites, can be used to alter the level, activity, or metabolism of target microorganisms as indicated in the sections for increasing the fitness of insects, such as honeybees and silkworms.

(a) Antibiotics

The modulating agent described herein may include an antibiotic. Any antibiotic known in the art may be used. Antibiotics are commonly classified based on their mechanism of action, chemical structure, or spectrum of activity.

The antibiotic described herein may target any bacterial function or growth processes and may be either bacteriostatic (e.g., slow or prevent bacterial growth) or bactericidal (e.g., kill bacteria). In some instances, the antibiotic is a bactericidal antibiotic. In some instances, the bactericidal antibiotic is one that targets the bacterial cell wall (e.g., penicillins and cephalosporins); one that targets the cell membrane (e.g., polymyxins); or one that inhibits essential bacterial enzymes (e.g., rifamycins, lipiarmycins, quinolones, and sulfonamides). In some instances, the bactericidal antibiotic is an aminoglycoside. In some instances, the antibiotic is a bacteriostatic antibiotic. In some instances the bacteriostatic antibiotic targets protein synthesis (e.g., macrolides, lincosamides and tetracyclines). Additional classes of antibiotics that may be used herein include cyclic lipopeptides (such as daptomycin), glycylcyclines (such as tigecycline), oxazolidinones (such as linezolid), or lipiarmycins (such as fidaxomicin). Examples of antibiotics include rifampicin, ciprofloxacin, doxycycline, ampicillin, and polymyxin B. Non-limiting examples of antibiotics are found in Table 9.

TABLE 9

Examples of Antibiotics

| Antibiotics | Action |
| --- | --- |
| Penicillins, cephalosporins, vancomycin | Cell wall synthesis |
| Polymixin, gramicidin | Membrane active agent, disrupt cell membrane |
| Tetracyclines, macrolides, chloramphenicol, clindamycin, spectinomycin | Inhibit protein synthesis |
| Sulfonamides | Inhibit folate-dependent pathways |
| Ciprofloxacin | Inhibit DNA-gyrase |
| Isoniazid, rifampicin, pyrazinamide, ethambutol, (myambutol)l, streptomycin | Antimycobacterial agents |

The antibiotic described herein may have any level of target specificity (e.g., narrow- or broad-spectrum). In some instances, the antibiotic is a narrow-spectrum antibiotic, and thus targets specific types of bacteria, such as gram-negative or gram-positive bacteria. Alternatively, the antibiotic may be a broad-spectrum antibiotic that targets a wide range of bacteria.

The antibiotics described herein may be formulated in a composition for any of the uses described herein. The compositions disclosed herein may include any number or type (e.g., classes) of antibiotics, such as at least about any one of 1 antibiotic, 2, 3, 4, 5, 10, 15, 20, or more antibiotics (e.g., a combination of rifampicin and doxycycline, or a combination of ampicillin and rifampicin). A suitable concentration of each antibiotic in the composition depends on factors such as efficacy, stability of the antibiotic, number of distinct antibiotics, the formulation, and methods of application of the composition. In some instances, wherein the composition includes at least two types of antibiotics, the concentration of each type of antibiotic may be the same or different.

A modulating agent including an antibiotic as described herein can be contacted with the target host in an amount and for a time sufficient to: (a) reach a target level (e.g., a predetermined or threshold level) of antibiotic concentration inside a target host; (b) reach a target level (e.g., a predetermined or threshold level) of antibiotic concentration inside a target host gut; (c) reach a target level (e.g., a predetermined or threshold level) of antibiotic concentration inside a target host bacteriocyte; (d) modulate the level, or an activity, of one or more microorganism (e.g., endosymbiont) in the target host; or/and (e) modulate fitness of the target host.

(b) Secondary Metabolites

In some instances, the modulating agent of the compositions and methods described herein includes a secondary metabolite. Secondary metabolites are derived from organic molecules produced by an organism. Secondary metabolites may act (i) as competitive agents used against bacteria, fungi, amoebae, plants, insects, and large animals; (ii) as metal transporting agents; (iii) as agents of symbiosis between microbes and plants, nematodes, insects, and higher animals; (iv) as sexual hormones; and (v) as differentiation effectors. Non-limiting examples of secondary metabolites are found in Table 10.

In some instances, the small molecule is an amino acid analog. In certain instances, the amino acid analog is L-canvanine, D-arginine, D-valine, D-methionine, D-phenylalanine, D-histidine, D-tryptophan, D-threonine, D-leucine, L-NG-nitroarginine, or a combination thereof.

In some instances, the small molecule is a natural antimicrobial compound, such as propionic acid, levulinic acid, trans-cinnemaldehyde, nisin, or low molecular weight chitosan. The secondary metabolite described herein may be formulated in a composition for any of the uses described herein. The compositions disclosed herein may include any number or type (e.g., classes) of secondary metabolites, such as at least about any one of 1 secondary metabolite, 2, 3, 4, 5, 10, 15, 20, or more secondary metabolites. A suitable concentration of each secondary metabolite in the composition depends on factors such as efficacy, stability of the secondary metabolite, number of distinct secondary metabo-

TABLE 10

Examples of Secondary Metabolites

| Phenylpropanoids | Alkaloids | Terpenoids | Quinones | Steroids | Polyketides |
|---|---|---|---|---|---|
| Anthocyanins | Acridines | Carotenes | Anthraquinones | Cardiac | Erythromycin |
| Coumarins | Betalaines | Monoterpenes | Bezoquinones | Glycosides | Lovastatin and other statins |
| Flavonoids | Quinolozidines | Sesquiterpenes | Naphthoquinones | Pregnenolone | Discodermolide |
| Hydroxycinnamoyl Derivatives | Furonoquinones | Diterpenes | | Derivatives | Aflatoxin B1 |
| Isoflavonoids | Harringtonines | Triterpenes | | | Avermectins |
| Lignans | Isoquinolines | | | | Nystatin |
| Phenolenones | Indoles | | | | Rifamycin |
| Proanthocyanidins | Purines | | | | |
| Stilbenes | Pyridines | | | | |
| Tanins | Tropane Alkaloids | | | | |

The secondary metabolite used herein may include a metabolite from any known group of secondary metabolites. For example, secondary metabolites can be categorized into the following groups: alkaloids, terpenoids, flavonoids, glycosides, natural phenols (e.g., gossypol acetic acid), enals (e.g., trans-cinnamaldehyde), phenazines, biphenols and dibenzofurans, polyketides, fatty acid synthase peptides, nonribosomal peptides, ribosomally synthesized and post-translationally modified peptides, polyphenols, polysaccharides (e.g., chitosan), and biopolymers. For an in-depth review of secondary metabolites see, for example, Vining, *Annu. Rev. Microbiol.* 44:395-427, 1990.

Secondary metabolites useful for compositions and methods described herein include those that alter a natural function of an endosymbiont (e.g., primary or secondary endosymbiont), bacteriocyte, or extracellular symbiont. In some instances, one or more secondary metabolites described herein is isolated from a high throughput screening (HTS) for antimicrobial compounds. For example, a HTS screen identified 49 antibacterial extracts that have specificity against gram positive and gram negative bacteria from over 39,000 crude extracts from organisms growing in diverse ecosystems of one specific region. In some instances, the secondary metabolite is transported inside a bacteriocyte.

In some instances, the small molecule is an inhibitor of vitamin synthesis. In some instances, the vitamin synthesis inhibitor is a vitamin precursor analog. In certain instances, the vitamin precursor analog is pantothenol.

lites, the formulation, and methods of application of the composition. In some instances, wherein the composition includes at least two types of secondary metabolites, the concentration of each type of secondary metabolite may be the same or different.

A modulating agent including a secondary metabolite as described herein can be contacted with the target host in an amount and for a time sufficient to: (a) reach a target level (e.g., a predetermined or threshold level) of secondary metabolite concentration inside a target host; (b) reach a target level (e.g., a predetermined or threshold level) of secondary metabolite concentration inside a target host gut; (c) reach a target level (e.g., a predetermined or threshold level) of secondary metabolite concentration inside a target host bacteriocyte; (d) modulate the level, or an activity, of one or more microorganism (e.g., endosymbiont) in the target host; or/and (e) modulate fitness of the target host.

iv. Bacteria as Modulating Agents

In some instances, the modulating agent described herein includes one or more bacteria. Numerous bacteria are useful in the compositions and methods described herein. In some instances, the agent is a bacterial species endogenously found in the host. In some instances, the bacterial modulating agent is an endosymbiotic bacterial species. Non-limiting examples of bacteria that may be used as modulating agents include all bacterial species described herein in Section II of the detailed description and those listed in Table 1 starting at page 15. For example, the modulating agent may be a bacterial species from any bacterial phyla present in insect guts, including Gammaproteobacteria, Alphaproteobacteria, Betaproteobacteria, Bacteroidetes, Firmicutes (e.g., *Lactobacillus* and *Bacillus* spp.), *Clostridia, Actinomycetes, Spirochetes, Verrucomicrobia*, and *Actinobacteria*.

In some instances, the modulating agent is a bacterium that promotes microbial diversity or otherwise alters the microbiota of the host in a favorable manner. In one instance, bacteria may be provided to promote microbiome development in honey bees. For example, the modulating agent may include, for example, *Bartonella apis, Parasaccharibacter apium, Frischella perrara, Snodgrassella alvi, Gilliamela apicola, Bifidobacterium* spp, or *Lactobacillus* spp.

The bacterial modulating agents discussed herein can be used to alter the level, activity, or metabolism of target microorganisms as indicated in the sections for increasing the fitness of insects, such as, honeybees and silkworms.

In some instances, such bacterial modulating agents are bacteria which are capable of degrading pesticides as laid out in Table 12 including insecticides. Such insecticides include neonicotinoids such as imidacloprid, or organophosphorus insecticides, such as fenitrothion. In some instances, the pesticide-metabolizing bacteria are at a concentration of at least 100,000 cells/ml (e.g., at least about 100,000 cells/ml, at least about 150,000 cells/ml, at least about 200,000 cells/ml, at least about 250,000 cells/ml, at least about 300,000 cells/ml, at least about 350,000 cells/ml, at least about 400,000 cells/ml, at least about 450,000 cells/ml, or at least about 500,000 cells/ml).

Examples 1 to 3, 5, and 6 describe how imidacloprid and fenitrothion degrading microorganisms can be identified which can then be used a modulating agents in insect hosts, such as honeybees, giving the treated insect hosts a competitive advantage. Administering such pesticide-degrading microorganisms, for example imidacloprid- or fenitrothion-degrading microorganisms to insect hosts such as honeybees is understood to be encompassed by the alteration of a level, activity, or metabolism of one or more microorganisms resident in the host.

In some instances, such bacterial modulating agents are bacteria which are capable of producing nutrients, including amino acids (e.g., methionine or glutamate). The nutrient-producing bacteria may be naturally occurring bacteria, e.g., naturally occurring bacteria exogenous to the insect host. Such bacteria may be isolated from a population of bacteria, such as that found in an environmental sample. Bacteria can be isolated that produce one or more amino acids in a manner that increases production of amino acids in the host relative to a host who has not been administered the amino-acid producing bacteria. Amino acids that can be produced by the bacteria in the host include methionine, alanine, arginine, asparagine, aspartic acid, cysteine, glutamine, glutamic acid, glutamate, glycine, histidine, isoleucine, leucine, lysine, methionine, phenylalanine, proline, serine, threonine, tryptophan, tyrosine, or valine. In certain instances, the amino acid-producing bacteria is a methionine-producing bacteria.

In some instances, the nutrient-producing bacteria (e.g., amino acid-producing bacteria, e.g., methionine-producing bacteria) are at a concentration of at least 100,000 cells/ml (e.g., at least about 100,000 cells/ml, at least about 150,000 cells/ml, at least about 200,000 cells/ml, at least about 250,000 cells/ml, at least about 300,000 cells/ml, at least about 350,000 cells/ml, at least about 400,000 cells/ml, at least about 450,000 cells/ml, or at least about 500,000 cells/ml).

Examples 8, 9, and 10 describe how methionine-producing microorganisms can be identified which can then be used as modulating agents in insect hosts, such as honeybees, or in the model organism *Drosophila*, to increase the fitness of the hosts (e.g., increase amino acid content (e.g., methionine content or glutamate content).

v. Modifications to Modulating Agents (a) Fusions

Any of the modulating agents described herein may be fused or linked to an additional moiety. In some instances, the modulating agent includes a fusion of one or more additional moieties (e.g., 1 additional moiety, 2, 3, 4, 5, 6, 7, 8, 9, 10, or more additional moieties). In some instances, the additional moiety is any one of the modulating agents described herein (e.g., a peptide, polypeptide, small molecule, or antibiotic). Alternatively, the additional moiety may not act as modulating agent itself but may instead serve a secondary function. For example, the additional moiety may to help the modulating agent access, bind, or become activated at a target site in the host (e.g., at a host gut or a host bacteriocyte) or at a target microorganism resident in the host (e.g., honeybee or silkworm).

In some instances, the additional moiety may help the modulating agent penetrate a target host cell or target microorganism resident in the host. For example, the additional moiety may include a cell penetrating peptide. Cell penetrating peptides (CPPs) may be natural sequences derived from proteins; chimeric peptides that are formed by the fusion of two natural sequences; or synthetic CPPs, which are synthetically designed sequences based on structure—activity studies. In some instances, CPPs have the capacity to ubiquitously cross cellular membranes (e.g., prokaryotic and eukaryotic cellular membranes) with limited toxicity. Further, CPPs may have the capacity to cross cellular membranes via energy-dependent and/or independent mechanisms, without the necessity of a chiral recognition by specific receptors. CPPs can be bound to any of the modulating agents described herein. For example, a CPP can be bound to an antimicrobial peptide (AMP), e.g., a scorpion peptide, e.g., UY192 fused to a cell penetrating peptide (e.g., YGRKKRRQRRRFLSTIWNGIKGLLFAM; SEQ ID NO: 198). Non-limiting examples of CPPs are listed in Table 11.

TABLE 11

| Examples of Cell Penetrating Peptides (CPPs) | | |
|---|---|---|
| Peptide | Origin | Sequence |
| Protein-derived | | |
| rit | Antennapedia | RQIKIWFQNRRMKWKK (SEQ ID NO: 178) |
| Tat peptide | Tat | GRKKRRQRRRPPQ (SEQ ID NO: 179) |
| pVEC | Cadherin | LLIILRRRIRKQAHAHSK (SEQ ID NO: 180) |
| Chimeric | | |
| Transportan | Galanine/Mastoparan | GWTLNSAGYLLGKINLKA LAALAKKIL (SEQ ID NO: 181) |

TABLE 11-continued

Examples of Cell Penetrating Peptides (CPPs)

| Peptide | Origin | Sequence |
|---|---|---|
| MPG | HIV-gp41/ SV40 T-antigen | GALFLGFLGAAGSTMGAW SQPKKKRKV (SEQ ID NO: 182) |
| Pep-1 | HIV-reverse transcriptase/ SV40 T-antigen | KETWWETWWTEWSQPKKK RKV (SEQ ID NO: 183) |
| Synthetic | | |
| Polyarginines | Based on Tat peptide | $(R)_n$; $6 < n < 12$ |
| MAP | de novo | KLALKLALKALKAALKLA (SEQ ID NO: 184) |
| $R_6W_3$ | Based on penetratin | RRWWRRWRR (SEQ ID NO: 185) |

In other instances, the additional moiety helps the modulating agent bind a target microorganism (e.g., a fungi or bacterium) resident in the host. The additional moiety may include one or more targeting domains. In some instances, the targeting domain may target the modulating agent to one or more microorganisms (e.g., bacterium or fungus) resident in the gut of the host. In some instances, the targeting domain may target the modulating agent to a specific region of the host (e.g., host gut or bacteriocyte) to access microorganisms that are generally present in said region of the host. For example, the targeting domain may target the modulating agent to the foregut, midgut, or hindgut of the host. In other instances, the targeting domain may target the modulating agent to a bacteriocyte in the host and/or one or more specific bacteria resident in a host bacteriocyte. For example, the targeting domain may be *Galanthus nivalis* lectin or agglutinin (GNA) bound to a modulating agent described herein, e.g., an AMP, e.g., a scorpion peptide, e.g., Uy192.

(b) Pre- or Pro-Domains

In some instances, the modulating agent may include a pre- or pro-amino acid sequence. For example, the modulating agent may be an inactive protein or peptide that can be activated by cleavage or post-translational modification of a pre- or pro-sequence. In some instances, the modulating agent is engineered with an inactivating pre- or pro-sequence. For example, the pre- or pro-sequence may obscure an activation site on the modulating agent, e.g., a receptor binding site, or may induce a conformational change in the modulating agent. Thus, upon cleavage of the pre- or pro-sequence, the modulating agent is activated.

Alternatively, the modulating agent may include a pre- or pro-small molecule, e.g., an antibiotic. The modulating agent may be an inactive small molecule described herein that can be activated in a target environment inside the host. For example, the small molecule may be activated upon reaching a certain pH in the host gut.

(c) Linkers

In instances where the modulating agent is connected to an additional moiety, the modulating agent may further include a linker. For example, the linker may be a chemical bond, e.g., one or more covalent bonds or non-covalent bonds. In some instances, the linker may be a peptide linker (e.g., 2, 3, 4, 5, 6, 8, 10, 12, 14, 16, 20, 25, 30, 35, 40, or more amino acids longer). The linker maybe include any flexible, rigid, or cleavable linkers described herein.

A flexible peptide linker may include any of those commonly used in the art, including linkers having sequences having primarily Gly and Ser residues ("GS" linker). Flexible linkers may be useful for joining domains that require a certain degree of movement or interaction and may include small, non-polar (e.g. Gly) or polar (e.g. Ser or Thr) amino acids.

Alternatively, a peptide linker may be a rigid linker. Rigid linkers are useful to keep a fixed distance between moieties and to maintain their independent functions. Rigid linkers may also be useful when a spatial separation of the domains is critical to preserve the stability or bioactivity of one or more components in the fusion. Rigid linkers may, for example, have an alpha helix-structure or Pro-rich sequence, $(XP)_n$, with X designating any amino acid, preferably Ala, Lys, or Glu.

In yet other instances, a peptide linker may be a cleavable linker. In some instances, linkers may be cleaved under specific conditions, such as the presence of reducing reagents or proteases. In vivo cleavable linkers may utilize the reversible nature of a disulfide bond. One example includes a thrombin-sensitive sequence (e.g., PRS) between two Cys residues. In vitro thrombin treatment of CPRSC results in the cleavage of the thrombin-sensitive sequence, while the reversible disulfide linkage remains intact. Such linkers are known and described, e.g., in Chen et al., *Adv. Drug Deliv. Rev.* 65(10):1357-1369, 2013. Cleavage of linkers in fusions may also be carried out by proteases that are expressed in vivo under conditions in specific cells or tissues of the host or microorganisms resident in the host. In some instances, cleavage of the linker may release a free functional, modulating agent upon reaching a target site or cell.

Fusions described herein may alternatively be linked by a linking molecule, including a hydrophobic linker, such as a negatively charged sulfonate group; lipids, such as a poly (—CH2-) hydrocarbon chains, such as polyethylene glycol (PEG) group, unsaturated variants thereof, hydroxylated variants thereof, amidated or otherwise N-containing variants thereof, non-carbon linkers; carbohydrate linkers; phosphodiester linkers, or other molecule capable of covalently linking two or more molecules, e.g., two modulating agents. Non-covalent linkers may be used, such as hydrophobic lipid globules to which the modulating agent is linked, for example, through a hydrophobic region of the modulating agent or a hydrophobic extension of the modulating agent, such as a series of residues rich in leucine, isoleucine, valine, or perhaps also alanine, phenylalanine, or even tyrosine, methionine, glycine or other hydrophobic residue. The modulating agent may be linked using charge-based chemistry, such that a positively charged moiety of the modulating agent is linked to a negative charge of another modulating agent or an additional moiety.

IV. Formulations and Compositions

The compositions described herein may be formulated either in pure form (e.g., the composition contains only the modulating agent) or together with one or more additional agents (such as excipient, delivery vehicle, carrier, diluent, stabilizer, etc.) to facilitate application or delivery of the compositions. Examples of suitable excipients and diluents include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline solution, syrup, methylcellulose, methyl- and propylhydroxybenzoates, talc, magnesium stearate, and mineral oil.

In some instances, the composition includes a delivery vehicle or carrier. In some instances, the delivery vehicle includes an excipient. Exemplary excipients include, but are not limited to, solid or liquid carrier materials, solvents, stabilizers, slow-release excipients, colorings, and surface-active substances (surfactants). In some instances, the delivery vehicle is a stabilizing vehicle. In some instances, the stabilizing vehicle includes a stabilizing excipient. Exemplary stabilizing excipients include, but are not limited to, epoxidized vegetable oils, antifoaming agents, e.g. silicone oil, preservatives, viscosity regulators, binding agents and tackifiers. In some instances, the stabilizing vehicle is a buffer suitable for the modulating agent. In some instances, the composition is microencapsulated in a polymer bead delivery vehicle. In some instances, the stabilizing vehicle protects the modulating agent against UV and/or acidic conditions. In some instances, the delivery vehicle contains a pH buffer. In some instances, the composition is formulated to have a pH in the range of about 4.5 to about 9.0, including for example pH ranges of about any one of 5.0 to about 8.0, about 6.5 to about 7.5, or about 6.5 to about 7.0.

Depending on the intended objectives and prevailing circumstances, the composition may be formulated into emulsifiable concentrates, suspension concentrates, directly sprayable or dilutable solutions, coatable pastes, diluted emulsions, spray powders, soluble powders, dispersible powders, wettable powders, dusts, granules, encapsulations in polymeric substances, microcapsules, foams, aerosols, carbon dioxide gas preparations, tablets, resin preparations, paper preparations, nonwoven fabric preparations, or knitted or woven fabric preparations. In some instances, the composition is a liquid. In some instances, the composition is a solid. In some instances, the composition is an aerosol, such as in a pressurized aerosol can. In some instances, the composition is present in the waste (such as feces) of the pest. In some instances, the composition is present in or on a live pest.

In some instances, the delivery vehicle is the food or water of the host. In other instances, the delivery vehicle is a food source for the host. In some instances, the delivery vehicle is a food bait for the host. In some instances, the composition is a comestible agent consumed by the host. In some instances, the composition is delivered by the host to a second host, and consumed by the second host. In some instances, the composition is consumed by the host or a second host, and the composition is released to the surrounding of the host or the second host via the waste (such as feces) of the host or the second host. In some instances, the modulating agent is included in food bait intended to be consumed by a host or carried back to its colony.

In some instances, the modulating agent may make up about 0.1% to about 100% of the composition, such as any one of about 0.01% to about 100%, about 1% to about 99.9%, about 0.1% to about 10%, about 1% to about 25%, about 10% to about 50%, about 50% to about 99%, or about 0.1% to about 90% of active ingredients (such as phage, lysin or bacteriocin). In some instances, the composition includes at least any of 0.1%, 0.5%, 1%, 5%, 10%, 20%, 30%, 40%, 50%, 60%, 70%, 80%, 90%, 95%, or more active ingredients (such as phage, lysin or bacteriocin). In some instances, the concentrated agents are preferred as commercial products, the final user normally uses diluted agents, which have a substantially lower concentration of active ingredient.

Any of the formulations described herein may be used in the form of a bait, a coil, an electric mat, a smoking preparation, a fumigant, or a sheet.

i. Liquid Formulations

The compositions provided herein may be in a liquid formulation. Liquid formulations are generally mixed with water, but in some instances may be used with crop oil, diesel fuel, kerosene or other light oil as a carrier. The amount of active ingredient often ranges from about 0.5 to about 80 percent by weight.

An emulsifiable concentrate formulation may contain a liquid active ingredient, one or more petroleum-based solvents, and an agent that allows the formulation to be mixed with water to form an emulsion. Such concentrates may be used in agricultural, ornamental and turf, forestry, structural, food processing, livestock, and public health pest formulations. These may be adaptable to application equipment from small portable sprayers to hydraulic sprayers, low-volume ground sprayers, mist blowers, and low-volume aircraft sprayers. Some active ingredients are readily dissolve in a liquid carrier. When mixed with a carrier, they form a solution that does not settle out or separate, e.g., a homogenous solution. Formulations of these types may include an active ingredient, a carrier, and one or more other ingredients. Solutions may be used in any type of sprayer, indoors and outdoors.

In some instances, the composition may be formulated as an invert emulsion. An invert emulsion is a water-soluble active ingredient dispersed in an oil carrier. Invert emulsions require an emulsifier that allows the active ingredient to be mixed with a large volume of petroleum-based carrier, usually fuel oil. Invert emulsions aid in reducing drift. With other formulations, some spray drift results when water droplets begin to evaporate before reaching target surfaces; as a result the droplets become very small and lightweight. Because oil evaporates more slowly than water, invert emulsion droplets shrink less and more active ingredient reaches the target. Oil further helps to reduce runoff and improve rain resistance. It further serves as a sticker-spreader by improving surface coverage and absorption. Because droplets are relatively large and heavy, it is difficult to get thorough coverage on the undersides of foliage. Invert emulsions are most commonly used along rights-of-way where drift to susceptible non-target areas can be a problem.

A flowable or liquid formulation combines many of the characteristics of emulsifiable concentrates and wettable powders. Manufacturers use these formulations when the active ingredient is a solid that does not dissolve in either water or oil. The active ingredient, impregnated on a substance such as clay, is ground to a very fine powder. The powder is then suspended in a small amount of liquid. The resulting liquid product is quite thick. Flowables and liquids share many of the features of emulsifiable concentrates, and they have similar disadvantages. They require moderate agitation to keep them in suspension and leave visible residues, similar to those of wettable powders.

Flowables/liquids are easy to handle and apply. Because they are liquids, they are subject to spilling and splashing. They contain solid particles, so they contribute to abrasive wear of nozzles and pumps. Flowable and liquid suspensions settle out in their containers. Because flowable and liquid formulations tend to settle, packaging in containers of five gallons or less makes remixing easier.

Aerosol formulations contain one or more active ingredients and a solvent. Most aerosols contain a low percentage of active ingredients. There are two types of aerosol formulations—the ready-to-use type commonly available in pressurized sealed containers and those products used in electrical or gasoline-powered aerosol generators that release the formulation as a smoke or fog.

Ready to use aerosol formulations are usually small, self-contained units that release the formulation when the nozzle valve is triggered. The formulation is driven through a fine opening by an inert gas under pressure, creating fine droplets. These products are used in greenhouses, in small areas inside buildings, or in localized outdoor areas. Commercial models, which hold five to 5 pounds of active ingredient, are usually refillable.

Smoke or fog aerosol formulations are not under pressure. They are used in machines that break the liquid formulation into a fine mist or fog (aerosol) using a rapidly whirling disk or heated surface.

ii. Dry or Solid Formulations

Dry formulations can be divided into two types: ready-to-use and concentrates that must be mixed with water to be applied as a spray. Most dust formulations are ready to use and contain a low percentage of active ingredients (less than about 10 percent by weight), plus a very fine, dry inert carrier made from talc, chalk, clay, nut hulls, or volcanic ash. The size of individual dust particles varies. A few dust formulations are concentrates and contain a high percentage of active ingredients. Mix these with dry inert carriers before applying. Dusts are always used dry and can easily drift to non-target sites.

iii. Granule or Pellet Formulations

In some instances, the composition is formulated as granules. Granular formulations are similar to dust formulations, except granular particles are larger and heavier. The coarse particles may be made from materials such as clay, corncobs, or walnut shells. The active ingredient either coats the outside of the granules or is absorbed into them. The amount of active ingredient may be relatively low, usually ranging from about 0.5 to about 15 percent by weight. Granular formulations are most often used to apply to the soil, insects or nematodes living in the soil, or absorption into plants through the roots. Granular formulations are sometimes applied by airplane or helicopter to minimize drift or to penetrate dense vegetation. Once applied, granules may release the active ingredient slowly. Some granules require soil moisture to release the active ingredient. Granular formulations also are used to control larval mosquitoes and other aquatic pests. Granules are used in agricultural, structural, ornamental, turf, aquatic, right-of-way, and public health (biting insect) pest-control operations.

In some instances, the composition is formulated as pellets. Most pellet formulations are very similar to granular formulations; the terms are used interchangeably. In a pellet formulation, however, all the particles are the same weight and shape. The uniformity of the particles allows use with precision application equipment.

iv. Powders

In some instances, the composition is formulated as a powder. In some instances, the composition is formulated as a wettable powder. Wettable powders are dry, finely ground formulations that look like dusts. They usually must be mixed with water for application as a spray. A few products, however, may be applied either as a dust or as a wettable powder—the choice is left to the applicator. Wettable powders have about 1 to about 95 percent active ingredient by weight; in some cases more than about 50 percent. The particles do not dissolve in water. They settle out quickly unless constantly agitated to keep them suspended. They can be used for most pest problems and in most types of spray equipment where agitation is possible. Wettable powders have excellent residual activity. Because of their physical properties, most of the formulation remains on the surface of treated porous materials such as concrete, plaster, and untreated wood. In such cases, only the water penetrates the material.

In some instances, the composition is formulated as a soluble powder. Soluble powder formulations look like wettable powders. However, when mixed with water, soluble powders dissolve readily and form a true solution. After they are mixed thoroughly, no additional agitation is necessary. The amount of active ingredient in soluble powders ranges from about 15 to about 95 percent by weight; in some cases more than about 50 percent. Soluble powders have all the advantages of wettable powders and none of the disadvantages, except the inhalation hazard during mixing.

In some instances, the composition is formulated as a water-dispersible granule. Water-dispersible granules, also known as dry flowables, are like wettable powders, except instead of being dust-like, they are formulated as small, easily measured granules. Water-dispersible granules must be mixed with water to be applied. Once in water, the granules break apart into fine particles similar to wettable powders. The formulation requires constant agitation to keep it suspended in water. The percentage of active ingredient is high, often as much as 90 percent by weight. Water-dispersible granules share many of the same advantages and disadvantages of wettable powders, except they are more easily measured and mixed. Because of low dust, they cause less inhalation hazard to the applicator during handling v. Bait In some instances, the composition includes a bait. The bait can be in any suitable form, such as a solid, paste, pellet or powdered form. The bait can also be carried away by the host back to a population of said host (e.g., a colony or hive). The bait can then act as a food source for other members of the colony, thus providing an effective modulating agent for a large number of hosts and potentially an entire host colony.

The baits can be provided in a suitable "housing" or "trap." Such housings and traps are commercially available and existing traps can be adapted to include the compositions described herein. The housing or trap can be box-shaped for example, and can be provided in pre-formed condition or can be formed of foldable cardboard for example. Suitable materials for a housing or trap include plastics and cardboard, particularly corrugated cardboard. The inside surfaces of the traps can be lined with a sticky substance in order to restrict movement of the host once inside the trap. The housing or trap can contain a suitable trough inside which can hold the bait in place. A trap is distinguished from a housing because the host cannot readily leave a trap following entry, whereas a housing acts as a "feeding station" which provides the host with a preferred environment in which they can feed and feel safe from predators.

vi. Attractants

In some instances, the composition includes an attractant (e.g., a chemoattractant). The attractant may attract an adult host or immature host (e.g., larva) to the vicinity of the composition. Attractants include pheromones, a chemical that is secreted by an animal, especially an insect, which influences the behavior or development of others of the same species. Other attractants include sugar and protein hydrolysate syrups, yeasts, and rotting meat. Attractants also can be combined with an active ingredient and sprayed onto foliage or other items in the treatment area.

Various attractants are known which influence host behavior as a host's search for food, oviposition or mating sites, or mates. Attractants useful in the methods and compositions described herein include, for example, eugenol, phenethyl propionate, ethyl dimethylisobutyl-cyclopropane carboxylate, propyl benszodioxancarboxylate, cis-7,8-epoxy-2-methyloctadecane, trans-8,trans-0-dodecadienol, cis-9-tetradecenal (with cis-11-hexadecenal), trans-11-tetradecenal, cis-11-hexadecenal, (Z)-11,12-hexadecadienal, cis-7-dodecenyl acetate, cis-8-dodecenyul acetate, cis-9-dodecenyl acetate, cis-9-tetradecenyl acetate, cis-11-tetradecenyl acetate, trans-11-tetradecenyl acetate (with cis-11), cis-9,trans-11-tetradecadienyl acetate (with cis-9,trans-12), cis-9,trans-1 2-tetradecadienyl acetate, cis-7,cis-11-hexadecadienyl acetate (with cis-7,trans-11), cis-3,cis-13-octadecadienyl acetate, trans-3,cis-13-octadecadienyl acetate, anethole and isoamyl salicylate.

Means other than chemoattractants may also be used to attract insects, including lights in various wavelengths or colors.

vii. Nanocapsules/Microencapsulation/Liposomes

In some instances, the composition is provided in a microencapsulated formulation. Microencapsulated formulations are mixed with water and sprayed in the same manner as other sprayable formulations. After spraying, the plastic coating breaks down and slowly releases the active ingredient.

viii. Carriers

Any of the compositions described herein may be formulated to include the modulating agent described herein and an inert carrier. Such carrier can be a solid carrier, a liquid carrier, a gel carrier, and/or a gaseous carrier. In certain instances, the carrier can be a seed coating. The seed coating is any non-naturally occurring formulation that adheres, in whole or part, to the surface of the seed. The formulation may further include an adjuvant or surfactant. The formulation can also include one or more modulating agents to enlarge the action spectrum.

A solid carrier used for formulation includes finely-divided powder or granules of clay (e.g. kaolin clay, diatomaceous earth, bentonite, Fubasami clay, acid clay, etc.), synthetic hydrated silicon oxide, talc, ceramics, other inorganic minerals (e.g., sericite, quartz, sulfur, activated carbon, calcium carbonate, hydrated silica, etc.), a substance which can be sublimated and is in the solid form at room temperature (e.g., 2,4,6-triisopropyl-1,3,5-trioxane, naphthalene, p-dichlorobenzene, camphor, adamantan, etc.); wool; silk; cotton; hemp; pulp; synthetic resins (e.g., polyethylene resins such as low-density polyethylene, straight low-density polyethylene and high-density polyethylene; ethylene-vinyl ester copolymers such as ethylene-vinyl acetate copolymers; ethylene-methacrylic acid ester copolymers such as ethylene-methyl methacrylate copolymers and ethylene-ethyl methacrylate copolymers; ethylene-acrylic acid ester copolymers such as ethylene-methyl acrylate copolymers and ethylene-ethyl acrylate copolymers; ethylene-vinylcarboxylic acid copolymers such as ethylene-acrylic acid copolymers; ethylene-tetracyclododecene copolymers; polypropylene resins such as propylene homopolymers and propylene-ethylene copolymers; poly-4-methylpentene-1, polybutene-1, polybutadiene, polystyrene; acrylonitrile-styrene resins; styrene elastomers such as acrylonitrile-butadiene-styrene resins, styrene-conjugated diene block copolymers, and styrene-conjugated diene block copolymer hydrides; fluororesins; acrylic resins such as poly(methyl methacrylate); polyamide resins such as nylon 6 and nylon 66; polyester resins such as polyethylene terephthalate, polyethylene naphthalate, polybutylene terephthalate, and polycyclohexylenedimethylene terephthalate; polycarbonates, polyacetals, polyacrylsulfones, polyarylates, hydroxybenzoic acid polyesters, polyetherimides, polyester carbonates, polyphenylene ether resins, polyvinyl chloride, polyvinylidene chloride, polyurethane, and porous resins such as foamed polyurethane, foamed polypropylene, or foamed ethylene, etc.), glasses, metals, ceramics, fibers, cloths, knitted fabrics, sheets, papers, yarn, foam, porous substances, and multifilaments.

A liquid carrier may include, for example, aromatic or aliphatic hydrocarbons (e.g., xylene, toluene, alkylnaphthalene, phenylxylylethane, kerosine, gas oil, hexane, cyclohexane, etc.), halogenated hydrocarbons (e.g., chlorobenzene, dichloromethane, dichloroethane, trichloroethane, etc.), alcohols (e.g., methanol, ethanol, isopropyl alcohol, butanol, hexanol, benzyl alcohol, ethylene glycol, etc.), ethers (e.g., diethyl ether, ethylene glycol dimethyl ether, diethylene glycol monomethyl ether, diethylene glycol monoethyl ether, propylene glycol monomethyl ether, tetrahydrofuran, dioxane, etc.), esters (e.g., ethyl acetate, butyl acetate, etc.), ketones (e.g., acetone, methyl ethyl ketone, methyl isobutyl ketone, cyclohexanone, etc.), nitriles (e.g., acetonitrile, isobutyronitrile, etc.), sulfoxides (e.g., dimethyl sulfoxide, etc.), amides (e.g., N,N-dimethylformamide, N,N-dimethylacetamide, cyclic imides (e.g. N-methylpyrrolidone) alkylidene carbonates (e.g., propylene carbonate, etc.), vegetable oil (e.g., soybean oil, cottonseed oil, etc.), vegetable essential oils (e.g., orange oil, hyssop oil, lemon oil, etc.), or water.

A gaseous carrier may include, for example, butane gas, flon gas, liquefied petroleum gas (LPG), dimethyl ether, and carbon dioxide gas.

ix. Adjuvants

In some instances, the composition provided herein may include an adjuvant. Adjuvants are chemicals that do not possess activity. Adjuvants are either pre-mixed in the formulation or added to the spray tank to improve mixing or application or to enhance performance. They are used extensively in products designed for foliar applications. Adjuvants can be used to customize the formulation to specific needs and compensate for local conditions. Adjuvants may be designed to perform specific functions, including wetting, spreading, sticking, reducing evaporation, reducing volatilization, buffering, emulsifying, dispersing, reducing spray drift, and reducing foaming. No single adjuvant can perform all these functions, but compatible adjuvants often can be combined to perform multiple functions simultaneously.

Among nonlimiting examples of adjuvants included in the formulation are binders, dispersants and stabilizers, specifically, for example, casein, gelatin, polysaccharides (e.g., starch, gum arabic, cellulose derivatives, alginic acid, etc.), lignin derivatives, bentonite, sugars, synthetic water-soluble polymers (e.g., polyvinyl alcohol, polyvinylpyrrolidone, polyacrylic acid, etc.), PAP (acidic isopropyl phosphate), BHT (2,6-di-t-butyl-4-methylphenol), BHA (a mixture of 2-t-butyl-4-methoxyphenol and 3-t-butyl-4-methoxyphenol), vegetable oils, mineral oils, fatty acids and fatty acid esters.

x. Surfactants

In some instances, the composition provided herein includes a surfactant. Surfactants, also called wetting agents and spreaders, physically alter the surface tension of a spray droplet. For a formulation to perform its function properly, a spray droplet must be able to wet the foliage and spread out evenly over a leaf. Surfactants enlarge the area of formulation coverage, thereby increasing the pest's exposure to the chemical. Surfactants are particularly important when applying a formulation to waxy or hairy leaves. Without proper wetting and spreading, spray droplets often run off or fail to cover leaf surfaces adequately. Too much surfactant, however, can cause excessive runoff and reduce efficacy.

Surfactants are classified by the way they ionize or split apart into electrically charged atoms or molecules called ions. A surfactant with a negative charge is anionic. One with a positive charge is cationic, and one with no electrical charge is nonionic. Formulation activity in the presence of a nonionic surfactant can be quite different from activity in the presence of a cationic or anionic surfactant. Selecting the wrong surfactant can reduce the efficacy of a pesticide product and injure the target plant. Anionic surfactants are most effective when used with contact pesticides (pesticides that control the pest by direct contact rather than being absorbed systemically). Cationic surfactants should never be used as stand-alone surfactants because they usually are phytotoxic.

Nonionic surfactants, often used with systemic pesticides, help pesticide sprays penetrate plant cuticles. Nonionic surfactants are compatible with most pesticides, and most EPA-registered pesticides that require a surfactant recommend a nonionic type. Adjuvants include, but are not limited to, stickers, extenders, plant penetrants, compatibility agents, buffers or pH modifiers, drift control additives, defoaming agents, and thickeners.

Among nonlimiting examples of surfactants included in the compositions described herein are alkyl sulfate ester salts, alkyl sulfonates, alkyl aryl sulfonates, alkyl aryl ethers and polyoxyethylenated products thereof, polyethylene glycol ethers, polyvalent alcohol esters and sugar alcohol derivatives.

xi. Combinations

In formulations and in the use forms prepared from these formulations, the modulating agent may be in a mixture with other active compounds, such as pesticidal agents (e.g., insecticides, sterilants, acaricides, nematicides, molluscicides, or fungicides; see, e.g., pesticides listed in Table 12), attractants, growth-regulating substances, or herbicides. As used herein, the term "pesticidal agent" refers to any substance or mixture of substances intended for preventing, destroying, repelling, or mitigating any pest. A pesticide can be a chemical substance or biological agent used against pests including insects, mollusks, pathogens, weeds, nematodes, and microbes that compete with humans for food, destroy property, spread disease, or are a nuisance. The term "pesticidal agent" may further encompass other bioactive molecules such as antibiotics, antivirals pesticides, antifungals, antihelminthics, nutrients, pollen, sucrose, and/or agents that stun or slow insect movement.

In instances where the modulating agent is applied to plants, a mixture with other known compounds, such as herbicides, fertilizers, growth regulators, safeners, semiochemicals, or else with agents for improving plant properties is also possible.

V. Delivery

A host described herein can be exposed to any of the compositions described herein in any suitable manner that permits delivering or administering the composition to the insect. The modulating agent may be delivered either alone or in combination with other active or inactive substances and may be applied by, for example, spraying, microinjection, through plants, pouring, dipping, in the form of concentrated liquids, gels, solutions, suspensions, sprays, powders, pellets, briquettes, bricks and the like, formulated to deliver an effective concentration of the modulating agent.

Amounts and locations for application of the compositions described herein are generally determined by the habits of the host, the lifecycle stage at which the microorganisms of the host can be targeted by the modulating agent, the site where the application is to be made, and the physical and functional characteristics of the modulating agent. The modulating agents described herein may be administered to the insect by oral ingestion, but may also be administered by means which permit penetration through the cuticle or penetration of the insect respiratory system.

In some instances, the insect can be simply "soaked" or "sprayed" with a solution including the modulating agent. Alternatively, the modulating agent can be linked to a food component (e.g., comestible) of the insect for ease of delivery and/or in order to increase uptake of the modulating agent by the insect. Methods for oral introduction include, for example, directly mixing a modulating agent with the insects food, spraying the modulating agent in the insect's habitat or field, as well as engineered approaches in which a species that is used as food is engineered to express a modulating agent, then fed to the insect to be affected. In some instances, for example, the modulating agent composition can be incorporated into, or overlaid on the top of, the insect's diet. For example, the modulating agent composition can be sprayed onto a field of crops which an insect inhabits.

In some instances, the composition is sprayed directly onto a plant e.g., crops, by e.g., backpack spraying, aerial spraying, crop spraying/dusting etc. In instances where the modulating agent is delivered to a plant, the plant receiving the modulating agent may be at any stage of plant growth. For example, formulated modulating agents can be applied as a seed-coating or root treatment in early stages of plant growth or as a total plant treatment at later stages of the crop cycle. In some instances, the modulating agent may be applied as a topical agent to a plant, such that the host insect ingests or otherwise comes in contact with the plant upon interacting with the plant.

Further, the modulating agent may be applied (e.g., in the soil in which a plant grows, or in the water that is used to water the plant) as a systemic agent that is absorbed and distributed through the tissues (e.g., stems or leafs) of a plant or animal host, such that an insect feeding thereon will obtain an effective dose of the modulating agent. In some instances, plants or food organisms may be genetically transformed to express the modulating agent such that a host feeding upon the plant or food organism will ingest the modulating agent.

Delayed or continuous release can also be accomplished by coating the modulating agent or a composition with the modulating agent(s) with a dissolvable or bioerodable coating layer, such as gelatin, which coating dissolves or erodes in the environment of use, to then make the modulating agent available, or by dispersing the agent in a dissolvable or erodable matrix. Such continuous release and/or dispensing means devices may be advantageously employed to consistently maintain an effective concentration of one or more of the modulating agents described herein in a specific host habitat.

The modulating agent can also be incorporated into the medium in which the insect grows, lives, reproduces, feeds, or infests. For example, a modulating agent can be incorporated into a food container, feeding station, protective wrapping, or a hive. For some applications the modulating agent may be bound to a solid support for application in powder form or in a "trap" or "feeding station." As an example, for applications where the composition is to be used in a trap or as bait for a particular host insect, the compositions may also be bound to a solid support or encapsulated in a time-release material. For example, in instances where the host is a honeybee, the compositions described herein can be administered by delivering the composition to a honeybee hive or at least one habitat where a honeybee grows, lives, reproduces, or feeds.

VI. Screening

Included herein are screening assays for identifying a modulating agent, wherein the modulating agent is effective to alter the microbiota of a host and thereby increase host fitness (e.g., insect or nematode fitness). For example, the screening assay may be used to identify one or more modulating agents that target specific microorganisms and/or specific hosts. Further, the screening assays may be used to identify one or more microorganisms with enhanced functionalities. For example, the screening assay may be effective to isolate one or more microorganisms with an enhanced ability to metabolize (e.g., degrade) a pesticide (e.g., a pesticide listed in Table 12 or an insecticide known in the art, e.g., a neonicotinoid (e.g., imidacloprid) or an organophosphorus insecticide (e.g., a phosphorothioate, e.g., fenitrothion)) or plant allelochemical (e.g., caffeine, soyacystatin N, monoterpenes, diterpene acids, or phenolic compounds). Delivery and colonization of an isolated microorganism in the host may increase the host's resistance to the pesticide (e.g., a pesticide listed in Table 12) or plant allelochemical, thereby increasing host fitness. The methods may also be useful for the isolation of microorganisms with an enhanced ability to colonize any of the hosts described herein.

For example, to screen for microorganisms that increase a host's resistance to a pesticide (e.g., a pesticide listed in Table 12), a starting culture may be used that includes microorganisms (e.g., bacteria) and high concentrations of a pesticide (e.g., a pesticide listed in Table 12 or an insecticide known in the art, e.g., a neonicotinoid (e.g., imidacloprid) or an organophosphorus insecticide (e.g., a phosphorothioate, e.g., fenitrothion)). In some instances, the pesticide may be provided in the form of an environmental sample enriched with the pesticide (e.g., a soil sample). Alternatively, the pesticide (e.g., a pesticide listed in Table 12) may be provided in pure form or in combination with other carriers. Further, the one or more microorganism isolates may be inoculated directly into the media (e.g., from a laboratory strain) or may be an environmental sample including one or more microorganism species. The growth media may be either liquid or solid. In some instances, the pesticide of interest is the sole carbon or nitrogen source for the microorganisms in the media. The culture may be sub-cultured (e.g., inoculated into fresh media with high levels of the pesticide) any number of times to enrich for and/or isolate microbial strains (e.g., bacterial strains) capable of metabolizing the pesticide. The original culture or the subcultures may be assessed using any methods known in the art to test for alterations (e.g., decrease) in the levels of the pesticide in the sample (e.g., using HPLC). Isolates that reduce the concentration of the pesticide (e.g., a pesticide listed in Table 12 or a pesticide known in the art, e.g., a neonicotinoid (e.g., imidacloprid) or an organophosphorus insecticide (e.g., a phosphorothioate, e.g., fenitrothion)) may be isolated for use as a modulating agent in any of the methods or compositions described herein.

The methods may be used to further select for microorganisms described herein, including those isolated from a screening assay, with an enhanced ability to colonize and survive in a host (e.g., insect, e.g., bee). For example, a host may be inoculated with a bacterial isolate (e.g., one with the ability to degrade a pesticide). The host may then be tested at regular intervals for the presence of the bacterial isolate (e.g., via culturing or 16s RNA from guts isolated from the host (e.g., honeybee)). Bacterial isolates that survive in the host (e.g., the midgut of the honeybee) may be isolated for use as a modulating agent in any of the methods or compositions described herein.

TABLE 12

| Pesticides |
| --- |
| Aclonifen |
| Acetamiprid |
| Alanycarb |
| Amidosulfuron |
| Aminocyclopyrachlor |
| Amisulbrom |
| Anthraquinone |
| Asulam, sodium salt |
| Benfuracarb |
| Bensulide |
| beta-HCH; beta-BCH |
| Bioresmethrin |
| Blasticidin-S |
| Borax; disodium tetraborate |
| Boric acid |
| Bromoxynil heptanoate |
| Bromoxynil octanoate |
| Carbosulfan |
| Chlorantraniliprole |
| Chlordimeform |
| Chlorfluazuron |
| Chlorphropham |
| Climbazole |
| Clopyralid |
| Copper (II) hydroxide |
| Cyflufenamid |
| Cyhalothrin |
| Cyhalothrin, gamma |
| Decahydrate |
| Diafenthiuron |
| Dimefuron |
| Dimoxystrobin |
| Dinotefuran |
| Diquat dichloride |
| Dithianon |
| E-Phosphamidon |
| EPTC |
| Ethaboxam |
| Ethirimol |
| Fenchlorazole-ethyl |
| Fenothiocarb |
| Fenitrothion |
| Fenpropidin |
| Fluazolate |
| Flufenoxuron |
| Flumetralin |
| Fluxapyroxad |
| Fuberidazole |
| Glufosinate-ammonium |
| Glyphosate |
| Group: Borax, borate salts (see |
| Group: Paraffin oils, Mineral |
| Halfenprox |
| Imiprothrin |
| Imidacloprid |
| Ipconazole |
| Isopyrazam |
| Isopyrazam |
| Lenacil |
| Magnesium phosphide |
| Metaflumizone |
| Metazachlor |
| Metazachlor |
| Metobromuron |
| Metoxuron |
| Metsulfuron-methyl |
| Milbemectin |
| Naled |
| Napropamide |
| Nicosulfuron |
| Nitenpyram |

TABLE 12-continued

Pesticides

Nitrobenzene
o-phenylphenol
Oils
Oxadiargyl
Oxycarboxin
Paraffin oil
Penconazole
Pendimethalin
Penflufen
Penflufen
Pentachlorbenzene
Penthiopyrad
Penthiopyrad
Pirimiphos-methyl
Prallethrin
Profenofos
Proquinazid
Prothiofos
Pyraclofos
Pyrazachlor
Pyrazophos
Pyridaben
Pyridalyl
Pyridiphenthion
Pyrifenox
Quinmerac
Rotenone
Sedaxane
Sedaxane
Silafluofen
Sintofen
Spinetoram
Sulfoxaflor
Temephos
Thiocloprid
Thiamethoxam
Tolfenpyrad
Tralomethrin
Tributyltin compounds
Tridiphane
Triflumizole
Validamycin
Zinc phosphide

EXAMPLES

The following is an example of the methods of the invention. It is understood that various other embodiments may be practiced, given the general description provided above.

Example 1

Isolation of Microorganisms that Degrade Imidacloprid, a Nicotinoid

This example demonstrates the acquisition of a library of microorganisms able to degrade imidacloprid, a neonicotinoid.

Experimental Design:

Four soil samples with elevated concentrations of imidacloprid are collected as described in Bonmatin et al. (*Environ. Sci. Pollut. Res. Int.* 22:35-67, 2015) and diluted in Kaufman and Kearney's minimal salts media (MSM) to enrich for imidacloprid-degrading microorganisms. Three variations of cultures for each soil sample include: 50 mL carbon-limited MSM with 83 mg/L imidacloprid as the sole carbon source; 50 mL nitrogen-limited MSM with imidacloprid as the sole nitrogen source and sodium citrate and sucrose added as supplemental carbon sources; and 50 mL MSM broth, with all components plus sodium citrate, sucrose, and imidacloprid. Each culture is inoculated with 2 g of the collected soil.

Cultures are maintained on a shaker at 100 rpm and 27° C. Subcultures (1 mL of the cultured solution diluted in 25 mL of new medium) are made monthly in order to obtain soil-free enrichments. Aliquots of the cultures are periodically removed from the shaker flasks for HPLC analysis as described in Tago et al. (*Microbes Environ.* 21:58-64, 2006). For the HPLC assay, $\approx 7.0 \times 10^7$ microorganisms are incubated in 1.0 mL of 20 mM sodium-potassium phosphate buffer (pH 7.0) with 1.0 mM imidacloprid. After 20 min of incubation at 30° C., 1.0 mL of methanol is added. Imidacloprid and products of its partial degradation are quantitatively analyzed on a HPLC system (a 600E pump and 2487 dual absorbance detector; Waters). Retention times and peak areas of the HPLC profiles are compared with those of known standards Bonmatin et al. (*Environ. Sci. Pollut. Res. Int.* 22:35-67, 2015).

Mixed enrichment cultures from the soil that show a decrease of imidacloprid via HPLC analysis during incubation are spread-plated using dilutions of $10^{-1}$ to $10^{-6}$ on nitrogen-limited agar plates with 36 mg/kg imidacloprid and streptomycin.

After a one-week incubation at 27° C., the plates are screened for colonies that morphologically appear different from one another (size differences). Individual colonies are grown into new agar plates with imidacloprid as the sole nitrogen source. After three weeks, single colonies are put into 25 mL of tryptic soy broth (TSB) with 25 mg/L imidacloprid.

After three days' growth, each of the isolates is centrifuged in conical Falcon tubes for 10 min at 6700×g. The supernatant is removed, and the isolates are re-suspended in sterile phosphate buffer for a total volume of 10 mL. A 2-mL sample of each isolate is inoculated into a nitrogen-limited MSM and a carbon-limited MSM cultures; both cultures with 30 mg/L of imidacloprid in 25 mL total. Non-inoculated controls are also made by inoculating 2 mL of phosphate buffer into each of the media types. All samples are wrapped in aluminum foil and placed on a shaker operated at 27° C. and 100 rpm. The samples are then analyzed for imidacloprid concentration by HPLC.

After seven days of incubation, 25 mL of methanol is added to the flasks. The samples are then sonicated for six minutes each at 50% duty cycle and centrifuged at 6700×g. The supernatant is then analyzed and the imidacloprid is quantitatively measured by HPLC as described herein.

Isolates that reduce the concentration of imidacloprid are stored at −80 C in a solution of 50% glycerol.

Example 2

Selection of Imidacloprid Degrading Isolates that Survive in Bees' Midgut

This example demonstrates the ability to select for an imidacloprid-degrading microorganism from isolates described in Example 1 that are able to survive in the bee midgut.

Therapeutic design: Ten isolates described in Example 1 are formulated with 0 (negative control), $10^2$, $10^5$, or $10^8$ cfu/ml in 10 mL of 50% sucrose syrup.

Experimental Design:

About fifty bees per bacterial isolate are collected and kept in a wooden cage. Bacterial strains isolated in the previous example are cultivated and prepared for feeding as followed. Cell from each isolate are washed and diluted to an OD600 at 0.1 in MSM supplemented with 50% (w/v) sucrose syrup and incubated at 30° C. for cell growth. The four concentrations of fresh bacterial cultures are administered to bees as feed (between $0$-$10^8$ cfu/ml) as follows. The different concentrations of isolates are placed in a 15 ml tube with six small pinched holes in which the bees project their proboscis and consume the isolate-containing solutions. Fresh isolate-containing cultures are prepared daily for use as feed and mortality of bees is scored every day during the entire course (7 days) of the experiment by counting and removing dead bees. After 7 days, the isolate-containing solution is replaced with 15% (w/v) sucrose for 48 h.

Ten bees are removed from each replicate every 24 hours for bacterial analysis; the first sample is removed before experiment onset, followed by seven additional sampling points. After each sampling, the bees are anaesthetized on ice and the midgut is removed. Replicates for each time point are pooled and homogenized in 150 µl 1×PBS, then serially diluted and plated on nitrogen-limited agar plates with 36 mg/kg imidacloprid to grow out bacteria under selective growth conditions at 30° C. for 2 days.

The bacterial isolates that survive in the bee midgut are selected for administration to increase bees' resistance to neonicotinoids.

Example 3

Increase Bees' Resistance to Neonicotinoids Through the Administration of Imidacloprid-Degrading Bacteria This example demonstrates the ability to increase the resistance of bees to insecticides, and more specifically to neonicotinoids. Bees play an important role in pollinating flowering plants, and are the major type of pollinator in many ecosystems that contain flowering plants. It is estimated that one third of the human food supply depends on pollination by insects, birds and bats, most of which is accomplished by bees, especially the domesticated European honey bee. The number of colonies kept by beekeepers has declined, through urbanization, systematic pesticide use, and tracheal and Varroa mites. Through direct consumption of contaminated nectar and pollen from insecticide treated plants, neonicotinoids in the insecticides affect foraging, learning, and memory in worker bees. By introducing imidacloprid degrading bacteria into their microbiome, bees are expected to increase their resistance to neonicotinoids through improved behavior, such as increased foraging, hygienic behavior, and survival.

Therapeutic design: The bacterial isolate selected in Example 2 and identified as surviving in bees' midgut is formulated at $10^8$ organisms in 10 mL of 50% sucrose syrup.

Experimental Design:

The isolate selected in Example 2 is prepared at a concentration of $10^8$ cells/mL (see Example 2) and placed in a 15 ml tube with six small pinched holes in which the bees project their proboscis and consume the isolate-containing solution. Fresh isolate-containing cultures are prepared daily for use as feed. The pretreatment lasts for seven days in total.

Approximately 1500, 3000, or 7000 worker hives estimated by weight of worker bees, *Apis mellifera*, (0.5, 1, and 2 lbs., respectively, or 0.23, 0.45, and 0.1 kg) are pretreated with the isolate selected in Example 2 prepared at a concentration of $10^8$ cells/mL and placed in a 15 ml tube with six small pinched holes in which the bees project their proboscis and consume the isolate-containing solution. Fresh isolate-containing cultures are prepared daily for use as feed. The pretreatment lasts for seven days in total.

After the 7 day pretreatment, each worker hive is fed 2 to 4 grams of pollen supplement and sugar syrup (1:1) for 1-2 days before imidacloprid treatment. Smaller colonies (1500- and 3000-bees) are placed in glass-walled observation hives. The larger colonies (7000-bees) are placed in Ulster observation hives (Brushy Mountain Bee Supply, N.C.) containing a bottom box holding 4 standard frames and a division board feeder where treatment syrup is provided. All observation hives are housed in sheds maintained at constant temperature and relative humidity (23-25° C. and 70%). Additionally, all hives contain an entrance leading to the outside allowing bees to freely forage in surrounding agricultural fields and urban residential neighborhoods.

When egg laying is visually confirmed, each colony is randomly assigned an imidacloprid treatment (0, 10, 20, 50, and 100 ppm) provided in 50% sucrose syrup. Colonies are given through a dispenser system similar to the one described in Example 2 with proportional amounts of sucrose solution with imidacloprid: 80, 160 and 320 mL for 1500-, 3000-, and 7000-bee colonies, respectively. Syrup is replenished every other day for 3 weeks. Syrup quantities are designed to supplement, but not sustain, the colonies, so bees are required to freely forage on other resources. Stock solutions of imidacloprid (100 ppm) are prepared using 99.5±0.5% technical grade imidacloprid purchased from Chem Service, Inc (PS-2086) dissolved with agitation in 50% sucrose overnight. Stock solutions are prepared every two weeks and treatment solutions are prepared every week. Samples of treatment solutions (3-6 per dose) are randomly selected and tested for residue concentrations to confirm accuracy of dosage.

Measurements of Behavioral Phenotypes:

Foraging activity is measured by recording the number of workers entering and exiting the entrance of the bee colony during one-minute observations twice a day. Hygienic behavior is used as a measure to assess worker activity inside the hive, and is defined as the ability of worker bees to detect and remove diseased and mite-infested brood thereby limiting within-colony transmission of pathogens and parasites. Hygienic behavior is measured using a freeze-killed brood assay, in which a 3-inch (7.6 cm) polyvinyl chloride tube is gently pushed into a section of comb containing a large area of sealed pupal cells (taken from non-experimental field colonies). The number of empty cells is counted and recorded before pouring 400 ml of liquid nitrogen to freeze-kill roughly 160 pupae. The frame is then temporarily put into the bee colony and the proportion of pupae completely or partially removed from the cells is quantified after 24 hours to assess hygienic behavior. The removal of freeze-killed brood is correlated with the removal of diseased and parasitized brood.

Bees pretreated with the bacterial isolate selected in Example 2 demonstrate higher activity than bees treated with the control.

Example 4

Treatment of Varroa Mites that Infect Bees with Oxytetracycline Solutions

This example demonstrates the ability to kill, decrease the fitness of Varroa mites by treating them with an antibiotic solution. This example demonstrates that the effect of oxytetracycline on Varroa mites is mediated through the alteration of bacterial populations endogenous, such as *Bacillus*, to the Varroa mites that are sensitive to oxytetracycline.

Varroa mites are thought to be a leading cause for the wide spread Colony Collapse Disorder (CCD) that decimates domesticated honey bee colonies of *Apis mellifera*, around the world. They attach to the bees' abdomen and suck on their blood, depriving them of nutrients, and eventually killing them. While Varroa mites can be killed with chemically synthesized miticides, these types of chemicals must be kept away from comestible honey.

Therapeutic design: Oxytetracycline solution is formulated with 0 (negative control), 1, 10, or 50 μg/ml in 10 mL of sterile water with 0.5% sucrose and essential amino acids.

Experimental Design:

To determine whether adult Varroa mites at the reproductive stage have different susceptibility compared to phoretic mites or their offspring because their cuticle is not hardened, Varroa mites living on adult bees, *Apis mellifera*, and mites associated with larvae and pupae are collected. This assay tests antibiotic solutions on different types of mites and determines how their fitness is altered by targeting endogenous microbes, such as *Bacillus*.

The brood mites are collected from combs (or pieces of combs) of Varroa mite-infested bee colonies. The mites are collected from cells where bee larvae develop.

Varroa mites are grouped per age of their brood host and assayed separately. The age of the brood is determined based on the morphology and pigmentation of the larva or the pupa as follows: Varroa mites collected from spinning larvae that are small enough to move around their cell are grouped into Group 1; Varroa mites collected from stretched larvae, which are too big to lay in the cell and start to stretch upright with their mouth in the direction of the cell opening, are grouped into Group 2; and Varroa mites collected from pupae are grouped into Group 3. Mites are stored on their host larva or pupa in glass Petri dishes until 50 units are collected. This ensures their feeding routine and physiological status remains unchanged. To prevent mites from straying from their host larva or pupa or climbing onto one another, only hosts at the same development stage are kept in the same dish.

The equipment—a stainless steel ring (56 mm inner diameter, 2-3 mm height) and 2 glass circles (62 mm diameter)—is cleaned with acetone and hexane or pentane to form the testing arena. The oxytetracycline solutions and control solution are applied on the equipment by spraying the glass disks and ring of the arena homogeneously. For this, a reservoir is loaded with 1 ml of the solutions; the distance of the sprayed surface from the bottom end of the tube is set at 11 mm and a 0.0275 inch nozzle is used. The pressure is adjusted (usually in the range 350-500 hPa) until the amount of solution deposited is 1±0.05 $mg/cm^2$. The antibiotic solutions are poured in their respective dishes, covering the whole bottom of the dishes, and residual liquid is evaporated under a fume hood. The ring is placed between the glass circles to build a cage. The cages are used within 60 hr of preparation, for not more than three assays, in order to control the exposure of mites to antibiotic solutions. 10 to 15 Varroa mites are introduced in this cage and the equipment pieces are bound together with droplets of melted wax. Mites collected from spinning larvae, stretched larvae, white eyed pupae and dark eyed with white and pale body are used.

After 4 hours, mites are transferred into a clean glass Petri dish (60 mm diameter) with two or three white eye pupae (4-5 days after capping) to feed on. The mites are observed under a dissecting microscope at 4 hr, 24 hr, and 48 hr after being treated with the antibiotic or the control solutions, and classified according to the following categories:

Mobile: they walk around when on their legs, whether after being poked by a needle.

Paralyzed: they move one or more appendages, unstimulated or after stimulation, but they cannot move around.

Dead: immobile and do not react to 3 subsequent stimulations.

A sterile toothpick or needle is used to stimulate the mites by touching their legs. New tooth picks or sterile needles are used for stimulating each group to avoid contamination between mite groups.

The assays are carried out at 32.5° C. and 60-70% relative humidity. If the mortality in the controls exceeds 30%, the replicate is excluded. Each experiment is replicated with four series of cages.

The status of *Bacillus* in Varroa mite groups is assessed by PCR. Total DNA is isolated from control (non-oxytetracycline treated) and oxytetracyline treated individuals (whole body) using a DNA Kit (OMEGA, Bio-tek) according to the manufacturer's protocol. The primers for *Bacillus*, forward primer 5'-GAGGTAGACGAAGCGACCTG-3' (SEQ ID NO: 186) and reverse primer 5'-TTCCCT-CACGGTACTGGTTC-3' (SEQ ID NO: 187), are designed based on 23S-5S rRNA sequences obtained from the *Bacillus* genome (Accession Number: AP007209.1) (Takeno et al., *J. Bacteriol.* 194(17):4767-4768, 2012) using Primer 5.0 software (Primer-E Ltd., Plymouth, UK). The PCR amplification cycles included an initial denaturation step at 95° C. for 5 min, 35 cycles of 95° C. for 1 min, 59° C. for 1 min, and 72° C. for 2 min, and a final extension step of 5 min at 72° C. Amplification products from oxytetracyline treated and control samples are analyzed on 1% agarose gels, stained with SYBR safe, and visualized using an imaging System.

The survival rates of Varroa mites treated with an oxytetracyline solution are compared to the Varroa mites treated with the negative control.

The survival rate and the mobility of Varroa mites treated with oxytetracyline solution are decreased compared to the control.

Example 5

Isolation of Microorganisms that Degrade Fenitrothion, an Organophosphorus Insecticide This Example demonstrates the acquisition of a library of microorganisms able to degrade fenitrothion, an organophosphorus insecticide.

Experimental Design

Soil samples are obtained from various regions where fenitrothion was previously utilized for insect control. Fenitrothion degrading bacteria will be isolated from the soil samples as described in (Microbes Environ. Vol. 21, No. 1, 58-64, 2006). Briefly, 1 g of the soil sample is mixed thoroughly with 9 ml of sterile distilled water. The soil particles are then centrifuged at 1000 rcf for 5 min, and 100 μl of the supernatant is then plated onto fenitrothion with mineral salts medium (0.4 g/l of yeast extract, 0.4 g/l fenitrothion, 15 g/l bacteriological agar). The plates are cloudy when prepared as the fenitrothion is an emulsion.

Colonies that develop clear zones around them and are likely to be degrading or metabolizing fenitrothion, and these colonies are isolated and regrown on LB agar, nutrient agar, yeast glucose agar, TSA agar, BHI agar, or MRS agar. Once unique bacterial colonies are identified, their genomes are extracted using a genomic DNA extraction kit, (Qiagen, DNeasy Blood and Tissue Kit) as per the manufacturer's protocol.

The 16S rRNA gene is amplified using universal bacterial primers 27F (5'-AGAGTTTGATCMTGGCTCAG-3'; SEQ ID NO: 188) and 1492R (5'-TACCTTGTTACGACTT-3'; SEQ ID NO: 189), and using PCR conditions of 94° C. for 2 min, 30 cycles of 94° C. for 1 min, 56° C. for 1 min, and 72° C. for 2 min, and a final extension of 72° C. for 5 min. Gel electrophoresis is used to confirm that the amplicons are of the correct size (~1500 bp), and the products are excised from the gel and purified using a gel extraction kit (Qiagen, QIAquick) as per the manufacturer's protocol. The correct size amplicons are Sanger sequenced and BLAST is used to match the sequence against various repositories of 16s rRNA gene sequences to identify the bacteria.

To determine whether the isolated bacteria is degrading fenitrothion, ~$10^7$ bacterial cells are incubated in 1 ml of 20 mM sodium-potassium phosphate buffer (pH 7) with 1 mM fenitrothion, as described in PNAS, Vol. 109, No. 22, 8618-8622, 2012. After 30 min of incubation at 30° C., the reaction is stopped by adding an equal volume of methanol. Then fenitrothion and its metabolite, 3-methyl-4-nitrophenol, are analyzed by HPLC. The retention times and peak areas of the HPLC profiles are compared to known standards.

Unique bacterial isolates that have fenitrothion degrading capabilities are then stored as frozen glycerol at −80° C.

Example 6

Increasing *Drosophila melanogaster*'s Resistance to Fenitrothion Through the Administration of Fenitrothion-Degrading Bacteria This Example demonstrates the ability to protect an insect model, *Drosophila melanogaster*, from one or more negative effects of insecticides in their diet, more specifically fenitrothion. The following approach is a surrogate for other insects, such as bees or other insects disclosed herein, e.g., insects that are important pollinators for many flowering plant crops and vegetables. Many insecticides including fenitrothion have been shown to be toxic to bees.

Experimental Design:

Therapeutic design: The bacterial isolates selected in Example 5 are formulated at $10^9$ organisms in 100 µl of fly food medium with and without fenitrothion.

The media used to rear flies is cornmeal, molasses and yeast medium (11 g/l yeast, 54 g/l yellow cornmeal, 5 g/l agar, 66 ml/l molasses, and 4.8 ml/l propionic acid). For experimental procedures, fenitrothion at 0, 10, and 100 p.p.m. or phosphate-buffered saline as negative controls are infused into sterile fly food medium.

Development Rate Assay

On day one, $10^9$ fenitrothion-degrading bacteria described in Example 5 are suspended in 100 µl phosphate-buffered saline or equal volumes of saline (negative controls) are added to sterile fly food medium with or without fenitrothion. All are left to dry for a day at 25° C. as described in *Appl. Environ. Microbiol.* Vol. 82, No. 20, 6204-6213, 2016.

On day two, fertilized embryos collected from flies are treated with 2% hypochlorite solution for 5 min and then washed with sterile water to remove any extracellular microbes from the embryos. 10 µl of the embryo suspension in water (1:3 embryo:water suspension) is added to the bacteria-seeded or negative control fly food with or without the fenitrothion. The fly food cohorts with the embryos are maintained at 25° C. with 12 h light and 12 dark cycle for the rest of the experiment.

The time to puparium formation and the number of pupa formed is measured in each cohort. The time to adult emergence and the rate of emergence is measured in each sample. From the time the first adult emerges from the pupa, the number of emerging adult flies are counted every 12 hours and rate of emergence is computed.

Embryos in the fenitrothion infused fly food seeded with Fenitrothion-degrading bacteria are expected to develop faster than the embryos on fenitrothion infused food without the fenitrothion-degrading bacteria.

Survival Assay

About 12 days before day one, sterile embryos are generated as described previously and raised on sterile fly food. Adults start to emerge from their pupae 11 days from embryo collection when raised in sterile fly food without fenitrothion at 25° C. with 12 h light and 12 h dark cycle. On day one, $10^9$ of the fenitrothion-degrading bacteria in phosphate-buffered saline are added to sterile fly food medium as described in a previous Example.

On day two, 10 newly emerged sterile adult males and females are introduced to bacteria-seeded or negative control fly food with or without fenitrothion. The fly food with the flies is maintained at 25° C. with 12 h light and 12 dark cycle for the rest of the experiment. The number of surviving male and female flies are counted every day until all the flies are dead. Survival analysis is performed to assess the fitness benefit of fenitrothion-degrading bacteria on the fly survival.

Flies raised on fenitrothion infused fly food seeded with fenitrothion-degrading bacteria are expected to survive longer than flies raised on fenitrothion infused food without the fenitrothion-degrading bacteria.

Example 7

Elimination of Entomopathogenic Bacteria from *Drosophila melanogaster* Using Naturally Occurring Phages This Example demonstrates the ability to eliminate insect bacterial pathogens (such as *Serratia marcescens, Erwinia carotovora*, and *Pseudomonas entomophila*) from *Drosophila melanogaster* using naturally occurring phages. This procedure can be useful as a surrogate assay for eliminating bacteria in other insect species, such as in bees.

Experimental Design:

Therapeutic design: Phage library collections are used having the following phage families: Myoviridae, Siphoviridae, Podoviridae, Lipothrixviridae, Rudiviridae, Ampullaviridae, Bicaudaviridae, Clavaviridae, Corticoviridae, Cystoviridae, Fuselloviridae, Globuloviridae, Guttaviridae, Inoviridae, Leviviridae, Microviridae, Plasmaviridae, Tectiviridae.

Multiple environmental samples (soil, pond sediments, and sewage water) are collected in sterile 1 L flasks over a period of 2 weeks and are immediately processed after collection and stored thereafter at 4° C. Solid samples are homogenized in sterile double-strength difco luria broth (LB) or tryptic soy broth (TSB) supplemented with 2 mM CaCl2 to a final volume of 100 mL. The pH and phosphate levels are measured using phosphate test strips. For purification, all samples are centrifuged at 3000-6000 g for 10-15 min at 4° C., and filtered through 0.2-µm low protein filters to remove all remaining bacterial cells. The supernatant that contains the phage library is then stored at 4° C. in the presence of chloroform in a glass bottle.

20-30 ml of the phage library is diluted to a volume of 30-40 ml with LB-broth. The target bacterial strain (e.g., *Serratia marcescens, Erwinia carotovora*, and *Pseudomonas entomophila*) is added (50-200 μl overnight culture grown in LB-broth) to enrich phages that target this specific bacterial strain in the culture. This culture is incubated overnight at 37° C., shaken at 230 rpm. Bacteria from this enrichment culture are removed by centrifugation (3000-6000 g 15-20 min, 4° C.) and filtered (0.2 or 0.45 μm filter). 2.5 ml of the bacteria free culture is added to 2.5 ml of LB-broth and 50-100 μl of the target bacteria are added back to the culture to further enrich the phages. The enrichment culture is grown overnight as above. A sample from this enrichment culture is centrifuged at 13,000 g for 15 min at room temperature and 10 μl of the supernatant is plated on an LB-agar petri dish along with 100-300 μl of the target bacteria and 3 ml of melted 0.7% soft-agar. The plates are incubated overnight at 37° C.

Each of the plaques observed on the bacterial lawn are picked and transferred into 500 μl of LB-broth. A sample from this plaque-stock is further plated on the target bacteria. Plaque-purification is performed three times for all discovered phages in order to isolate a single homogenous phage from the heterogeneous phage mix.

Lysates from plates with high-titer phages (>1×10^10 PFU/ml) are prepared by harvesting overlay plates of a host bacterium strain exhibiting confluent lysis. After being flooded with 5 ml of buffer, the soft agar overlay is macerated, clarified by centrifugation, and filter sterilized. The resulting lysates are stored at 4° C. High-titer phage lysates are further purified by isopycnic CsCl centrifugation, as described in Summer et al., *J. Bacteriol.* 192:179-190, 2010.

DNA is isolated from CsCl-purified phage suspensions as described in Summer, *Methods Mol. Biol.* 502:27-46, 2009. An individual isolated phage is sequenced as part of two pools of phage genomes by using a 454 pyrosequencing method. Briefly, phage genomic DNA is mixed in equimolar amounts to a final concentration of about 100 ng/L. The pooled DNA is sheared, ligated with a multiplex identifier (MID) tag specific for each of the pools, and sequenced by pyrosequencing using a full-plate reaction on a sequencer (Roche) according to the manufacturer's protocols. The pooled phage DNA is present in two sequencing reactions. The output corresponding to each of the pools is assembled individually by using software (454 Life Sciences), by adjusting the settings to include only reads with a single MID per assembly. The identity of individual contigs is determined by PCR using primers generated against contig sequences and individual phage genomic DNA preparations as the template. Sequence software (Gene Codes Corporation) is used for sequence assembly and editing.

Phage chromosomal end structures are determined experimentally. Cohesive (cos) ends for phages are determined by sequencing off the ends of the phage genome and sequencing the PCR products derived by amplification through the ligated junction of circularized genomic DNA, as described in Summer, *Methods Mol. Biol.* 502:27-46, 2009. Protein-coding regions are initially predicted using gene prediction software (Lukashin et al. *Nucleic Acids Res.* 26:1107-1115, 1998), refined through manual analysis in Artemis (Rutherford et al., *Bioinformatics* 16:944-945, 2000), and analyzed through the use of BLAST (E value cutoff of 0.005) (Camacho et al., *BMC Bioinformatics* 10:421, 2009). Proteins of particular interest are additionally analyzed by sequence searching software (Hunter et al., *Nucleic Acids Res.* 40:D306-D312, 2012).

Electron microscopy of CsCl-purified phage (>1×10^11 PFU/ml) that lysed the *Drosophila*'s pathogenic bacterial species is performed by diluting phage stock with the tryptic soy broth buffer. Phages are applied onto thin 400-mesh carbon-coated grids, stained with 2% (wt/vol) uranyl acetate, and air dried. Specimens are observed on a transmission electron microscope operating at an acceleration voltage of 100 kV. Five virions of each phage are measured to calculate mean values and standard deviations for dimensions of capsid and tail, where appropriate.

Incorporating Phages into a Meal

The media used to rear flies is cornmeal, molasses and yeast medium (11 g/l yeast, 54 g/l yellow cornmeal, 5 g/l agar, 66 ml/l molasses, and 4.8 ml/l propionic acid). Phage solutions are infused into the fly food to obtain final concentrations of phages between 0 and $10^8$ pfu/ml.

*S. Marcescens, Erwinia carotovora*, and *Pseudomonas entomphila* bacteria are grown at 30° C. in nutrient broth or LB broth.

Sterile fly embryos are generated by treating fertilized embryos collected from flies with 2% hypochlorite solution for 5 min and then washed with sterile water to remove any extracellular microbes. Fly larvae with the target bacteria are generated by seeding $10^9$ CFUs of bacteria in sterile fly food and adding sterile fly embryos to this food. After 2 days, ten *S. marcescens* infected first instar fly larvae are added to the fly food with a range (0-$10^8$ pfu/ml) of the phage concentrations. The larvae are left to grow in the food with the phages for 3 days until they become third instars. The larvae are then collected and individually homogenized in nutrient broth or LB broth, and plated on nutrient agar or LB agar plates, and incubated at 30° C. The number of CFUs of *S. marcescens* obtained from larvae in fly food with varying phage concentrations are recorded. This shows the number of live bacteria that were present in the flies.

The number of live bacteria are expected to be reduced in the larvae grown on fly food with the phages against the bacteria.

Example 8

Generation of a Library of Natural Microbes

This Example demonstrates the isolation of bacteria from soil that naturally produce the amino acid, methionine.

The medium used for isolation of microorganisms is Starch-Casein-Nitrate agar (Starch, 10.0 g; Casein, 0.003 g; $KNO_3$, 0.02 g; NaCl, 0.02 g; $MgSO_4$, 0.5 mg; $CaCO_3$, 0.2 mg; $FeSO_4$, 0.1 mg; Agar, 12.0 g; $H_2O$, 1 L; pH 7.0) (Kuster and Williams, 1964). Each environmental soil sample (1.0 g) is suspended in 9 ml of sterile water, and 1 ml of the suspension is serially diluted ten-fold in sterile distilled water. One milliliter of the $10^{-5}$ dilution is inoculated onto the agar medium and incubated for 7 days at 30° C. At the end of this period, the plates are observed for growth. White discrete and leathery colonies are picked and grown on new Starch-Casein-Nitrate agar plates to create a library of isolates. After 7 days of growth at 30° C., the plates are kept at 4° C.

Example 9

Screen for Isolates that Produce Methionine

This Example demonstrates the screening assay of isolates from Example 8 that naturally produce the amino acid, methionine.

Screening for Methionine Production:

A modified basal medium ($K_2HPO_4$, 0.3 g; $KH_2PO_4$, 0.7 g; $Na_2CO_3$, 1.0 g; $CaCl_2$, 5.0 mg; $MgSO_4$, 0.3 g; $FeSO_4$, 1.0 mg; $H_2O$, 1 L) with sucrose (20.0 g) and $NH_4Cl$ (10.0 g) is used for fermentation (Chay, B. P., Galvez, F. C. F., and Padolina, W. G. P. U. L. B. P. (1992). Methionine production by batch fermentation from various carbohydrates. ASEAN Food Journal (Malaysia)). The pH of the medium is 7.2.

Culture conditions: Two loops of the 7 day isolate culture of Example 8 are inoculated into a 250 ml Erlenmeyer flask with 30 ml of the fermentation medium. Methionine production is assayed after incubation of the flask for 5 days on a rotary shaker (160 rpm) at 30° C. Duplicate flasks are prepared and non-inoculated flasks served as control in all experiments.

The presence of methionine in the culture broths of the isolates is examined by paper chromatography following a modified method of Khanna and Nag (Khanna et al., "Production of amino acids in vitro tissue culture," *Indian Journal of Experimental Biology* (1973)). The broth culture is centrifuged at 5000×g for 20 min and 2 µL of the supernatant is applied 1.5 cm above one edge of Whatman No. 1 filter paper, with dimensions of 18 cm×22 cm. 1 µL of volume of a standard methionine solution (0.1 mg/mL) is applied alongside with the supernatant, and the chromatogram is developed in a solvent mixture of n-butanol, acetic acid and water (4:1:1) for 18 h. The chromatogram is air-dried at room temperature, sprayed with 0.15% ninhydrin solution in butanol and dried again before heating at 60° C. for 5 min in an oven. The value of the ninhydrin-positive spot (bluish-violet) of the supernatant that corresponds with the value of the standard methionine solution indicates presence of methionine in the broth culture. The concentration of methionine produced in the broth culture of the isolate is estimated as follows. The ninhydrin-positive spot of the supernatant of the isolate on the chromatogram is eluted in 10% ethanol and the spectrophotometric reading of the eluate at 520 nm recorded. The methionine concentration in the supernatant is determined from a standard curve. A plot of the values of optical densities against varying concentrations (0.1 to 0.9 mg/ml) of a methionine solution serve as the standard methionine curve.

Isolates that produce methionine are kept on fresh agar plates and a stock solution is created by suspending two loopfuls of microorganism in an aliquot of 50% glycerol solution.

Example 10

Administration of Amino Acid Producing Strain of Bacteria to *Drosophila melanogaster* through Diet to Increase their Development Rate This example demonstrates the ability to treat *Drosophila melanogaster* with amino acid producing bacteria to increase their development rate when raised on nutrient deprived diets. This experimental design can be extended to aid in the development of other insects, such as honeybees, which may lack nutrients in their diets.

Therapeutic Design:

Isolated bacteria *Corynebacterium glutamicum* that are glutamate or methionine producing, are formulated with a solution of $10^9$ colony forming units (CFUs) mixed to the feeding substrate for *Drosophila* flies.

Experimental Design:

*Corynebacterium glutamicum* strains that produce glutamate or methionine were grown in nutrient broth at 30° C. The media used to rear flies is cornmeal, molasses and yeast medium (11 g/l yeast, 54 g/l yellow cornmeal, 5 g/l agar, 66 ml/l molasses, and 4.8 ml/l propionic acid). All the components of the diet except propionic acid are heated together to 80° C. in deionized water with constant mixing for 30 minutes and let to cool to 60° C. Propionic acid is then mixed in and 50 ml of the diet is aliquoted into individual bottles and allowed to cool down and solidify. The flies are raised at 26° C., 16:8 hour light:dark cycle, at around 60% humidity.

For the experimental setup to measure the larval growth rate, defined diet was used (Piper et al., 2014, Nature Methods). Defined diet eliminates the effects of batch to batch variation in the ingredients used for the cornmeal based diet. In addition, the defined diet allows for the exclusion of individual components to test their effects on fly development.

Development Rate Assay

On day one, 100 ul of a *Corynebacterium glutamicum* suspension in nutrient broth consisting of $10^9$ colony forming units (CFUs) were added to five replicates of fly food. As controls, nutrient broth without the bacteria was added to five more bottles of fly food. Fertilized embryos collected from fruit flies were treated with 2% hypochlorite solution for five minutes and then washed with sterile water to remove any extracellular microbes from the embryos. 10 ul of the embryo suspension in water (one:three embryo:water suspension) was added to all the bacteria seeded and control fly food bottles. The fly food with the embryos was maintained at 26° C., 16:8 hour light:dark cycle, at around 60% humidity for the rest of the experiment. The time to adult emergence and the rate of emergence was measured in every replicate. From the time the first adult emerges from the pupa, the number of adult flies emerging was counted every 12 hours and rate of emergence was be computed.

Larval Mass Assay

To test whether the presence of bacteria producing amino acids can increase the body mass of developing larvae when raised on defined diet, we produced larvae that are axenic, and mono-associated with a single strain of bacterium. For these assays, three different bacteria were used, *Corynebacterium glutamicum*—a strain that produces glutamate, *Corynebacterium glutamicum*—a strain that produces methionine, and *E. coli*.

First, axenic embryos were generated. Fertilized embryos were collected from fruit flies over a 6 hour period on grape juice agar plates with yeast. To eliminate any bacterial contamination, the embryos were treated with 2% hypochlorite solution for five minutes and then washed thrice with sterile water. One volume of embryos was then suspended in 3 volumes of water.

The defined diet was aliquoted into vials and nine replicates were used for every condition being tested. The conditions were:

1. No bacteria added to the food
2. Food containing *C. glutamicum*, strain that produces glutamate (C.glu-Glu)
3. Food containing *C. glutamicum*, a strain that produces methionine (C.glu-Met)
4. Food containing *E. coli*

To each vial of the food that were in conditions 2, 3, and 4, 100 ul of overnight stationary phase cultures was added. To each of the nine replicates in every condition, 10 ul of the sterile embryo+water suspension was added. The vials were then incubated at 26° C., 60% humidity, 16:8 light:dark cycle.

After 13 days, 10-15 randomly chosen larvae from each replicate were sampled, and their areas were measured, as a proxy to their biomass and weight. The larvae were scooped out from the food with a sterile spatula, rinsed in water to clean the food from their bodies, and an image of every larvae sampled was acquired individually for every replicate in each condition. An Image J script was used to identify, outline, and measure the area of the larva in every image.

Amino Acid Producing Bacteria Treatment Increases Insect Development Rate.

Figure 2:
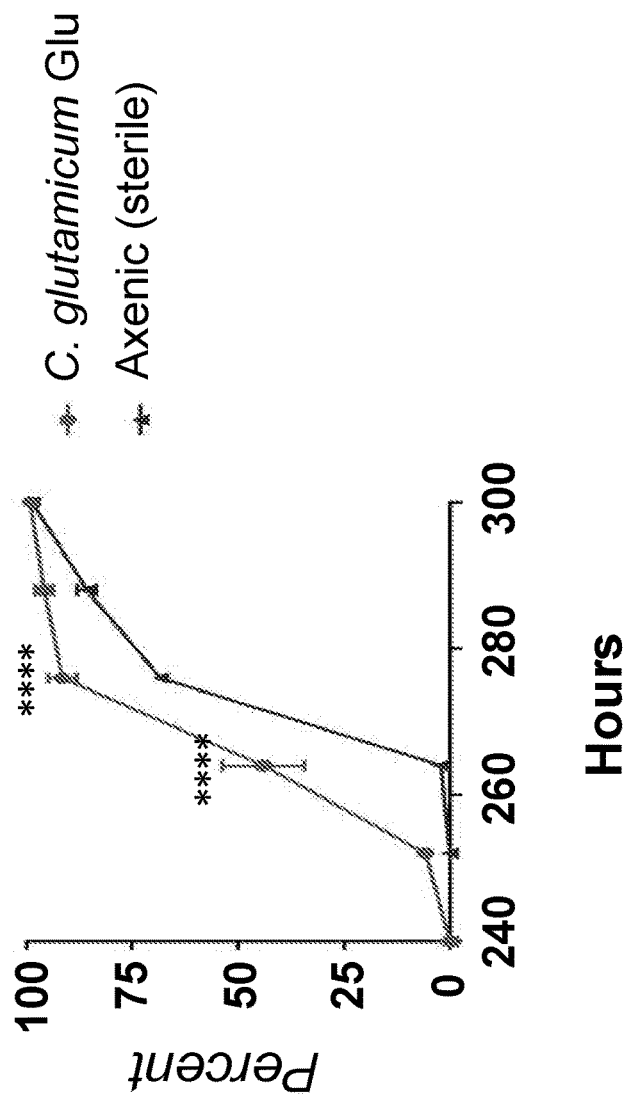
FIG. 2A is a graph showing the effects of male gender on the developmental rate differences in *Drosophila melanogaster*. The adults emerging from FIG. 1 were sexed and their rate of emergence was plotted.
FIG. 2B is a graph showing the effects of female gender on the developmental rate differences in *Drosophila melanogaster*. The adults emerging from FIG. 1 were sexed and their rate of emergence was plotted. The enhancement in the rate of development in the females due to the presence of bacteria in the diet is significantly more than in their male counterparts. The benefits of the presence of bacteria in the fly diet are higher in the females compared to the males.

Embryos that developed on diet that was seeded with the amino acid producing strain of bacterium reached adulthood significantly faster than those that were raised on the sterile diet (FIG. 1). Further, this effect was slightly stronger in female flies than in male files (FIGS. 2A and 2B).

Amino Acid Producing Bacteria Treatment Increases Larval Body Mass.

Figure 3:
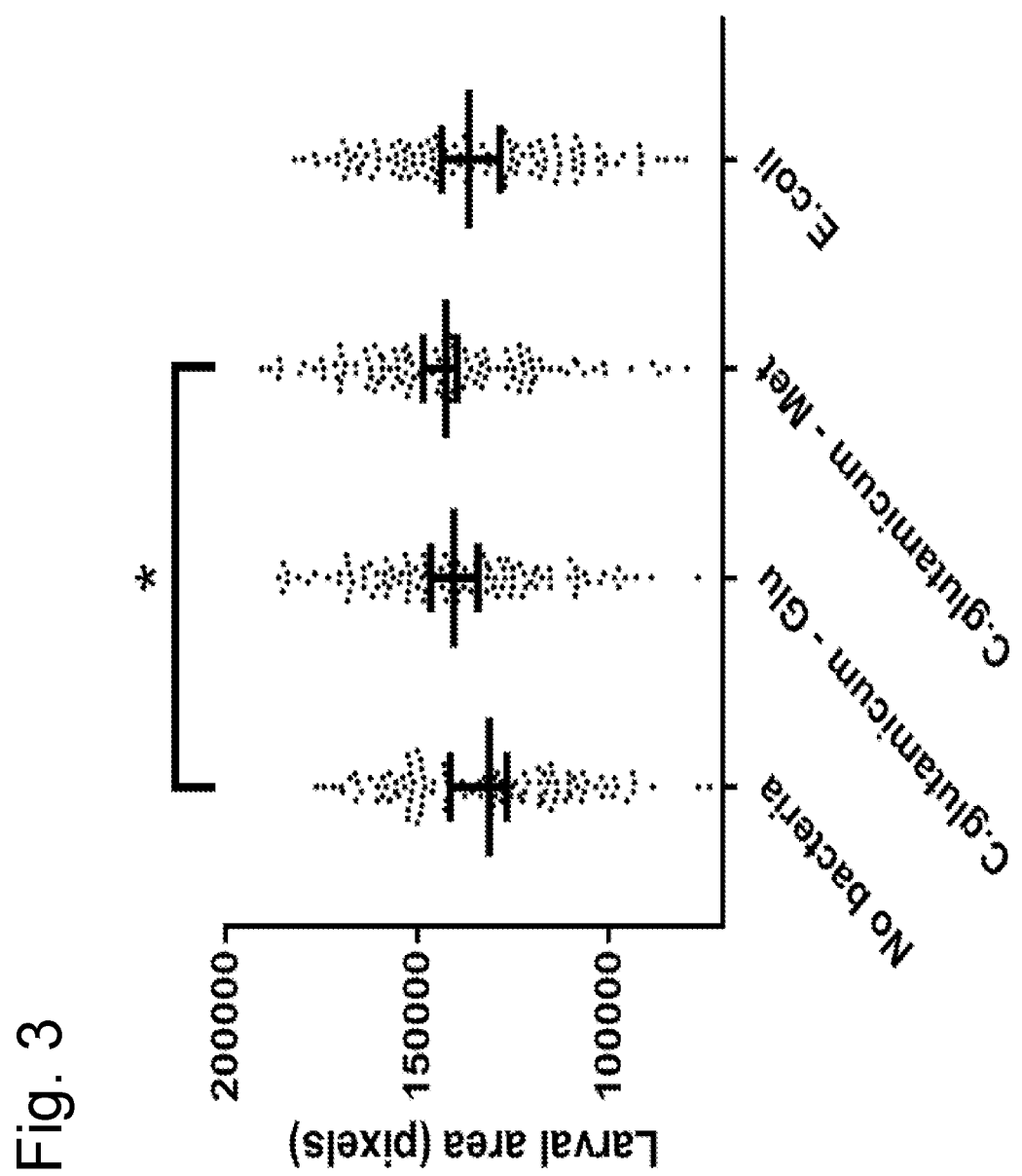
FIG. 3 is a graph showing *C. glutamicum* strains promoted larval biomass. Larvae raised on diet supplemented with *C. glutamicum* strains either producing glutamate or methionine are bigger than those raised on sterile diet or diet supplemented with *Escherichia coli*. The areas of the larvae are measured as the number of pixels in the images of the larvae. The medians and the 95% confidence intervals are shown as lines on the graph.

Larvae from the diet supplemented with C. glu-Met had the largest body size on average, followed by those in diet with C.glu-Glu, *E. coli*, and no bacteria (FIG. 3). This shows that augmenting the diet of insects with bacteria that produce amino acids produced insect biomass faster than un-supplemented diet.

Together this data demonstrates that augmenting the diet of insects with bacteria that were capable of producing amino acids produced insect biomass faster than un-supplemented diet. Extending this to other insects such as bees, supplementing their diet with bacteria that are capable of producing methionine can increase their fitness.

Example 11

Insects Treated with a Solution of Purified Phage

This Example demonstrates the isolation and purification of phages from environmental samples that targeted specific insect bacteria. This Example also demonstrates the efficacy of isolated phages against the target bacteria in vitro by plaque assays, by measuring their oxygen consumption rate, and the extracellular acidification rate. Finally, this Example demonstrates the efficacy of the phages in vivo, by measuring the ability of the phage to the target bacteria from flies by treating them with a phage isolated against the bacteria. This Example demonstrates that a pathogenic bacterium that decreased the fitness of an insect can be cleared using a phage to target the bacteria. Specifically, *Serratia marcescens* which is a pathogenic bacterium in flies can be cleared with the use of a phage that was isolated from garden compost.

Experimental Design

Isolation of Specific Bacteriophages from Natural Samples:

Bacteriophages against target bacteria were isolated from environmental source material. Briefly, a saturated culture of *Serratia marcescens* was diluted into fresh double-strength tryptic soy broth (TSB) and grown for ~120 minutes to early log-phase at 24-26° C., or into double-strength Luria-Bertani (LB) broth and grown for ~90 min at 37° C. Garden compost was prepared by homogenization in PBS and sterilized by 0.2 μm filtration. Raw sewage was sterilized by 0.2 μm filtration. One volume of filtered source material was added to log-phase bacterial cultures and incubation was continued for 24 h. Enriched source material was prepared by pelleting cultures and filtering supernatant fluid through 0.45 μm membranes.

Phages were isolated by plating samples onto double-agar bacterial lawns. Stationary bacterial cultures were combined with molten 0.6% agar LB or TSB and poured onto 1.5% agar LB or TSB plates. After solidification, 2.5 μL of phage sample dilutions were spotted onto the double-agar plates and allowed to absorb. Plates were then wrapped and incubated overnight at 25° C. (TSA) or 37° C. (LB), then assessed for the formation of visible plaques. Newly isolated plaques were purified by serial passaging of individual plaques on the target strain by picking plaques into SM Buffer (50 mM Tris-HCl [pH 7.4], 10 mM MgSO4, 100 mM NaCl) and incubating for 15 min at 55° C., then repeating the double-agar spotting method from above using the plaque suspension.

Bacteriophages were successfully isolated from both sewage and compost, as detailed above. Plaque formation was clearly evident after spotting samples onto lawns of the *S. marcescens* bacteria used for the enrichments.

Passaging, Quantification, and Propagation of Bacteriophages:

Propagation and generation of phage lysates for use in subsequent experiments was performed using bacteriophages isolated and purified as above. Briefly, saturated bacterial cultures were diluted 100-fold into fresh medium and grown for 60-120 minutes to achieve an early-logarithmic growth state for effective phage infection. Phage suspensions or lysates were added to early log phase cultures and incubation was continued until broth clearing, indicative of phage propagation and bacterial lysis, was observed, or until up to 24 h post-infection. Lysates were harvested by pelleting cells at 7,197×g for 20 min, then filtering the supernatant fluid through 0.45 or 0.2 μm membranes. Filtered lysates were stored at 4° C.

Enumeration of infective phage particles was performed using the double-agar spotting method. Briefly, a 1:10 dilution series of samples was performed in PBS and dilutions were spotted onto solidified double-agar plates prepared with the host bacteria as above. Plaque-forming units (PFU) were counted after overnight incubation to determine the approximate titer of samples.

In Vitro Analysis of Isolated Phages Measuring Bacterial Respiration:

A Seahorse XFe96 Analyzer (Agilent) was used to measure the effects of phages on bacteria by monitoring oxygen consumption rate (OCR) and extracellular acidification rate (ECAR) during infection. XFe96 plates were coated the day prior to experiments by 15 μL of a 1 mg/mL poly-L-lysine stock per well and dried overnight at 28° C. and XFe96 probes were equilibrated by placing into wells containing 200 μL of XF Calibrant and incubating in the dark at room temperature. The following day, poly-L-lysine coated plates were washed twice with ddH2O. Saturated overnight cultures of *E. coli* BL21 (LB, 37° C.) or *S. marcescens* (TSB, 25° C.) were subcultured at 1:100 into the same media and grown with aeration for ~2.5 h at 30° C. Cultures were then diluted to O.D. 600 nm~0.02 using the same media. Treatments were prepared by diluting stocks into SM Buffer at 10× final concentration and loading 20 μL of the 10× solutions into the appropriate injection ports of the probe plate. While the probes were equilibrating in the XFe96 Flux Analyzer, bacterial plates were prepared by adding 90 μL of bacterial suspensions or media controls and spun at 3,000 rpm for 10 min. Following centrifugation, an additional 90 μL of the appropriate media were added gently to the wells so as not to disturb bacterial adherence, bringing the total volume to 180 μL per well.

The XFe96 Flux Analyzer was run at ~30° C., following a Mix, Wait, Read cycling of 1:00, 0:30, 3:00. Four cycles were completed to permit equilibration/normalization of bacteria, then the 20 μL treatments were injected and cycling continued as above, for a total time of approximately 6 h. Data were analyzed using the Seahorse XFe96 Wave software package.

Figure 4:
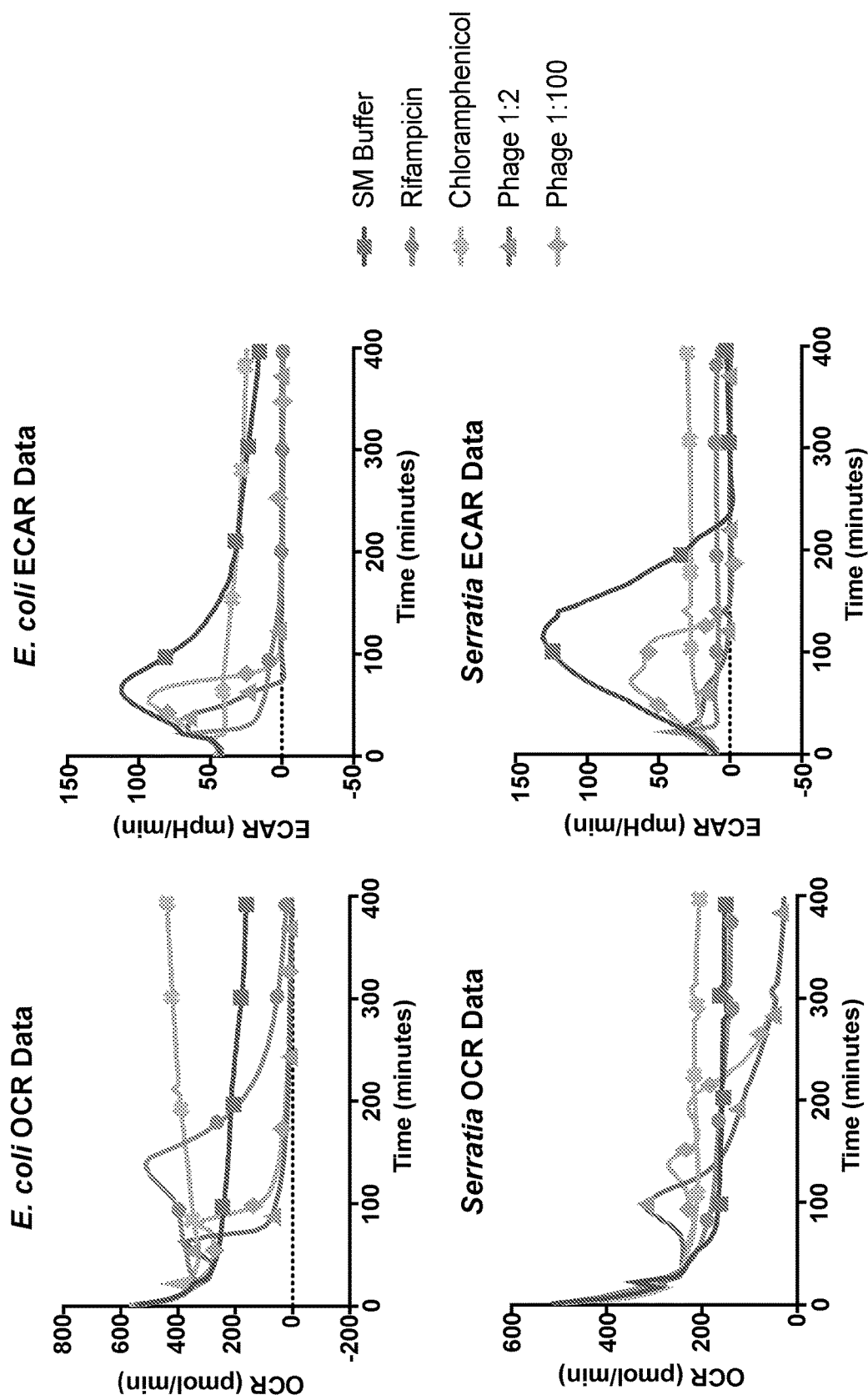
FIG. 4 is a panel of graphs showing the results of a Seahorse flux assay for bacterial respiration. Bacteria were grown to logarithmic phase and loaded into Seahorse XFe96 plates for temporal measurements of oxygen consumption rate (OCR) and extracellular acidification rate (ECAR) as described in methods. Treatments were injected into the wells after approximately 20 minutes and bacteria were monitored to detect changes in growth. Rifampicin=100 µg/mL; Chloramphenicol=25 µg/mL; Phages (T7 for *E. coli* and ɸSmVL-C1 for *Serratia marcescens*) were lysates diluted either 1:2 or 1:100 in SM Buffer. The markers on each line are solely provided as indicators of the condition to which each line corresponds, and are not indicative of data points

The effects of isolated bacteriophages were assayed by measuring oxygen consumption rate (OCR) and extracellular acidification rate (ECAR) of bacteria with a Seahorse XFe96 Analyzer. When $E.$ $coli$ was infected with phage T7 and $S.$ $marcescens$ infected with the newly isolated ϕSmVL-C1, dramatic decreases in OCR were observed following brief bursts in this rate (FIG. 4). For both phages with both host organisms, the Seahorse assay permitted the detection of successful phage infection without the need for plaque assays. Thus, this method is applicable for detecting phage infection of a host organism not amenable to traditional phage detection methods.

SYBR Gold Transduction Assay for Infection Identification:

Bacteriophage preparations were prepared for staining by pretreating with nucleases to remove extraviral nucleic acids that could interfere with fluorescent signal interpretation. Briefly, MgCl2 was added to 10 mL of phage lysate at 10 mM final concentration, and RNase A (Qiagen) and DNase I (Sigma) were both added to final concentrations of 10 μg/mL. Samples were incubated for 1 h at room temperature. After nuclease treatment, 5 mL of lysates were combined with 1 μL of SYBR Gold (Thermo, 10,000×) and incubated at room temperature for ~1.5 h. Excess dye was subsequently removed from samples using Amicon ultrafiltration columns. Briefly, Amicon columns (15 mL, 10 k MWCO) were washed by adding 10 mL of SM Buffer and spinning at 5,000×g, 4° C. for 5 min. Labeled phage samples were then spun through the columns at 5,000×g, 4° C. until the volume had decreased by approximately 10-fold (15-30 min). To wash samples, 5 mL SM Buffer was added to each reservoir and the spin repeated, followed by two additional washes. After the third wash, the retained samples were pipetted out from the Amicon reservoirs and brought up to approximately 1 mL using SM Buffer. To remove larger contaminants, washed and labeled phage samples were spun at 10,000×g for 2 min, and the supernatants were subsequently filtered through 0.2 μm membranes into black microtubes and stored at 4° C.

Saturated bacterial cultures ($E.$ $coli$ MG1655 grown in LB at 37° C., $S.$ $marcescens$ and $S.$ $symbiotica$ grown in TSB at 26° C.) were prepared by spinning down 1 mL aliquots and washing once with 1 mL PBS before a final resuspension using 1 mL PBS. Positive control labeled bacteria were stained by combining 500 μL of washed bacteria with 1 μL of SYBR Gold and incubating for 1 h in the dark at room temperature. Bacteria were pelleted by spinning at 8,000×g for 5 min and washed twice with an equal volume of PBS, followed by resuspension in a final volume of 500 μL PBS. A volume of 25 μL of stained bacteria was combined with 25 μL of SM Buffer in a black microtube, to which 50 μL of 10% formalin (5% final volume, ~2% formaldehyde) was added and mixed by flicking. Samples were fixed at room temperature for ~3 h and then washed using Amicon ultrafiltration columns. Briefly, 500 μL of picopure water was added to Amicon columns (0.5 mL, 100 k MWCO) and spun at 14,000×g for 5 min to wash membranes. Fixed samples were diluted by adding 400 μL of PBS and then transferred to pre-washed spin columns and spun at 14,000×g for 10 min. Columns were transferred to fresh collection tubes, and 500 μL of PBS was added to dilute out fixative remaining in the retentate. Subsequently, two additional PBS dilutions were performed, for a total of three washes. The final retentates were diluted to roughly 100 μL, then columns were inverted into fresh collection tubes and spun at 1,000×g for 2 min to collect samples. Washed samples were transferred to black microtubes and stored at 4° C.

For transduction experiments and controls, 25 μL of bacteria (or PBS) and 25 μL of SYBR Gold labeled phage (or SM Buffer) were combined in black microtubes and incubated static for 15-20 min at room temperature to permit phage adsorption and injection into recipient bacteria. Immediately after incubation, 50 μL of 10% formalin was added to samples and fixation was performed at room temperature for ~4 h. Samples were washed with PBS using Amicon columns, as above.

Injection of bacteriophage nucleic acid was required for a phage to successfully infect a host bacterial cell. Coliphage P1kc labeled with SYBR Gold and co-incubated with $S.$ $marcescens$ revealed the presence of fluorescent bacteria by microscopy, validating the use of this assay in a phage isolation pipeline. As with the Seahorse assay, this approach provided an alternative to traditional phage methods to permit expansion to organisms not amenable to plaque assay. Additionally, the SYBR Gold transduction assay did not require bacterial growth, so is applicable to analysis of phages targeting difficult or even non-culturable organisms, including endosymbionts such as $Buchnera$.

Testing in Vivo Efficacy of the Phages Against $S.$ $Marcescens$ in $Drosophila$ $melanogaster$ Flies $S.$ $marcescens$ cultures were grown in Tryptic Soy Broth (TSB) at 30° C. with constant shaking at 200 rpm.

The media used to rear fly stocks was cornmeal, molasses and yeast medium (11 g/l yeast, 54 g/l yellow cornmeal, 5 g/l agar, 66 ml/l molasses, and 4.8 ml/l propionic acid). All the components of the diet except propionic acid were heated together to 80° C. in deionized water with constant mixing for 30 minutes and let to cool to 60° C. Propionic acid was then mixed in and 50 ml of the diet was aliquoted into individual bottles and allowed to cool down and solidify. The flies were raised at 26° C., 16:8 hour light:dark cycle, at around 60% humidity.

To infect the flies with $S.$ $marcescens$, a fine needle (About 10 um wide tip) was dipped in a dense overnight stationary phase culture and the thorax of the flies was punctured. For this experiment, four replicates of 10 males and 10 females each were infected with $S.$ $marcescens$ using the needle puncturing method as the positive control for fly mortality. For the treatment group, four replicates of 10 males and 10 females each were pricked with $S.$ $marcescens$ and a phage solution containing about 108 phage particles/ml. Finally, two replicates of 10 males and 10 females each that were not pricked or treated in anyway were used as a negative control for mortality.

Figure 5:
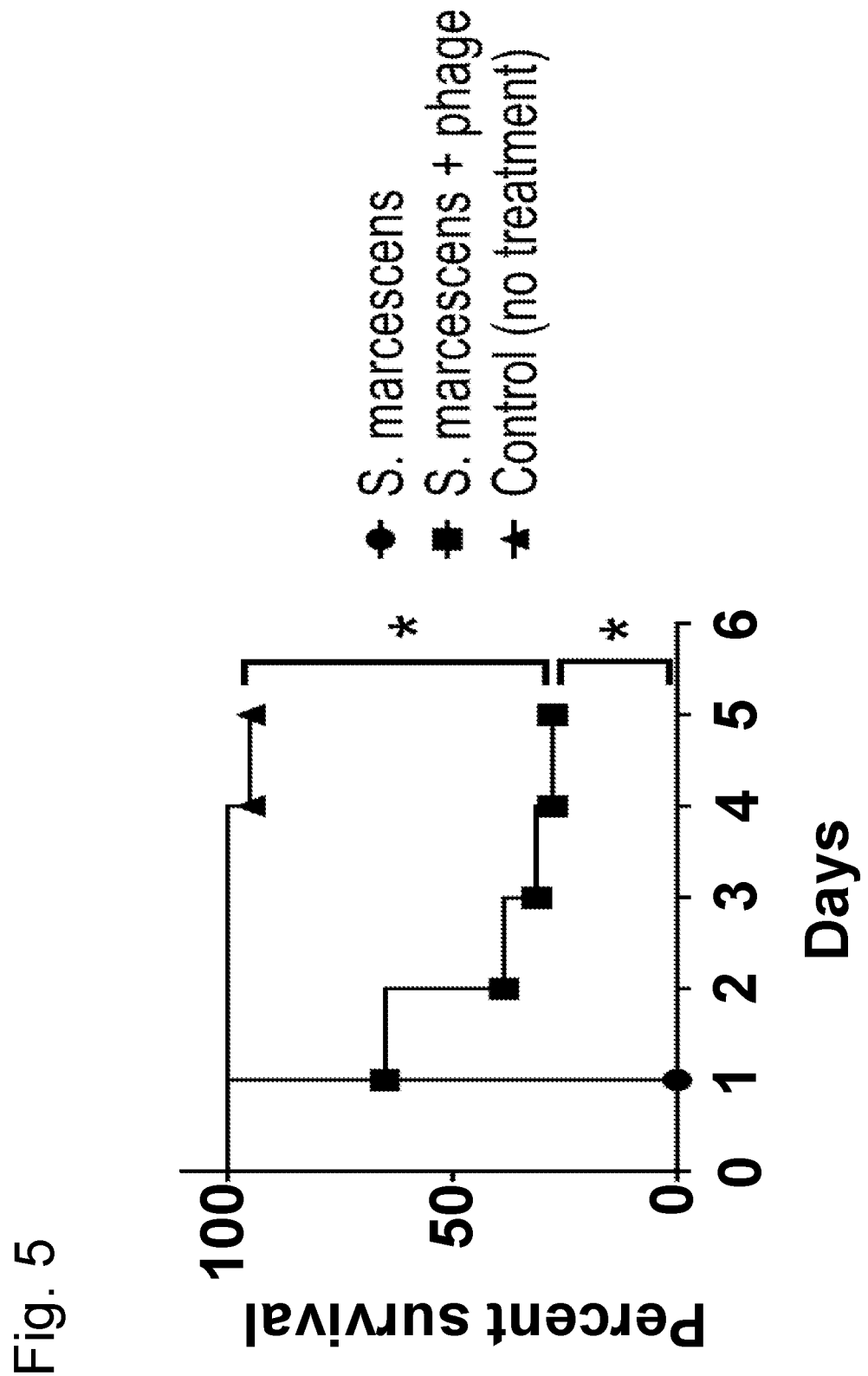
FIG. 5 is a graph showing phage against *S. marcescens* reduced fly mortality. Flies that were pricked with *S. marcescens* were all dead within a day, whereas a sizeable portion of the flies that were pricked with both *S. marcescens* and the phage survived for five days after the treatment. Almost all of the control flies which were not treated in anyway survived till the end of the experiment. Log-rank test was used to compare the curves for statistical significance, asterisk denotes $p<0.0001$.

Flies in all conditions were placed in food bottles and incubated at 26° C., 16:8 light:dark cycle, at 60% humidity. The number of alive and dead flies were counted every day for four days after the pricking. All The flies pricked with $S.$ $marcescens$ alone were all dead within 24 hours of the treatment. In comparison, more than 60% of the flies in the phage treatment group, and all the flies in the untreated control group were alive at that time point (FIG. 5). Further, most of the flies in the phage treatment group and the negative control group went on to survive for four more days when the experiment was terminated.

To ascertain the reason of death of the flies, dead flies from both the *S. marcescens* and *S. marcescens*+phage pricked flies were homogenized and plated out. Four dead flies from each of the four replicates of both the *S. marcescens* and the *S. marcescens*+phage treatment were homogenized in 100 ul of TSB. A 1:100 dilution was also produced by diluting the homogenate in TSB. 10 ul of the concentrated homogenate as well as the 1:100 dilution was plated out onto TSA plates, and incubated overnight at 30° C. Upon inspection of the plates for bacteria growth, all the plates from the dead *S. marcescens* pricked flies had a lawn of bacteria growing on them, whereas the plates from the dead *S. marcescens*+phage pricked flies had no bacteria on them.

This shows that in the absence of the phage, *S. marcescens* likely induced septic shock in the flies leading to their fatality. However, in the presence of the phage, the mortality may have been due to injury caused by the pricking with the needle.

Other Embodiments

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

---

The invention claimed is:

1. A method for increasing fitness of a honeybee, the method comprising:
   administering to the honeybee a composition comprising an effective amount of organophosphorous insecticide-metabolizing bacteria formulated with an insect comestible carrier.

2. The method of claim 1, wherein the administration comprises delivering the composition to a honeybee hive or at least one habitat where the honeybee grows, lives, reproduces, or feeds.

3. The method of claim 1, wherein the composition is a liquid, a solid, an aerosol, a paste, a gel, or a gas.

4. The method of claim 1, wherein the organophosphorous insecticide is fenitrothion.

5. The method of claim 1, wherein the carrier is a seed coating.

6. The method of claim 1, wherein the honeybee is in a honeybee colony.

* * * * *